US010065941B2

(12) United States Patent
Kai

(10) Patent No.: US 10,065,941 B2
(45) Date of Patent: *Sep. 4, 2018

(54) AMINOTRIAZINE DERIVATIVE AND PHARMACEUTICAL COMPOSITION COMPRISING THE SAME

(71) Applicant: Shionogi & Co., Ltd., Osaka-shi, Osaka (JP)

(72) Inventor: Hiroyuki Kai, Osaka (JP)

(73) Assignee: SHIONOGI & CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/637,967

(22) Filed: Jun. 29, 2017

(65) Prior Publication Data

US 2017/0362199 A1 Dec. 21, 2017

Related U.S. Application Data

(63) Continuation of application No. 14/897,836, filed as application No. PCT/JP2014/065678 on Jun. 13, 2014, now Pat. No. 9,732,060.

(30) Foreign Application Priority Data

Jun. 14, 2013 (JP) ................................. 2013-125134

(51) Int. Cl.

| C07D 401/12 | (2006.01) |
|---|---|
| C07D 405/14 | (2006.01) |
| C07D 409/14 | (2006.01) |
| A61K 31/53 | (2006.01) |
| A61P 25/04 | (2006.01) |

(52) U.S. Cl.
CPC ............ *C07D 401/12* (2013.01); *A61K 31/53* (2013.01); *C07D 405/14* (2013.01); *C07D 409/14* (2013.01)

(58) Field of Classification Search
CPC .. C07D 401/12; C07D 405/14; C07D 409/14; A61K 31/53
USPC .................. 544/211, 212; 514/245
See application file for complete search history.

(56) References Cited

U.S. PATENT DOCUMENTS

| 3,598,815 A | 8/1971 | Gilles |
| 4,021,249 A | 5/1977 | Noguchi et al. |
| 4,127,718 A | 11/1978 | Lily et al. |
| 4,156,002 A | 5/1979 | Brown et al. |
| 4,158,724 A | 6/1979 | Lily et al. |
| 4,254,122 A | 3/1981 | Brown |
| 4,317,911 A | 3/1982 | Rasburger et al. |
| 4,518,688 A | 5/1985 | Leppard et al. |
| 5,232,924 A | 8/1993 | Watanabe et al. |
| 5,389,599 A | 2/1995 | Schallner et al. |
| 6,177,437 B1 | 1/2001 | Wright |
| 7,745,451 B2 | 6/2010 | Kelly et al. |

(Continued)

FOREIGN PATENT DOCUMENTS

| EP | 5911 | 12/1979 |
| EP | 547461 | 12/1996 |

(Continued)

OTHER PUBLICATIONS

Adriaensen et al., "Functional Morphology of Pulmonary Neuroepithelial Bodies: Extremely Complex Airway Receptors," The Anatomical Record Part A, vol. 270A, pp. 25-40, (2003).
Akteries et al., "Reactions of Carbonyl Diisocynate with Amides and Acids," Chemische Berichte, vol. 119, pp. 669-682 (1986).
Balboni et al., "Triazine Compounds as Antagonists at BvB-Prokineticin Receptors," J. Med. Chem., vol. 51, pp. 7635-7639, (2008).
Baraldi et al., "Recent Developments in the field of $A_{2A}$ and $A_3$ Adenosine Receptor Anatagonists," European Journal of Medicinal Chemistry vol. 38, pp. 367-382, 2003.
Basoclu et al., "Effects of Aerosolized Adenosine 5'-Triphosphate vs Adenosine 5'-Monophosphate on Dyspnea and Airway Caliber in Healthy Nonsmokers and Patients with Asthma," Chest, vol. 128, No. 4, pp. 1905-1909. (2005).
Bernatowicz et al., "1H-Pyrazole-1-Carboxamidine Hydrochloride," J.Org. Chem., 57:2497-2502 (1992).

(Continued)

*Primary Examiner* — Venkataraman Balasubramanian
(74) *Attorney, Agent, or Firm* — Finnegan, Henderson, Farabow, Garrett & Dunner, LLP

(57) ABSTRACT

The present invention provides novel compounds having a $P2X_3$ and/or $P2X_{2/3}$ receptor antagonistic activity.
A compound of Formula (I):

[Chemical Formula 1]

(I)

wherein $R^a$ and $R^b$, and $R^d$ and $R^e$ are taken together to form oxo or the like; $R^{4a}$ and $R^{4b}$ are hydrogen or the like; n is 1 or the like; $R^2$ is aryl or the like; s and s' is 0 or the like; $R^9$ and $R^{9'}$ are halogen or the like; $R^{20a}$ and $R^{20b}$ are hydrogen, alkyl or the like; u is 1 to 4; $R^{13}$ is hydrogen or the like, or its pharmaceutically acceptable salt.

4 Claims, No Drawings

(56) References Cited

U.S. PATENT DOCUMENTS

| | | | |
|---|---|---|---|
| 7,858,632 | B2 | 12/2010 | Broka et al. |
| 9,732,060 | B2* | 8/2017 | Kai .................. C07D 401/12 |
| 2002/0049320 | A1 | 4/2002 | Gopalsamy et al. |
| 2007/0037974 | A1 | 2/2007 | Brotherton-Pleiss et al. |
| 2007/0049534 | A1 | 3/2007 | Dillon et al. |
| 2007/0049609 | A1 | 3/2007 | Dillon et al. |
| 2007/0049610 | A1 | 3/2007 | Dillon et al. |
| 2007/0049758 | A1 | 3/2007 | Dillon et al. |
| 2009/0099195 | A1 | 4/2009 | Bayrakdarian et al. |
| 2009/0270369 | A1 | 10/2009 | Ozaki et al. |
| 2010/0317676 | A1 | 12/2010 | Kelly et al. |
| 2011/0077242 | A1 | 3/2011 | Broka et al. |
| 2011/0237578 | A1 | 9/2011 | Wei et al. |
| 2013/0172317 | A1 | 7/2013 | Kai |
| 2016/0024072 | A1 | 1/2016 | Kai et al. |

FOREIGN PATENT DOCUMENTS

| | | |
|---|---|---|
| EP | 2 399 910 | 12/2011 |
| EP | 2 604 260 | 6/2013 |
| EP | 2 604 595 | 6/2013 |
| JP | 57144269 | 6/1982 |
| JP | 62-156110 | 11/1987 |
| JP | 11-189577 | 7/1999 |
| JP | 2000-72757 | 3/2000 |
| JP | 2001-131156 | 5/2001 |
| JP | 2006528640 | 12/2006 |
| JP | 2007-526268 | 9/2007 |
| JP | 2008-546639 | 12/2008 |
| JP | 2009-7258 | 1/2009 |
| JP | 2010-523667 | 7/2010 |
| JP | 2010-526138 | 7/2010 |
| RU | 2057754 | 4/1996 |
| SU | 867303 | 2/1979 |
| WO | WO 1999/52881 | 10/1999 |
| WO | WO 2000/39101 | 7/2000 |
| WO | WO 2000/51990 | 9/2000 |
| WO | WO 2001/55093 | 2/2001 |
| WO | WO 2002/094767 | 11/2002 |
| WO | WO 2004/054617 | 1/2004 |
| WO | WO 2005/009980 | 2/2005 |
| WO | WO 2005/095359 | 10/2005 |
| WO | WO 2006/012639 | 2/2006 |
| WO | WO 2006/074057 | 7/2006 |
| WO | WO 2006/102112 | 9/2006 |
| WO | WO 2006/104713 | 10/2006 |
| WO | WO 2006/104715 | 10/2006 |
| WO | WO 2006/119502 | 11/2006 |
| WO | WO 2006/119504 | 11/2006 |
| WO | WO 2007/079214 | 7/2007 |
| WO | WO 2008/005538 | 1/2008 |
| WO | WO 2008/016522 | 2/2008 |
| WO | WO 2008/089051 | 7/2008 |
| WO | WO 2008/127591 | 10/2008 |
| WO | WO 2008/136756 | 11/2008 |
| WO | WO 2009/058653 | 5/2009 |
| WO | WO 2010/051188 | 5/2010 |
| WO | WO 2010/149578 | 12/2010 |
| WO | WO 2011/017347 | 2/2011 |
| WO | WO 2012/016182 | 2/2012 |
| WO | WO 2012/020749 | 2/2012 |
| WO | WO 2012/135800 | 10/2012 |
| WO | WO 2013/089212 | 6/2013 |
| WO | WO 2013/118855 | 8/2013 |

OTHER PUBLICATIONS

Brouns et al., "Intraepithelial Vagal Sensory Nerve Terminals in Rat Pulmonary Neuroepthelial Bodies Express P2X$_3$ Receptors," Am J. Respir. Cell Mol. Biol. vol. 23, pp. 52-61, (2002).
Cantin et al., "Discovery of P2X3 Selective Antagonists for the Treatment of Chronic Pain," Bioorganic & Medicinal Chemistry Letters, vol. 22, pp. 2565-2571, (2012).
Carter et al., "Identification and SAR of Novel Diaminopyrimidines," Bioorganic & Medicinal Chemistry Letters, 19, 1628-1631 (2009).
CAS Registry No. 857972-98-6, (2016).
CAS Registry No. RN 343346-65-6 (Entered STN: Jun. 26, 2001).
CAS Registry No. RN 887 418-38-4 (Entered STN: Jun. 12, 2006).
Cecil Textbook of Medicine, edited by Bennet, J.C., and Plum F., 20th edition, vol. 1, pp. 1004-1010, 1996.
Cockayne et al., "P2X$_2$ Knockout Mice and P2X$_2$, P2X$_3$ Double Knockout Mice Reveal a Role for the P2X$_2$ Receptor Subunit in Mediating Multiple Sensory Effects of ATP," J. Physiol., vol. 567, No. 2, pp. 621-639, (2005).
Drager et al, "A New Reagent and its Polymer-Supported Variant for the Aminidation of Amides," Tetrahedron Lett. vol. 43, pp. 1401-1403 (2002).
English-language International Search Report from the Japanese Patent Office for International Application No. PCT/JP2014/065678, dated Aug. 12, 1914.
Freshney et al.,Culture of Animal Cells, A Manual of Basic Technique, Alan R. Liss, Inc., 1983, New York, p. 4.
Fukuchi et al., "2-Anilino-4(3H)-pyrimidinone derivatives, Pesticidally/Herbicidally Active, Useful in Agriculture/Horticulture and Their Preparation," STN Accession No. 2003-318151.
Fukuchi et al., "A Novel 2-Substituted Amino-5,6-Dihydro-4(3H)-Pyrimidinone Derivative," STN Accession No. 2001-491646.
Fukuchi et al., "Novel 2-Substituted Aminopyrimidinone Derivatives, useful as Insecticide and Acaricide," STN Accession No. 2001-468100.
Gao, Z., et al. "Emerging Adenosine Receptor Agonist," Expert Opin. Emerging Drugs 12(3), pp. 479-492, 2008.
Gever et al., "AF-353, A Novel, Potent and Orally Bioavailable P2X3/P2X2/3 Receptor Antagonist," British Journal of Pharmacology (2010), vol. 160, pp. 1387-1398.
Gever et al., "Pharmacology of P2X Channels," Pflugers Arch—Eur. J. Physiol., vol. 452, pp. 513-537 (2006).
Gopalsamy et al, "Combinatorial Synthesis of Heterocycles: Solid-Phase Synthesis of 6-Amino-2,4-Dioxo-3,4-Dihydro-1 ,3,5-Triazine Derivatives," Journal of Combinatorial Chemistry vol. 3, pp. 278-283 (2001).
Han et al., "Advances in Characterization of Pharmaceutical Hydrates," Trends in Bio/Pharmaceutical Industry, pp. 25-29, Mar. 2006.
Jahangir et al., "Identification and Sar of Novel Diaminopyrimidines. Part 2: The Discovery of Ro-51, A Potent and Selective, Dual P2X$_3$ and P2X$_{2/3}$ Antagonist for the Treatment of Pain," Bioorganic & Medicinal Chemistry Letters, vol. 19, pp. 1632-1635, (2009).
Jarvis et al., "A-317491, A Novel Potent and Selective Non-Nucleotide Antagonist of P2X$_3$ and P2X$_{2/3}$ Receptors, Reduces Chronic Inflammatory and Neuropathic Pain in the Rat," PNAS, vol. 99, No. 26, pp. 17179-17184, (2002).
Ji-Zhen et al., "Polymer Supported Synthesis of Multi-substituted Pyrimidine-4-one Derivatives via Pbf activated Thiourea," Chem. Research in Chinese Universities, vol. 27, No. 2, pp. 221-223 (2011).
Kai et al. WO 2012020749,Feb. 16, 2012; STN Search Answer Set 3 pp. 243-274, provided.
Kappe, T., et al., "Rearrangements of heterocycles. VIII. Mesoionic siX-membered-ring heterocycles. XII. Ketenoid rearrangements of mesoionic pyrimidines", Chemische Berichte, vol. 112, No. 10, 1979, pp. 3424-3431.
Kennedy et al., "Crossing the Pain Barrier: P2 Receptors as Targets for Novel Analgesics," J. Physiol., vol. 553, No. 3, pp. 683-694, (2003).
Kennedy, "P2X Receptors: Targets for Novel Analgesics," Review , The Neuroscientist, vol. 11, No. 4, pp. 345-356, (2005).
Kong et al., "A Versatile Thiouronium-Based Solid-Phase Synthesis of 1,3,5-Triazines." Chem Eur. J., vol. 18, pp. 1476-1486, (2012).
Kurzer et al, "Triazines: the interaction of biguanide and its homologs with isocyanate esters," Chemical Abstract, vol. 67, pp. 10245 (1967), Abstract No. 108644, CAS Registry No. 14943-99-8, 16120-41-5.

(56) References Cited

OTHER PUBLICATIONS

Lerchova et al., "Antioxidants and Stabilizers," Angewandte Makromolekulare Chemie, vol. 39, No. 1 pp. 107-118 (1974).
Non-final Office Action, U.S. Appl. No. 14/931,807, dated Jan. 17, 2017.
North, "P2X$_3$ Receptors and Peripheral Pain Mechanisms," J. Physiol., vol. 554, No. 2, pp. 301-308, (2003).
Notification of Transmittal of Translation of the International Preliminary Report on Patentability dated Dec. 23, 2015, and International Preliminary Report on Patentability dated Dec. 15, 2015, from the International Bureau.
Okano et al., "Preparation of 2-Phenylaminopyrimidinones, Intermediates as Pesticides and Herbicides in Agriculture," STN Accession No. 1999-672770.
Pecchi et al., "Identification and Structure-Activity Relationship of 2-Morpholino-6-3-Hydroxyphenyl Pyrimidines, a Class of Potent and Selective PI3 Kinase Inhibitors," Bioorganic & Medicinal Chemistry Letters, vol. 20, No. 23, pp. 6895-6898 (201 0).
Schroif-Gregoire et al, "Preparation of N-alkyi-N-Carboalkoxy Guanidines," Tetrahedron Lett., vol. 48, pp. 2357-2359 (2007).
Shao et al., "Strapped Porphyrin Rosettes Based on the Melamine-Cyanuric Acid Motif," Tetrahedron, vol. 60, No. 41, pp. 9155-9162 (2004).
Shieh et al., "P2X Receptor Ligands and Pain," Review, Expert Opin. Ther. Patents, vol. 16, No. 8, pp. 1113-1127, (2006).
Sitkovsky et al., "Adenosine A2A Receptor Antagonists: Blockade of Adenosinergic Effects and T Regulatory Cells," British Journal of Pharmacology, vol. 153, pp. 5457-S464, 2008.
Somogyi et al, "Cyclisierungsreaktionen von mono- und disubstituierten Biguaniden mit Phenylisothiocyanat, " Chemische Berichte, vol. 100, pp. 1975-1982 (1967).
Suyama et al, "The Reaction of 3-Cyano-2-methyl-1-phenylisothiourea with isocyanate, isothiocyanate and carboiimide," Nippon Kagaku Kaishi, vol. 9, pp. 845-848 (1996).
Vippagunta et al., "Crystalline Solids," Advanced Drug Delivery Reviews vol. 48, pp. 3-26 (2001).
Written Opinion of the International Searching Authority from the European Patent Office for International Application No. PCT/JP2014/065678, dated Dec. 15, 2015.
Yessayan et al, "Synthesis and Hydrolysis Gamma-Chlorcrothylbibenzyl-Aklkyl-Isocianurates," Armyanskii Khimicheskii Zhurna, vol. 28, No. 4, pp. 332-337 (1975).
Zigeuner, "1-Chlormethylisatain, Ein Ausgezeichnetes Reagens Zur Identifizierung Von Carbonstturen Und NH-Aciden Verbindungen," Scientia Pharmaceutica, vol. 38, No. 4, pp. 227-233 (1970).
Zuen et al., "Crystalline Furanic Polyisocyanates," Polymer Bulletin, vol. 26, No. 4, pp. 383-390 (1991).

* cited by examiner

AMINOTRIAZINE DERIVATIVE AND PHARMACEUTICAL COMPOSITION COMPRISING THE SAME

TECHNICAL FIELD

The invention relates to a compound useful for the treatment of diseases or conditions associated with P2X receptor, specifically to P2X$_3$ and/or P2X$_{2/3}$ receptor, and a pharmaceutical composition comprising such compound.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 4, Non-Patent Document 5).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 6).

ATP is known to cause pain, and studies with P2X$_3$ knockout and knockdown methodologies have shown that P2X$_3$ receptor mediates transmission of chronic pain. P2X$_3$ receptors are expressed in a specific manner on peripheral sensory nerve to form a homo-complex or hetero-complex with P2X$_2$ (P2X$_{2/3}$) (Non-Patent Document 1).

Later, the compound A-317491 was reported as a specific antagonist to P2X$_3$ and P2X$_{2/3}$ receptors. A-317491 is tri-substituted-N-[(1S)-1,2,3,4-tetrahydro-1-naphthalenyl]benzamide derivative represented by the formula:

[Chemical Formula 1]

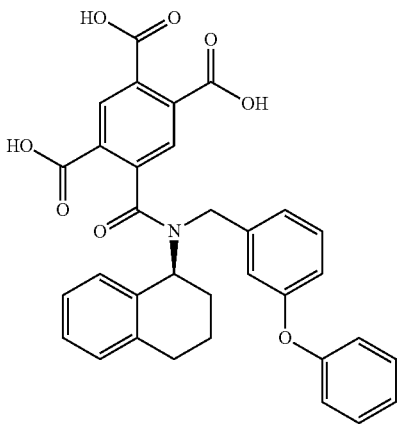

(Patent Document 1). It was reported to exhibit an antagonist activity to P2X$_3$ and P2X$_{2/3}$ receptors and analgesic action in neuropathic pain model and inflammatory pain model in rats (Non-Patent Document 7). This indicates that pain sensation is transmitted via P2X$_3$ or P2X$_{2/3}$ receptor and that a compound having a P2X$_3$ or P2X$_{2/3}$ receptor antagonistic activity is useful as an analgesic. Also, compounds that exhibit P2X$_3$ or P2X$_{2/3}$ receptor antagonistic activity are described in Patent Documents 2-7.

Additionally, it was recently reported that vesical reflex was strongly reduced in P2X$_3$ knockout mouse (Non-Patent Document 2), suggesting that a compound having P2X$_3$ antagonistic activity is useful in the treatment of diseases caused by overactive bladder. Also, compounds that exhibit P2X$_3$ or P2X$_{2/3}$ receptor antagonistic activity are described in Patent Documents 2-7.

In addition, P2X$_3$ receptor is expressed in neuroepithelial bodies (NEB) of the lung (Non-Patent Document 9), ATP induces cough (Non-Patent Document 10), and the like, therefore it ie suggested that P2X$_3$ receptor participates in signal transduction in the respiratory system (Non-Patent Document 11). These reports suggest the possibility that compounds that exhibit P2X$_3$ receptor antagonistic activity are useful in the treatment of respiratory diseases.

Later, the compound A-317491 known as a specific antagonist to P2X$_3$ and P2X$_{2/3}$ receptors was reported inhibiting an activity of afferent vagal A fiber in pulmonary diseases (Patent Document 16). Additionally, biphenyl and phenyl-pyridine derivatives were reported as a specific antagonist to P2X$_3$ and P2X$_{2/3}$ receptors, and it is suggested that the biphenyl and phenyl-pyridine derivatives exhibit improving effect on respiratory diseases in asthma and lung model (Patent Document 17). Also, compounds that exhibit P2X$_3$ or P2X$_{2/3}$ receptor antagonistic activity are described in Patent Documents 2-7.

Patent Documents 8, 9, 10, 11, and 15 and Non-Patent Document 14 disclose compounds having similar structure to the compounds of the present invention but they do not disclose analgesic effect and P2X$_3$ or P2X$_{2/3}$ receptor antagonistic activity. Non-Patent Document 8 discloses compounds having similar structure to the compounds of the present invention and having analgesic effect, but it does not discloses P2X$_3$ nor P2X$_{2/3}$ receptor antagonistic activity. Patent Document 12 and Non-Patent Documents 12 and 13 disclose compounds having P2X$_3$ receptor antagonistic activity but the structures are different with those of the compounds of the present invention. Patent Documents 13, 14, and 18 disclose compounds having P2X$_3$ or P2X$_{2/3}$ receptor antagonistic activity with a triazine structure.

PRIOR ART

Patent Document

[Patent Document 1] WO02/094767
[Patent Document 2] WO2005/095359
[Patent Document 3] US2007/0037974
[Patent Document 4] US2007/0049758
[Patent Document 5] US2007/0049610
[Patent Document 6] US2007/0049609
[Patent Document 7] US2007/0049534
[Patent Document 8] JP12-072757A
[Patent Document 9] WO2006/104713
[Patent Document 10] WO2006/104715
[Patent Document 11] WO2006/102112
[Patent Document 12] WO2010/051188
[Patent Document 13] WO2010/092966
[Patent Document 14] WO2012/020749
[Patent Document 15] WO2011/017347
[Patent Document 16] WO2006/012639
[Patent Document 17] WO2010/149578
[Patent Document 18] WO2013/089212

Non-Patent Document

[Non-Patent Document 1] Neuroscientist (2005), 11, pp. 345-356
[Non-Patent Document 2] J. Physiol. 567.2 (2005), pp. 621-639
[Non-Patent Document 3] Expert Opin. Ther. Patens (2006), 16(8), pp. 113-1127
[Non-Patent Document 4] J. Physiology (2003), 554(2), pp. 301-308
[Non-Patent Document 5] J. Physiology (2003), 553(3), pp. 683-694
[Non-Patent Document 6] Pflungers Arch Eur J physiol (2006), p. 452, 513-537
[Non-Patent Document 7] PNAS (2002), 99(26), pp. 17179-17184
[Non-Patent Document 8] Journal of Medicinal Chemistry (2008), 51(23), pp. 7635-7639
[Non-Patent Document 9] Brouns et al. Am J Respir Cell Mol Biol (2000), 23, pp. 52-61
[Non-Patent Document 10] Basoglu et al. Chest. (2005), 128(4), pp. 1905-9
[Non-Patent Document 11] Adriaensen et al. THE ANATOMICAL RECORD PART A (2003), 270A, pp. 25-40
[Non-Patent Document 12] Cantin, L.-D. et al. Bioorg. Med. Chem. Lett. (2012), 22(7), pp. 2565-2571
[Non-Patent Document 13] Jahangir, A. et al. Bioorg. Med. Chem. Lett. (2009), 19, pp. 1632-1635
[Non-Patent Document 14] Chemistry—A European Journal (2012), 18(5), pp. 1476-1486

SUMMARY OF THE INVENTION

Problems to be Solved by the Invention

The present invention provides a novel compound having a $P2X_3$ and/or $P2X_{2/3}$ receptor antagonistic activity. It also provides a pharmaceutical composition having a $P2X_3$ and/or $P2X_{2/3}$ receptor antagonistic activity.

Means for Solving the Problem

Through their extensive research to solve the aforementioned problems, the inventors have found novel compounds that bind specifically to $P2X_3$ and/or $P2X_{2/3}$ receptor and exhibit an antagonistic activity, and novel compounds that bind specifically to $P2X_3$ and/or $P2X_{2/3}$ receptor. Additionally, they have discovered pharmaceutical compositions that have $P2X_3$ and/or $P2X_{2/3}$ antagonistic activity.

The compounds and pharmaceutical compositions encompassed by the present invention produced excellent results of $P2X_3$ receptor inhibitory effect, $P2X_3$ receptor inhibitory effect in the presence of rat serum albumin (hereinafter referred to as RSA) and the like. The compounds encompassed by the present invention or the pharmaceutical compositions encompassed by the present invention also produced excellent results in CYP enzyme inhibition assay, FAT assay, solubility assay, metabolic stability assay, hERG inhibitory activity assay, pharmacokinetic assay (bioavailability assay, total body clearance assay, etc.) and/or protein binding assay and the like.

This invention relates to the following (1) to (44):
(1) A compound of Formula (I):

[Chemical Formula 2]

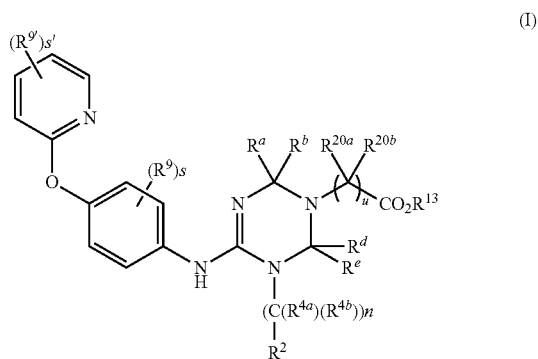

wherein,
$R^a$ and $R^b$ are both hydrogen atoms, or $R^a$ and $R^b$ are taken together to form oxo, thioxo or =N—$R^x$;
$R^d$ and $R^e$ are both hydrogen atoms, or $R^d$ and $R^e$ are taken together to form oxo, thioxo or =N—$R^y$;
$R^x$ and $R^y$ are each independently a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^{4a}$ is each independently a hydrogen atom or substituted or unsubstituted alkyl; $R^{4b}$ is each independently a hydrogen atom or substituted or unsubstituted alkyl;
or $R^{4a}$ and $R^{4b}$ attached to the same carbon atom are taken together to form oxo or thioxo;
n is an integer of 1 to 4;
$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy;
$R^{9'}$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy;

s and s' are each independently an integer of 0 to 3;

$R^{20a}$ is each independently a hydrogen atom, hydroxy, substituted or unsubstituted alkyl, substituted or unsubstituted alkenyl, substituted or unsubstituted alkynyl, or substituted or unsubstituted alkyloxy;

$R^{20b}$ is each independently a hydrogen atom, hydroxy, substituted or unsubstituted alkyl, substituted or unsubstituted alkenyl, substituted or unsubstituted alkynyl, or substituted or unsubstituted alkyloxy; or $R^{20a}$ and $R^{20b}$ attached to the same carbon atom or the different carbon atoms are taken together to form substituted or unsubstituted cycloalkane, substituted or unsubstituted cycloalkene, or a substituted or unsubstituted non-aromatic heterocyclic ring; provided that all $R^{20a}$ and $R^{20b}$ are not hydrogen atoms at the same time;

u is an integer of 1 to 4; and $R^{13}$ is a hydrogen atom or substituted or unsubstituted alkyl, provided that the following compounds:

[Chemical Formula 3]

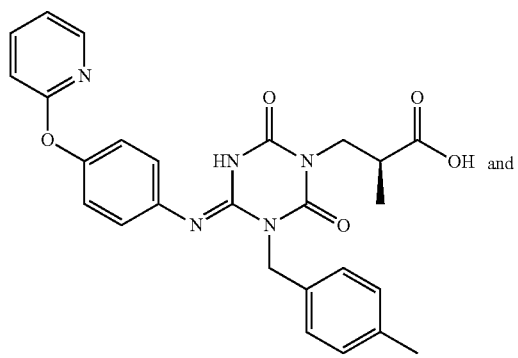

and

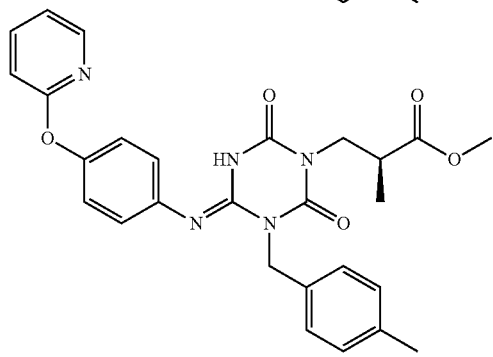

are excluded,
or its pharmaceutically acceptable salt.

(2) The compound according to the above (1), wherein the group represented by the formula:

[Chemical Formula 4]

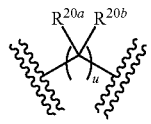

is a group represented by the formula:

[Chemical Formula 5]

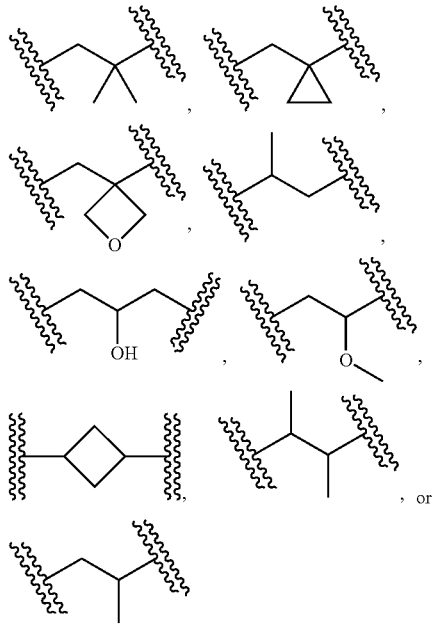

, or or its pharmaceutically acceptable salt.

(3) The compound according to the above (1), wherein the group represented by the formula:

[Chemical Formula 6]

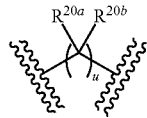

is a group represented by the formula:

[Chemical Formula 7]

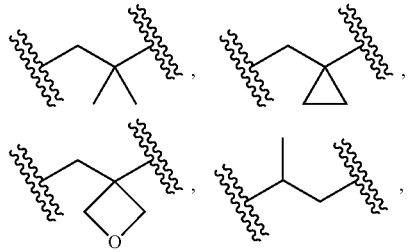

-continued

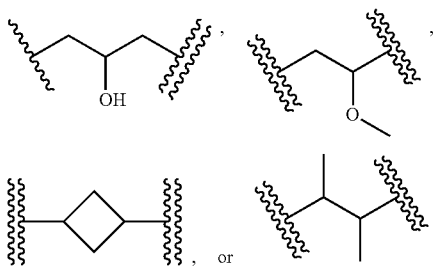

or its pharmaceutically acceptable salt.

(4) The compound according to the above (1), wherein the group represented by the formula:

[Chemical Formula 8]

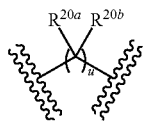

is a group represented by the formula:

[Chemical Formula 9]

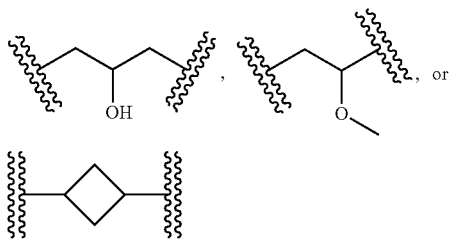

or its pharmaceutically acceptable salt.

(5) The compound according to the above (1), wherein the group represented by the formula:

[Chemical Formula 10]

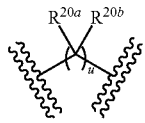

is a group represented by the formula:

[Chemical Formula 11]

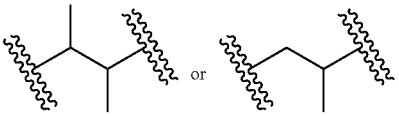

or its pharmaceutically acceptable salt.

(6) The compound according to the above (1), wherein the group represented by the formula:

[Chemical Formula 12]

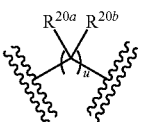

is a group represented by the formula:

[Chemical Formula 13]

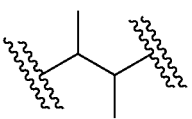

or its pharmaceutically acceptable salt.

(7) The compound according to any one of the above (1) to (6), wherein n is 1, $R^{4a}$ and $R^{4b}$ are both hydrogen atoms, and $R^2$ is substituted or unsubstituted phenyl or substituted or unsubstituted cycloalkyl, or its pharmaceutically acceptable salt.

(8) The compound according to any one of the above (1) to (7), wherein n is 1, $R^{4a}$ and $R^{4b}$ are both hydrogen atoms, and $R^2$ is substituted or unsubstituted phenyl, or its pharmaceutically acceptable salt.

(9) The compound according to any one of the above (1) to (8), wherein n is 1, $R^{4a}$ and $R^{4b}$ are both hydrogen atoms, and $R^2$ is phenyl substituted with chloro or methyl, or its pharmaceutically acceptable salt.

(10) The compound according to any one of the above (1) to (9), wherein n is 1, $R^{4a}$ and $R^{4b}$ are both hydrogen atoms, and $R^2$ is phenyl substituted with methyl, or its pharmaceutically acceptable salt.

(11) The compound according to any one of the above (1) to (8), wherein n is 1, $R^{4a}$ and $R^{4b}$ are both hydrogen atoms, and $R^2$ is phenyl substituted with halogen, or its pharmaceutically acceptable salt.

(12) The compound according to any one of the above (1) to (8), wherein n is 1, $R^{4a}$ and $R^{4b}$ are both hydrogen atoms, and $R^2$ is 4-methylphenyl, 4-chlorophenyl, 2, 4-dichlorophenyl, or 4-methylcyclohexyl, or its pharmaceutically acceptable salt.

(13) The compound according to any one of the above (1) to (10) and (12), wherein n is 1, $R^{4a}$ and $R^{4b}$ are both hydrogen atoms, and $R^2$ is 4-methylphenyl, or its pharmaceutically acceptable salt.

(14) The compound according to any one of the above (1) to (9), (11) and (12), wherein n is 1, $R^{4a}$ and $R^{4b}$ are both hydrogen atoms, and $R^2$ is 4-chlorophenyl, or its pharmaceutically acceptable salt.

(15) The compound according to any one of the above (1) to (14), wherein $R^a$ and $R^b$ are taken together to form oxo, or its pharmaceutically acceptable salt.

(16) The compound according to any one of the above (1) to (15), wherein $R^d$ and $R^e$ are taken together to form oxo, or its pharmaceutically acceptable salt.
(17) The compound according to any one of the above (1) to (16), wherein s is 0, or its pharmaceutically acceptable salt.
(18) The compound according to any one of the above (1) to (16), wherein s is 1 or 2, and $R^9$ is each independently halogen, unsubstituted alkyl, haloalkyl, unsubstituted alkenyl, or unsubstituted alkynyl, or its pharmaceutically acceptable salt.
(19) The compound according to the above (18), wherein s is 1, $R^9$ is fluoro, chloro or methyl, or its pharmaceutically acceptable salt.
(20) The compound according to any one of the above (1) to (19), wherein s' is 0, or its pharmaceutically acceptable salt.
(21) The compound according to any one of the above (1) to (19), wherein s' is an integer of 1 to 3, or its pharmaceutically acceptable salt.
(22) The compound according to the above (21), wherein s' is 1 or 2, and $R^{9'}$ is each independently halogen, carboxy, cyano, substituted or unsubstituted alkyl, substituted or unsubstituted alkyloxy, substituted or unsubstituted alkyloxycarbonyl, or substituted or unsubstituted aryl, or its pharmaceutically acceptable salt.
(23) The compound according to the above (21) or (22), wherein s' is 1, and $R^{9'}$ is fluoro, chloro, bromo, iodo, carboxy, cyano, methyl, ethyl, propyl, isopropyl, hydroxymethyl, fluoromethyl, difluoromethyl, trifluoromethyl, methyloxy, ethyloxy, propyloxy, isopropyloxy, methyloxycarbonyl, or ethyloxycarbonyl, or its pharmaceutically acceptable salt.
(24) The compound according to any one of the above (21) to (23), wherein s' is 1, and $R^{9'}$ is fluoro, chloro, carboxy, cyano, methyl, hydroxymethyl, trifluoromethyl, methyloxy, isopropyloxy, difluoromethyl, methyloxycarbonyl, or ethyloxycarbonyl, or its pharmaceutically acceptable salt.
(25) The compound according to the above (1), wherein
$R^a$ and $R^b$ are taken together to form oxo:
$R^d$ and $R^e$ are taken together to form oxo;
$R^{4a}$ and $R^{4b}$ are both hydrogen atoms;
n is 1;
$R^2$ is phenyl substituted with methyl;
s is 0; and
s' is 1,
or its pharmaceutically acceptable salt.
(26) The compound according to the above (1), wherein
$R^a$ and $R^b$ are taken together to form oxo:
$R^d$ and $R^e$ are taken together to form oxo;
$R^{4a}$ and $R^{4b}$ are both hydrogen atoms;
n is 1;
$R^2$ is phenyl substituted with halogen; and
s and s' are both 0,
or its pharmaceutically acceptable salt.
(27) The compound according to the above (26), wherein $R^{13}$ is a hydrogen atom and the group represented by the formula:

[Chemical Formula 14]

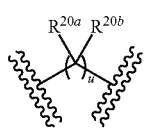

is a group represented by the formula:

[Chemical Formula 15]

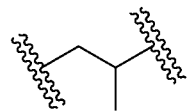

or its pharmaceutically acceptable salt.

(28) A compound of formula:

[Chemical Formula 16]

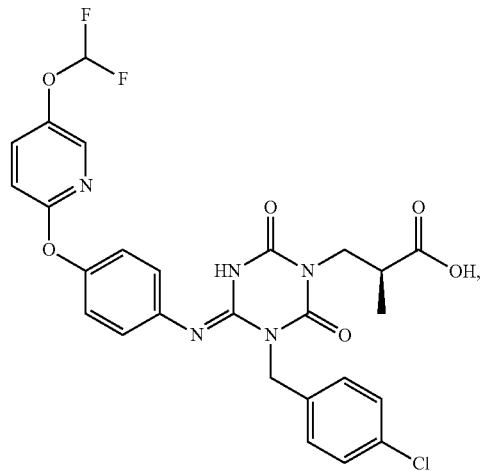

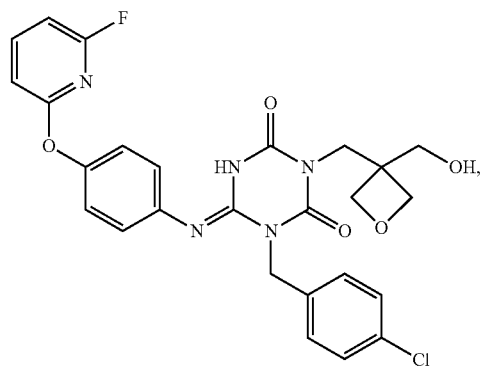

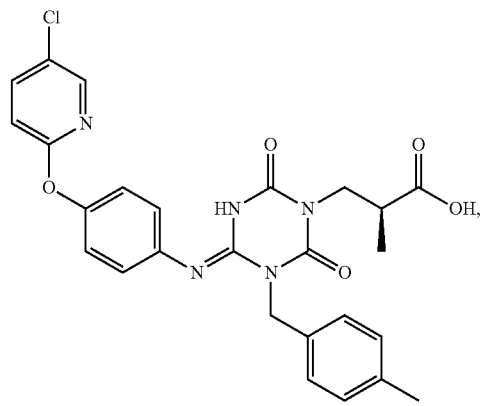

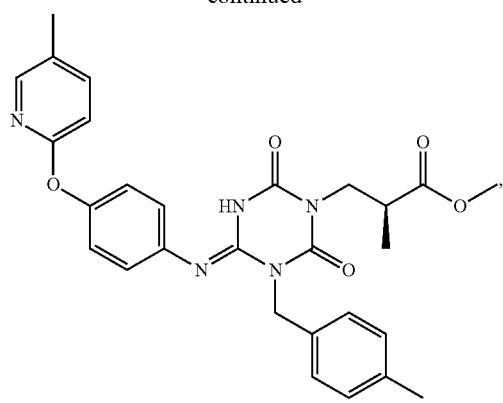
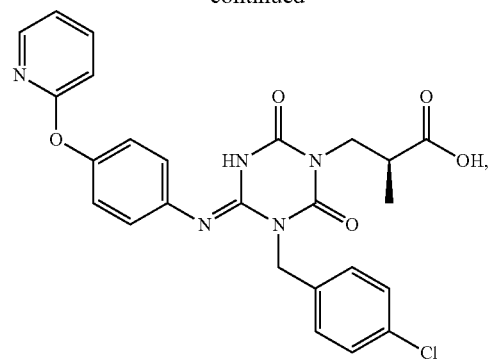
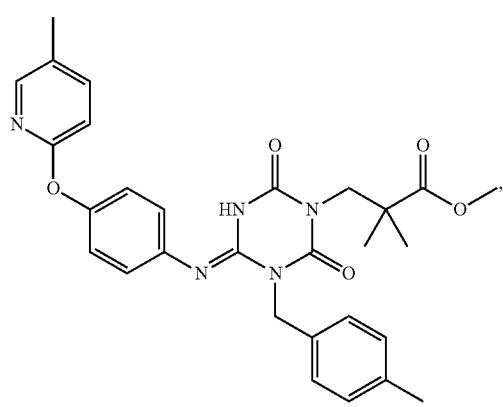
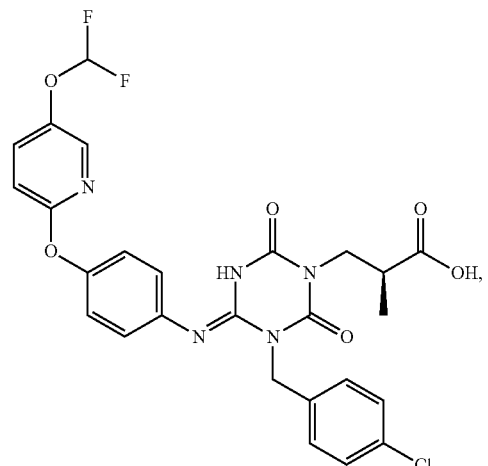
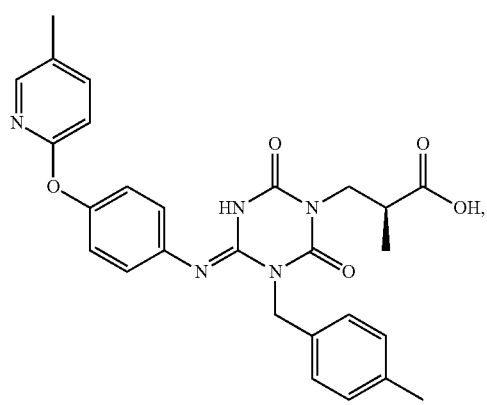
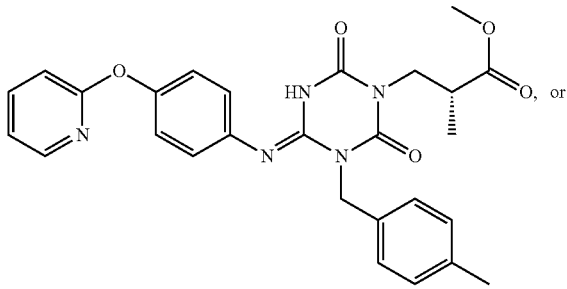
or
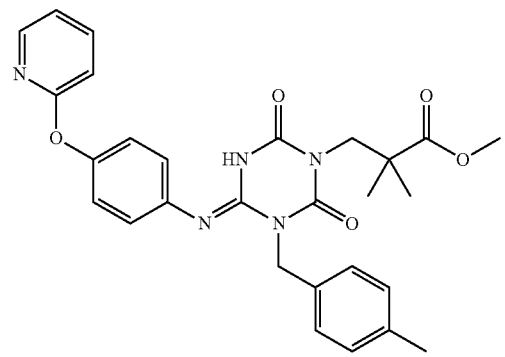
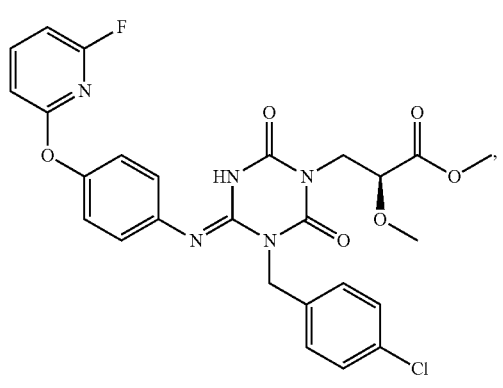
or its pharmaceutically acceptable salt.
(29) A pharmaceutical composition comprising the compound according to any one of the above (1) to (28), or its pharmaceutically acceptable salt.
(30) The pharmaceutical composition according to the above (29), wherein the composition has a $P2X_3$ and/or $P2X_{2/3}$ receptor antagonistic activity.

(31) The pharmaceutical composition according to the above (30), wherein the composition has an effect of treatment for and/or prevention of chronic pain, urination disorder, or respiratory disease.
(32) A compound according to any one of the above (1) to (28), or its pharmaceutically acceptable salt, for use in a method for treating and/or preventing a disease related to $P2X_3$ and/or $P2X_{2/3}$ receptor.
(33) The compound according to the above (32), or its pharmaceutically acceptable salt, for use in a method for treating and/or preventing chronic pain, urination disorder, or respiratory disease.
(34) A method for treating and/or preventing a disease related to $P2X_3$ and/or $P2X_{2/3}$ receptor comprising administering the compound according to any one of the above (1) to (28), or its pharmaceutically acceptable salt.
(35) The method according to the above (34), for treating and/or preventing chronic pain, urination disorder, or respiratory disease.
(36) Use of the compound of any one of the above (1) to (28), or its pharmaceutically acceptable salt, in the manufacturing of an agent for treating and/or preventing a disease related to $P2X_3$ and/or $P2X_{2/3}$ receptor.
(37) The use according to the above (36), in the manufacturing of an agent for treating and/or preventing chronic pain, urination disorder, or respiratory disease.
(38) A pharmaceutical composition comprising the compound of any one of the above (1) to (28), or a pharmaceutically acceptable salt thereof, for oral administration.
(39) The pharmaceutical composition of the above (38), which is a tablet, powder, granule, capsule, pill, film, suspension, emulsion, elixir, syrup, lemonade, spirit, aromatic water, extract, decoction or tincture.
(40) The pharmaceutical composition of the above (39), which is a sugar-coated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.
(41) A pharmaceutical composition comprising the compound of any one of the above (1) to (28), or a pharmaceutically acceptable salt thereof, for parenteral administration.
(42) The pharmaceutical composition of the above (41), for dermal, subcutaneous, intravenous, intraarterial, intramuscular, intraperitoneal, transmucosal, inhalation, transnasal, ophthalmic, inner ear or vaginal administration.
(43) The pharmaceutical composition of the above (41) or (42), which is injection, infusion, eye drop, nose drop, ear drop, aerosol, inhalation, lotion, impregnation, liniment, mouthwash, enema, ointment, plaster, jelly, cream, patch, cataplasm, external powder or suppository.
(44) A pharmaceutical composition comprising the compound of any one of the above (1) to (28), or a pharmaceutically acceptable salt thereof, for a pediatric or geriatric patient.

Effect of the Invention

The compound of the invention has a $P2X_3$ and/or $P2X_{2/3}$ receptor antagonistic activity and is useful in the treatment of diseases or conditions associated with a $P2X_3$ and/or $P2X_{2/3}$ receptor.

MODE FOR CARRYING OUT THE INVENTION

As used throughout the specification, the following terms have the following meaning unless specifically indicated.

The term "halogen" means fluoro, chloro, bromo and iodo.

The halogen moiety in said "haloalkyl", "haloalkylcarbamoyl" and "haloalkyloxy" is as defined above for "halogen".

The term "alkyl" includes a straight or branched chain monovalent hydrocarbon group of a carbon number of 1 to 15, as one embodiment a carbon number of 1 to 10, and as another embodiment a carbon number of 1 to 6. Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl, n-undecanyl, dodecanyl, tridecanyl, and the like.

In the present specification, the carbon number in the term "alkyl" may be limited. For example, C3-C6 alkyl means "alkyl" of a carbon number of 3 to 6.

Examples of "alkyl" for $R^{13}$ are methyl, ethyl, and the like.

The alkyl moiety in said "haloalkyl", "hydroxyalkyl", "aminoalkyl", "alkylaminoalkyl", "alkylamino", "alkylimino", "alkylsulfonyl", "alkylsulfamoyl", "alkylcarbamoyl", "arylalkyl", "alkylsilylalkynyl", "alkylsulfonyl", "alkylsulfinyl", "alkylcarbamoyl", "alkylcarbamoylalkyl", "alkylcarbamoylalkyloxy", "alkylsulfamoyl", "alkylsulfamoylalkyl", "haloalkylcarbamoyl", "hydroxyalkylcarbamoyl", "alkyloxycarbonylalkyl", "alkylcarbamoylamino", "alkyloxycarbonylamino", "alkylsulfonylcarbamoyl", and "arylalkylamino" is as defined above for "alkyl".

The term "alkyloxy" includes an alkyloxy group of which alkyl moiety is as defined above for "alkyl". For example, methoxy, ethoxy, propoxy, isopropoxy, butoxy, isobutoxy, sec-butoxy, tert-butoxy, pentyloxy, isopentyloxy, neopentyloxy, hexyloxy, etc are exemplified as alkyloxy.

The alkyloxy moiety in said "haloalkyloxy", "arylalkyloxy", "alkyloxycarbonyl", "alkyloxycarbonylalkyl", "alkyloxyalkyloxy", "alkylcarbamoylalkyloxy", "carbamoylalkyloxy", "carboxyalkyloxy", and "alkyloxyimino" is as defined above for "alkyloxy".

For example, methylthio, ethylthio, propylthio, isopropylthio, butylthio, isobutylthio, sec-butylthio, tert-butylthio, pentylthio, isopentylthio, neopentylthio, hexylthio, and the like are exemplified as "alkylthio".

For example, methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, and the like are exemplified as "alkyloxycarbonyl".

For example, mono- or di-alkylcarbamoyl, such as methylcarbamoyl, ethylcarbamoyl, n-propylcarbamoyl, isopropylcarbamoyl, cyclopropylcarbamoyl, n-butylcarbamoyl, dimethylcarbamoyl, diethylcarbamoyl, dipropylcarbamoyl, and the like are exemplified as "alkylcarbamoyl".

The term "alkenyl" includes linear or branched alkenyl of a carbon number of 2 to 15, as one embodiment a carbon number of 2 to 10, and as another embodiment a carbon number of 2 to 6 having one or more double bonds at any available position. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl and the like.

In the present specification, the carbon number in the term "alkenyl" may be limited. For example, C3-C6 alkenyl means "alkenyl" of a carbon number of 3 to 6.

The alkenyl moiety in said "alkenyloxy", "alkenylthio", "alkenylcarbamoyl", "alkenylsulfamoyl" and "alkenyloxycarbonyl" is as defined above for "alkenyl".

The term "alkynyl" includes a linear or branched alkynyl of a carbon number of 2 to 15, as one embodiment a carbon number of 2 to 10, as another embodiment a carbon number 2 to 6. Examples include ethynyl, propynyl, butynyl, pentynyl, hexynyl, heptynyl, octynyl, nonynyl and decynyl. These have one or more triple bonds at any available position and may further a double bond.

In the present specification, the carbon number in the term "alkynyl" may be limited. For example, C3-C6 alkynyl means "alkynyl" of a carbon number of 3 to 6.

The alkynyl moiety in said "alkynyloxy", "alkynylthio" and "alkynyloxycarbonyl" is as defined above for "alkynyl".

The term "acyl" includes a group of the formula R—C (=O)—, wherein R is, for example, "hydrogen", "alkyl", "alkenyl" or "alkynyl" as defined above and "cycloalkyl", "cycloalkenyl", "non-aromatic heterocyclic group", "aryl" or "heteroaryl" as defined below.

The acyl moiety in "acylamino" and "acylimino" is as defined above for "acyl".

The term "cycloalkane" includes a monocyclic or polycyclic saturated cyclic carbocyclic ring containing from 3 to 10 carbons. Monocyclic cycloalkane includes, for example, cyclopropane, cyclobutane, cyclopentane, cyclohexane, cycloheptane, cyclooctane, cyclononane, cyclodecane, etc. Polycyclic cycloalkane includes norbornanane, tetrahydronaphthalene, etc.

The term "cycloalkyl" includes a monovalent group derived from "cycloalkane" as defined above. Monocyclic cycloalkyl includes, for example, cyclopropyl, cyclobutyl, cyclopentyl, cyclohexyl, cycloheptyl, cyclooctyl, cyclononyl, cyclodecyl, etc. As one embodiment, C3 to C8 cycloalkane is exemplified. As another embodiment, C3 to C7 cycloalkane is exemplified. Polycyclic cycloalkyl includes norbornyl, tetrahydronaphthalene-5-yl, tetrahydronaphthalene-6-yl, etc.

Examples of "cycloalkyl" for $R^2$ are cyclopentyl, cyclohexyl, cycloheptyl, cyclooctyl and the like.

The cycloalkyl moiety in said "cycloaokylcarbonyl", "cycloalkyloxycarbonyl" and "cycloalkyloxy" is as defined above for "cycloalkyl".

The term "cycloalkene" includes a non-aromatic monocyclic or polycyclic ring of 3 to 10 carbons containing at least one carbon-carbon double bond. As one embodiment C3 to C8 cycloalkene is exemplified. As another embodiment C3 to C7 cycloalkene is exemplified. Monocyclic cycloalkene includes, for example, cyclopentene, cyclohexene, etc. Polycyclic cycloalkene includes norbornene, indene, etc.

The term "cycloalkenyl" includes a monovalent group derived from "cycloalkene" as defined above. Monocyclic cycloalkenyl includes cyclopentenyl, cyclohexenyl, etc. As one embodiment, C3 to C8 cycloalkyl is exemplified. As another embodiment, C3 to C7 cycloalkyl is exemplified. Polycyclic cycloalkenyl includes norbornenyl, indene-1-yl, indene-2-yl, indene-3-yl, etc.

The cycloalkenyl moiety in said "cycloalkenyloxycarbonyl" and "cyclolalkenyloxy" is as defined above for "cycloalkenyl".

The term "aromatic carbocyclic ring" includes an aromatic hydrocarbocyclic ring which is monocyclic or fused-cyclic, such as benzene, naphthalene, anthracene, phenanthrene, etc.

The term "aryl" includes a monovalent group derived from "aromatic carbocyclic ring" as defined above. For example, phenyl, 1-naphthyl, 2-naphthyl, anthryl, phenanthryl, etc. are exemplified.

Preferable "aryl" for $R^2$ is phenyl.

The aryl moiety in said "aryloxy", "arylthio" and "aryloxycarbonyl" is as defined above for "aryl".

The term "heterocyclic ring" includes an aromatic or a non-aromatic monocyclic or fused-cyclic ring, which includes a five- to seven-membered ring having at least one nitrogen atom, oxygen atom, and/or sulfur atom in the ring;
a fused ring consisting of two or more said five- to seven-membered rings; or a fused ring consisting of said five- to seven-membered ring having at least one nitrogen atom, oxygen atom, and/or sulfur atom in the ring fused to one or more "aromatic carbocyclic ring", "cycloalkene" or "cycloalkene" as defined above.

For example, a monocyclic non-aromatic heterocyclic ring such as pyrroline, pyrrolidine, piperidine, piperazine, morpholine, thiomorpholine, tetrahydropyrane, dihydropyridine, dihydropyridazine, dioxane, oxathiolane, thiane, tetrahydrofuran, tetrahydropyran, tetrahydrothiazole, tetrahydroisothiazole, etc.;
a monocyclic aromatic heterocyclic ring such as pyrrole, pyrazine, pyrazole, tetrazole, furan, thiophene, pyridine, imidazole, triazole, tetrazole, triazine, pyridazine, pyrimidine, isoxazole, thiazole, isothiazole, thiadiazole, oxazole, oxadiazole, etc; and
a fused heterocyclic ring such as indole, isoindole, indazole, indolizine, indoline, isoindoline, quinoline, isoquinoline, cinnoline, phthalazine, quinazoline, naphthyridine, quinoxaline, purine, pteridine, benzopyrane, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazole, benzodioxane, tetrahydroquinoline, tetrahydrobenzothiophene, etc. are exemplified.

The term "heterocyclic group" includes a monovalent group derived from "heterocyclic ring" as defined above.

For example, monocyclic non-aromatic heterocyclic groups such as pyrrolinyl, pyrrolidino, pyrrolidinyl, imidazolinyl, imidazolidinyl, pyrazolinyl, pyrazolidinyl, piperidino, piperidyl, piperazino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.;
monocyclic aromatic heterocyclic groups such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and
fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, benzodioxanyl, tetrahydroquinoline, tetrahydrobenzothienyl, etc. are exemplified.

The term "non-aromatic carbocyclic ring" includes "cycloalkane" as defined above, "cycloalkene" as defined above, a fused ring consisting of "aromatic carbocyclic ring" as defined above fused to "cycloalkane" or "cycloalkene" as defined above. As a fused ring, indene and the like are exemplified.

The term "non-aromatic carbocyclic group" includes a monovalent group derived from "non-aromatic carbocyclic ring" as defined above. For example, cyclopropyl, cyclobutyl, cyclopentyl, cyclohexyl, cycloheptyl, cyclooctyl, cyclononyl, cyclodecyl, cyclopentenyl, cyclohexenyl, norbornyl, tetrahydronaphthalene-5-yl, tetrahydronaphthalene-6-yl, norbornenyl, inden-1-yl, inden-2-yl, inden-3-yl and the like are exemplified.

The non-aromatic carbocyclyl moiety in said "non-aromatic carbocyclyloxy" and "non-aromatic carbocyclylalkyloxy" is as defined above for "non-aromatic carbocyclic ring".

The term "aromatic heterocyclic ring" includes aromatic rings of "heterocyclic ring" as defined above.

"Aromatic heterocyclic ring" includes a five- to seven-membered aromatic ring having at least one nitrogen atom, oxygen atom, and/or sulfur atom in the ring;
a fused aromatic ring consisting of two or more said rings; and
a fused ring consisting of a five- to seven-membered aromatic ring having at least one nitrogen atom, oxygen atom, and/or sulfur atom in the ring fused to one or more "aromatic carbocyclic ring" as defined above.

For example, a monocyclic aromatic heterocyclic ring such as pyrazine, pyrazole, tetrazole, furan, thiophene, pyridine, imidazole, triazole, triazine, pyridazine, pyrimidine, pyrazine, isoxazole, thiazole, isothiazole, thiadiazole, oxazole, oxadiazole, etc; and a fused aromatic heterocyclic ring such as indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, benzimidazoline, etc. are exemplified.

The term "heteroaryl" includes a monovalent group derived from "aromatic heterocyclic ring" as defined above. "Heteroaryl" includes a five- to seven-membered aromatic group having at least one nitrogen atom, oxygen atom, and/or sulfur atom in the ring;
a fused aromatic group consisting of two or more said rings; and
a fused ring consisting of a five- to seven-membered aromatic group having at least one nitrogen atom, oxygen atom, and/or sulfur atom in the ring fused to one or more "aromatic carbocyclic ring" as defined above.

For example, monocyclic heteroaryl such as pyrrolyl, pyrazinyl, pyrazolyl, indolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and fused heteroaryl such as isoindolyl, indazolyl, indolizinyl, isoindolinyl, quinolyl, isoquinolyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, etc. are exemplified.

One of examples of "heteroaryl" for $R^2$ is pyridyl.

The heteroaryl moiety in said "heteroaryloxy" and "heteroaryloxycarbonyl" is as defined above for "heteroaryl".

The term "non-aromatic heterocyclic ring" includes non-aromatic rings of "heterocyclic ring" as defined above.

"Non-aromatic heterocyclic ring" includes, a four- to seven-membered non-aromatic ring having at least one nitrogen atom, oxygen atom, and/or sulfur atom in the ring;
a fused non-aromatic ring consisting of two or more said rings;
a fused ring consisting of a five- to seven-membered aromatic ring having at least one nitrogen atom, oxygen atom, and/or sulfur atom in the ring fused to one or more "cycloalkane" or "cycloalkene" as defined above; and
a fused ring consisting of a five- to seven-membered non-aromatic heterocyclic ring having at least one nitrogen atom, oxygen atom, and/or sulfur atom in the ring fused to one or more "aromatic carbocyclic ring" or "non-aromatic carbocyclic ring" as defined above.

For example, monocyclic non-aromatic heterocyclic ring such as oxetane, thietane, azetidine, pyrroline, pyrrolidine, imidazoline, imidazolidine, pyrazoline, pyrazolidine, piperidine, piperazine, morpholine, thiomorpholine, thiomorpholine, tetrahydropyran, for example, 2-tetrahydropyran, 3-tetrahydropyran, 4-tetrahydropyran, dihydropyridine, dihydropyridazine, dihydropyrazine, dioxane, oxathiolane, thiane, tetrahydrofuran, tetrahydropyran, tetrahydrothiazoline, tetrahydroisothiazoline etc.; a fused non-aromatic heterocyclic ring such as indoline, isoindoline, benzopyrane, benzodioxane, tetrahydroquinoline, benzo[d]oxazole-2(3H)-one, tetrahydrobenzothiophene etc. are exemplified.

"Non-aromatic heterocyclic group" includes a monovalent group derived from "non-aromatic heterocyclic ring" as defined above.

Examples are monocyclic non-aromatic heterocyclic group such as pyrrolinyl, pyrrolidino, pyrrolidinyl, imidazolinyl, imidazolidinyl, pyrazolinyl, pyrazolidinyl, piperidino, piperidyl, piperazino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl etc. and
a fused heterocyclic group such as benzodioxane, tetrahydroquinoline, benzo[d]oxazole-2(3H)-one, tetrahydfobenzothiophene etc.

The non-aromatic heterocyclyl moiety in said "non-aromatic heterocyclyloxy" and "non-aromatic heterocyclyloxycarbonyl" is as defined above for "non-aromatic heterocyclic ring".

The term "nitrogen-containing non-aromatic heterocyclic group" includes a group derived from a four- to seven-membered non-aromatic ring which contains at least one nitrogen atom in the ring and may contain one or more atoms arbitrarily selected from an oxygen atom and a sulfur atom in the ring, or a fused ring consisting of two or more said rings. Examples are pyrrolinyl, pyrrolidino, pyrrolidinyl, piperidino, piperidyl, piperazino, piperazinyl, morpholinyl, morpholino, thiomorpholino etc.

The non-aromatic heterocyclyl moiety in said "non-aromatic heterocyclyloxycarbonyl" is as defined above for "non-aromatic heterocyclic ring".

Substituents for "substituted alkyl", "substituted alkenyl", "substituted alkynyl", "substituted alkyloxy", "substituted alkenyloxy", "substituted alkynyloxy", "substituted alkylthio", "substituted alkenylthio", "substituted alkynylthio", "substituted alkyloxycarbonyl", "substituted alkenyloxycarbonyl", "substituted alkynyloxycarbonyl" and "substituted alkylcarbamoyl" include but are not limited to one or more same or different substituents selected from the group consisting of:

hydroxy, carboxy, halogen (F, Cl, Br, I), haloalkyloxy (e.g., $CF_3O$), cycloalkyl (e.g., cyclopropyl), cycloalkenyl (e.g., cyclopropenyl), alkyloxy (e.g., methoxy, ethoxy, propoxy, butoxy, etc.), alkenyloxy (e.g., vinyloxy, allyloxy, etc.), alkyloxycarbonyl (e.g., methoxycarbonyl, ethoxycarbonyl, tert-butoxycarbonyl, etc.), nitro, nitroso, amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, alkylsulfonylamino (e.g., methanesulfonylamino), alkylsulfinylamino (e.g., methanesulfinylamino), non-aromatic heterocyclylamino (e.g. 4-tetrahydropyranylamino etc.) imino, hydroxyimino, alkylimino (e.g., methylimino, ethylimino, dimethylimino, etc.), alkyloxyimino (e.g., methoxyimino, ethoxyimino, etc.), acylimino (e.g., acetylimino, benzoylimino, etc.), azido, aryl (e.g., phenyl, etc.), arylalkyl (e.g., benzyl, phenylethyl etc.), arylalkyloxy (e.g., benzyloxy), a non-aromatic heterocyclic group (e.g., pyrrolinyl, piperidyl, piperazinopyrrolidino, pyrrolidinyl, morpholinyl, morpholino, 2,2-dimethyl-1,3-dioxopyranyl etc.), heteroaryl (e.g., furyl, thienyl, pyridyl, isoxazolyl, thiazolyl, thiadiazolyl, oxazolyl, oxadiazolyl, tetrazolyl, indolyl, benzofuryl etc.), heteroarylalkyl (e.g., pyridylmethyl, pyridylethyl etc.), cyano, isocyano, isocyanato, thiocyanato, isothiocyanato, mercapto, alkylthio (e.g., methylthio, etc.), alkylsulfonyl (e.g., methanesulfonyl, ethanesulfonyl), carbamoyl, alkylcarbamoyl (e.g., methylcarbamoyl, ethylcarbamoyl, dimethylcarbamoyl, etc.), sulfamoyl, alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido, tri-alkylsilyl (e.g., trimethylsilyl, etc.), hydroxyalkylcarbamoyl (hydroxyethylcarbamoyl, etc.), tetrahydropyranyloxy, carbamoylamino, alkylcarbamoylamino (e.g., methylcarbamoylamino, etc.), haloalkylcarbamoyl (e.g., trifluoroethylcarbamoyl, etc.), alkyloxyalkyloxy (e.g., methyloxymethyloxy, etc.), carbamoylcarbamoyl, alkylsulfonylcarbamoyl (e.g., methanesulfonylcarbamoyl) and oxo.

Substituents for "substituted acyl" are selected from the substituents as defined above for "substituted alkyl", the above "alkyl", the above "alkenyl" and the above "alkynyl". If R in acyl (R—C(=O)—) is "cycloalkyl", "cycloalkenyl", "non-aromatic heterocyclic group", "aryl", or "heteroaryl", then each ring may be substituted with alkyl (e.g., methyl, ethyl, isopropyl, tert-butyl, etc.), haloalkyl (e.g., $CF_3$, $CH_2CF_3$, $CH_2CCl_3$, etc.), alkenyl, alkynyl (e.g., ethynyl), alkyloxy (e.g., methoxy, ethoxy, isopropyloxy), halogen (e.g., fluoro, chloro etc.) or the like.

Substituents for "substituted carbamoyl" or "substituted sulfamoyl" are one or more same or different groups selected from, but are not limited to, the group consisting of:

hydroxy, carboxy, carboxyalkyl (e.g., carboxymethyl, carboxyethyl etc.), halogen (F, Cl, Br, I), alkyl (e.g., methyl, ethyl), alkenyl (e.g., vinyl), alkynyl (e.g., ethynyl), cycloalkyl (e.g., cyclopropyl), cycloalkenyl (e.g., cyclopropenyl), alkyloxycarbonyl (e.g., methoxycarbonyl, ethoxycarbonyl, tert-butoxycarbonyl, etc.), alkyloxycarbonylalkyl (e.g., methoxycarbonylmethyl, ethoxycarbonylmethyl etc.), amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, aryl (e.g., phenyl, etc.), a non-aromatic heterocyclic group (e.g., 4-tetrahydropyranyl etc.), heteroaryl (e.g., pyridyl etc.), cyano, isocyano, isocyanato, thiocyanato, isothiocyanato and acyl (e.g., formyl, acetyl, etc.).

Substituents for "substituted sulfonyl" or "substituted sulfinyl" are selected from the above "substituted or unsubstituted alkyl", the above "substituted or unsubstituted alkenyl", the above "substituted or unsubstituted alkynyl", the after-mentioned "substituted or unsubstituted cycloalkyl", the after-mentioned "substituted or unsubstituted cycloalkenyl", the after-mentioned "a substituted or unsubstituted non-aromatic heterocyclic group", the after-mentioned "substituted or unsubstituted aryl", and the after-mentioned "substituted or unsubstituted heteroaryl". If R in R—S(=O)$_2$— or R—S(=O)— is "cycloalkyl", "cycloalkenyl", "non-aromatic heterocyclic group", "aryl", "heteroaryl" or the like, then each ring may be substituted with alkyl (e.g., methyl, ethyl, isopropyl, tert-butyl, etc.), haloalkyl (e.g., $CF_3$, $CH_2CF_3$, $CH_2CCl_3$, etc.), alkenyl, alkynyl (e.g., ethynyl), alkyloxy (e.g., methoxy, ethoxy, isopropyloxy), halogen (e.g., fluoro, chloro etc.) or the like.

Substituents for "substituted amino", "substituted imino" and "substituted guanidyl" are one or more same or different groups selected from, but are not limited to, the group consisting of: alkyl (e.g., methyl, ethyl, isopropyl, tert-butyl etc.), haloalkyl (e.g., $CF_3$, $CH_2CF_3$, $CH_2CCl_3$, etc.), hydroxyalkyl (e.g., hydroxyethyl, —C(CH$_3$)$_2$CH$_2$OH, etc.), alkenyl (e.g., vinyl), alkynyl (e.g., ethynyl), cycloalkyl (e.g., cyclopropyl), cycloalkenyl (e.g., cyclopropenyl), alkyloxy (e.g., methoxy, ethoxy, propoxy, butoxy, etc.), haloalkyloxy (e.g., $CF_3O$), alkenyloxy (e.g., vinyloxy, allyloxy, etc.), alkyloxycarbonyl (methoxycarbonyl, tert-butyloxycarbonyl, etc.), alkyloxycarbonylalkyl, amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, imino, hydroxyimino, alkylimino (e.g., methylimino, ethylimino, dimethylimino, etc.), alkyloxyimino (e.g., methoxyimino, ethoxyimino, etc.), acylimino (e.g., acetylimino, benzoylimino, etc.), aryl (e.g., phenyl, etc.), arylalkyl (e.g., benzyl, etc.), aryloxy (e.g., phenoxy etc.), a non-aromatic heterocyclic group (e.g., pyrrolinyl, pyrrolidino, piperidino, piperidyl, piperazino, piperazinyl, morpholinyl, morpholino etc.), heteroaryl (e.g., pyridyl, thienyl, thiazolyl, furyl etc.), heteroarylalkyl (e.g., pyridylmethyl, thienylmethyl, thiazolylmethyl, furylmethyl etc.), non-aromatic heterocyclyloxy (pipierazinooxy, piperidinooxy etc.), heteroaryloxy (pyridyloxy etc.), hydroxy, halogen, (F, Cl, Br, I), cyano, acyl (e.g., formyl, acetyl, etc.), non-aromatic heterocyclicylcarbonyl (e.g., 4-tetrahydropyranylcarbonyl etc.), alkylsulfonyl (e.g., methanesulfonyl etc.), non-aromatic heterocyclicylsulfonyl (e.g., 4-tetrahydropyranylsulfonyl etc.), alkylsulfinyl (e.g., methansulfinyl), carbamoyl, alkylcarbamoyl (e.g., methylcarbamoyl etc.), alkylcarbamoylalkyl (e.g., methylcarbamoylmethyl etc.), carbamoylalkyl (e.g., carbamoylmethyl etc.), carboxyalkyl (e.g., carboxymethyl etc.), sulfamoyl, alkylsulfamoyl (e.g., methylsulfamoyl etc.), alkylsulfamoylalkyl (e.g., methylsulfamoylmethyl etc.), and sulfamoylalkyl (e.g, sulfamoylmethyl etc.).

Substituents for "substituted cycloalkyl", "substituted cycloalkenyl", "substituted aryl", "substituted phenyl", "a substituted heterocyclic group", "substituted heteroaryl", "a substituted non-aromatic carbocyclic group", "a substituted non-aromatic heterocyclic group", "a substituted nitrogen-containing non-aromatic heterocyclic group", "substituted cycloalkyloxycarbonyl", "substituted cycloalkyenyloxycarbonyl", "substituted non-aromatic heterocyclyloxycarbonyl", "substituted aryloxycarbonyl", "substituted heteroaryloxycarbonyl", "a substituted cyclopropane ring", "a substituted cyclopropene ring", "a substituted oxetane ring", "a substituted thietane ring" and "a substituted azetizine ring" are one or more same or different groups selected from, but are not limited to, the group consisting of: alkyl (e.g., methyl, ethyl, isopropyl, tert-butyl etc.), haloalkyl (e.g., $CF_3$, $CH_2CF_3$, $CH_2CCl_3$, etc.), haloalkyloxy (e.g., $CF_3O$, $CHCF_2O$ etc.), alkenyl (e.g., vinyl), alkynyl (e.g., ethynyl), cycloalkyl (e.g., cyclopropyl), cycloalkenyl (e.g., cyclopropenyl), alkyloxy (e.g., methoxy, ethoxy, propoxy, butoxy, etc.), alkenyloxy (e.g., vinyloxy, allyloxy, etc.), alkyloxycarbonyl (e.g., methoxycarbonyl, ethoxycarbonyl, tert-butoxycarbonyl, etc.), nitro, nitroso, amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, amino substituted with one or two same or different substituent selected from the after-mentioned substituent Group Y, imino, hydroxyimino, alkylimino (e.g., methylimino, ethylimino, dimethylimino etc.), alkyloxyimino (e.g., methoxyimino, ethoxyimino etc.), acylimino (e.g., acetylimino, benzoylimino etc.), azido, aryl (e.g., phenyl etc.), arylalkyl (e.g., benzyl etc.), unsubstituted non-aromatic carbocyclyloxy (e.g., cyclopropyloxy etc.), non-aromatic carbocyclyloxy substituted with one or more same or different substituents selected from the after-mentioned Substituent Group Z, unsubstituted non-aromatic carbocyclylalkyloxy (e.g., cyclopropylmethyloxy etc.), non-aromatic carbocyclylalkyloxy substituted with one or more same or different substituents selected from the after-mentioned Substituent Group Z, unsubstituted aryloxy (e.g., phenoxy etc.), aryloxy substituted with one or more same or different substituents selected from the after-mentioned Substituent Group Z, unsubstituted arylalkyloxy (e.g., benzyloxy etc.), arylalkyloxy substituted with one or more same or different substituents selected from the after-mentioned Substituent Group Z, a non-aromatic heterocyclic group (e.g., pyrrolinyl, pyrrolidino, piperidino, piperidyl, piperazino, piperazinyl, morpholinyl, morpholino etc.), heteroaryl (e.g., pyridyl, thienyl, thiazolyl, furyl etc.), heteroarylalkyl (e.g., pyridylmethyl, thienylmethyl, thiazolylmethyl, furylmethyl etc.), unsubstituted non-aromatic heterocyclyloxy (e.g., piperazinooxy, piperizinooxy etc.), non-aromatic heterocyclyloxy substituted with one or more same or different substituents selected from the after-mentioned Substituent Group Z, unsubstituted heteroaryloxy (e.g., pyridyloxy, pyridazinyloxy, pyrimidinyloxy, pyrazinyloxy, oxazolyloxy, isoxazolyloxy, oxadiazolyloxy, thiazolyloxy, isothiazolyloxy, thiadiazolyloxy, furyloxy, thienyloxy, etc.), heteroaryloxy substituted with one or more same or different substituents selected from the after-mentioned Substituent Group Z, cyano, isocyano, isocyanato, thiocyanato, isothiocyanato, mercapto, alkylthio (e.g., methylthio etc.), alkylsulfonyl (e.g., methanesulfonyl, ethanesulfonyl), substituted or unsubstituted carbamoyl (e.g., carbamoyl, N-methyl-N-methoxycarbamoyl etc.), substituted or unsubstituted alkylcarbamoyl (e.g., methylcarbamoyl, ethylcarbamoyl, dimethylcarbamoyl, hydroxyethylcarbamoyl, trifluoromethylcarbamoyl, trifluoroethylcarbamoyl etc.), sulfamoyl, alkylsulfamoyl, hydroxy, carboxy, halogen (F, Cl, Br, I), acyl (e.g., formyl, acetyl etc.), formyloxy, thioformyl, thiocarboxy, dithiocarboxy, thiocarbamoyl, sulfino, sulfo, hydrazino, azido, ureido, amidino, guanidino, phthalimido and oxo.

A substituent Group Y includes hydroxyalkyl (e.g., hydroxyethyl, —$C(CH_3)_2CH_2OH$ etc.), alkyloxycarbonyl (methoxycarbonyl, tert-butyloxycarbonyl etc.), alkyloxycarbonylalkyl, alkylsulfonyl (e.g., methanesulfonyl etc.), alkylsulfinyl (e.g., methanesulfinyl etc.), carbamoyl, alkylcarbamoyl (e.g., methylcarbamoyl etc.), alkylcarbamoylalkyl (e.g., methylcarbamoylmethyl etc.), carbamoylalkyl (e.g., carbamoylmethyl etc.), carboxyalkyl (e.g., carboxymethyl etc.), sulfamoyl, alkylsulfamoyl (e.g., methylsulfamoyl etc.), alkylsulfamoylalkyl (e.g., methylsulfamoylmethyl etc.) and sulfamoylalkyl (e.g., sulfamoylmethyl etc.).

A substituent Group Z includes halogen (e.g., F, Cl etc.), hydroxy, carboxy, carboxyalkyloxy (e.g., carboxymethyloxy etc.), cyano, nitro, alkyl (e.g., methyl etc.), hydroxyalkyl (e.g., hydroxymethyl etc.), aminoalkyl, alkylaminoalkyl, alkenyl, alkynyl, alkyloxy, alkenyloxy, alkynyloxy, alkylthio, alkenylthio, alkynylthio, acyl, alkyloxycarbonyl (e.g., methyloxycarbonyl, ethyloxycarbonyl etc.), alkenyloxycarbonyl, alkynyloxycarbonyl, carbamoyl, carbamoylalkyloxy (e.g., carbamoylmethyloxy etc.), alkylcarbamoyl (e.g., methylcarbamoyl, ethylcarbamoyl etc.), haloalkylcarbamoyl, cycloalkylcarbamoyl (e.g., cyclopropylcarbamoyl etc), alkylcarbamoylalkyloxy (e.g., methylcarbamoylmethyloxy etc), hydroxyalkylcarbamoyl (e.g., hydroxyethylcarbamoyl etc), cyanocarbamoyl, amino, acylamino, amino substituted with one or two same or different substituent selected from the above substituent Group Y, sulfamoyl, methylsulfonyl, methylsulfinyl, cycloalkyl, cycloalkenyl, a non-aromatic heterocyclic group, aryl, heteroaryl (e.g., tetrazolyl etc), cycloalkyloxy, cycloalkenyloxy, non-aromatic heterocyclyloxy, aryloxy heteroaryloxy and oxo.

As substituents for "substituted aryl" and "substituted heteroaryl" for $R^2$, halogen, alkyl, alkenyl, alkynyl, alkyloxy, haloalkyl, cycloalkyl, alkylsilylalkynyl and the like are exemplified.

As substituents for "substituted aryl" and "substituted heteroaryl" for $R^2$, alkyl, haloalkyl, and the like are exemplified.

As substituents for "substituted aryl" and "substituted heteroaryl" for $R^2$, halogen and the like are exemplified.

As substituents for "substituted aryl" and "substituted heteroaryl" for $R^2$, fluoro, chloro, bromo, iodo, methyl, ethyl, propyl, isopropyl, propenyl, vinyl, ethynyl, methyloxy, fluoromethyl, difluoromethyl, trifluoromethyl, cyclopropyl, trimethylsilylethynyl and the like are exemplified.

As substituents for "substituted aryl" and "substituted heteroaryl" for $R^2$, fluoro, chloro, methyl, fluoromethyl, difluoromethyl and the like are exemplified.

As substituents for "substituted aryl" and "substituted heteroaryl" for $R^2$, fluoro, chloro, methyl, difluoromethyl and the like are exemplified.

As substituents for "substituted aryl" and "substituted heteroaryl" for $R^2$, chloro, methyl and the like are exemplified.

As substituents for "substituted aryl" and "substituted heteroaryl" for $R^2$, methyl and the like are exemplified.

As substituents for "substituted aryl" and "substituted heteroaryl" for $R^2$, chloro and the like are exemplified.

Examples of $R^2$ are 4-methylphenyl, 4-chlorophenyl, 4-fluoromethyl, 4-difluoromethylphenyl, 2,4-difluorophenyl, 2,4-dichloromethyl, 4-methylcyclohexyl and the like.

Examples of $R^2$ are 4-methylphenyl, 4-chlorophenyl, 2,4-difluorophenyl, 4-methylcyclohexyl and the like.

Examples of $R^2$ are 4-methylphenyl and the like.

Examples of $R^2$ are 4-chlorophenyl and the like.

Examples of $R^9$ are halogen, alkyl, haloalkyl, alkenyl, alkynyl and the like.

Examples of $R^9$ are fluoro, chloro, bromo, iodo, methyl, ethyl, propyl, isopropyl and the like.

Examples of $R^9$ are fluoro, chloro, methyl and the like.

Examples of $R^{9'}$ are halogen, carboxy, cyano, substituted or unsubstituted alkyl, substituted or unsubstituted alkyloxy, substituted or unsubstituted acyl, substituted or unsubstituted alkyloxycarbonyl, substituted sulfonyl, or substituted or unsubstituted aryl, and the like.

Examples of $R^{9'}$ are halogen, carboxy, cyano, substituted or unsubstituted alkyl, substituted or unsubstituted alkyloxy, substituted or unsubstituted alkyloxycarbonyl, substituted or unsubstituted aryl, and the like.

Examples of $R^{9'}$ are fluoro, chloro, bromo, iodo, carboxy, cyano, methyl, ethyl, propyl, isopropyl, hydroxymethyl, hydroxyethyl, methyloxymethyl, ethyloxymethyl, fluoromethyl, difluoromethyl, trifluoromethyl, methyloxy, ethyloxy, propyloxy, isopropyloxy, formyl, acetyl, methyloxycarbonyl, ethyloxycarbonyl, methanesulfonyl, ethanesulfonyl, and the like.

Examples of $R^{9'}$ are fluoro, chloro, bromo, iodo, carboxy, cyano, methyl, ethyl, propyl, isopropyl, hydroxymethyl, fluoromethyl, difluoromethyl, trifluoromethyl, methyloxy, ethyloxy, propyloxy, isopropyloxy, methyloxycarbonyl, ethyloxycarbonyl, and the like.

Examples of $R^{9'}$ are fluoro, chloro, carboxy, cyano, methyl, ethyl, hydroxymethyl, hydroxyethyl, methyloxymethyl, fluoromethyl, difluoromethyl, trifluoromethyl, methyloxy, isopropyloxy, acetyl, methyloxycarbonyl, ethyloxycarbonyl, methanesulfonyl, and the like.

Examples of $R^{9'}$ are fluoro, chloro, carboxy, cyano, methyl, hydroxymethyl, trifluoromethyl, methyloxy, isopropyloxy, difluoromethyl, methyloxycarbonyl, ethyloxycarbonyl, and the like.

Examples of $R^{9'}$ are carboxy, hydroxymethyl, isopropyloxy, difluoromethyl, methyloxycarbonyl, ethyloxycarbonyl, and the like.

In Formula (I), "$R^{4a}$ and $R^{ob}$ attached to the same carbon atom are taken together to form oxo or thioxo" includes the followings:

[Chemical Formula 17]

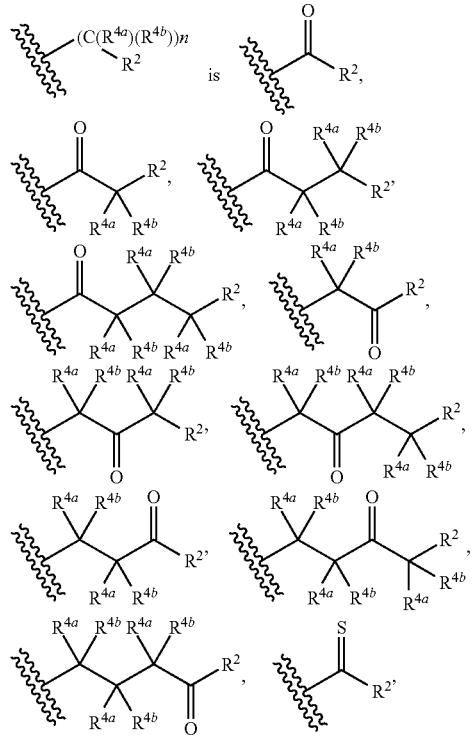

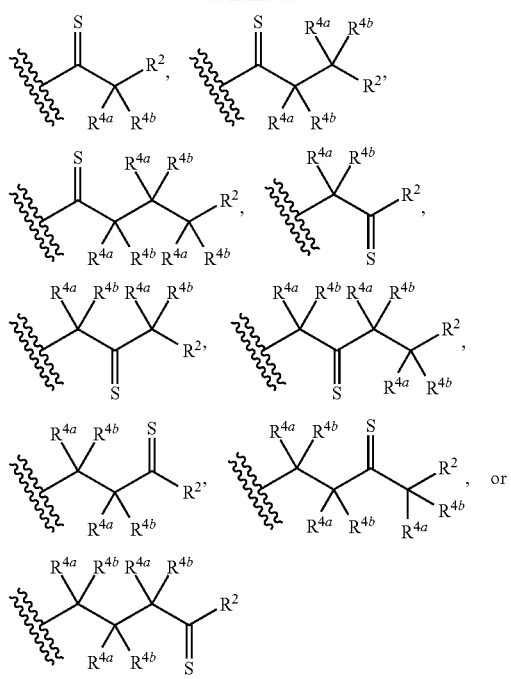

wherein n, $R^{4a}$, $R^{4b}$ and $R^2$ are as defined in the above (1) or the like.

Examples of the group represented by the following formula:

[Chemical Formula 18]

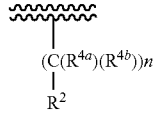

are groups represented by the following formula:

[Chemical Formula 19]

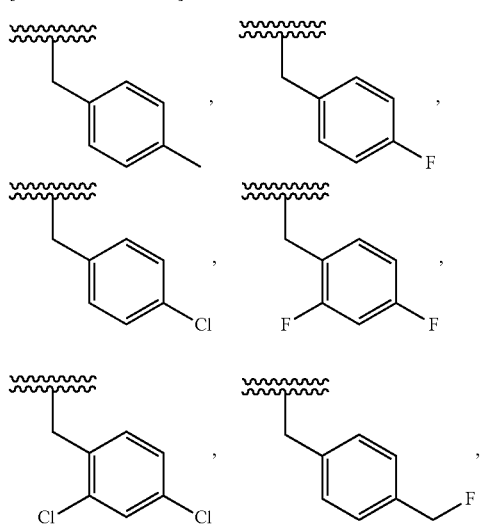

-continued

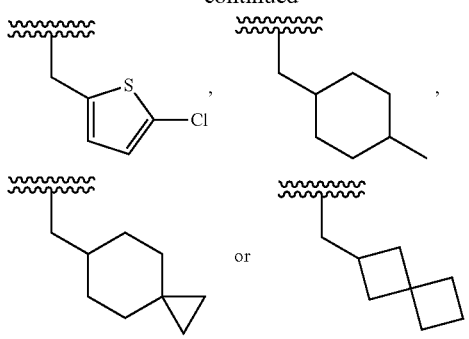

Examples of the group represented by the following formula:

[Chemical Formula 20]

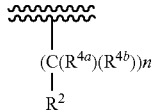

are groups represented by the following formula:

[Chemical Formula 21]

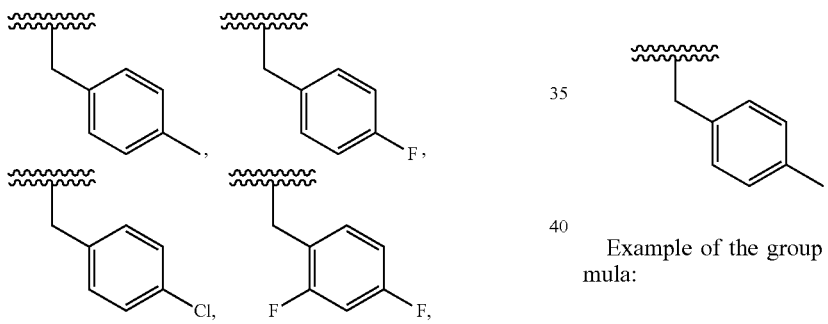

Examples of the group represented by the following formula:

[Chemical Formula 22]

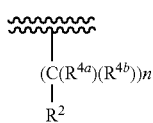

are groups represented by the following formula:

[Chemical Formula 23]

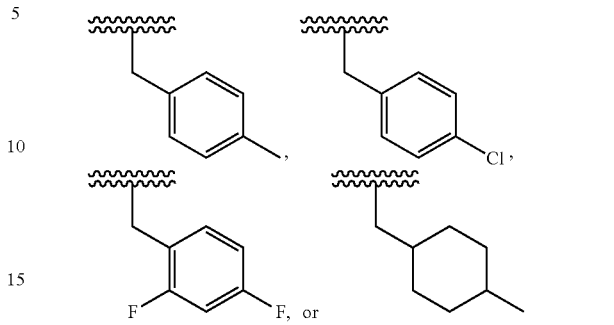

Example of the group represented by the following formula:

[Chemical Formula 24]

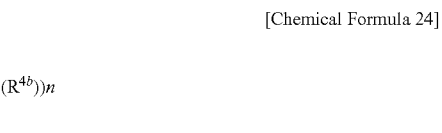

is a group represented by the following formula:

[Chemical Formula 25]

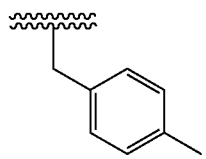

Example of the group represented by the following formula:

[Chemical Formula 26]

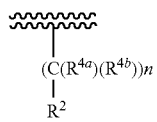

is a group represented by the following formula:

[Chemical Formula 27]

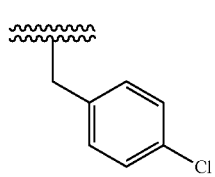

In Formula (I), "$R^{20a}$ and $R^{20b}$ attached to the same carbon atom are taken together to form substituted or unsubstituted cycloalkane, substituted or unsubstituted cycloalkene, or a substituted or unsubstituted non-aromatic heterocyclic ring" includes the followings:

[Chemical Formula 28]

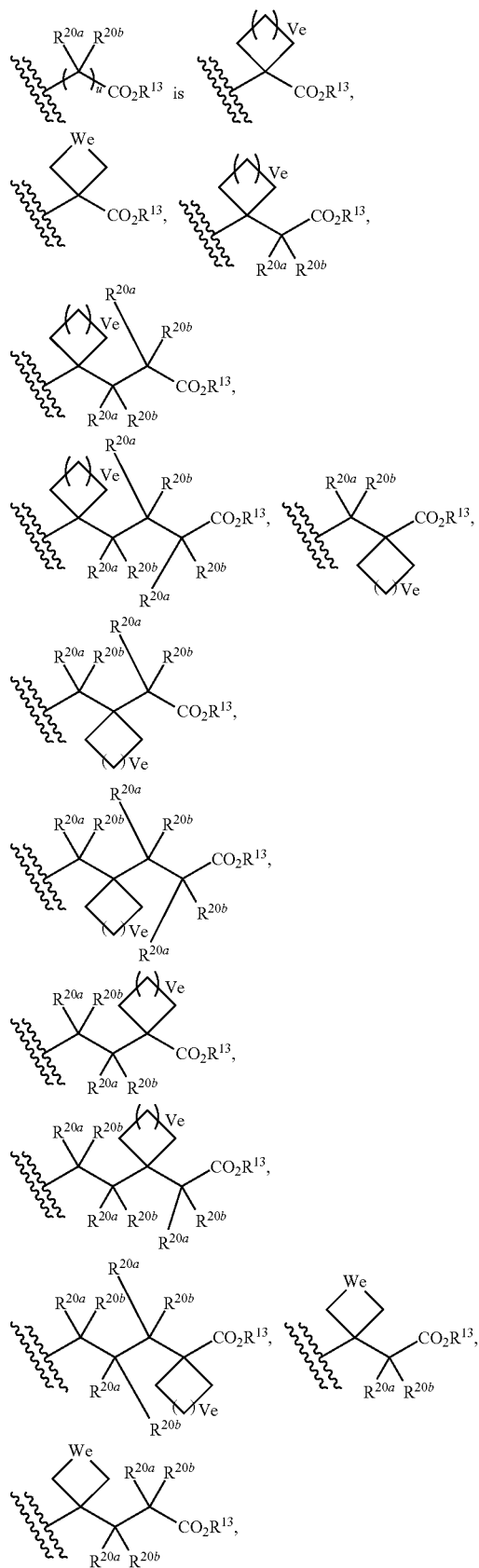
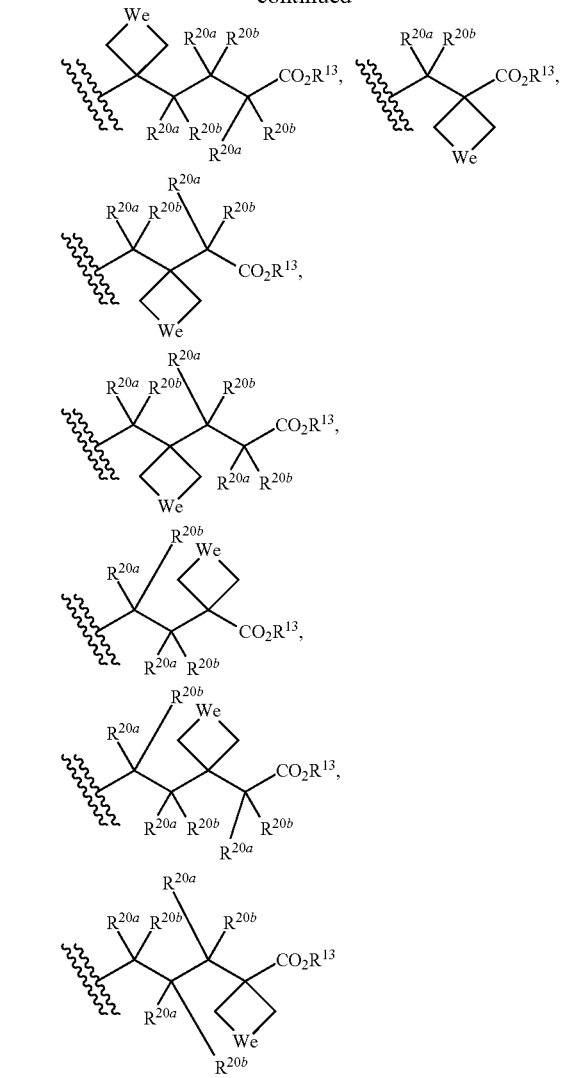

wherein u, $R^{20a}$ and $R^{20b}$ are as defined in the above (1);
Ve is an integer of 0 to 3 (e.g., 0 or 1, and e.g., 0);
-We- is —O—, —S— or —N($R^{17d}$)— (e.g., —O—);
$R^{17d}$ is a hydrogen atom, substituted or unsubstituted alkyl, substituted or unsubstituted alkenyl, substituted or unsubstituted alkynyl, substituted or unsubstituted acyl or the like.

In Formula (I), "$R^{20a}$ and $R^{20b}$ attached to the different carbon atoms are taken together to form substituted or unsubstituted cycloalkane, substituted or unsubstituted cycloalkene, or a substituted or unsubstituted non-aromatic heterocyclic ring" includes the followings:

[Chemical Formula 29]

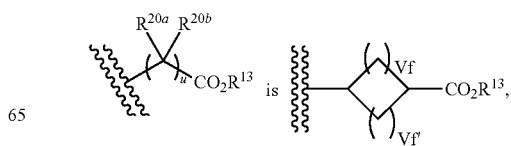

-continued

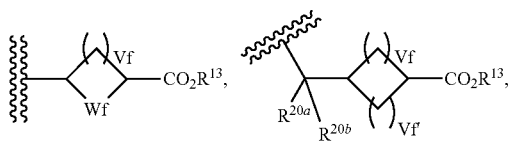

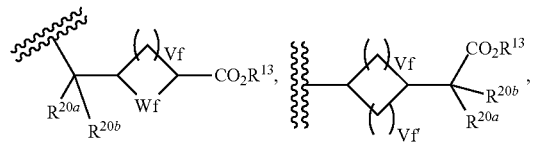

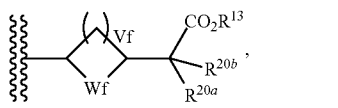

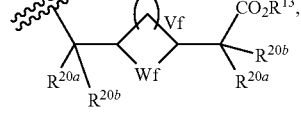

wherein u, $R^{20a}$ and $R^{20b}$ are as defined in the above (1);
Vf is an integer of 0 to 3 (e.g., 0 or 1, and e.g., 1);
Vf' is an integer of 1 to 3 (e.g., 1);
-Wf- is —O—, —S— or —N($R^{1d7}$)— (e.g., —O—);
$R^{17d}$ is a hydrogen atom, substituted or unsubstituted alkyl, substituted or unsubstituted alkenyl, substituted or unsubstituted alkynyl, substituted or unsubstituted acyl or the like.

In Formula (I), the group represented by the following formula:

[Chemical Formula 30]

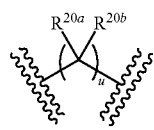

is the same as a group represented by the following formula:

[Chemical Formula 31]

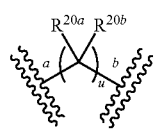

wherein the bond a is attached to the nitrogen atom of the triazine ring, and the bond b is attached to the "C" atom of the "—$CO_2R^{13}$" group.

Examples of the group represented by the following formula:

[Chemical Formula 32]

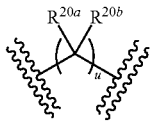

are groups represented by the following formula:

[Chemical Formula 33]

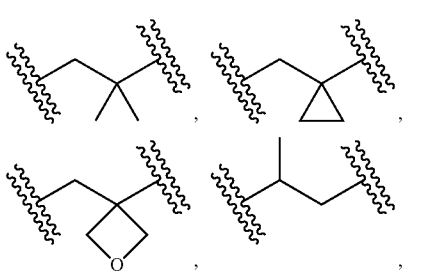

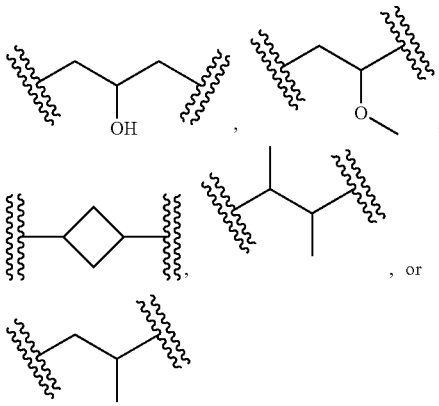

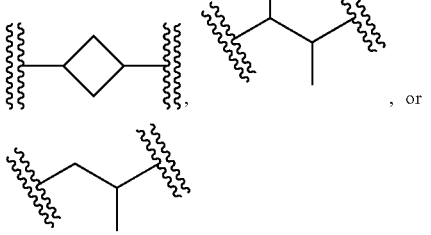

As described above, the above formulae are the same as groups represented by the following formula:

[Chemical Formula 34]

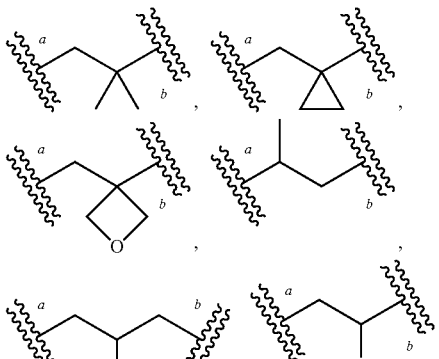

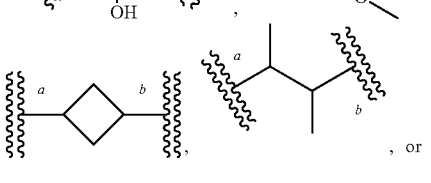

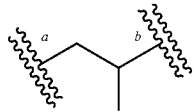

wherein the bond a is attached to the nitrogen atom of the triazine ring, and the bond b is attached to the "C" atom of the "—CO$_2$R$^{13}$" group. The binding mode is the same also in the below formula.

Examples of the group represented by the following formula:

[Chemical Formula 35]

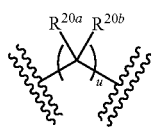

are groups represented by the following formula:

[Chemical Formula 36]

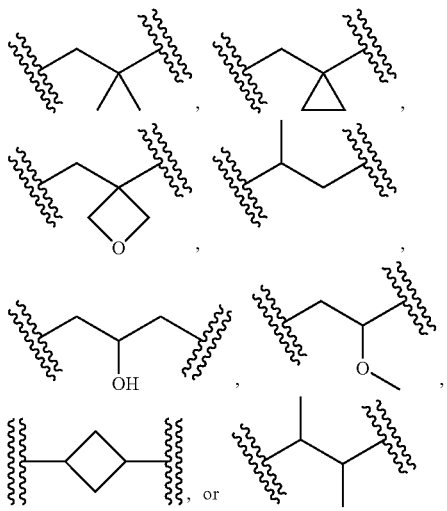

Examples of the group represented by the following formula:

[Chemical Formula 37]

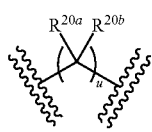

are groups represented by the following formula:

[Chemical Formula 38]

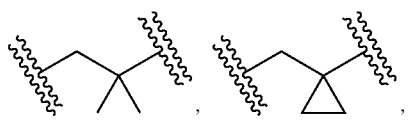

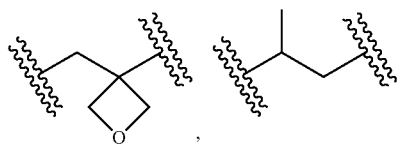

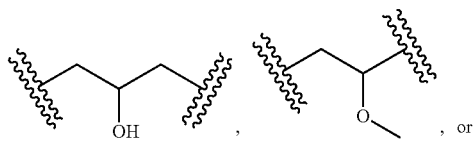

Examples of the group represented by the following formula:

[Chemical Formula 39]

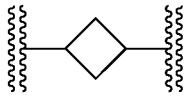

are groups represented by the following formula:

[Chemical Formula 40]

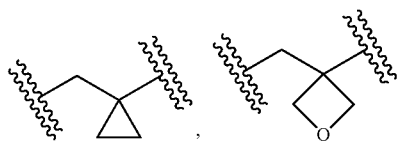

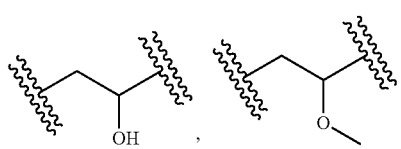

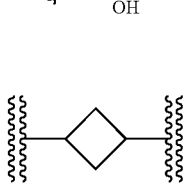

Examples of the group represented by the following formula:

[Chemical Formula 41]

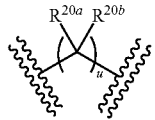

are groups represented by the following formula:

[Chemical Formula 42]

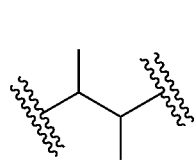 or 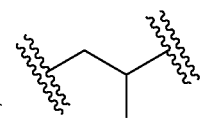

Example of the group represented by the following formula:

[Chemical Formula 43]

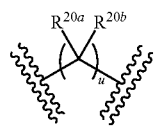

is a group represented by the following formula:

[Chemical Formula 44]

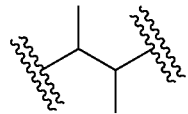

Example of the group represented by the following formula:

[Chemical Formula 45]

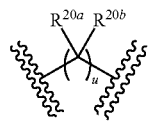

is a group represented by the following formula:

[Chemical Formula 46]

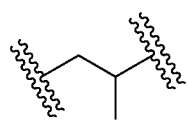

The following is a general method for synthesizing the compounds of this invention. The starting materials and reagents used for synthesizing these compounds are commercially available or can be manufactured in accordance with a widely known method in this field using commercially available compounds.

For example, the compounds of the Formula (I) described in this invention can be manufactured by the following synthesis route, or by reference to what is described in WO2010/092966 and WO2012/020749 if necessary.

[Method A]

[Chemical Formula 47]

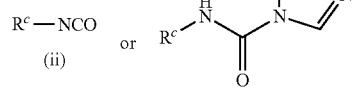

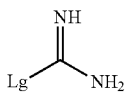

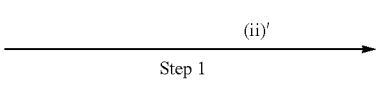

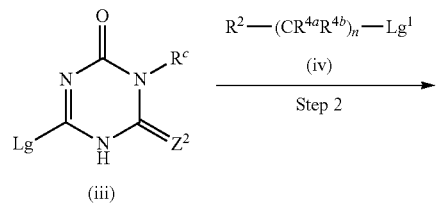

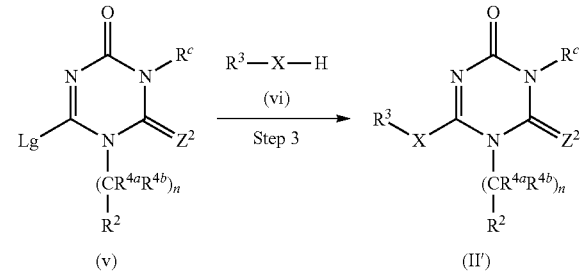

wherein, Lg is a leaving group represented by the formula:

[Chemical Formula 48]

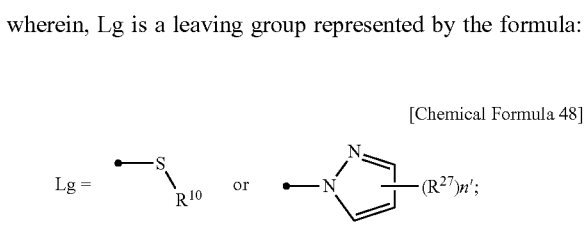

$R^3$ is a group represented by the formula:

[Chemical Formula 49]

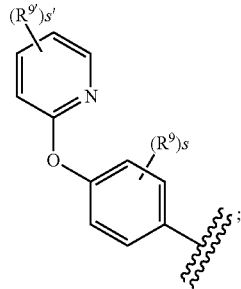

$R^c$ is a group represented by the formula:

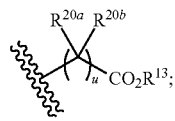

[Chemical Formula 50]

$R^{10}$ is alkyl, $R^{27}$ is alkyl, $Z^2$ is an oxygen atom or a sulfur atom, X is NH, n' is an integer of 0 to 3, $Lg^1$ is a leaving group and other symbols are as defined above.

(Step 1)

The compound (i) or its hydrochloride or bromate is reacted with isocyanate (ii) or 1-carbamoyl imidazole (ii)' in a solvent, such as N,N-dimethylformamide, N,N-dimethylacetamide, N,N'-dimethyl imidazolidinone and dimethylsulfoxide, in the presence of a base, such as DBU, triethylamine and pyridine (preferably DBU) at a temperature between −20 and 50° C., preferably at a temperature between −10° C. and below zero. After that, the compound (iii) can be manufactured by reacting the reactive mixture with a carbonylating or thiocarbonylating agent, such as 1,1'-carbonyldiimidazole, 1,1'-thiocarbonyldiimidazole, phosgene, thiophosgene and triphosgene, etc., and a base, such as DBU, triethylamine or pyridine (preferably DBU) at a temperature between −20 and 50° C., preferably at a temperature between −10° C. and below zero.

(Step 2)

The compound (v) can be manufactured by reacting the compound (iii) with the compound (iv) in a solvent, such as acetonitrile, acetone, DMF and DMSO, in the presence of a base, such as potassium carbonate and sodium carbonate, at a temperature between 50° C. to reflux, preferably at reflux.

The examples of a leaving group include halogen and —OSO$_2$ (C$_t$F$_{2t+1}$) wherein t is an integer of 1 to 4. As halogen, chloro, iodo and bromo are preferred. As —OSO$_2$ (C$_t$F$_{2t+1}$) group, —OTf group (trifluoromethanesulfonate) is preferred.

(Step 3)

The compound indicated by Formula (II') can be manufactured by reacting the compound (v) with the compound (vii) in a solvent, such as NMP, DMF and DMSO, or under solvent-free conditions under microwave irradiation at a temperature between 150° C. and 250° C., preferably at a temperature between 200° C. and 230° C., or in a solvent, such as t-butanol, in the presence of an acid, such as acetic acid, at a temperature between 60° C. and 150° C., preferably at a temperature between 80° C. and 120° C.

Using optically active isocyanate (ii) enables to synthesize optically active compound (II').

[Method B]

[Chemical Formula 51]

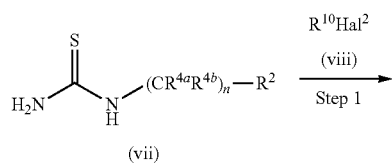

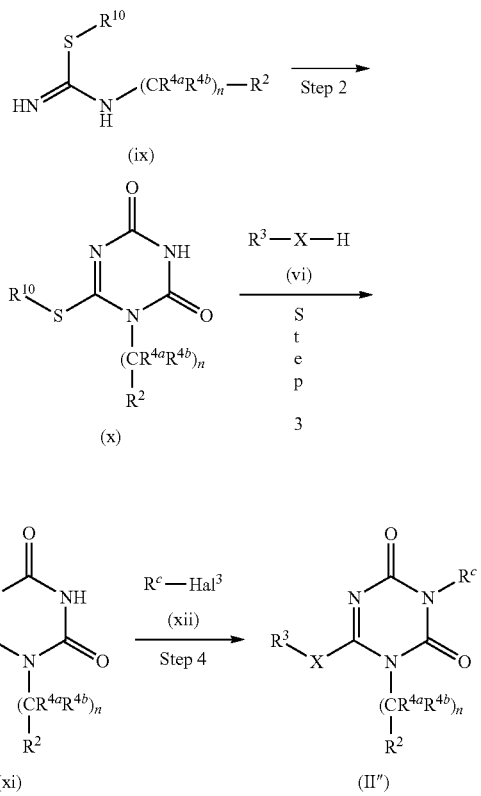

wherein Hal$^2$ and Hal$^3$ are halogen and other symbols are as defined above.

(Step 1)

The compound (ix) can be manufactured by reacting the compound (vii) with alkylating agent (viii), such as methyl iodide and ethyl iodide, in a solvent, such as methanol and ethanol, at a temperature between −40° C. and 30° C., preferably below zero.

(Step 2)

The compound (x) can be manufactured by reacting the compound (ix) with isocyanate, such as N-(chlorocarbonyl) isocyanate, in a solvent, such as dichloromethane, chloroform, 1,2-dichloroethane, in the presence of a base, such as triethylamine and N,N-diisopropylethylamine, at a temperature between −20° C. and 30° C., preferably below zero.

(Step 3)

The compound (xi) can be manufactured by reacting the compound (x) with the compound (vi) in a solvent, such as t-butanol, isopropanol, ethanol and acetonitrile, in the presence of an acid, such as acetic acid, formic acid and methanesulfonic acid, at reflux.

(Step 4)

The compound represented by Formula (II'') can be manufactured by reacting the compound (xi) with the compound (xii) in a solvent, such as DMF or NMP, etc, in the presence of a base, such as potassium t-butoxide, or sodium hydride, at a temperature between 40° C. and 100° C., preferably at a temperature between 50° C. and 70° C.

Using optically-active compound (xii) enables to synthesize optically-active compound (II'').

[Method C]

[Chemical Formula 52]

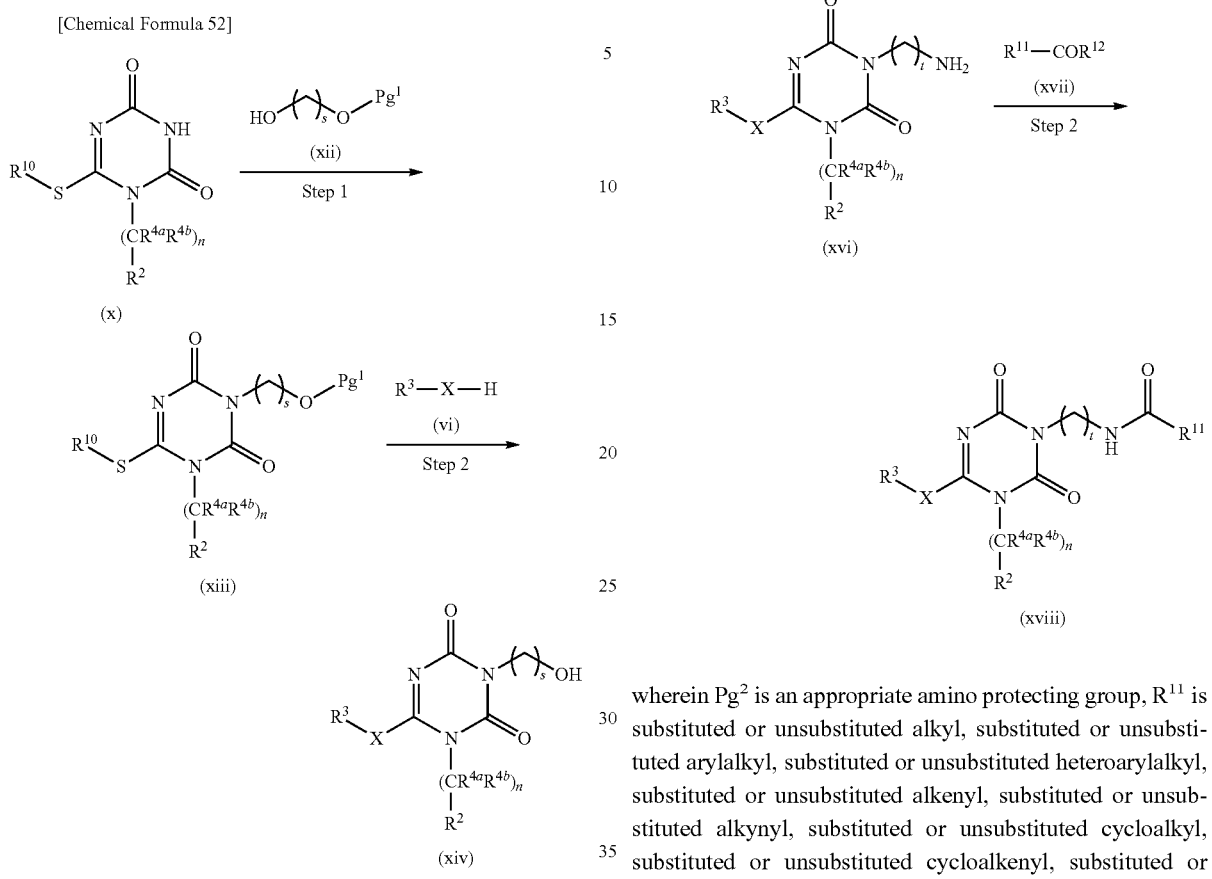

wherein $Pg^1$ is an appropriate hydroxy protecting group, s is an integer of 1 to 4 and other symbols are as defined above.

(Step 1)

The compound (xiii) can be manufactured by reacting a mixture of the compound (x) obtained by the method B, and the alcohol (xii) whose one hydroxyl group is protected, such as 2-(tetrahydro-2H-pyran-2-yloxy) ethanol in a solvent, such as THF or dioxane, etc, with triphenylphosphine, and diethyl azodicarboxylate, etc.

(Step 2)

The compound (xiv) can be manufactured by reacting the compound (xiii) with the compound (vi) in the presence of an acid, such as formic acid or acetic acid, etc., at reflux.

[Method D]

[Chemical Formula 53]

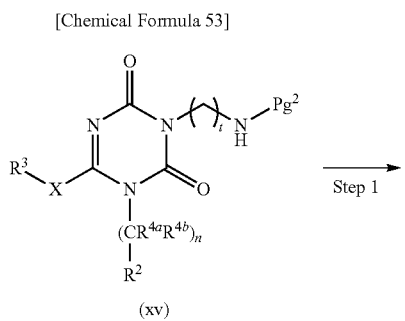

wherein $Pg^2$ is an appropriate amino protecting group, $R^{11}$ is substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, substituted or unsubstituted acyl, a substituted or unsubstituted non-aromatic heterocyclic group, substituted or unsubstituted aryl or substituted or unsubstituted heteroaryl, $R^{12}$ is hydroxy or halogen, t is an integer of 1 to 4 and other symbols are as defined above.)

(Step 1)

The compound (xvi) can be manufactured by reacting the compound (xv) obtained by the method A or B with acid, such as hydrochloric acid-dioxane solution, hydrochloric acid-methanol, hydrochloric acid-ethyl acetate solution and trifluoroacetic acid, etc.

(Step 2)

The compound (xviii) can be manufactured by reacting the compound (xvi) with the acid halide (xvii) ($R^{12}$ is halogen) in a solvent, such as THF or dioxane, etc., in the presence of a base, such as triethylamine or diisopropylethylamine, etc. If necessary, dimethylaminopyridine, etc., can be added.

Alternatively, the compound (xviii) can be manufactured by reacting the compound (xvi) with the carboxylic acid (xvii, $R^{12}$ is hydroxy) in a solvent, such as THF or DMF, in the presence of a condensing agent, such as 1-hydroxybenzotriazole and 1-ethyl-3-(3-dimethylaminopropyl) carbodiimide hydrochloride, and a base, such as triethylamine or diisopropylethylamine, etc.

[Method E]

[Chemical Formula 54]

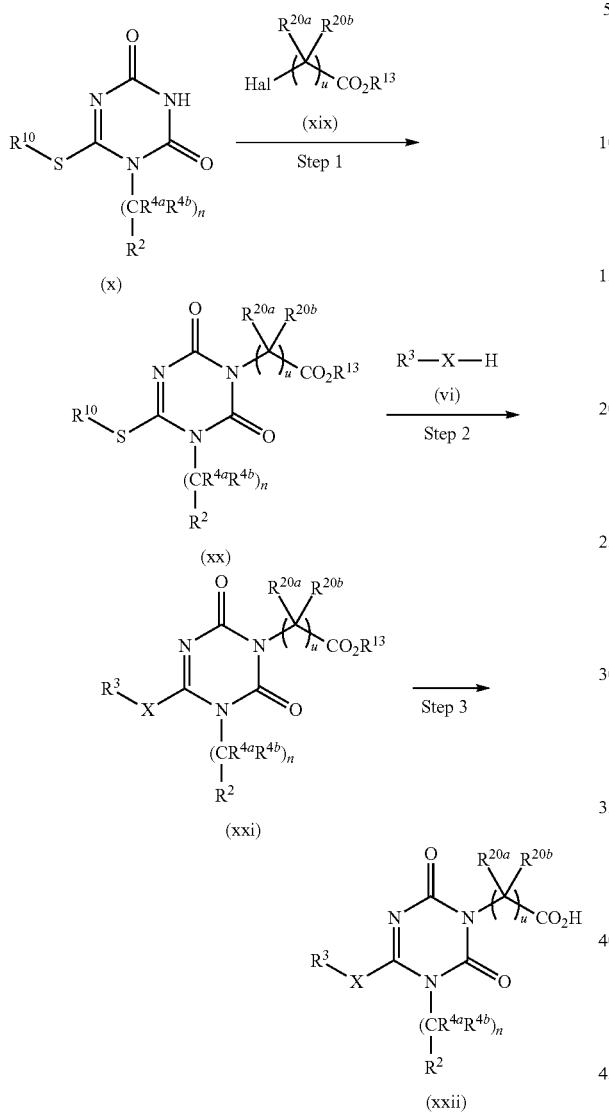

(xix) in a solvent, such as DMF, NMP or THF, etc., in the presence of a base, such as DBU, potassium t-butoxide or sodium hydride, etc., at a temperature between 0° C. and 80° C., preferably at a temperature between 30° C. and 50° C.

(Step 2)

The compound (xxi) can be manufactured by reacting the compound (xx) with the compound (vi) in a solvent, such as t-butanol, isopropanol, ethanol or acetonitrile, etc., in the presence of an acid such as formic acid, acetic acid or methanesulfonic acid, etc., at reflux.

(Step 3)

The compound (xxii) can be manufactured by reacting the compound (xxi) with a solution, such as lithium hydroxide aqueous solution, sodium hydroxide aqueous solution and potassium hydroxide aqueous solution, in a solvent, such as methanol or ethanol, etc., or in a mixture of such solvent and a solvent, such as THF or dioxane, etc.

[Method F]

[Chemical Formula 55]

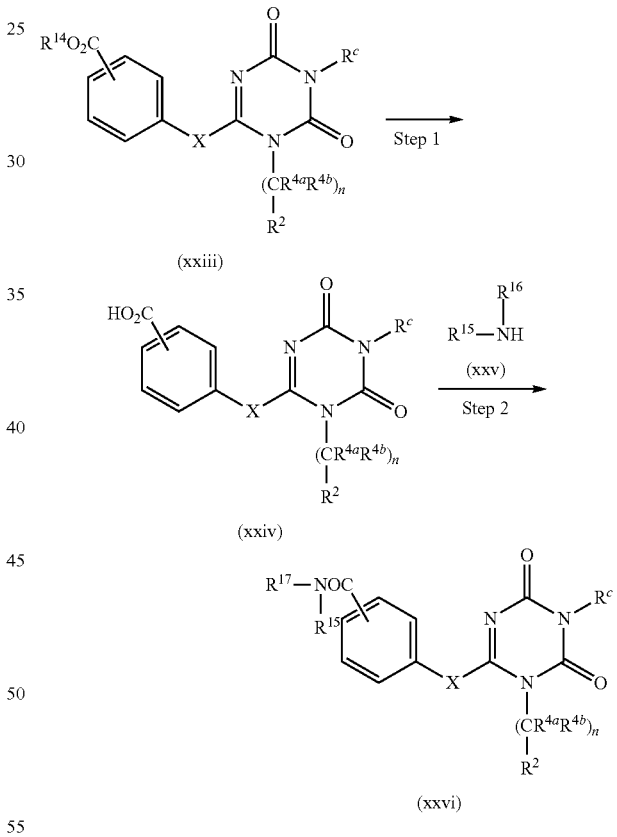

wherein $R^{13}$ is substituted or unsubstituted alkyl, $R^{20a}$ and $R^{20b}$ are hydrogen, halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl or $R^{20a}$ and $R^{20b}$ are taken together to form oxo or thioxo, u is an integer of 1 to 4, and other symbols are as defined above.

(Step 1)

The compound (xx) can be manufactured by reacting the compound (x) obtained by the method B with the compound wherein $R^{14}$ is substituted or unsubstituted alkyl, $R^{15}$ and $R^{16}$ are each independently substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, substituted or unsubstituted acyl, a substituted or unsubstituted non-aromatic heterocyclic group, substituted or unsubstituted aryl or substituted or unsubstituted heteroaryl, u is an integer of 1 to 4 and other symbols are as defined above.

(Step 1)

The compound (xxiv) can be manufactured by reacting the compound (xxiii) obtainored by the method A or B with a solution, such as lithium hydroxide aqueous solution, sodium hydroxide aqueous solution and potassium hydroxide aqueous solution, in a solvent, such as methanol or ethanol, etc., or in a mixture of such solvent and a solvent, such as dioxane THF, etc.

(Step 2)

The compound (xxvi) can be manufactured by reacting the compound (xxiv) with the compound (xxv) in a solvent, such as THF, DMF or NMP, etc., in the presence of a condensing agent, such as 1-hydroxybenzotriazole, HOAt, 1-ethyl-3-(3-dimethylaminopropyl)carbodiimide hydrochloride, HATU or PyBOP, etc., and a base, such as triethylamine or diisopropylethylamine, etc.

[Method L]

[Chemical Formula 56]

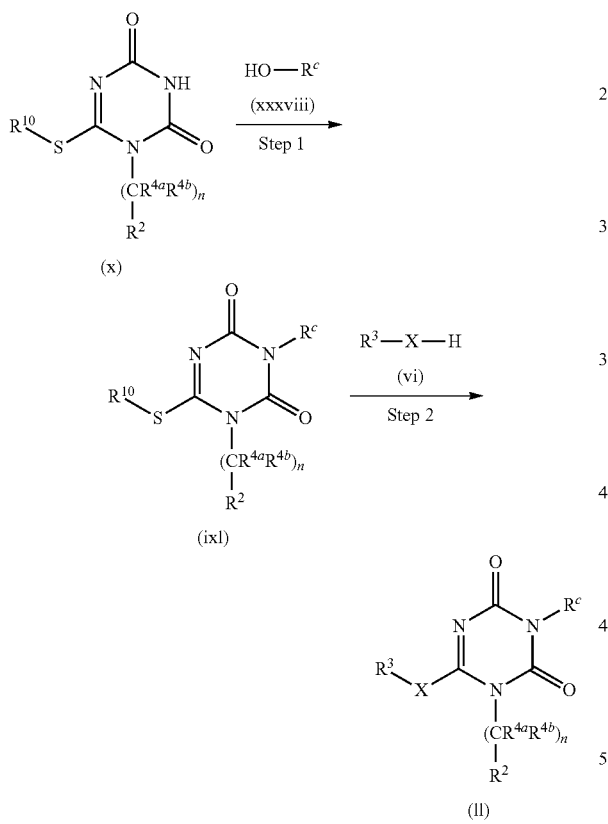

wherein the symbols in the formula are as defined above.

(Step 1)

The compound (ix1) can be manufactured by reacting a mixture of the compound (x) obtained by the method B and the alcohol (xxxviii) in a solvent, such as THF or dioxane, etc., with triphenylphosphine, etc., and diethyl azodicarboxylate, etc.

(Step 2)

The compound (II) can be manufactured by reacting the compound (ix1) with the compound (vi) in the presence of an acid, such as formic acid or acetic acid, etc., at reflux.

Using the optically-active alcohol (xxxviii) enables to synthesize the optically-active compound (II).

The alcohol used as an intermediate (xxxviii) is commercially available or can be manufactured according to a method specified in the following documents:

Tetrahedron (1993), 49(11), 2325-44.
Chemical Communications (2008), (47), 6408-6410.
Tetrahedron (1990), 46(24), 8207-28.
Synlett (1994), (3), 199-200.
Bulletin of the Chemical Society of Japan (1994), 67(8), 2244-7
Canadian Journal of Chemistry (1996), 74, 1731-1737
Chemistry—A European Journal (2010), 16(2), 577-587
Bioorganic & Medicinal Chemistry Letters (2009), 19(21), 6196-6199.
Chemische Berichte (1985), 118(10), 3966-79.
Tetrahedron: Asymmetry (1992), 3(4), 515-16.
Organic Letters (1999), 1(6), 957-959.
Chimia (1986), 40(5), 172-3.

[Method M]

[Chemical Formula 57]

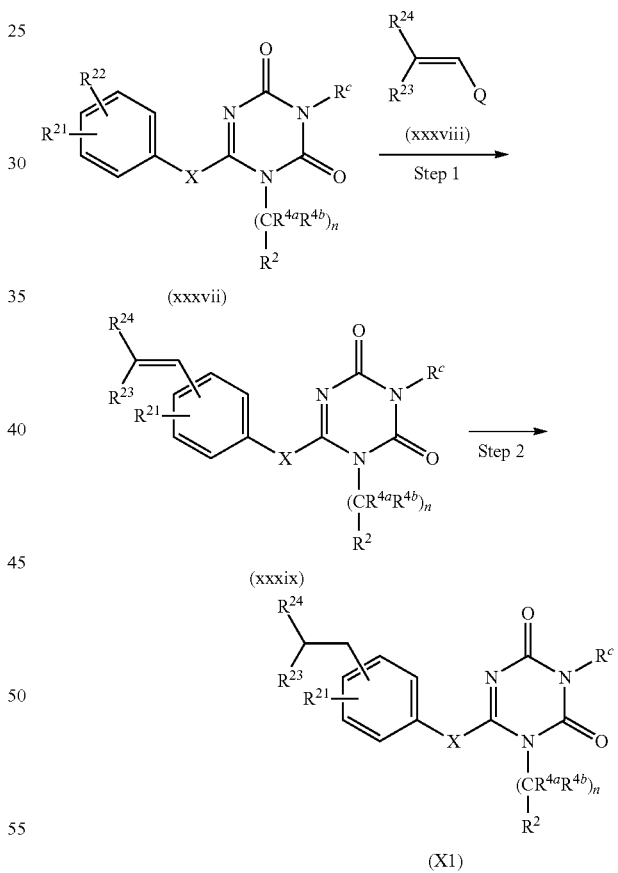

wherein $R^{21}$ is hydrogen, substituted or unsubstituted alkyl or substituted or unsubstituted alkoxy, etc., $R^{22}$ is bromo or iodo, $R^{23}$ and $R^{24}$ are each independently substituted or unsubstituted alkyl, substituted or unsubstituted arylalkyl, substituted or unsubstituted heteroarylalkyl, substituted or unsubstituted cycloalkyl, a substituted or unsubstituted non-aromatic heterocyclic group, substituted or unsubstituted aryl or substituted or unsubstituted heteroaryl, and other symbols are as defined above.

(Step 1)

The compound (xxxix) can be manufactured by reacting the compound (xxxvii) obtained by the method from A to F or L with the compound (xxxviii) in a solvent, such as THF or dioxane, etc., in the presence of a palladium catalyst and a solution, such as potassium carbonate, cesium carbonate or sodium carbonate aqueous solution, etc., at a temperature between 50° C. and reflux, preferably at reflux, or under microwave irradiation at a temperature between 120° C. and 200° C., preferably at a temperature between 130° C. and 150° C.

(Step 2)

The compound (xl) can be obtained by dissolving the compound (xxxix) in an alcohols solvent, such as methanol or ethanol, etc., and performing catalytic reduction using a hydrogenation reactor (such as H-Cube (10% Pt—C, H2=1 atm)) or a metallic catalyst, such as palladium-carbon, platinum oxide, chlorotris (triphenylphosphine) rhodium (I), etc.

[Method N]

[Chemical Formula 58]

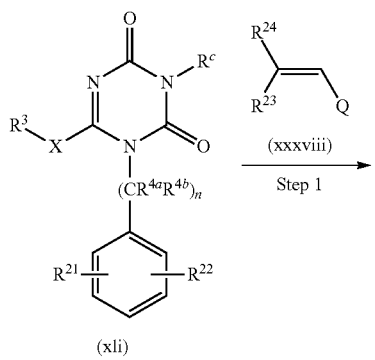

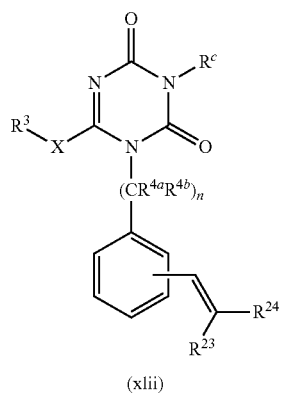

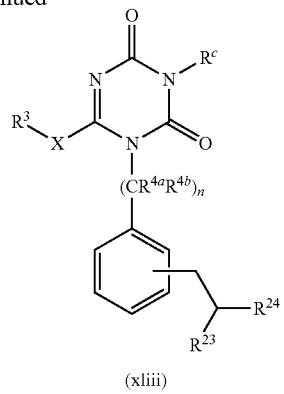

wherein the symbols in the formula are as defined above.

(Step 1)

The compound (xlii) can be manufactured by reacting the compound (xli) obtained by the method from A to F or L with the compound (xxxviii) in a solvent, such as THF or dioxane, etc., in the presence of a palladium catalyst and a solution, such as potassium carbonate, cesium carbonate or sodium carbonate aqueous solution, etc., at a temperature between 50° C. and reflux, preferably at reflux, or under microwave irradiation at a temperature between 120° C. and 200° C., preferably at a temperature between 130° C. and 150° C.

(Step 2)

The compound (xliii) can be obtained by dissolving the compound (xlii) in an alcohols solvent, such as methanol or ethanol, etc., and performing catalytic reduction using a hydrogenation reactor (such as H-Cube (10% Pt—C, H2=1 atm)) or a metallic catalyst, such as palladium-carbon, platinum oxide or chlorotris (triphenylphosphine) rhodium (I), etc.

[Method O]

[Chemical Formula 59]

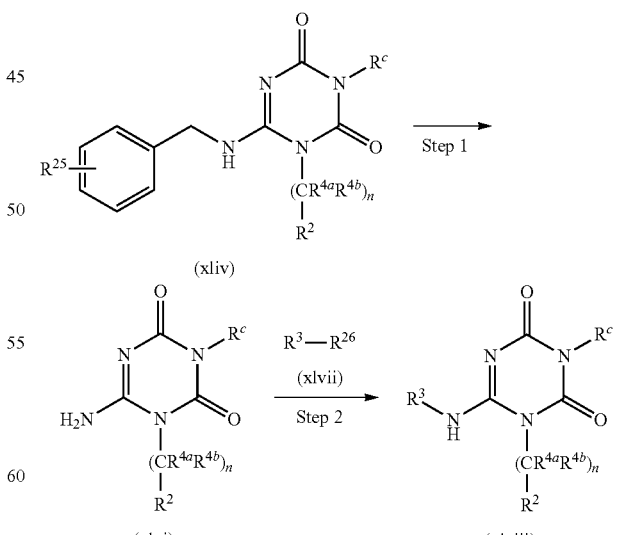

wherein $R^{25}$ is substituted or unsubstituted alkyl or substituted or unsubstituted alkoxy, $R^{26}$ is bromo or iodo, and other symbols are as defined above.

(Step 1)

The compound (xlvi) can be obtained from the compound (xliv) in the presence of Lewis acid or trifluoroacetic acid, etc., under solvent-free conditions or in an appropriate solvent at a temperature between 0° C. and reflux.

(Step 2)

The compound (xlviii) can be manufactured by reacting the compound (xlvi) with the compound (xlvii) in a solvent, such as THF or dioxane, etc., in the presence of a palladium catalyst and a solution, such as potassium carbonate, cesium carbonate or sodium carbonate aqueous solution, etc., at a temperature between 50° C. and reflux, preferably at reflux, or under microwave irradiation at a temperature of 120° C. and 200° C., preferably at a temperature between 130° C. and 150° C.

[Method P]

[Chemical Formula 60]

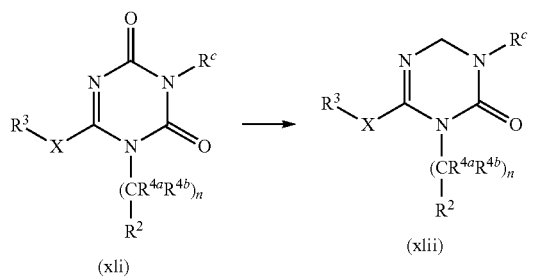

(xli)     (xlii)

wherein the symbols in the formula are as defined above.

The compound (xlii) can be manufactured by reacting the compound (xli) or its hydrochloride or bromate with a reducing agent, such as lithium aluminum hydride, diisobutylaluminum hydride, diborane, lithium borohydride, sodium borohydride etc., in a solvent, such as THF, dioxane, methanol etc., in the presence or absence of Lewis acid or acid, such as titanium tetrachloride, cobalt chloride (II), methane sulfonic acid etc., at a temperature between −20° C. and reflux, preferably at room temperature.

The preferred embodiment of the present invention is a compound or its pharmaceutically acceptable salt as mentioned below.

A compound of Formula (I):

[Chemical Formula 61]

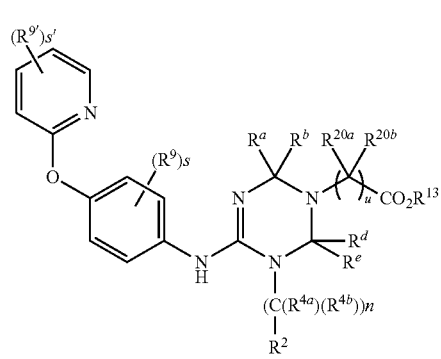

(I)

or its pharmaceutically acceptable salt.

1) The compound of Formula (I), wherein the group represented by the following formula:

[Chemical Formula 62]

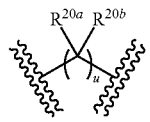

is a group represented by the following formula:

[Chemical Formula 63]

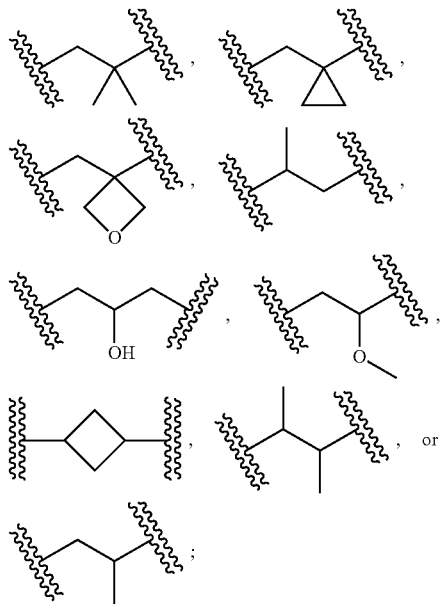

and the group represented by the following formula:

[Chemical Formula 64]

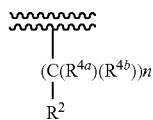

is a group represented by the following formula:

[Chemical Formula 65]

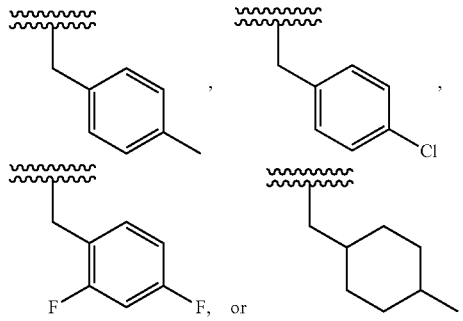

or its pharmaceutically acceptable salt.

2) The compound of Formula (I), wherein
the group represented by the following formula:

[Chemical Formula 66]

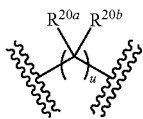

is a group represented by the following formula:

[Chemical Formula 67]

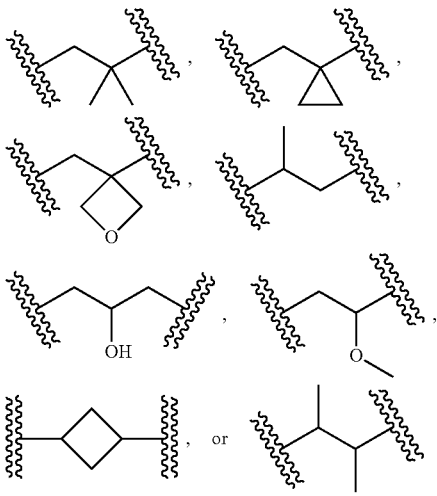, or and the group represented by the following formula:

[Chemical Formula 68]

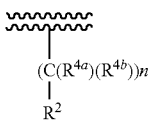

is a group represented by the following formula:

[Chemical Formula 69]

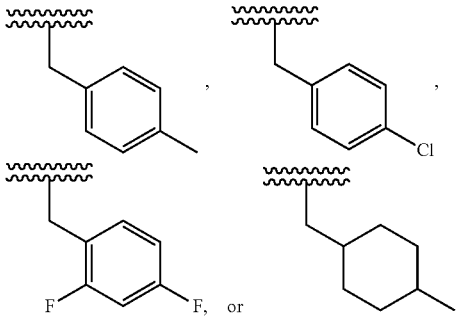, or or its pharmaceutically acceptable salt.

3) The compound of Formula (I), wherein
the group represented by the following formula:

[Chemical Formula 70]

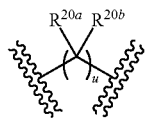

is a group represented by the following formula:

[Chemical Formula 71]

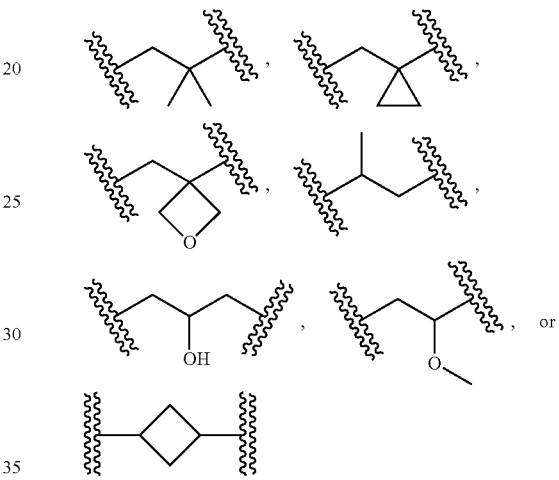, or and the group represented by the following formula:

[Chemical Formula 72]

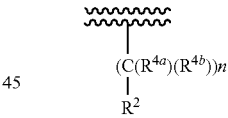

is a group represented by the following formula:

[Chemical Formula 73]

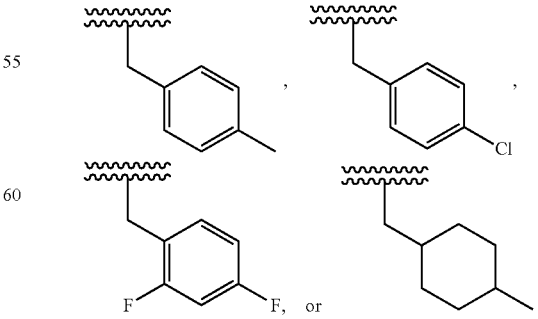, or or its pharmaceutically acceptable salt.

4) The compound of Formula (I), wherein
the group represented by the following formula:

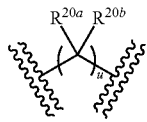

[Chemical Formula 74]

is a group represented by the following formula:

[Chemical Formula 75]

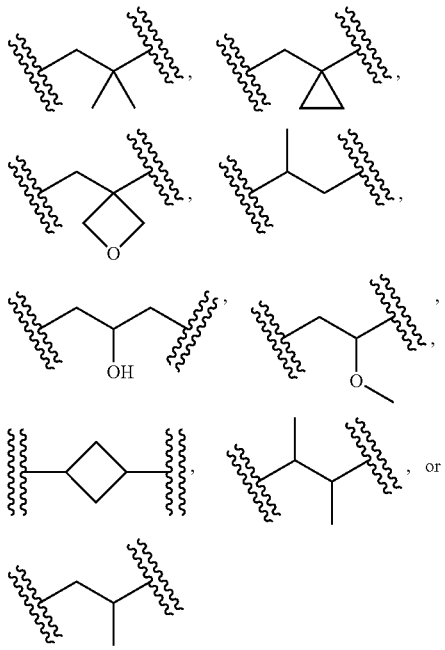

and the group represented by the following formula:

[Chemical Formula 76]

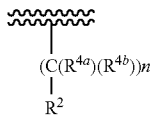

is a group represented by the following formula:

[Chemical Formula 77]

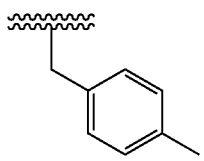

or its pharmaceutically acceptable salt.

5) The compound Formula (I), wherein
the group represented by the following formula:

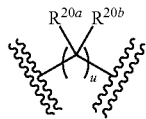

[Chemical Formula 78]

is a group represented by the following formula:

[Chemical Formula 79]

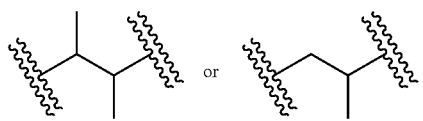

and the group represented by the following formula:

[Chemical Formula 80]

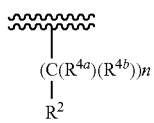

is a group represented by the following formula:

[Chemical Formula 81]

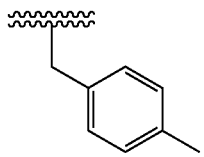

or its pharmaceutically acceptable salt.

6) The compound of Formula (I), wherein
the group represented by the following formula:

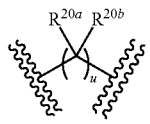

[Chemical Formula 82]

is a group represetnted by the following formula:

[Chemical Formula 83]

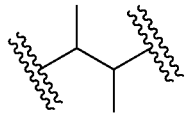

and the group represented by the following formula:

[Chemical Formula 84]

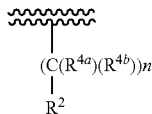

is a group represented by the following formula:

[Chemical Formula 85]

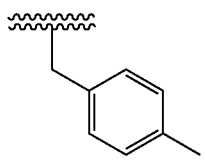

or its pharmaceutically acceptable salt.
7) The compound of Formula (I), wherein
$R^a$ and $R^b$ are taken together to form oxo:
$R^d$ and $R^e$ are taken together to form oxo;
$R^{4a}$ and $R^{4b}$ are both hydrogen atoms;
n is 1;
$R^2$ is phenyl substituted with methyl;
s is 0; and
s' is 1,
or its pharmaceutically acceptable salt.
8) The compound of Formula (I), wherein
$R^a$ and $R^b$ are taken together to form oxo:
$R^d$ and $R^e$ are taken together to form oxo;
$R^{4a}$ and $R^{ob}$ are both hydrogen atoms;
n is 1;
$R^2$ is phenyl substituted with halogen; and
s and s' are both 0,
or its pharmaceutically acceptable salt.
(Subtituent groups not specially defined in the above 1)-8) are as defined in the above (1))

When the group represented by the following formula in the compound of Formula (I):

[Chemical Formula 86]

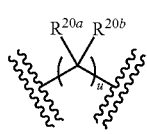

is the group represented by the following formula:

[Chemical Formula 87]

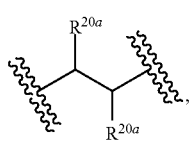

the absolute configuration of the formula is exemplified by the following configration:

[Chemical Formula 88]

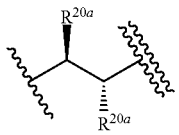

When the group represented by the following formula in the compound of Formula (I):

[Chemical Formula 89]

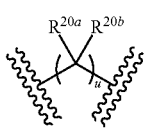

is the group represented by the following formula:

[Chemical Formula 90]

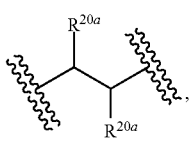

the absolute configuration of the formula is exemplified by the following configration:

[Chemical Formula 91]

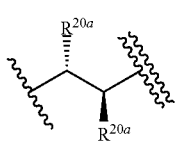

Particularly, when the group represented by the following formula:

[Chemical Formula 92]

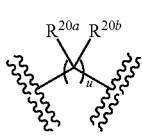

is the group represented by the following formula:

[Chemical Formula 93]

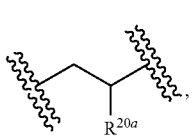

the absolute configuration of the formula is preferably the following configration:

[Chemical Formula 94]

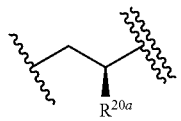

wherein $R^{20a}$ is preferably methyl.

The compounds of Formula (I) are not limited to specific isomers but include all possible isomers (e.g., keto-enol isomers, imine-enamine isomers, diastereoisomers, enantiomers, rotamers or the like), racemates or mixtures thereof. For example, a compound of Formula (I) includes the following tautomer.

[Chemical Formula 95]

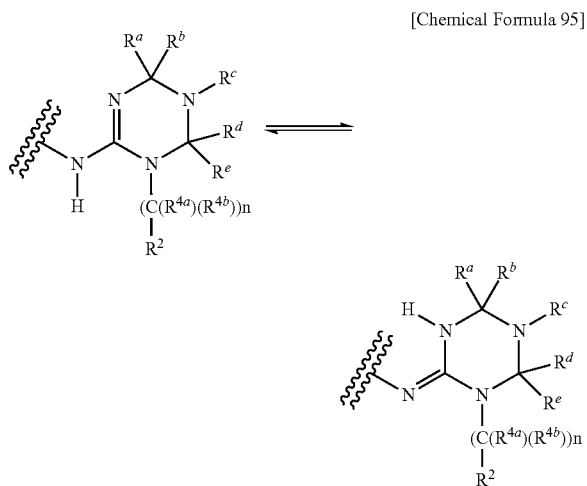

In addition, one or more hydrogen atoms, carbon atoms or other atoms of the compound of Formula (I) can be replaced by an isotope of the hydrogen atom, carbon atom or other atoms. Compounds of Formula (I) include all radiolabeled forms of compounds of Formula (I). The "radiolabeled," "radiolabeled form" and the like of the compound of Formula (I) are encompassed by the present invention and useful as a research and/or diagnostic tool in metabolism pharmacokinetic studies and in binding assays. It is also useful for a medicament.

One or more hydrogen, carbon and/or other atoms in the compounds of Formula (I) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of Formula (I) include the compounds replaced with these isotopes. The compounds replaced with the above isotopes are useful as medicines and include all of radiolabeled compounds of the compound of Formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of Formula (I) can be prepared using well-known methods in this field of the invention. For example, a tritium-labeled compound of Formula (I) can be prepared by introducing a tritium to a certain compound of Formula (I), through a catalytic dehalogenation reaction using a tritium. This method comprises reacting with an appropriately-halogenated precursor of the compound of Formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds of Formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of Formula (I) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of Formula (I). When the compounds of Formula (I) or pharmaceutically acceptable salts thereof are allowed to stand in the atmosphere, the compounds may absorb water, resulting in attachment of adsorbed water or formation of hydrates. Recrystallization of the compounds of Formula (I) or pharmaceutically acceptable salts thereof may produce crystal polymorphs.

The compounds of Formula (I) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of Formula (I) through enzymatic oxidation, reduction, hydrolysis or the like under physiological conditions in vivo, compounds that are converted to the compounds of Formula (I) through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of Formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3$.

The compound of the Formula (I) has an antagonistic activity on $P2X_3$ and/or $P2X_{2/3}$ receptor, and therefore, is useful as a therapeutic agent for diseases associated with a $P2X_3$ and/or $P2X_{2/3}$ receptor. Since $P2X_3$ and/or $P2X_{2/3}$ receptor is believed to associate with pain, diseases in urinary system and respiratory disease (Nature 407, 26, 1011-1015 (2000), Nature, Vol. 407, No. 26, 1015-1017 (2000), Non-Patent Document 1, Non-Patent Document 2, Non-Patent Documents 9-11 etc.), the compound of the invention is useful in the treatment, alleviation of symptoms or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, complex regional pain syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, ABC syndrome, multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, pains associated with endometriosis, and the like; Overactive bladder, urge incontinence, stress urinary incontinence, reflex incontinence, urinary urgency, neurogenic bladder, unstable bladder, urethritis, urinary tract infections, interstitial cystitis, cystitis, bladder cancer, chemotherapy-induced urinary tract disorder, urinary tract disorders associated with brain disorders such as stroke etc., voiding dysfunction, pain, etc. associated with prostatic hyperplasia, prostatitis, etc., and the like. And chronic obstructive pulmonary disease (COPD), asthma, bronchospasm, chronic cough, and the like.

"A pharmaceutical composition having an improving effect of urination disorder" includes a pharmaceutical composition for use to improve the treatment and/or prevention of urination disorder.

The compound of the present invention or the pharmaceutical composition of the present invention can be a drug with reduced side-effect such as effect on motor function because it has a high affinity for ATP receptor, especially $P2X_3$ receptor, and also has high subtype selectivity and high selectivity for other receptors. Also, the compound encompassed by the present invention or the pharmaceutical composition encompassed by the present invention is advantageous because of its high P2X3 receptor inhibitor activity in the presence of RSA, high metabolic stability, high oral absorption, high solubility, good bioavailability, low total body clearance, long half-life, prolonged duration of action, low activity of hepatic enzyme inhibition, high unbound fraction in serum and/or high safety etc.

The compound of the present invention or the pharmaceutical composition of the present invention can be a drug with high persistence after administration because of its low total body clearance.

When administering the pharmaceutical composition of the present invention, it can be administered in any method of orally and parenterally methods. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

Various pharmaceutical additives such as excipients, binders, disintegrating agents and lubricants suitable for the dosage form can be mixed as necessary in an effective amount of the compound of the present invention, to make the compound into a pharmaceutical composition. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old.

The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The dosage amount of the concomitant drug can be appropriately selected based on the clinically used dose. In addition, the blending ratio of the compound of the present invention to the concomitant drug can be appropriately selected depending on the administration subject, administration route, target disease, symptoms, combination and the like. For example, when the administration subject is a human, 0.01 to 100 parts by weight of the concomitant drug may be used, based on 1 part by weight of the compound of the present invention.

Following examples illustrate the present invention in more detail, but the present invention is not limited by these examples. The meaning of each abbreviation is as folllows:
Me: methyl
TMS: tetramethylsilane
DMSO: dimethyl sulfoxide
DMA: dimethyl acetamide
DMF: dimethylformamide
THF: tetrahydrofuran
DBU: 1,8-diazabicyclo [5.4.0]undeca-7-ene
NMP: N-methyl-2-pyrrolidone
HOAt: 1-hydroxy-7-azabenzotriazole
HATU: 2-(7-azabenzotriazole-1-yl)-1,1,3,3-tetramethyluronium hexafluorophosphate
PyBOP: benzotriazole-1-yl-oxytrispyrrolidinophosphonium hexafluorophosphate
rt: room temperature
M: mol/L Example 1

(1) Preparation of trans-3-(4-ethoxycarbonylcyclobutyl)-6-(1-pyrazolyl)-1,3,5-triazine-2,4(1H,3H)-dione

[Chemical Formula 96]

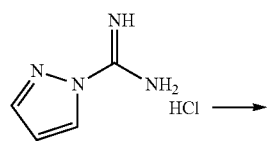

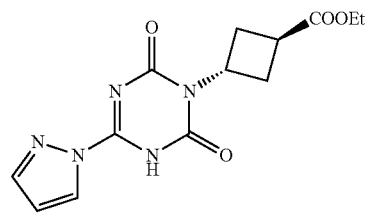

To a solution of ethyl trans-3-aminocyclobutanecarboxylate hydrochloride (340 mg, 2.3 mmol) in DMA (3.4 mL) were added 1,1'-Carbonyldiimidazole (496 g, 3.1 mmol) and DBU (0.46 mL, 3.1 mmol) under ice-cooling. The reaction mixture was stirred at room temperature for 4.5 hours, then 1-amidinopyrazole hydrochloride (340 mg, 2.3 mmol) and DBU (0.37 mL, 2.4 mmol) were added. The reaction mixture was stirred at room temperature for 7.5 hours. 1,1'-Carbonyldiimidazole (564 mg, 3.5 mmol) was added to the reaction mixture under ice-cooling, then DBU (0.52 mL, 3.5 mmol) was added. The reaction mixture was stirred at 50° C. for 15 hours. 4 mol/L Hydrochloric acid (7.5 mL) was added to the reaction mixture under ice-cooling. The resulting powder was collected by filtration to give trans-3-(4-ethoxycarbonylcyclobutyl)-6-(1-pyrazolyl)-1,3,5-triazine-2,4(1H,3H)-dione (376 mg, yield: 53%) as white powder.

1H-NMR (δ ppm TMS/DMSO-d6): 1.21 (3H, t, J=6.9 Hz), 2.40 (2H, t, J=9.4 Hz), 3.03 (2H, dd, J=19.4, 9.9 Hz), 3.09-3.17 (1H, m), 4.12 (2H, q, J=6.8 Hz), 5.13-5.31 (1H, m), 6.72 (1H, s), 8.05 (1H, s), 8.56 (1H, s), 13.05 (1H, br s).

(2) Preparation of trans-3-(4-ethoxycarbonylcyclobutyl)-1-(4-methylbenzyl)-6-(1-pyrazolyl)-1,3,5-triazine-2,4(1H,3H)-dione

[Chemical Formula 97]

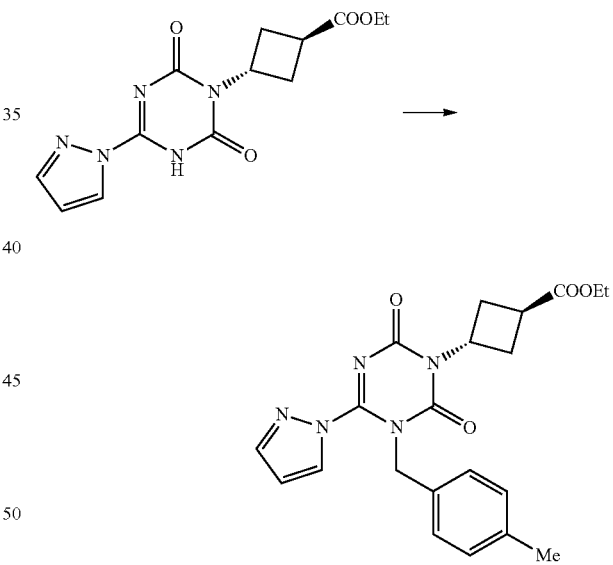

Diisopropylethylamine (0.19 mL, 1.1 mmol) was added to mixture of trans-3-(4-ethoxycarbonylcyclobutyl)-6-(1-pyrazolyl)-1,3,5-triazine-2,4(1H,3H)-dione (279 mg, 0.9 mmol), 4-methylbenzyl bromide (203 mg, 1.1 mmol), and DMA (2.8 mL), and the reaction mixture was stirred at 60° C. for 7 hours. The reaction mixture was acidified by 5% aqueous solution of citric acid, and extracted with ethyl acetate. The organic layer was washed by brine, dried over anhydrous sodium sulfate, and concentrated in vacuo to give crude trans-3-(4-ethoxycarbonylcyclobutyl)-1-(4-methylbenzyl)-6-(1-pyrazolyl)-1,3,5-triazine-2,4(1H,3H)-dione (371 mg, yield:99%) as yellow solid.

(3) Preparation of 6-[4-(5-chloro-2-pyridyloxy)phenylimino]-3-(4-ethoxycarbonylcyclobutyl)-1-(4-methylbenzyl)-1,3,5-triazinane-2,4-dione (I-172)

[Chemical Formula 98]

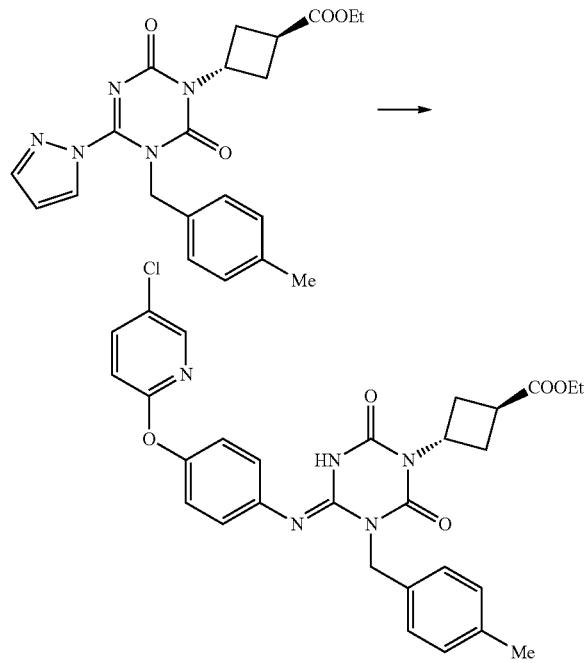

Mixture of trans-3-(4-ethoxycarbonylcyclobutyl)-1-(4-methylbenzyl)-6-(1-pyrazolyl)-1,3,5-triazine-2,4(1H,3H)-dione (123 mg, 0.3 mmol), 4-(5-chloro-2-pyridyloxy)aniline (73 mg, 0.33 mmol), and t-butanol (1.2 mL) was heated under reflux with stirring for 2 hours. The reaction mixture was concentrated in vacuo, and the residue was purified by silica-gel chromatography(ethyl acetate/hexane) to give 6-[4-(5-chloro-2-pyridyloxy)phenylimino]-3-(4-ethoxycarbonylcyclobutyl)-1-(4-methylbenzyl)-1,3,5-triazinane-2,4-dione (I-172, 140 mg, yield:83%) as pale yellow amorphous.

1H-NMR (CDCl3) δ: 1.28 (3H, t, J=6.8 Hz), 2.35 (3H, s), 2.50-2.70 (2H, m), 3.03-3.15 (2H, m), 3.16-3.30 (1H, m), 4.17 (2H, q, J=7.0 Hz), 5.20 (2H, s), 5.34-5.58 (1H, m), 6.59-7.08 (4H, m), 7.14 (3H, dd, J=14.4, 7.8 Hz), 7.49 (2H, d, J=7.4 Hz), 7.56-7.71 (2H, m), 8.10 (1H, s).

Example 2

Preparation of 6-[4-(5-chloro-2-pyridyloxy)phenylimino]-3-(4-hydroxycarbonylcyclobutyl)-1-(4-methylbenzyl)-1,3,5-triazinane-2,4-dione (I-178)

[Chemical Formula 99]

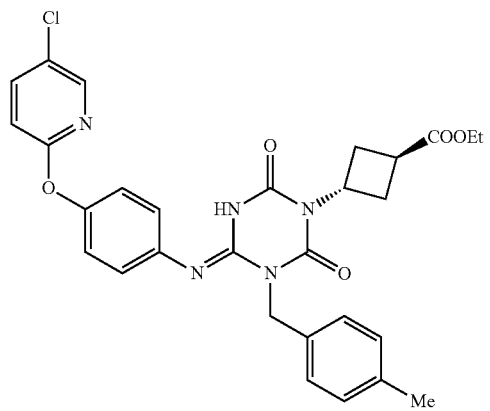

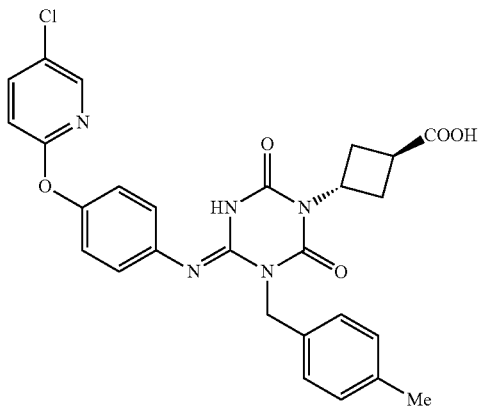

4 mol/L Lithium hydroxide (0.24 mL, 0.96 mmol) was added to mixture of 6-[4-(5-chloro-2-pyridyloxy)phenylimino]-3-(4-ethoxycarbonylcyclobutyl)-1-(4-methylbenzyl)-1,3,5-triazinane-2,4-dione (135 mg, 0.24 mmol), methanol (0.7 mL), and THF (0.7 mL), and stirred at 50° C. for 3 hours. 2 mol/L Hydrochloric acid (0.43 mL) was added to the reaction mixture, and the resulting mixture was concentrated in vacuo. The residue was purified by silica-gel chromatography (chloroform/methanol) and powderized by ethyl acetate and hexane to give 6-[4-(5-chloro-2-pyridyloxy)phenylimino]-3-(4-hydroxycarbonylcyclobutyl)-1-(4-methylbenzyl)-1,3,5-triazinane-2,4-dione (I-178, 103 mg, yield:80%) as white powder.

1H-NMR (CDCl3) δ: 2.35 (3H, s), 2.52-2.72 (2H, m), 3.08-3.42 (3H, m), 5.20 (2H, s), 5.37-5.61 (1H, m), 6.82-6.95 (3H, m), 7.01-7.20 (4H, m), 7.48 (2H, d, J=7.3 Hz), 7.61-7.81 (2H, m), 8.11 (1H, s).

Reference Example 1

(1) Preparation of 1-(4-chlorobenzyl)-6-(ethylthio)-1,3,5-triazine-2,4(1H,3H)-dione

[Chemical Formula 100]

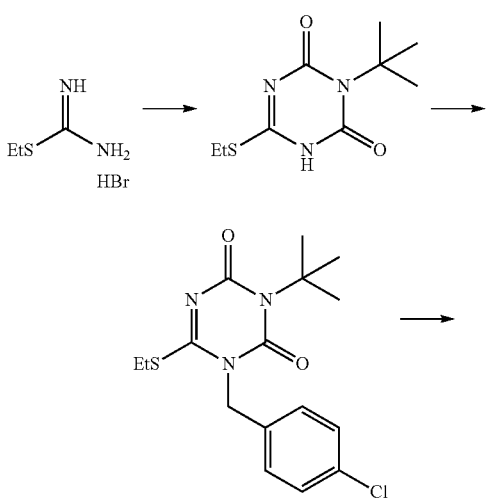

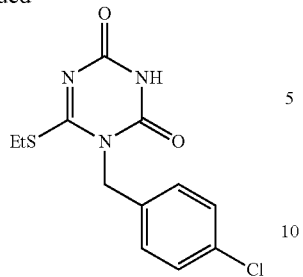

t-Butyl isocyanate (1.2 mL, 10.5 mmol) and DBU (1.9 mL, 12.8 mmol) were added to mixture of S-ethylthiourea hydrobromate (1.85 g, 10 mmol) and DMF (9.3 mL) under ice-cooling, and the resulting mixture was stirred for 6 hours. 1,1'-Carbonyldiimidazole (1.95 g, 12 mmol) and DBU (1.9 mL, 12.8 mmol) were added to the reaction mixture under ice-cooling and the mixture was stirred for 2 hours. 2 mol/L Hydrochloric acid (80 mL) was added to the reaction mixture under ice-cooling over 50 minutes, and the generated powder was collected by filtration. The powder was dissolved in ethyl acetate, dried over anhydrous magnesium sulfate, and concentrated in vacuo to give 6-(ethylthio)-3-t-butyl-1,3,5-triazine-2,4(1H,3H)-dione (1.15 g, yield:50%) as pale brown powder.

1H-NMR (δ ppm TMS/DMSO-d6): 1.27 (3H, t, J=7.3 Hz), 1.55 (9H, s), 3.03 (2H, q, J=7.3), 12.30 (1H, brs)

Potassium carbonate (17.97 g, 130 mmol) was added to mixture of 6-(ethylthio)-3-t-butyl-1,3,5-triazine-2,4(1H,3H)-dione (22.93 g, 100 mmol), 4-chlorobenzyl bromide (22.60 g, 110 mmol), and acetonitrile (200 mL), and the resulting mixture was heated at reflux and stirred for 3 hours. The reaction mixture was filtered, and the filtrate was concentrated in vacuo to give the crude product (39.9 g) of 3-t-butyl-1-(4-chlorobenzyl)-6-(ethylthio)-1,3,5-triazine-2,4(1H,3H)-dione as pale brown oil.

Trifluoroacetic acid (100 mL) was added to the resulting crude product, the resulting mixture was stirred at room temperature for 17 hours. The reaction mixture was concentrated in vacuo to give 1-(4-chlorobenzyl)-6-(ethylthio)-1,3,5-triazine-2,4(1H,3H)-dione (29.03 g, yield: 97%) as pale brown powder.

1H-NMR (δ ppm TMS/d6-DMSO): 1.25 (3H, t, J=7.3 Hz), 3.08 (2H, q, J=7.3 Hz), 5.02 (2H, s), 7.30-7.33 (2H, m), 7.39-7.42 (2H, m), 11.61 (1H, s).

(2) Preparation of 1-(4-chlorobenzyl)-3-(methoxycarbonylmethyl)-6-[4-(2-pyridyloxy)phenylimino]-1,3,5-triazinane-2,4-dione (R-238)

[Chemical Formula 101]

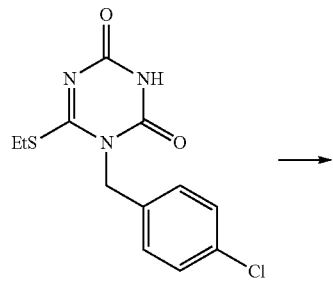

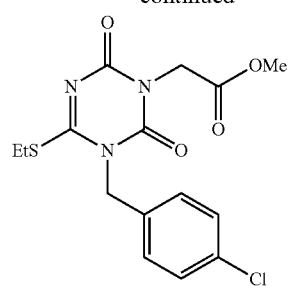

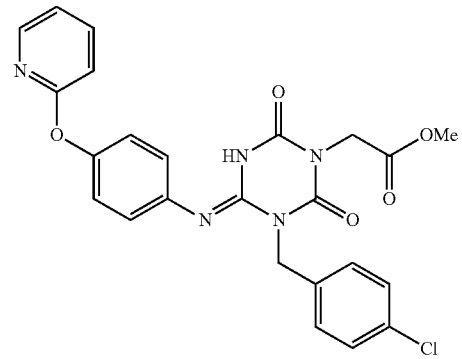

Potassium carbonate (1.80 g, 13 mmol) was added to mixture of 1-(4-chlorobenzyl)-6-(ethylthio)-1,3,5-triazine-2,4(1H,3H)-dione (2.98 g, 10 mmol), methyl bromoacetate (1.04 mL, 11 mmol), and DMF (30 mL), and the resulting mixture was stired at room temperature for 4 hours. Water (250 mL) was added to the reaction mixture, and the resulting mixture was extracted with ethyl acetate (200 mL). The organic layer was washed by brine (250 mL), and dried over anhydrous magnesium sulfate. After concentrated in vacuo, to the residue were added ethyl acetate and hexane. The generated powder was collected by filtration to give 1-(4-chlorobenzyl)-3-(methoxycarbonylmethyl)-6-(ethylthio)-1,3,5-triazine-2,4(1H,3H)-dione (3.26 g, yield: 88%) as colorless powder.

1H-NMR (δ ppm TMS/CDCl$_3$): 1.37 (3H, t, J=7.2 Hz), 3.23 (2H, q, J=7.2 Hz), 3.78 (3H, s), 4.68 (2H, s), 5.11 (2H, s), 7.27-7.35 (4H, m).

Mixture of 1-(4-chlorobenzyl)-3-(methoxycarbonylmethyl)-6-(ethylthio)-1,3,5-triazine-2,4(1H,3H)-dione (1.0 g, 2.70 mmol), 4-(2-pyridyloxy)aniline (1.0 g, 5.4 mmol), t-butanol (10.0 mL), and acetic acid (2.3 mL) was heated under reflux with stirring for 8 hours. Saturated aqueous solution of sodium hydrogen carbonate (30 mL) was added to the reaction mixture, and the resulting mixture was extracted with ethyl acetate (20 mL×3). The organic layer was washed by water (20 mL) and brine (20 mL) and dried over anhydrous magnesium sulfate. After concentrated in vacuo, the residue was purified by silica-gel chromatography (ethyl acetate/hexane) to give 1-(4-chlorobenzyl)-3-(methoxycarbonylmethyl)-6-[4-(2-pyridyloxy)phenylimino]-1,3,5-triazinane-2,4-dione (R-238, 1.24 g, yield: 93%) as pale yellow amorphous.

1H-NMR (CDCl3) δ: 3.78 (3H, s), 4.59 (2H, s), 5.23 (2H, s), 6.86 (2H, d, J=7.8 Hz), 6.96 (1H, d, J=8.1 Hz), 7.00 (1H, t, J=6.0 Hz), 7.15 (2H, d, J=8.1 Hz), 7.31 (2H, d, J=7.8 Hz), 7.49 (2H, d, J=7.8 Hz), 7.71 (1H, t, J=7.8 Hz), 7.86 (1H, s), 8.15 (1H, s).

(3) Preparation of 1-(4-chlorobenzyl)-3-(hydroxylcarbonylmethyl)-6-[4-(2-pyridyloxy)phenylimino]-1,3,5-triazinane-2,4-dione (R-239)

(4) Preparation of 1-(4-chlorobenzyl)-3-(carbamoylmethyl)-6-[4-(2-pyridyloxy)phenylimino]-1,3,5-triazinane-2,4-dione (R-240)

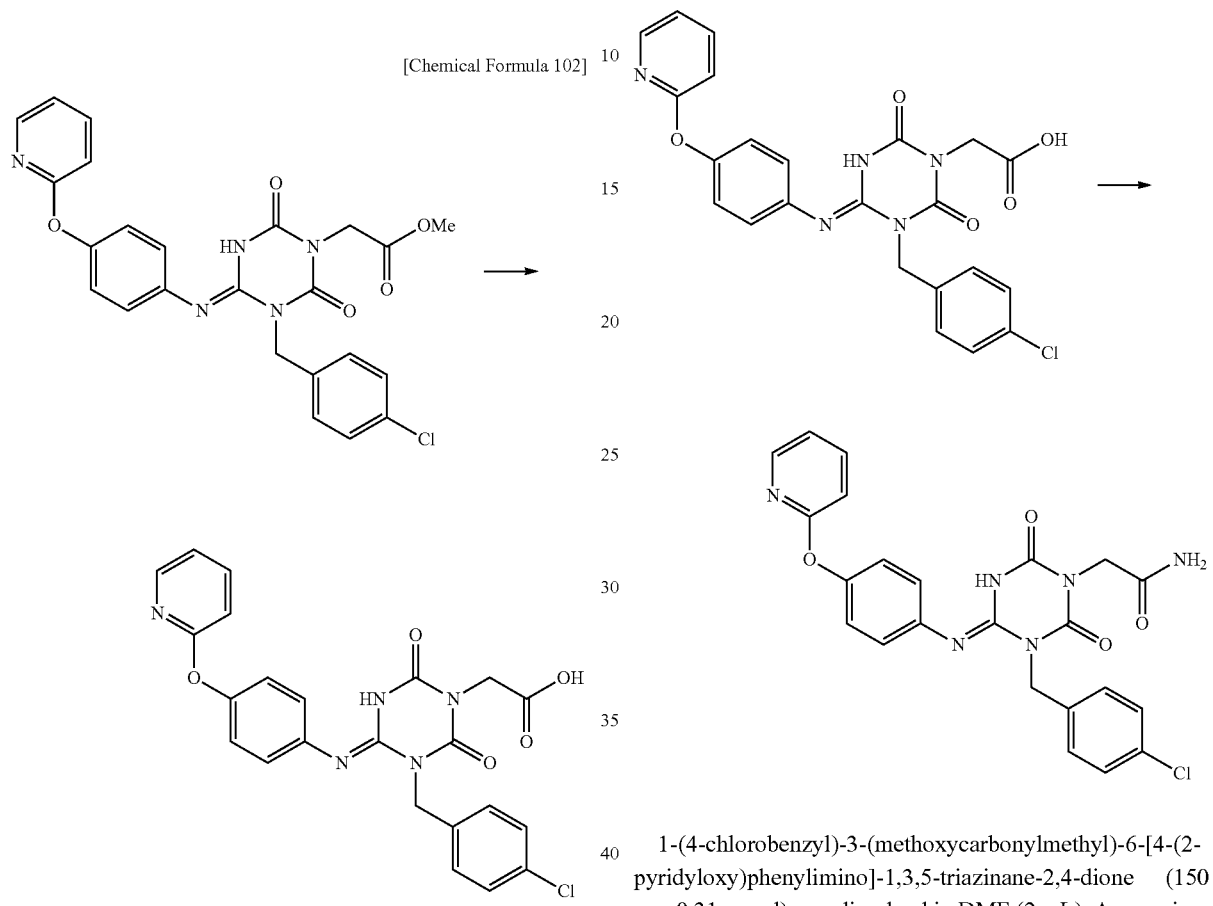

[Chemical Formula 102]

[Chemical Formula 103]

4 mol/L Lithium hydroxide (2.43 mL, 9.7 mmol) was added to mixture of 1-(4-chlorobenzyl)-3-(methoxycarbonylmethyl)-6-[4-(2-pyridyloxy)phenylimino]-1,3,5-triazinane-2,4-dione (1.2 g, 2.43 mmol), methanol (12 mL), THF (12 mL), and water (12 mL), and the resulting mixture was stirred under ice-cooling for 1 hour. The reaction mixture was poured into ice water, acidified by 1 mol/L hydrochloric acid, and extracted with ethyl acetate (100 mL). The organic layer was washed by water (50 mL) and brine (50 mL) and dried over anhydrous magnesium sulfate. After concentrated in vacuo, to the residue were added ethyl acetate and diethylether, and the generated powder was collected by filtration to give 1-(4-chlorobenzyl)-3-(hydroxylcarbonylmethyl)-6-[4-(2-pyridyloxy)phenylimino]-1,3,5-triazinane-2,4-dione (R-239, 2.23 mg, yield:92%) as pale brown powder.

1H-NMR (δ ppm TMS/d6-DMSO): 4.40 (2H, s), 5.30 (2H, s), 7.03 (2H, d, J=7.8 Hz), 7.12 (2H, s), 7.13 (1H, s), 7.37 (4H, d, J=7.5 Hz), 7.45 (4H, d, J=7.5 Hz), 7.84 (1H, t, J=7.8 Hz), 8.16 (1H, s), 9.48 (1H, brs).

1-(4-chlorobenzyl)-3-(methoxycarbonylmethyl)-6-[4-(2-pyridyloxy)phenylimino]-1,3,5-triazinane-2,4-dione (150 mg, 0.31 mmol) was dissolved in DMF (2 mL). Ammonium chloride (16.7 mg, 0.31 mmol), 1-hydroxybenzotriazole hydrate (57.4 mg, 0.38 mmol), 4-dimethylaminopyridine (3.8 mg, 0.03 mmol), 1-ethyl-3-(3-dimethylaminopropyl)carbodiimide hydrochloride (71.9 mg, 0.38 mmol), and triethylamine (0.05 mL, 0.38 mmol) were added to the reaction mixture, and the resulting mixture was stirred at room temperature for 16 hours. To the reaction mixture was added saturated aqueous solution of sodium hydrogen carbonate (20 mL) and extracted with ethyl acetate (30 mL). The organic phase was washed by water (10 mL) and brine (10 mL) and dried over anhydrous magnesium sulfate. After concentrated in vacuo, to the residue was added ethyl acetate, and the generated powder was collected by filtration to give 1-(4-chlorobenzyl)-3-(carbamoylmethyl)-6-[4-(2-pyridyloxy)phenylimino]-1,3,5-triazinane-2,4-dione (R-240, 79 mg, yield:53%) as pale yellow powder.

1H-NMR (δ ppm TMS/DMSO-d6): 4.28 (2H, s), 5.29 (2H, s), 7.03 (2H, d, J=7.2 Hz), 7.12 (4H, s), 7.35 (1H, s), 7.38 (1H, d, J=7.2 Hz), 7.42 (4H, d, J=9.3 Hz), 7.54 (1H, s), 7.85 (1H, t, J=7.2 Hz), 8.16 (1H, s), 9.37 (1H, s).

Reference Example 2

(1) Preparation of 3-ethyl-6-(1-pyrazolyl)-1,3,5-triazine-2,4(1H,3H)-dione

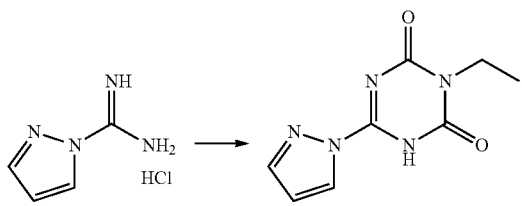

[Chemical Formula 104]

DBU (63.3 mL, 420 mmol) was added dropwise to mixture of 1-amidinopyrazole hydrochloride (58.6 g, 400 mmol), ethyl isocyanate (33.2 mL, 420 mmol), and DMA (240 mL) at −10° C. over 15 minutes, and the resulting mixture was stirred under ice-cooling for 30 minutes. 1,1'-Carbonyldiimidazole (97.2 g, 600 mmol) was added to the reaction mixture under ice-cooling, and then DBU (93 mL, 620 mmol) was added at −5° C. over 30 minutes. The reaction mixture was stirred under ice-cooling for 1 hour and then stirred at room temperature for 1 hour. 2 mol/L Hydrochloric acid (1.16 L) was added to the reaction mixture at 20° C. over 1 hour. The resulting powder was collected by filtration to give 3-ethyl-6-(1-pyrazolyl)-1,3,5-triazine-2,4(1H,3H)-dione (73.0 g, yield:88%) as pale brown powder. 1H-NMR (δ ppm TMS/CDCl3): 1.30 (6H, t, J=7.0 Hz), 4.02 (2H, q, J=7.0 Hz), 6.59 (1H, m), 7.34 (1H, m), 8.48 (1H, m), 9.79 (1H, brs).

(2) Preparation of 1-(4-chlorobenzyl)-3-ethyl-6-(1-pyrazolyl)-1,3,5-triazine-2,4(1H,3H)-dione

[Chemical Formula 105]

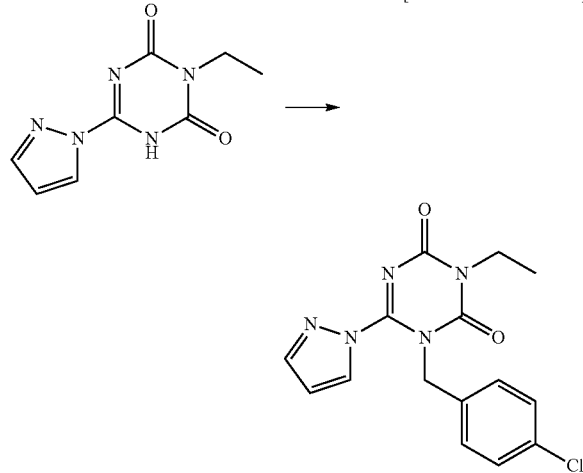

Diisopropylethylamine (92 mL, 528 mmol) was added dropwise to mixture of 3-ethyl-6-(1-pyrazolyl)-1,3,5-triazine-2,4(1H,3H)-dione (89 g, 480 mmol), 4-chlorobenzyl bromide (108 g, 528 mmol), and DMA (400 mL) at room temperature over 10 minutes, and the resulting mixture was stirred at 60° C. for 2 hours. Water (800 mL) was added dropwise to the reaction mixture under ice-cooling over 40 minutes, and then hexane (200 mL) was added. The resulting powder was collected by filtration to give 1-(4-chlorobenzyl)-3-ethyl-6-(1-pyrazolyl)-1,3,5-triazine-2,4(1H,3H)-dione (156 g, yield:97.6%) as pale brown powder.

1H-NMR (δ ppm TMS/CDCl$_3$): 1.30 (3H, t, J=7.1 Hz), 4.04 (2H, q, J=7.1 Hz), 5.86 (2H, s), 6.48 (1H, m), 7.02 (2H, d, J=8.6 Hz), 7.20-7.25 (2H, m), 7.84 (1H, m), 8.33 (1H, m).

(3) Preparation of 1-(4-chlorobenzyl)-6-[4-(3-chloro-5-ethoxycarbonyl-2-pyridyloxy)phenylimino]-3-ethyl-1,3,5-triazinane-2,4-dione (R-015)

[Chemical Formula 106]

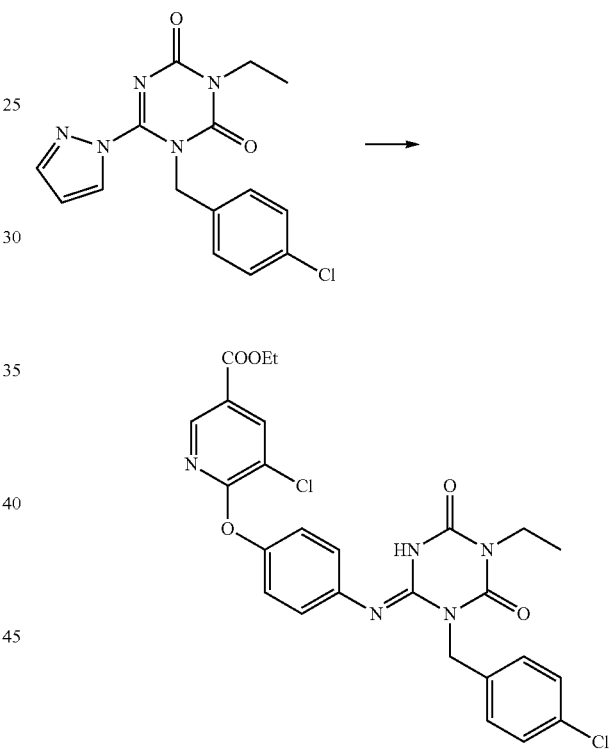

Mixture of 1-(4-chlorobenzyl)-2-ethyl-6-(1-pyrazolyl)-1,3,5-triazine-2,4(1H,3H)-dione (200 mg, 0.6 mmol), 4-(3-chloro-5-ethoxycarbonyl-2-pyridyloxy)aniline (176 mg, 0.6 mmol), and t-butanol (4 mL) was stirred at 80° C. for 1 hour. The reaction mixture was concentrated in vacuo, and the residue was purified by silica-gel chromatography (ethyl acetate/hexane) to give 1-(4-chlorobenzyl)-6-[4-(3-chloro-5-ethoxycarbonyl-2-pyridyloxy)phenylimino]-3-ethyl-1,3,5-triazinane-2,4-dione (R-015, 321 mg, yield:96%) as white powder.

1H-NMR (CDCl3) δ: 1.24 (3H, t, J=7.2 Hz), 1.39 (3H, t, J=7.2 Hz), 3.90 (2H, q, J=7.1 Hz), 4.39 (2H, q, J=7.1 Hz), 5.21 (2H, s), 6.88 (2H, dd, J=6.5, 2.0 Hz), 7.16 (2H, dd, J=6.7, 2.1 Hz), 7.30-7.33 (2H, m), 7.52 (2H, t, J=4.1 Hz), 7.89 (1H, s), 8.35 (1H, d, J=2.0 Hz), 8.63 (1H, d, J=2.0 Hz).

(4) Preparation of 1-(4-chlorobenzyl)-6-[4-(3-chloro-5-hydroxycarbonyl-2-pyridyloxy)phenylimino]-3-ethyl-1,3,5-triazinane-2,4-dione (R-016)

Reference Example 3

(1) Preparation of (S)-1-(4-chlorobenzyl)-6-(4-hydroxyphenylimino)-3-(2-hydroxycarbonylpropyl)-1,3,5-triazinane-2,4-dione

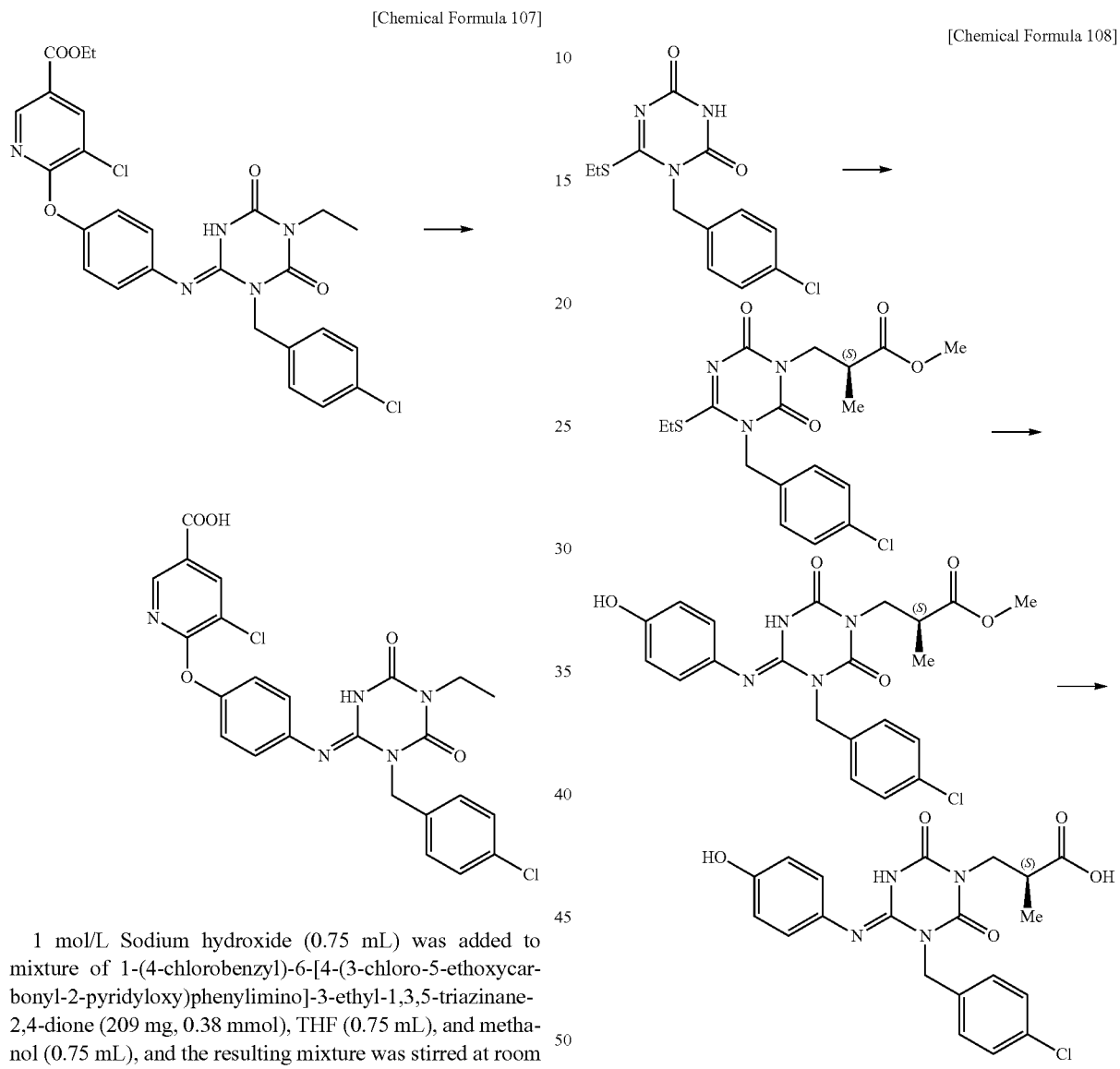

[Chemical Formula 107]

[Chemical Formula 108]

1 mol/L Sodium hydroxide (0.75 mL) was added to mixture of 1-(4-chlorobenzyl)-6-[4-(3-chloro-5-ethoxycarbonyl-2-pyridyloxy)phenylimino]-3-ethyl-1,3,5-triazinane-2,4-dione (209 mg, 0.38 mmol), THF (0.75 mL), and methanol (0.75 mL), and the resulting mixture was stirred at room temperature for overnight. The reaction mixture was poured into water, acidified by 5% aqueous solution of citric acid, and then extracted with ethyl acetate. The organic phase was dried over anhydrous sodium sulfate. After concentrated in vacuo, to the residue was added diethylether, and the generated powder was collected by filtration to give 1-(4-chlorobenzyl)-6-[4-(3-chloro-5-hydroxycarbonyl-2-pyridyloxy)phenylimino]-3-ethyl-1,3,5-triazinane-2,4-dione (R-016, 125 mg, yield:63%) as white powder.

$^1$H-NMR (CDCl$_3$) δ: 1.24 (3H, q, J=8.3 Hz), 3.93 (2H, q, J=7.0 Hz), 5.23 (2H, s), 6.91 (2H, d, J=8.5 Hz), 7.14 (2H, dd, J=6.8, 2.0 Hz), 7.32 (2H, d, J=8.3 Hz), 7.53 (2H, d, J=8.3 Hz), 8.36 (1H, d, J=2.0 Hz), 8.74 (1H, d, J=1.8 Hz), 9.78 (1H, s).

Di-2-methoxyethylazo dicarboxylate (56.2 g, 240 mmol) was gradually added to mixture of 1-(4-chlorobenzyl)-6-(ethylthio)-1,3,5-triazine-2,4(1H,3H)-dione (59.6 g, 200 mmol), methyl (S)-(+)-3-hydroxyisolactate (28.4 g, 240 mmol), triphenylphosphine (62.9 g, 240 mmol) and dioxane (400 mL), and the resulting mixture was stirred at room temperature for 3 hours. The reaction mixture was added to ice water (1000 mL) and extracted with toluene (500 mL). The organic phase was washed by brine (700 mL) and dried over anhydrous magnesium sulfate. After concentrated in vacuo, the residue was purified by silica-gel column chromatography (ethyl acetate/hexane) to give (S)-1-(4-chlorobenzyl)-6-(ethylthio)-3-(2-methoxycarbonylpropyl)-1,3,5-triazine-2,4(1H,3H)-dione (64.44 g, yield:81%) as white solid.

1H-NMR (δ ppm TMS/CDCl$_3$): 1.19 (3H, d, J=5.7 Hz), 1.37 (3H, t, J=7.1 Hz), 2.96 (1H, m), 3.12 (2H, q, J=7.1 Hz), 3.60 (3H, s), 3.98 (1H, m), 4.21 (1H, m), 5.08 (2H, s), 7.29-7.34 (4H, m).

Mixture of (S)-1-(4-chlorobenzyl)-6-(ethylthio)-3-(2-methoxycarbonylpropyl)-1,3,5-triazine-2,4(1H,3H)-dione (5.0 g, 12.6 mmol), 4-aminophenol (2.06 g, 18.9 mmol), acetic acid (11.32 g, 189 mmol), and t-butanol (100 mL) was stirred under heating at reflux for 3 hours. After the reaction, the reaction mixture was added to saturated aqueous solution of sodium hydrogen carbonate (500 mL) and extracted with ethyl acetate (500 mL). The organic layer was washed by 1mol/L hydrochloric acid (500 mL), dried over anhydrous sodium sulfate. After concentrated in vacuo, to the residue were added toluene and ethyl acetate, and heated, and the generated powder was collected by filtration to give (S)-1-(4-chlorobenzyl)-6-(4-hydroxyphenylimino)-3-(2-methoxycarbonylpropyl)-1,3,5-triazinane-2,4-dione (5.17 g, yield: 92%) as white powder.

2 mol/L Sodium hydroxide (25 mL) was added to mixture of (S)-1-(4-chlorobenzyl)-6-(4-hydroxyphenylimino)-3-(2-methoxycarbonylpropyl)-1,3,5-triazinane-2,4-dione (5.13 g, 11.5 mmol) and DMSO (50 mL), the resulting mixture was stirred at room temperature for 1 hour. To the reaction mixture was added 2 mol/L hydrochloric acid (25 mL), then the mixture was poured into water and extracted with ethyl acetate. The organic phase was washed by brine (700 mL) and dried over anhydrous sodium sulfate. After concentrated in vacuo, to the residue was added ethyl acetate, and the generated powder was collected by filtration to give (S)-1-(4-chlorobenzyl)-6-(4-hydroxyphenylimino)-3-(2-hydroxycarbonylpropyl)-1,3,5-triazinane-2,4-dione (3.92 g, yield: 79%) as white powder.

1H-NMR (δ ppm TMS/d6 DMSO): 0.99 (3H, d, J=7.0 Hz), 2.50 (1H, t, J=1.8 Hz), 2.74 (1H, td, J=14.5, 7.2 Hz), 3.89-3.95 (1H, m), 5.21 (2H, s), 6.70-6.75 (2H, m), 7.01 (2H, d, J=7.8 Hz), 7.29 (2H, d, J=8.5 Hz), 7.41 (2H, d, J=8.5 Hz), 9.16 (1H, br s), 9.66 (1H, br s).

(2) Preparation of (S)-1-(4-chlorobenzyl)-6-[4-(2-benzoxazolyloxy)phenylimino]-3-(2-methoxycarbonylpropyl)-1,3,5-triazinane-2,4-dione (R-144)

[Chemical Formula 109]

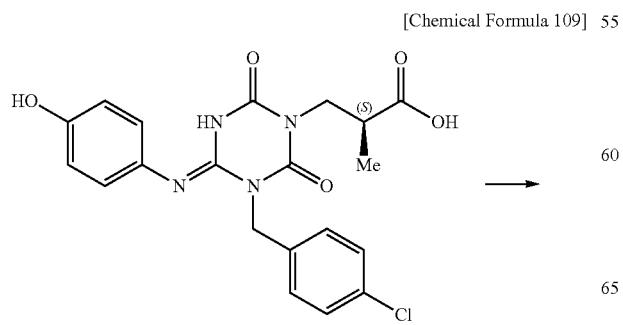

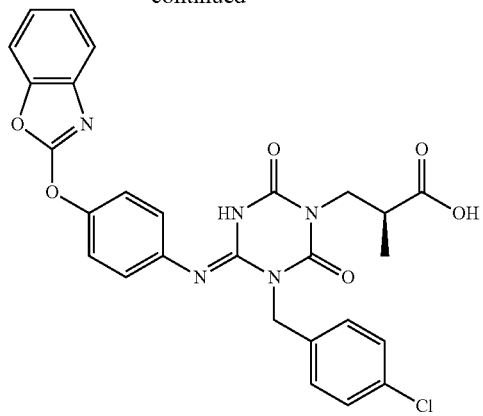

Cesium carbonate (454 mg, 1.39 mmol) was added to mixture of (S)-1-(4-chlorobenzyl)-6-(4-hydroxyphenylimino)-3-(2-hydroxycarbonylpropyl)-1,3,5-triazinane-2,4-dione (200 mg, 0.46 mmol), 2-chlorobenzoxazol (78 mg, 0.51 mmol), and DMSO (1 mL), and the resulting mixture was stirred overnight at room temperature. The reaction mixture was poured into water, acidified by 5% aqueous solution of citric acid, and then extracted with ethyl acetate. The organic phase was washed by brine and dried over anhydrous sodium sulfate. After concentrated in vacuo, the residue was purified by high-performance liquid chromatography (acetonitrile/water containing 0.3% formic acid) to give (S)-1-(4-chlorobenzyl)-6-[4-(2-benzoxazolyloxy)phenylimino]-3-(2-methoxycarbonylpropyl)-1,3,5-triazinane-2, 4-dione (R-144, 55.3 mg, yield:22%) as white powder.

$^1$H-NMR (CDCl$_3$) δ: 1.13 (3H, d, J=6.8 Hz), 2.74-2.79 (1H, m), 3.82 (1H, dd, J=13.3, 5.4 Hz), 4.04 (1H, dd, J=12.8, 9.2 Hz), 5.13 (1H, d, J=14.4 Hz), 5.22 (1H, d, J=14.3 Hz), 6.88 (2H, d, J=7.5 Hz), 7.23-7.49 (10H, m), 8.96 (1H, s).

Reference Example 4

(1) Preparation of 1-(4-chlorobenzyl)-3-(2-hydroxymethyl-2-propenyl)-6-[4-(2-pyridyloxy)phenylimino]-1,3,5-triazinane-2,4-dione (R-254)

[Chemical Formula 110]

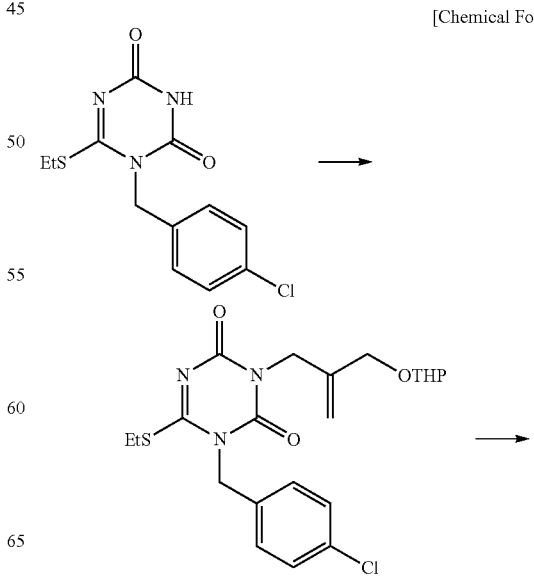

-continued

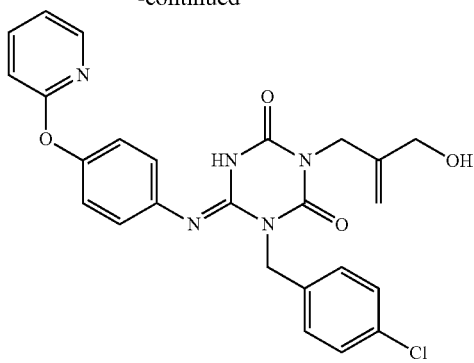

1-(4-Chlorobenzyl)-6-(ethylthio)-1,3,5-triazine-2,4(1H,3H)-dione (1090 mg, 3.65 mmol), 2-(tetrahydropyran-2-yloxy)methyl-2-propenol (628 mg, 3.65 mmol), and triphenylphosphine (956 mg, 3.65 mmol) were dissolved in 1,4-dioxane (5.0 mL). Dimethoxyethylazadicarboxylate (854 mg, 3.65 mmol) was added to the reaction mixture, the resulting mixture was stirred at room temperature for 3 hours. Then, triphenylphosphine (478 mg, 1.82 mmol) and dimethoxyethylazadicarboxylate (478 mg, 1.82 mmol) were added to the reaction mixture, and the resulting mixture was stirred at room temperature for 4 hours. The reaction mixture was concentrated in vacuo, and to the resulting residue was added diethylether. The generated powder was removed by filtration. The filtrate was washed by water and brine, dried over anhydrous sodium sulfate, and concentrated in vacuo. The resulting residue was purified by silica-gel chromatography (ethyl acetate/hexane) to give 1-(4-chlorobenzyl)-6-(ethylthio)-3-(2-tetrahydropyran-2-yloxymethyl-2-propenyl)-1,3,5-triazine-2,4(1H,3H)-dione (1589 mg, yield:96%) as colorless oil.

t-Butanol (2.4 mL), 4-(2-pyridyloxy)aniline (148 mg, 0.8 mmol) and acetic acid (0.58 mL, 10 mmol) were added to 1-(4-chlorobenzyl)-6-(ethylthio)-3-(2-tetrahydropyran-2-yloxymethyl-2-propenyl)-1,3,5-triazine-2,4(1H,3H)-dione (300 mg, 0.66 mmol), and the reaction mixture was heated at reflux for 15 hours. To the reaction mixture was added 2 mol/L hydrochloric acid (0.33 mL) and stirred at room temperature for 8 hours. To the reaction mixture was added saturated aqueous solution of sodium hydrogen carbonate and extracted with ethyl acetate. The organic phase was washed by brine (30 mL) and dried over anhydrous sodium sulfate. After concentrated in vacuo, the residue was purified by silica-gel chromatography (ethyl acetate/hexane) to give 1-(4-chlorobenzyl)-3-(2-hydroxymethyl-2-propenyl)-6-[4-(2-pyridyloxy)phenylimino]-1,3,5-triazinane-2,4-dione (R-254, 206 mg, yield:63%) as white amorphous.

1H-NMR (CDCl3) δ: 0.52-2.66 (1H, m), 4.08 (2H, d, J=5.0 Hz), 4.50 (2H, s), 5.16 (2H, d, J=21.1 Hz), 5.21 (2H, s), 6.86 (2H, d, J=8.5 Hz), 6.96-7.01 (2H, m), 7.13 (2H, d, J=8.8 Hz), 7.31 (2H, d, J=8.3 Hz), 7.51 (2H, d, J=8.5 Hz), 7.69-7.73 (1H, m), 8.10 (1H, d, J=3.5 Hz), 8.14-8.40 (1H, m).

(2) Preparation of 1-(4-chlorobenzyl)-3-(2-hydroxymethyl-2,3-dihydroxypropyl)-6-[4-(2-pyridyloxy)phenylimino]-1,3,5-triazinane-2,4-dione (R-255)

[Chemical Formula 111]

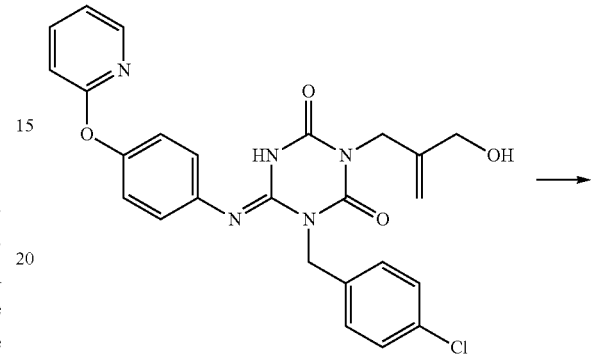

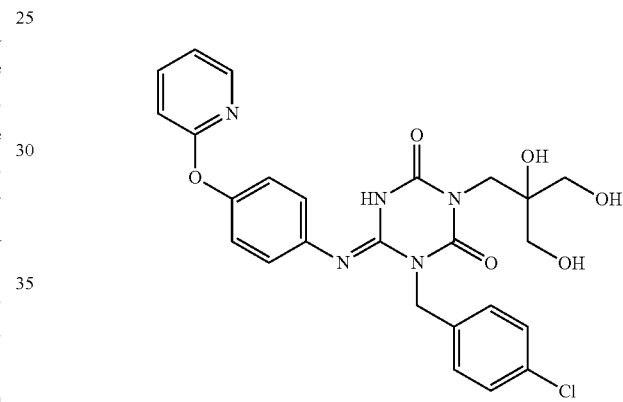

1-(4-chlorobenzyl)-3-(2-hydroxymethyl-2-propenyl)-6-[4-(2-pyridyloxy)phenylimino]-1,3,5-triazinane-2,4-dione (192 mg, 0.39 mmol) was dissolved in 95% aqueous solution of THF (2.2 mL). Potassium osmate (VI) dehydrate (14.4 mg, 0.04 mmol) and N-methylmorpholine (92 mg, 0.78 mmol) were added to the reaction mixture, the resulting mixture was stirred at room temperature for 2 hours. To the reaction mixture was added 5% aqueous solution of sodium sulfite (1.0 mL) and water (50 mL) and extracted with ethyl acetate (50 mL). The organic phase was washed by brine (50 mL) and dried over anhydrous sodium sulfate. After concentrated in vacuo, the residue was purified by silica-gel chromatography (chloroform/methanol) and powdered with ethyl acetate and hexane to give 1-(4-chlorobenzyl)-3-(2-hydroxymethyl-2,3-dihydroxypropyl)-6-[4-(2-pyridyloxy) phenylimino]-1,3,5-triazinane-2,4-dione (R-255, 155 mg, yield:75%) as white powder.

$^1$H-NMR (DMSO-d$_6$) δ: 3.26-3.31 (4H, m), 3.94 (2H, s), 4.31 (1H, s), 4.42 (2H, t, J=6.0 Hz), 5.29 (2H, s), 6.97-7.18 (4H, m), 7.30-7.52 (6H, m), 7.85 (1H, t, J=7.3 Hz), 8.16 (1H, d, J=3.3 Hz), 9.39 (1H, s).

Reference Example 5

Preparation of 1-(4-chlorobenzyl)-3-(2-hydroxyethyl)-6-[4-(2-pyridyloxy)phenylimino]-1,3,5-triazinane-2,4-dione (R-257)

Reference Example 6

(1) Preparation of 1-(4-chlorobenzyl)-3-(3-tetrahydropyran-2-yloxypropyl)-6-[4-(2-pyridyloxy)phenylimino]-1,3,5-triazinane-2,4-dione

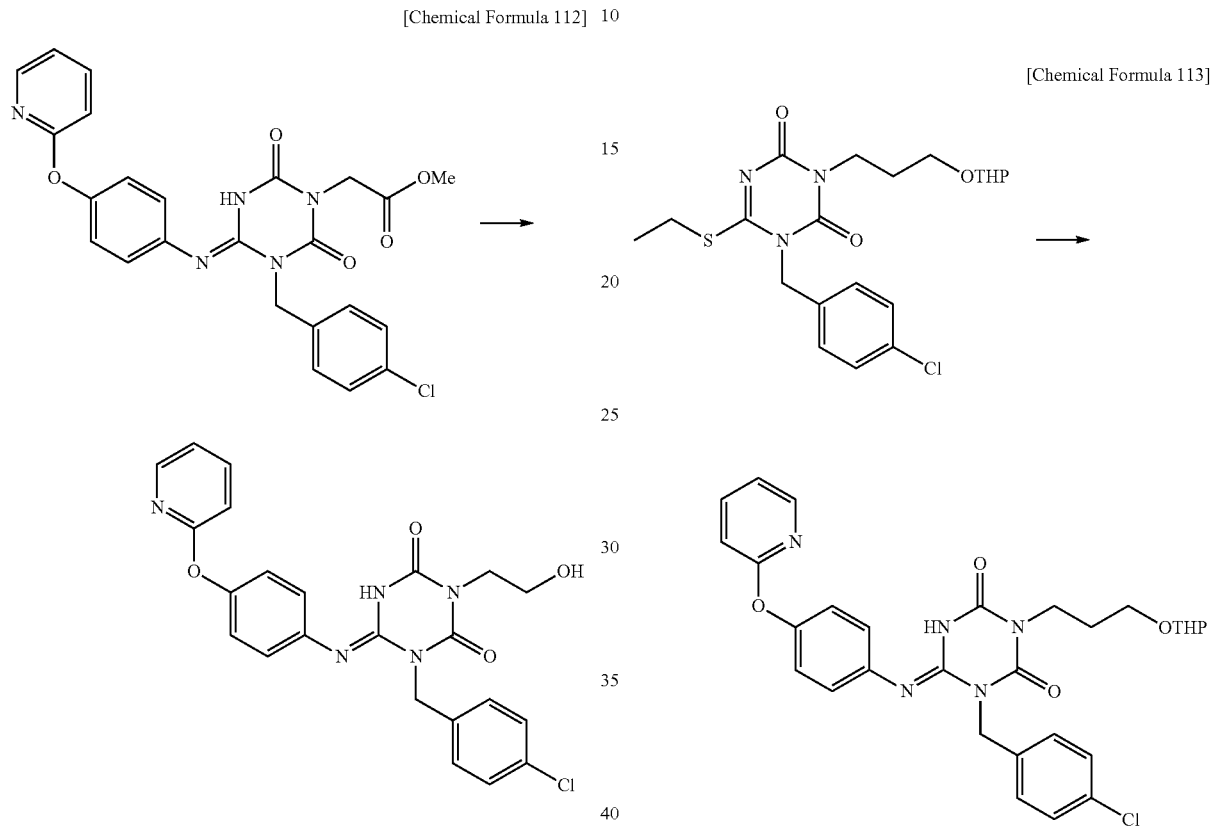

[Chemical Formula 112]

[Chemical Formula 113]

Lithium aluminum hydride (38 mg, 1 mmol) was added to 1-(4-chlorobenzyl)-3-(methoxycarbonylmethyl)-6-[4-(2-pyridyloxy)phenylimino]-1,3,5-triazinane-2,4-dione (248 mg, 0.5 mmol) in THF (6 mL) under ice-cooling, and the resulting mixture was stirred at room temperature for 1.5 hours. To the reaction mixture were added water (0.04 ml) and 10% aqueous solution of sodium hydroxide (0.04 ml) and stirred at room temperature for 1 hour. The reaction mixture was filtrated through Celite, washed by ethyl acetate, and dried over anhydrous magnesium sulfate. After concentrated in vacuo, the residue was purified by silica-gel chromatography (ethyl acetate/hexane) to give 1-(4-chlorobenzyl)-3-(2-hydroxyethyl)-6-[4-(2-pyridyloxy)phenylimino]-1,3,5-triazinane-2,4-dione (R-257, 65.4 mg, yield:28%) as white solid.

1H-NMR (CDCl3) δ: 2.25 (1H, t, J=5.7 Hz), 3.80 (2H, q, J=5.4 Hz), 4.05 (2H, t, J=5.1 Hz), 5.20 (2H, s), 6.85 (2H, d, J=8.5 Hz), 6.97 (1H, d, J=8.3 Hz), 7.00 (1H, dd, J=6.8, 5.3 Hz), 7.13 (2H, d, J=8.5 Hz), 7.30 (2H, d, J=8.3 Hz), 7.51 (2H, d, J=8.3 Hz), 7.71 (1H, t, J=8.0 Hz), 8.07 (1H, brs), 8.16 (1H, dd, J=4.8, 1.2 Hz).

Mixture of 1-(4-chlorobenzyl)-6-(ethylthio)-3-(3-tetrahydropyran-2-yloxypropyl)-1,3,5-triazine-2,4(1H,3H)-dione (230 mg, 0.52 mol), 4-(2-pyridyloxy)aniline (146 mg, 0.78 mmol), acetic acid (0.45 mL), and t-butanol (4 ml) was stirred overnight under heating at reflux. To the reaction mixture was added saturated aqueous solution of sodium hydrogen carbonate (50 mL) and extracted with ethyl acetate (50 mL). The organic phase was washed by brine and dried over anhydrous sodium sulfate. After concentrated in vacuo, the residue was purified by silica-gel column chromatography (hexane/ethyl acetate) to give 1-(4-chlorobenzyl)-3-(3-tetrahydropyran-2-yloxypropyl)-6-[4-(2-pyridyloxy)phenylimino]-1,3,5-triazinane-2,4-dione (188 mg, yield:64%) as colorless amorphous.

1H-NMR (CDCl$_3$) δ: 1.47-1.66 (6H, m), 1.95 (2H, td, J=12.3, 6.6 Hz), 3.42-3.49 (2H, m), 3.80-3.84 (2H, m), 3.96-4.00 (2H, m), 4.52 (1H, br s), 5.20 (2H, s), 6.84 (2H, d, J=8.6 Hz), 6.95-7.01 (2H, m), 7.13 (2H, d, J=8.6 Hz), 7.30 (2H, d, J=8.3 Hz), 7.52 (2H, d, J=8.3 Hz), 7.68-7.73 (1H, m), 7.95 (1H, s), 8.13 (1H, t, J=2.5 Hz).

(2) Preparation of 1-(4-chlorobenzyl)-3-(3-hydroxypropyl)-6-[4-(2-pyridyloxy)phenylimino]-1,3,5-triazinane-2,4-dione (R-251)

[Chemical Formula 114]

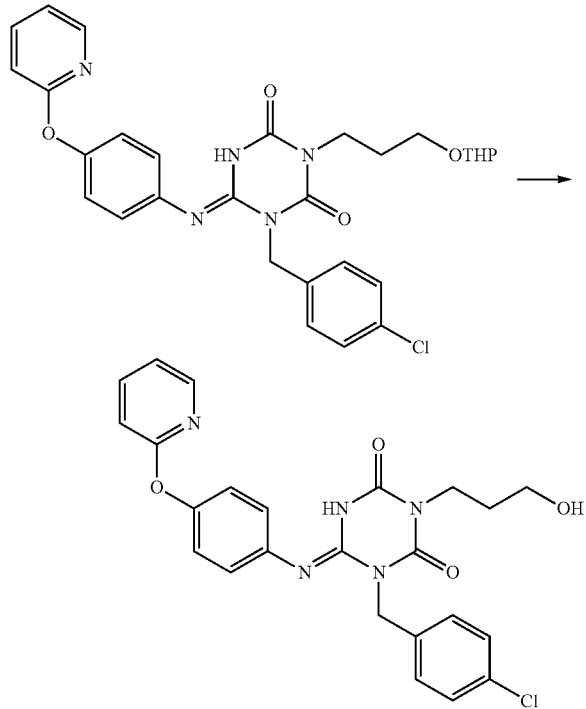

p-Toluenesulfonic acid hydrate (12 mg, 0.064 mmol) was added to 1-(4-chlorobenzyl)-3-(3-tetrahydropyran-2-yloxypropyl)-6-[4-(2-pyridyloxy)phenylimino]-1,3,5-triazinane-2,4-dione (180 mg, 0.32 mol) in methanol (2 ml), and the resulting mixture was stirred at 50° C. for 2 hours. To the reaction mixture was added triethylamine and concentrated in vacuo. The residue was purified by silica-gel column chromatography (hexane/ethyl acetate) to give 1-(4-chlorobenzyl)-3-(3-hydroxypropyl)-6-[4-(2-pyridyloxy)phenylimino]-1,3,5-triazinane-2,4-dione (R-251, 150 mg, yield: 99%) as colorless amorphous.

1H-NMR (CDCl$_3$) δ: 1.83-1.89 (2H, m), 2.63 (1H, t, J=6.5 Hz), 3.59 (2H, q, J=5.9 Hz), 4.00 (2H, t, J=6.1 Hz), 5.22 (2H, s), 6.86 (2H, d, J=8.8 Hz), 6.97-7.01 (2H, m), 7.13 (2H, d, J=8.5 Hz), 7.31 (2H, d, J=8.5 Hz), 7.52 (2H, d, J=8.3 Hz), 7.69-7.74 (1H, m), 8.10 (1H, dd, J=4.9, 1.4 Hz).

The following compounds of the invention were synthesized in a similar manner to those described in the above general procedures for the synthesis of the compound of the invention and Examples, with reference to the contents described in WO2010/092966 and WO2012/020749 as needed. The chemical structure of the compounds and the physical properties of them are described below.

(Method of Identification for the Compound)

LC/MS data of compound of the present invention were measured under any one of the following 2 conditions (Methods 1 and 2), and a retention time (RT) (unit: min) and [M+H]$^+$ are shown.

(Method 1)
Column: Shim-pack XR-ODS (2.2 μm, i.d.50×3.0 mm) (Shimadzu)
Flow rate: 1.6 mL/min
UV detection wavelength: 254 nm
Mobile phase: [A] is 0.1% formic acid-containing aqueous solution, and [B] is 0.1% formic acid-containing acetnitrile solution.
Gradient: Linear gradient of 10% to 100% solvent [B] for 3 minutes was performed, and 100% solvent [B] was maintained for 1 minute.

(Method 2)
Column: ACQUITY UPLC (registered trademark) BEH C18 (1.7 μm, i.d.2. 1×50 mm) (Waters)
Flow rate: 0.8 mL/min
UV detection wavelength: 254 nm
Mobile phase: [A] is 10 mM ammonium carbonate-containing aqueous solution, and [B] is acetonitrile
Gradient: Linear gradient of 5% to 100% solvent [B] for 3.5 minutes was performed, and 100% solvent [B] was maintained for 0.5 minute.

TABLE 1

| Compound No | Structure | [M+H]+ | RT | Method |
|---|---|---|---|---|
| I-001 | 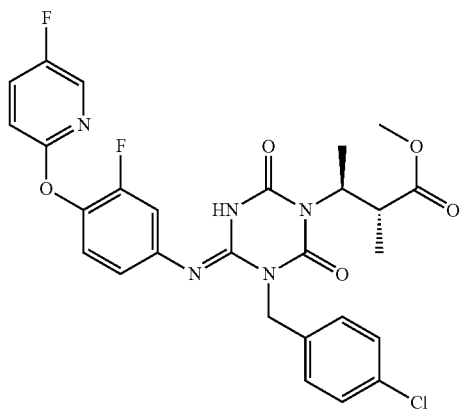 [SMILES: COC(=O)[C@H](C)[C@H](C)n1c(=O)[nH]/c(=N\c2ccc(Oc3ccc(F)cn3)c(F)c2)n(Cc2ccc(Cl)cc2)c1=O] | 572 | 2.61 | 1 |

TABLE 1-continued
| Compound No | Structure | [M+H]+ | RT | Method |
|---|---|---|---|---|
| I-002 | 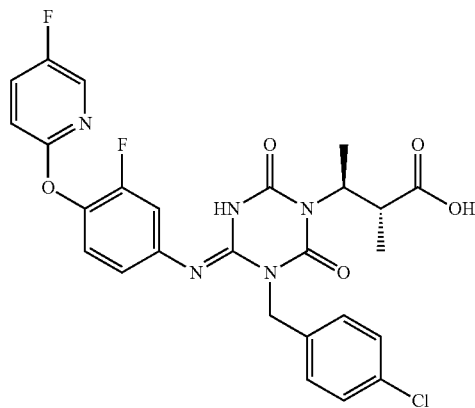 [SMILES: C[C@@H](C(=O)O)[C@H](C)n1c(=O)[nH]/c(=N\c2ccc(Oc3ccc(F)cn3)c(F)c2)n(Cc2ccc(Cl)cc2)c1=O] | 558 | 2.33 | 1 |
| I-003 | 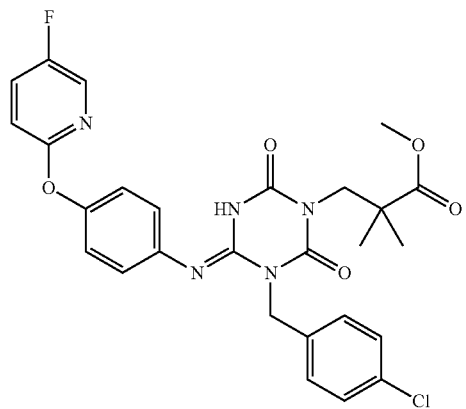 [SMILES: COC(=O)C(C)(C)Cn1c(=O)[nH]/c(=N\c2ccc(Oc3ccc(F)cn3)cc2)n(Cc2ccc(Cl)cc2)c1=O] | 554 | 2.43 | 1 |
| I-004 | 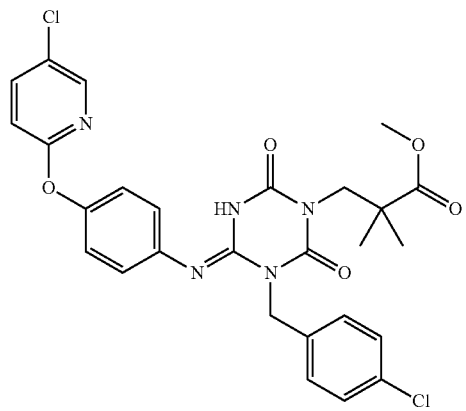 | 570 | 2.57 | 1 |

TABLE 1-continued

| Compound No | Structure | [M+H]+ | RT | Method |
|---|---|---|---|---|
| I-005 | 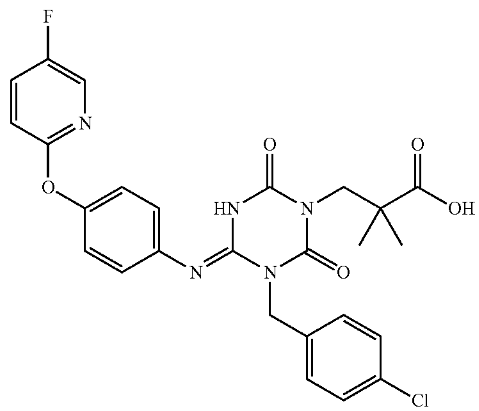 [SMILES: CC(C)(Cn1c(=O)[nH]/c(=N\c2ccc(Oc3ccc(F)cn3)cc2)n(Cc2ccc(Cl)cc2)c1=O)C(=O)O] | 540 | 2.15 | 1 |

TABLE 2

| Compound No | Structure | [M+H]+ | RT | Method |
|---|---|---|---|---|
| I-006 | 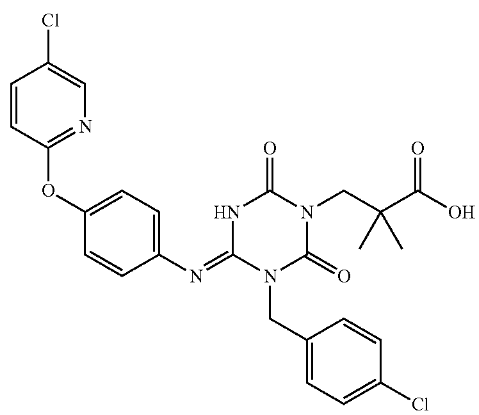 [SMILES: CC(C)(Cn1c(=O)[nH]/c(=N\c2ccc(Oc3ccc(Cl)cn3)cc2)n(Cc2ccc(Cl)cc2)c1=O)C(=O)O] | 556 | 2.28 | 1 |
| I-007 | 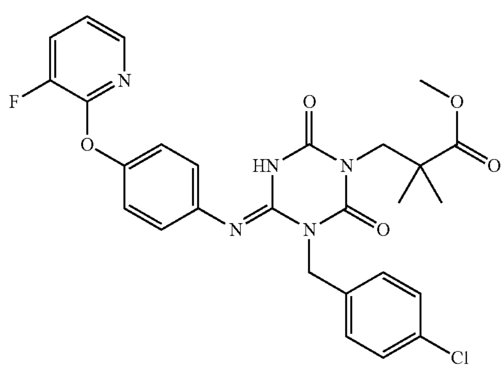 [SMILES: COC(=O)C(C)(C)Cn1c(=O)[nH]/c(=N\c2ccc(Oc3ncccc3F)cc2)n(Cc2ccc(Cl)cc2)c1=O] | 554 | 2.43 | 1 |

TABLE 2-continued

| Compound No | Structure | [M+H]+ | RT | Method |
|---|---|---|---|---|
| I-008 | 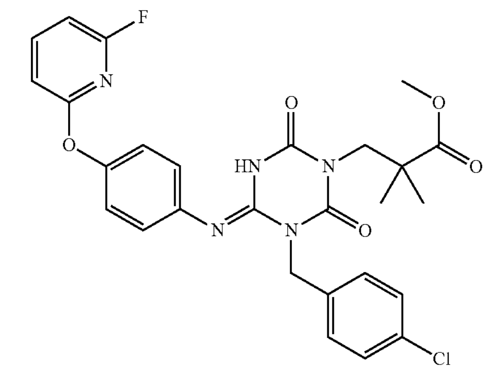 [SMILES: COC(=O)C(C)(C)Cn1c(=O)[nH]/c(=N\c2ccc(Oc3cccc(F)n3)cc2)n(Cc2ccc(Cl)cc2)c1=O] | 554 | 2.45 | 1 |
| I-009 | 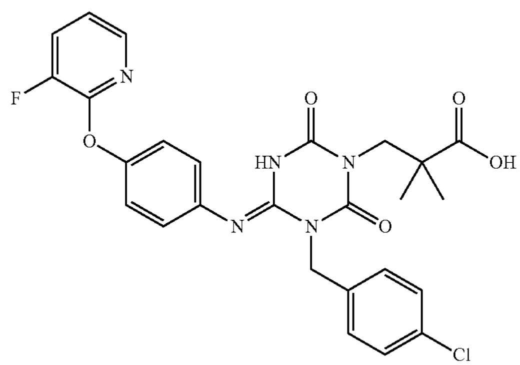 [SMILES: CC(C)(Cn1c(=O)[nH]/c(=N\c2ccc(Oc3ncccc3F)cc2)n(Cc2ccc(Cl)cc2)c1=O)C(=O)O] | 540 | 2.2 | 1 |
| I-010 | 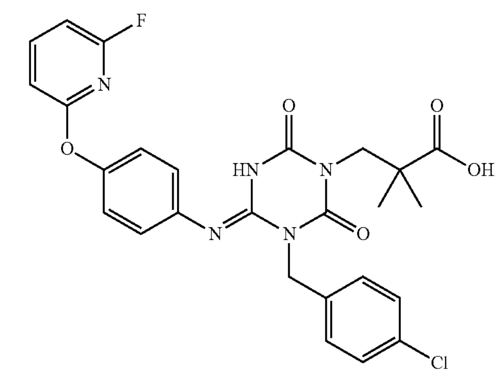 [SMILES: CC(C)(Cn1c(=O)[nH]/c(=N\c2ccc(Oc3cccc(F)n3)cc2)n(Cc2ccc(Cl)cc2)c1=O)C(=O)O] | 540 | 2.21 | 1 |

TABLE 3

| Compound No | Structure | [M+H]+ | RT | Method |
|---|---|---|---|---|
| I-011 | 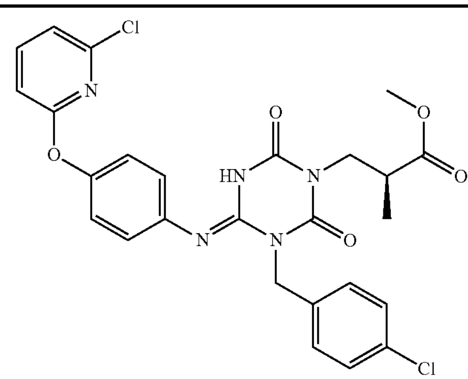 | 556 | 2.43 | 1 |

TABLE 3-continued

| Compound No | Structure | [M+H]+ | RT | Method |
|---|---|---|---|---|
| I-012 | 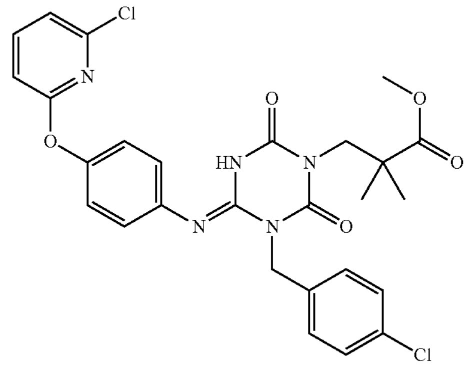 | 570 | 2.58 | 1 |
| I-013 | 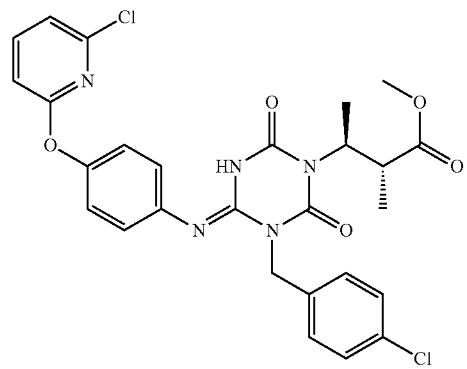 [SMILES: COC(=O)[C@H](C)[C@H](C)n1c(=O)[nH]/c(=N\c2ccc(Oc3cccc(Cl)n3)cc2)n(Cc2ccc(Cl)cc2)c1=O] | 570 | 2.56 | 1 |
| I-014 | 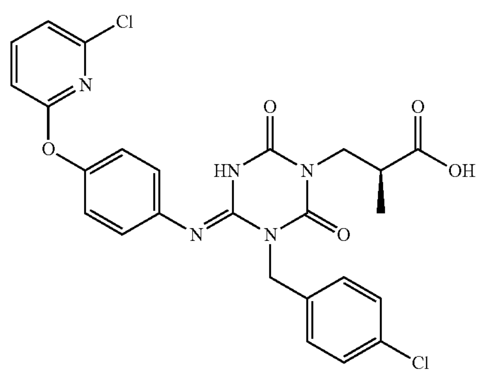 [SMILES: C[C@@H](Cn1c(=O)[nH]/c(=N\c2ccc(Oc3cccc(Cl)n3)cc2)n(Cc2ccc(Cl)cc2)c1=O)C(=O)O] | 542 | 2.18 | 1 |
| I-015 | 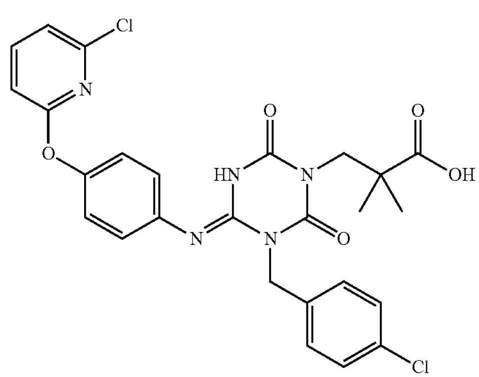 [SMILES: CC(C)(Cn1c(=O)[nH]/c(=N\c2ccc(Oc3cccc(Cl)n3)cc2)n(Cc2ccc(Cl)cc2)c1=O)C(=O)O] | 556 | 2.25 | 1 |

TABLE 4

| Compound No | Structure | [M+H]+ | RT | Method |
|---|---|---|---|---|
| I-016 | 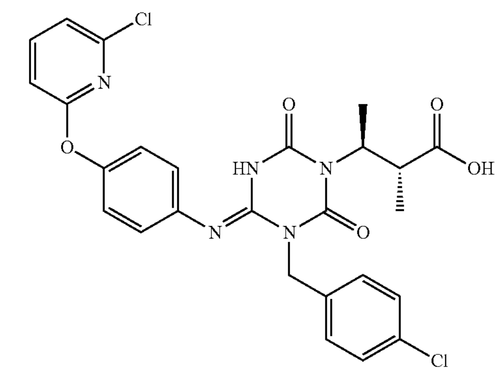 [SMILES: C[C@@H](C(=O)O)[C@H](C)n1c(=O)[nH]/c(=N\c2ccc(Oc3cccc(Cl)n3)cc2)n(Cc2ccc(Cl)cc2)c1=O] | 556 | 2.28 | 1 |
| I-017 | 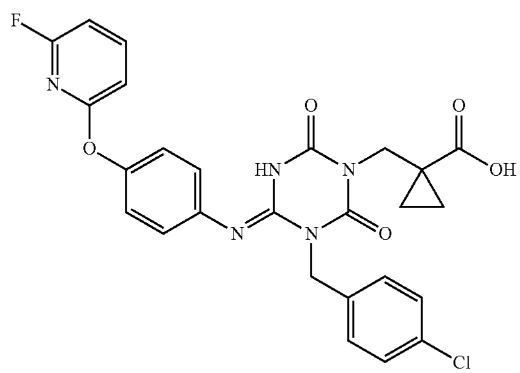 [SMILES: O=C(O)C1(Cn2c(=O)[nH]/c(=N\c3ccc(Oc4cccc(F)n4)cc3)n(Cc3ccc(Cl)cc3)c2=O)CC1] | 538 | 2.13 | 1 |
| I-018 | 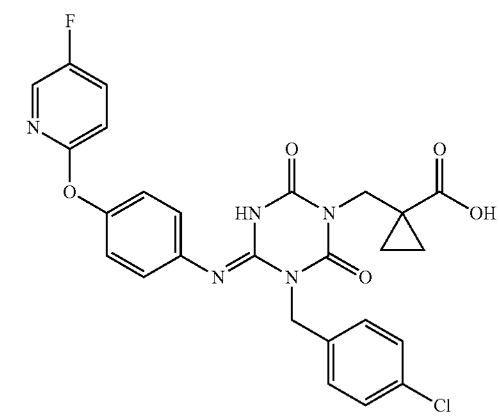 [SMILES: O=C(O)C1(Cn2c(=O)[nH]/c(=N\c3ccc(Oc4ccc(F)cn4)cc3)n(Cc3ccc(Cl)cc3)c2=O)CC1] | 538 | 2.11 | 1 |
| I-019 | 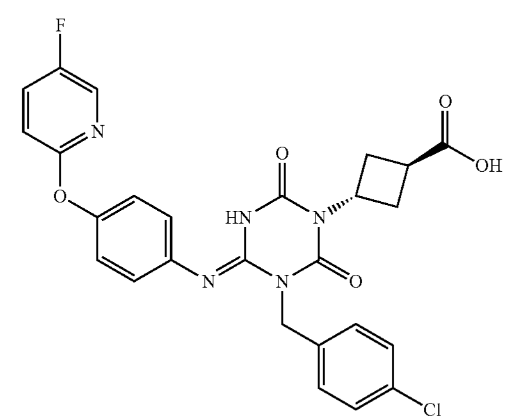 [SMILES: O=c1[nH]/c(=N\c2ccc(Oc3ccc(F)cn3)cc2)n(Cc2ccc(Cl)cc2)c(=O)n1[C@H]1C[C@H](C(=O)O)C1] | 538 | 2.13 | 1 |

TABLE 4-continued

| Compound No | Structure | [M+H]+ | RT | Method |
|---|---|---|---|---|
| I-020 | 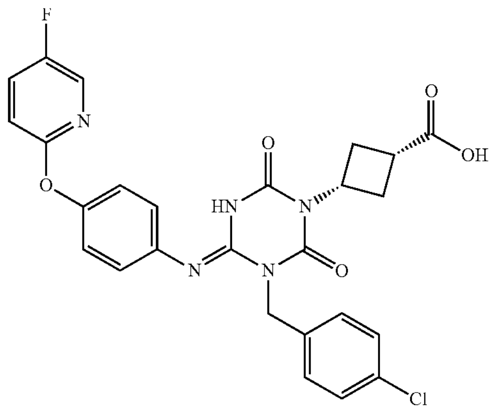 [SMILES: O=c1[nH]/c(=N\c2ccc(Oc3ccc(F)cn3)cc2)n(Cc2ccc(Cl)cc2)c(=O)n1[C@H]1C[C@@H](C(=O)O)C1] | 538 | 2.08 | 1 |

TABLE 5

| Compound No | Structure | [M+H]+ | RT | Method |
|---|---|---|---|---|
| I-021 | 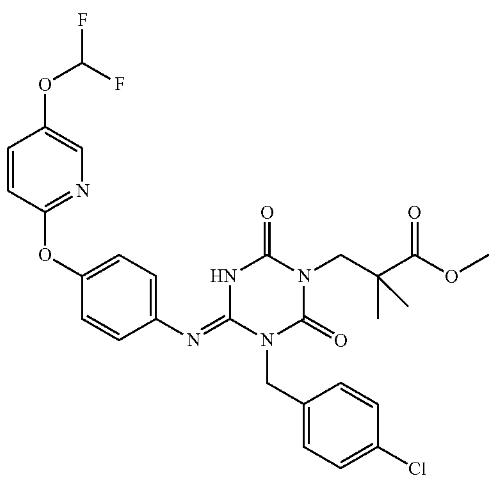 [SMILES: COC(=O)C(C)(C)Cn1c(=O)[nH]/c(=N\c2ccc(Oc3ccc(OC(F)F)cn3)cc2)n(Cc2ccc(Cl)cc2)c1=O] | 602 | 2.48 | 1 |
| I-022 | 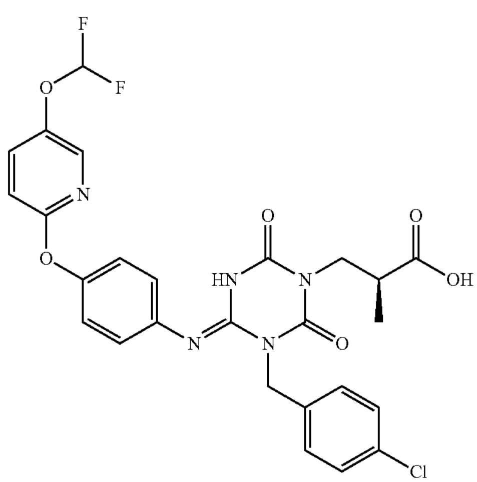 [SMILES: C[C@@H](Cn1c(=O)[nH]/c(=N\c2ccc(Oc3ccc(OC(F)F)cn3)cc2)n(Cc2ccc(Cl)cc2)c1=O)C(=O)O] | 574 | 2.15 | 1 |

TABLE 5-continued

| Compound No | Structure | [M+H]+ | RT | Method |
|---|---|---|---|---|
| I-023 | 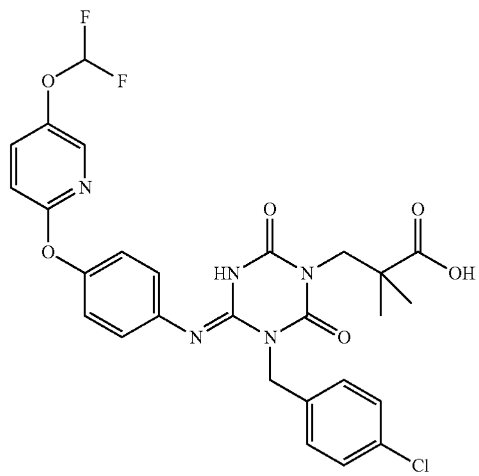 [SMILES: CC(C)(Cn1c(=O)[nH]/c(=N\c2ccc(Oc3ccc(OC(F)F)cn3)cc2)n(Cc2ccc(Cl)cc2)c1=O)C(=O)O] | 588 | 2.22 | 1 |
| I-024 | 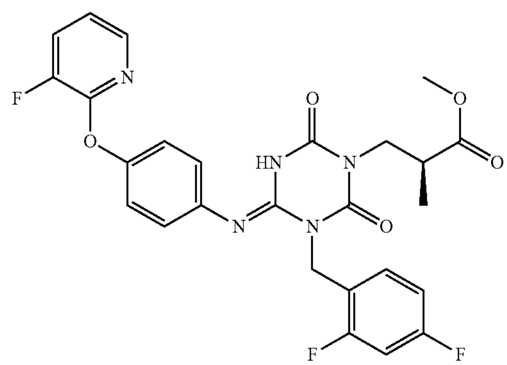 [SMILES: COC(=O)[C@@H](C)Cn1c(=O)[nH]/c(=N\c2ccc(Oc3ncccc3F)cc2)n(Cc2ccc(F)cc2F)c1=O] | 542 | 2.23 | 1 |
| I-025 | 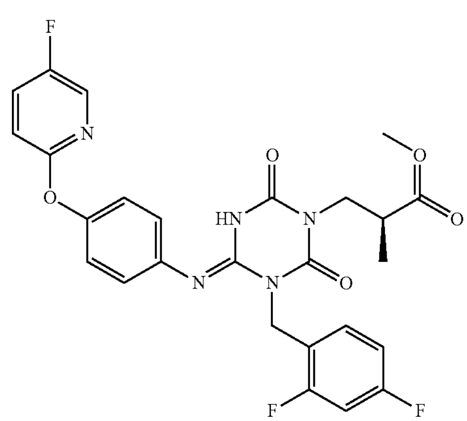 | 542 | 2.22 | 1 |

TABLE 6

| Compound No | Structure | [M+H]+ | RT | Method |
|---|---|---|---|---|
| I-026 | 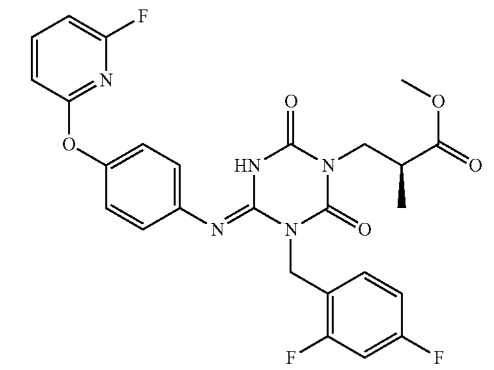 [SMILES: COC(=O)[C@@H](C)Cn1c(=O)[nH]/c(=N\c2ccc(Oc3cccc(F)n3)cc2)n(Cc2ccc(F)cc2F)c1=O] | 542 | 2.24 | 1 |
| I-027 | 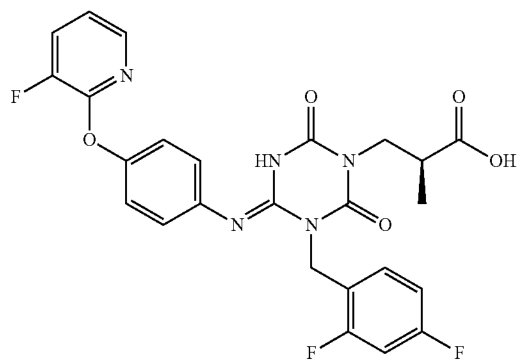 [SMILES: C[C@@H](Cn1c(=O)[nH]/c(=N\c2ccc(Oc3ncccc3F)cc2)n(Cc2ccc(F)cc2F)c1=O)C(=O)O] | 528 | 1.99 | 1 |
| I-028 | 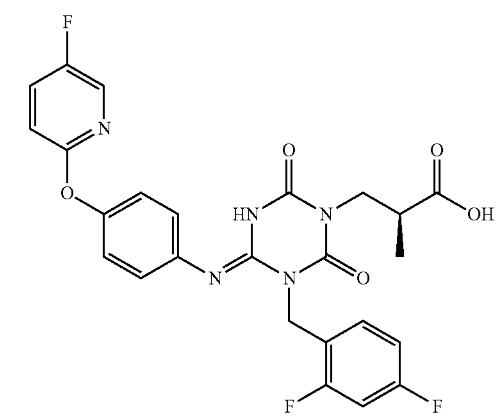 [SMILES: C[C@@H](Cn1c(=O)[nH]/c(=N\c2ccc(Oc3ccc(F)cn3)cc2)n(Cc2ccc(F)cc2F)c1=O)C(=O)O] | 528 | 1.98 | 1 |
| I-029 | 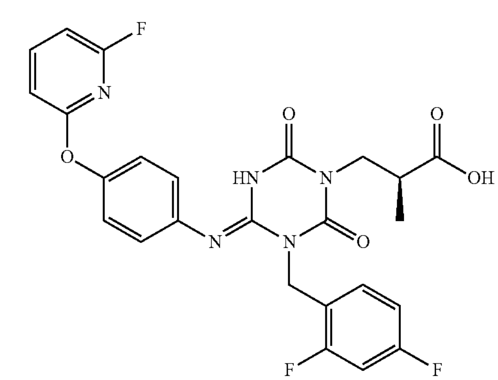 [SMILES: C[C@@H](Cn1c(=O)[nH]/c(=N\c2ccc(Oc3cccc(F)n3)cc2)n(Cc2ccc(F)cc2F)c1=O)C(=O)O] | 528 | 2 | 1 |

TABLE 6-continued

| Compound No | Structure | [M+H]+ | RT | Method |
|---|---|---|---|---|
| I-030 | 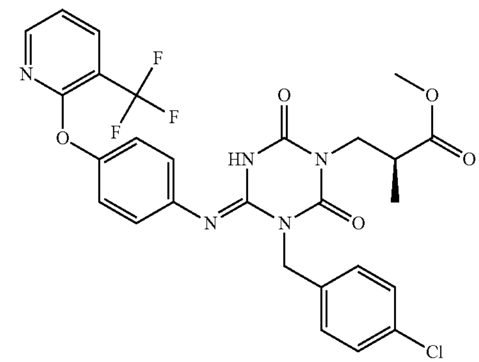 [SMILES: COC(=O)[C@@H](C)Cn1c(=O)[nH]/c(=N\c2ccc(Oc3ncccc3C(F)(F)F)cc2)n(Cc2ccc(Cl)cc2)c1=O] | 590 | 2.52 | 1 |

TABLE 7

| Compound No | Structure | [M+H]+ | RT | Method |
|---|---|---|---|---|
| I-031 | 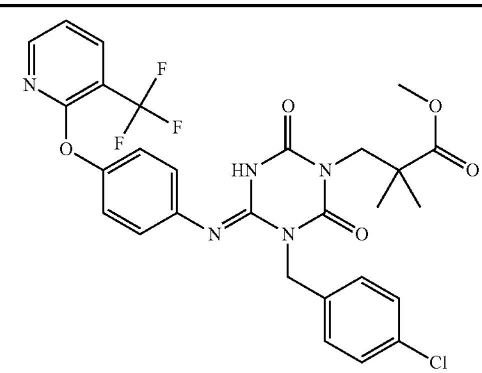 | 604 | 2.61 | 1 |
| I-032 | 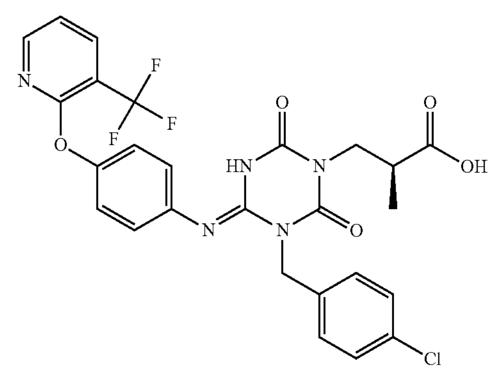 [SMILES: C[C@@H](Cn1c(=O)[nH]/c(=N\c2ccc(Oc3ncccc3C(F)(F)F)cc2)n(Cc2ccc(Cl)cc2)c1=O)C(=O)O] | 576 | 2.28 | 1 |
| I-033 | 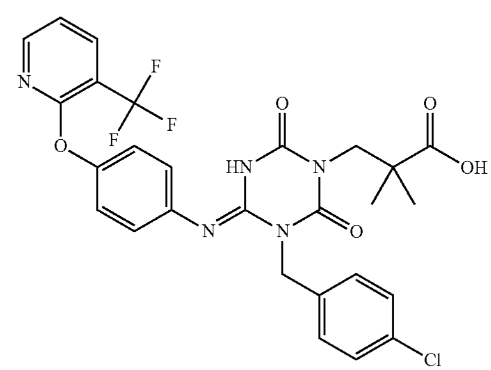 [SMILES: CC(C)(Cn1c(=O)[nH]/c(=N\c2ccc(Oc3ncccc3C(F)(F)F)cc2)n(Cc2ccc(Cl)cc2)c1=O)C(=O)O] | 590 | 2.35 | 1 |

TABLE 7-continued
| Compound No | Structure | [M+H]+ | RT | Method |
|---|---|---|---|---|
| I-034 | 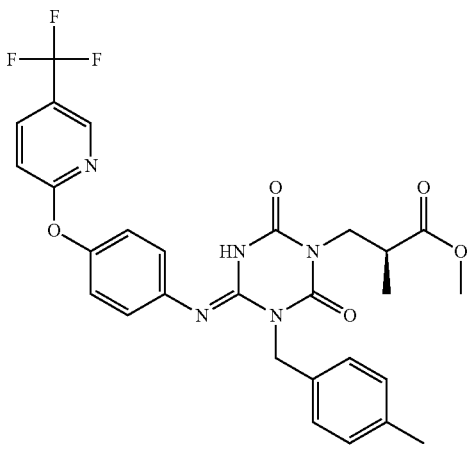 [SMILES: COC(=O)[C@@H](C)Cn1c(=O)[nH]/c(=N\c2ccc(Oc3ccc(C(F)(F)F)cn3)cc2)n(Cc2ccc(C)cc2)c1=O] | 570 | 2.46 | 1 |
| I-035 | 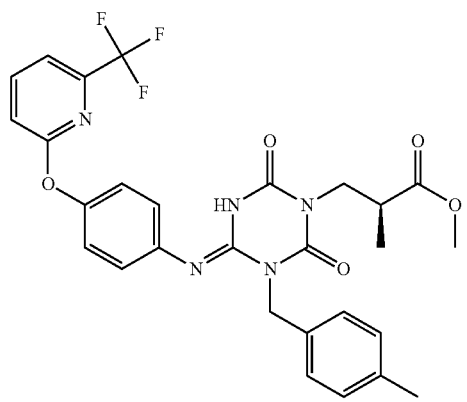 [SMILES: COC(=O)[C@@H](C)Cn1c(=O)[nH]/c(=N\c2ccc(Oc3cccc(C(F)(F)F)n3)cc2)n(Cc2ccc(C)cc2)c1=O] | 570 | 2.4 | 1 |
TABLE 8
| Compound No | Structure | [M+H]+ | RT | Method |
|---|---|---|---|---|
| I-036 | 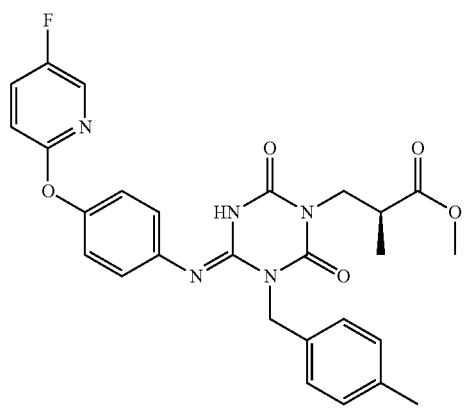 [SMILES: COC(=O)[C@@H](C)Cn1c(=O)[nH]/c(=N\c2ccc(Oc3ccc(F)cn3)cc2)n(Cc2ccc(C)cc2)c1=O] | 520 | 2.24 | 1 |

TABLE 8-continued

| Compound No | Structure | [M+H]+ | RT | Method |
|---|---|---|---|---|
| I-037 | 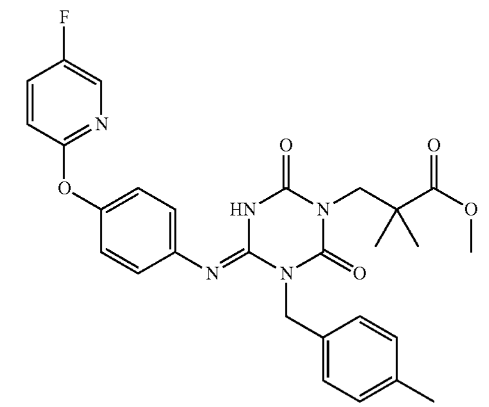 [SMILES: COC(=O)C(C)(C)Cn1c(=O)[nH]/c(=N\c2ccc(Oc3ccc(F)cn3)cc2)n(Cc2ccc(C)cc2)c1=O] | 534 | 2.34 | 1 |
| I-038 | 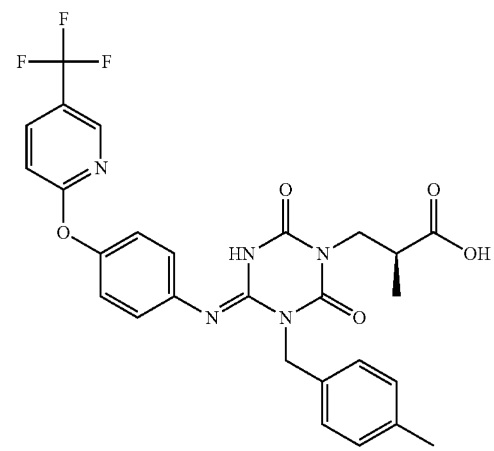 [SMILES: Cc1ccc(Cn2c(=O)n(C[C@H](C)C(=O)O)c(=O)[nH]/c2=N\c2ccc(Oc3ccc(C(F)(F)F)cn3)cc2)cc1] | 556 | 2.21 | 1 |
| I-039 | 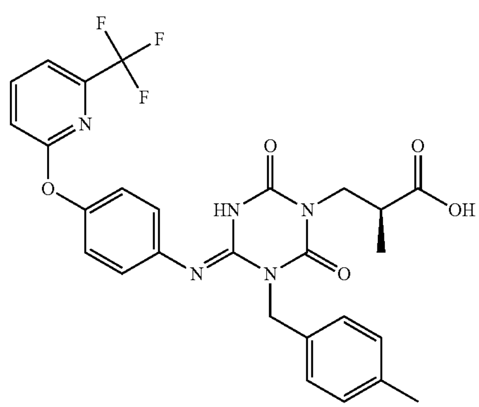 [SMILES: Cc1ccc(Cn2c(=O)n(C[C@H](C)C(=O)O)c(=O)[nH]/c2=N\c2ccc(Oc3cccc(C(F)(F)F)n3)cc2)cc1] | 556 | 2.17 | 1 |

TABLE 8-continued
| Compound No | Structure | [M+H]+ | RT | Method |
|---|---|---|---|---|
| I-040 | 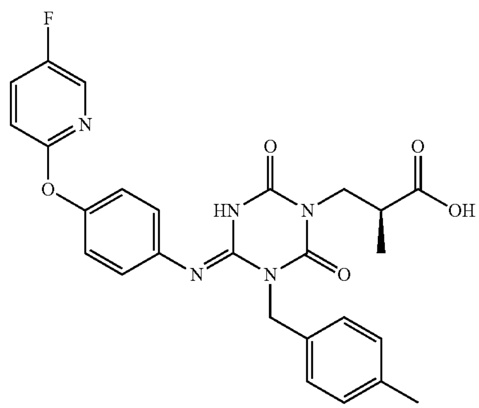 [SMILES: Cc1ccc(Cn2c(=O)n(C[C@H](C)C(=O)O)c(=O)[nH]/c2=N\c2ccc(Oc3ccc(F)cn3)cc2)cc1] | 506 | 1.98 | 1 |
TABLE 9
| Compound No | Structure | [M+H]+ | RT | Method |
|---|---|---|---|---|
| I-041 | 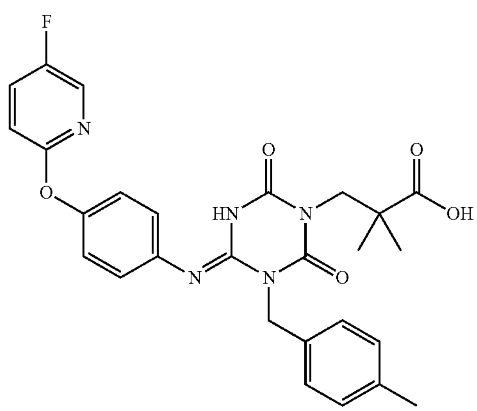 [SMILES: Cc1ccc(Cn2c(=O)n(CC(C)(C)C(=O)O)c(=O)[nH]/c2=N\c2ccc(Oc3ccc(F)cn3)cc2)cc1] | 520 | 2.06 | 1 |
| I-042 | 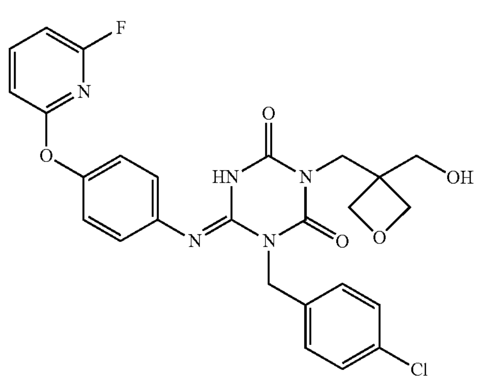 [SMILES: O=c1[nH]/c(=N\c2ccc(Oc3cccc(F)n3)cc2)n(Cc2ccc(Cl)cc2)c(=O)n1CC1(CO)COC1] | 540 | 2 | 1 |
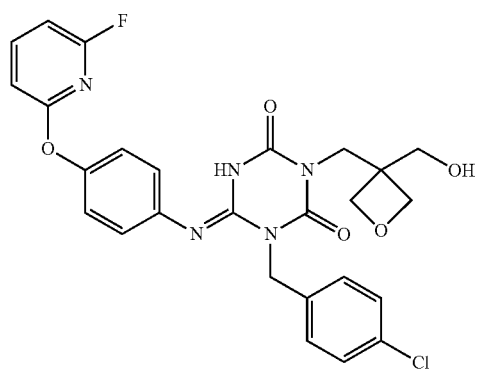

TABLE 9-continued
| Compound No | Structure | [M+H]+ | RT | Method |
|---|---|---|---|---|
| I-043 | 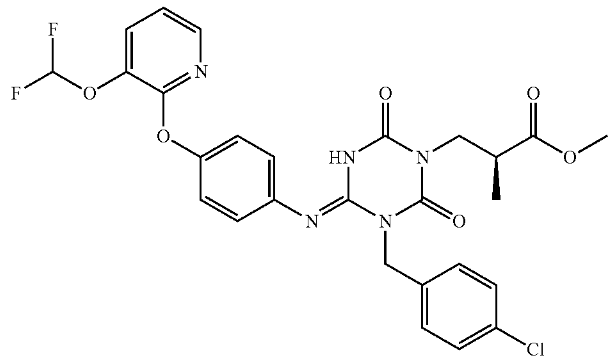 [SMILES: COC(=O)[C@@H](C)Cn1c(=O)[nH]/c(=N\c2ccc(Oc3ncccc3OC(F)F)cc2)n(Cc2ccc(Cl)cc2)c1=O] | 588 | 2.36 | 1 |
| I-044 | 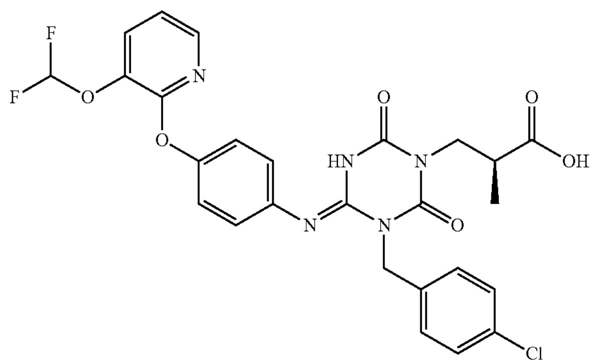 [SMILES: C[C@@H](Cn1c(=O)[nH]/c(=N\c2ccc(Oc3ncccc3OC(F)F)cc2)n(Cc2ccc(Cl)cc2)c1=O)C(=O)O] | 574 | 2.13 | 1 |
| I-045 | 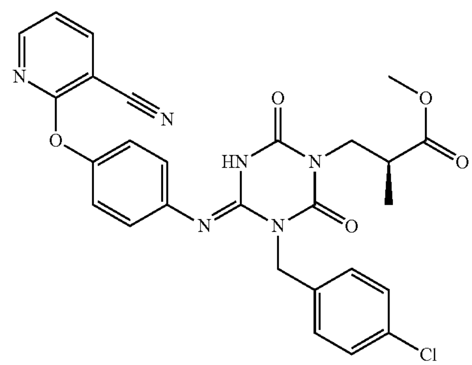 [SMILES: COC(=O)[C@@H](C)Cn1c(=O)[nH]/c(=N\c2ccc(Oc3ncccc3C#N)cc2)n(Cc2ccc(Cl)cc2)c1=O] | 547 | 2.24 | 1 |
TABLE 10
| Compound No | Structure | [M+H]+ | RT | Method |
|---|---|---|---|---|
| I-046 | 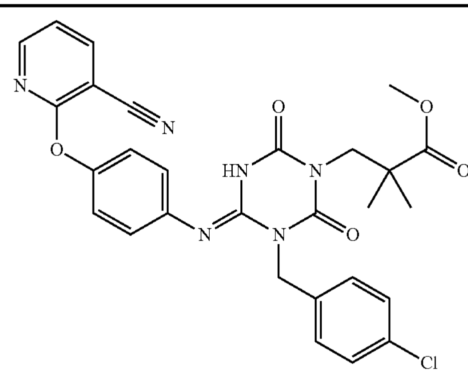 | 561 | 2.34 | 1 |

TABLE 10-continued

| Compound No | Structure | [M+H]+ | RT | Method |
|---|---|---|---|---|
| I-047 | 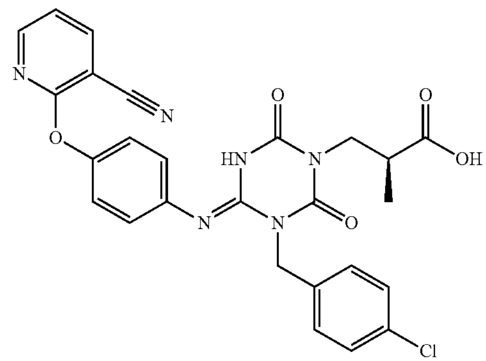 [SMILES: C[C@@H](Cn1c(=O)[nH]/c(=N\c2ccc(Oc3ncccc3C#N)cc2)n(Cc2ccc(Cl)cc2)c1=O)C(=O)O] | 533 | 1.99 | 1 |
| I-048 | 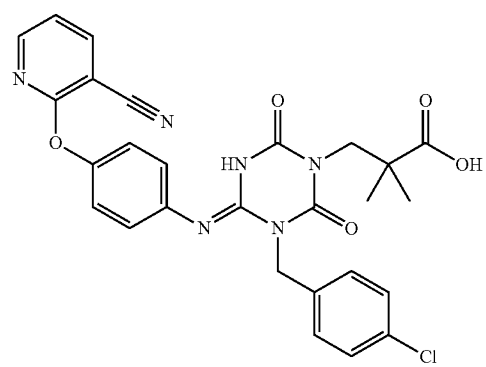 [SMILES: CC(C)(Cn1c(=O)[nH]/c(=N\c2ccc(Oc3ncccc3C#N)cc2)n(Cc2ccc(Cl)cc2)c1=O)C(=O)O] | 547 | 2.07 | 1 |
| I-049 | 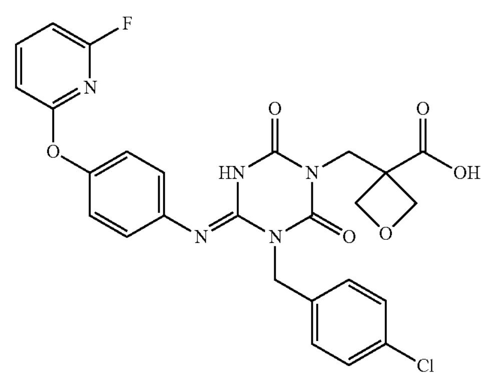 [SMILES: O=C(O)C1(Cn2c(=O)[nH]/c(=N\c3ccc(Oc4cccc(F)n4)cc3)n(Cc3ccc(Cl)cc3)c2=O)COC1] | 554 | 1.97 | 1 |
| I-050 | 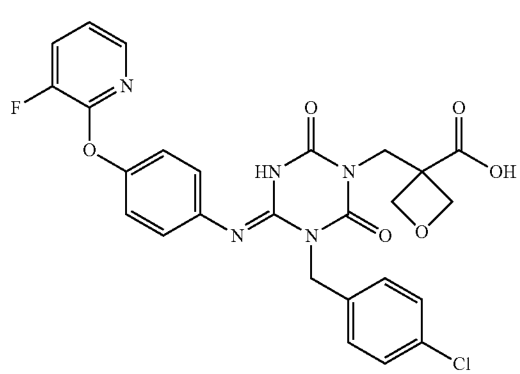 [SMILES: O=C(O)C1(Cn2c(=O)[nH]/c(=N\c3ccc(Oc4ncccc4F)cc3)n(Cc3ccc(Cl)cc3)c2=O)COC1] | 554 | 1.95 | 1 |

TABLE 11

| Compound No | Structure | [M+H]+ | RT | Method |
|---|---|---|---|---|
| I-051 | 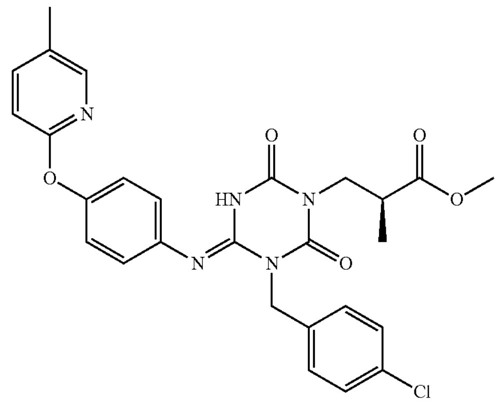 [SMILES: COC(=O)[C@@H](C)Cn1c(=O)[nH]/c(=N\c2ccc(Oc3ccc(C)cn3)cc2)n(Cc2ccc(Cl)cc2)c1=O] | 536 | 2.37 | 1 |
| I-052 | 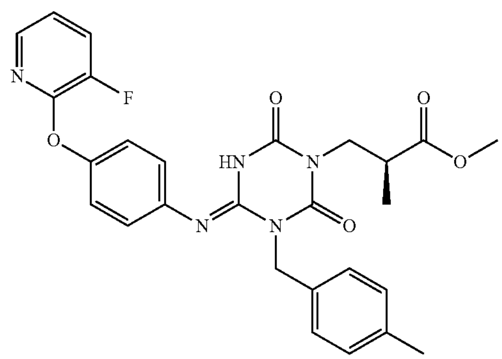 [SMILES: COC(=O)[C@@H](C)Cn1c(=O)[nH]/c(=N\c2ccc(Oc3ncccc3F)cc2)n(Cc2ccc(C)cc2)c1=O] | 520 | 2.25 | 1 |
| I-053 | 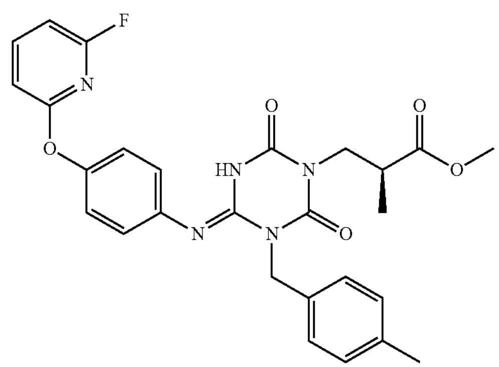 | 520 | 2.27 | 1 |
| I-054 | 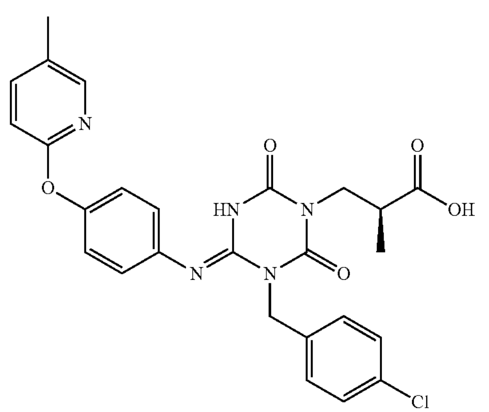 [SMILES: Cc1ccc(Oc2ccc(/N=c3\[nH]c(=O)n(C[C@H](C)C(=O)O)c(=O)n3Cc3ccc(Cl)cc3)cc2)nc1] | 522 | 2.12 | 1 |

TABLE 11-continued

| Compound No | Structure | [M+H]+ | RT | Method |
|---|---|---|---|---|
| I-055 | 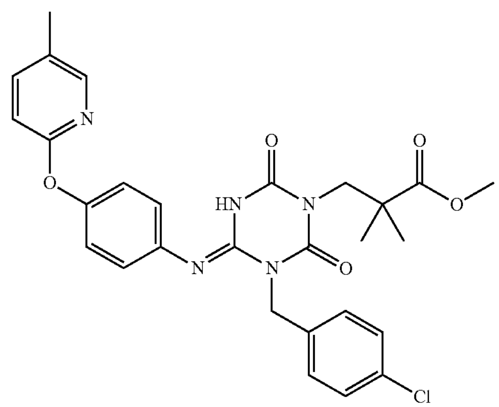 [SMILES: COC(=O)C(C)(C)Cn1c(=O)[nH]/c(=N\c2ccc(Oc3ccc(C)cn3)cc2)n(Cc2ccc(Cl)cc2)c1=O] | 550 | 2.48 | 1 |

TABLE 12

| Compound No | Structure | [M+H]+ | RT | Method |
|---|---|---|---|---|
| I-056 | 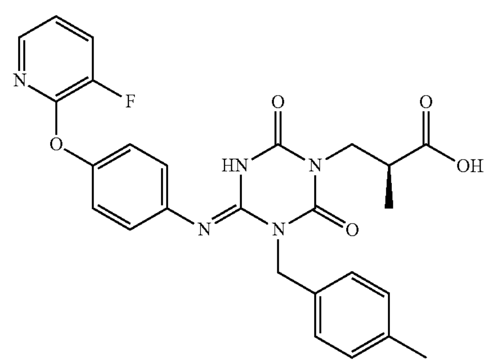 [SMILES: Cc1ccc(Cn2c(=O)n(C[C@H](C)C(=O)O)c(=O)[nH]/c2=N\c2ccc(Oc3ncccc3F)cc2)cc1] | 506 | 2 | 1 |
| I-057 | 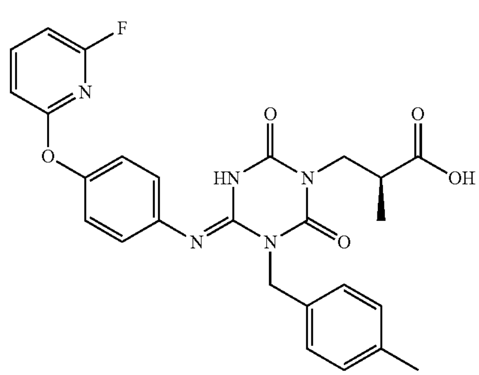 [SMILES: Cc1ccc(Cn2c(=O)n(C[C@H](C)C(=O)O)c(=O)[nH]/c2=N\c2ccc(Oc3cccc(F)n3)cc2)cc1] | 506 | 2.02 | 1 |

TABLE 12-continued

| Compound No | Structure | [M+H]+ | RT | Method |
|---|---|---|---|---|
| I-058 | 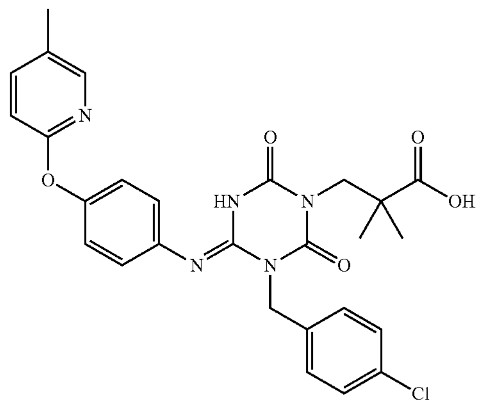 [SMILES: Cc1ccc(Oc2ccc(/N=c3\[nH]c(=O)n(CC(C)(C)C(=O)O)c(=O)n3Cc3ccc(Cl)cc3)cc2)nc1] | 536 | 2.2 | 1 |
| I-059 | 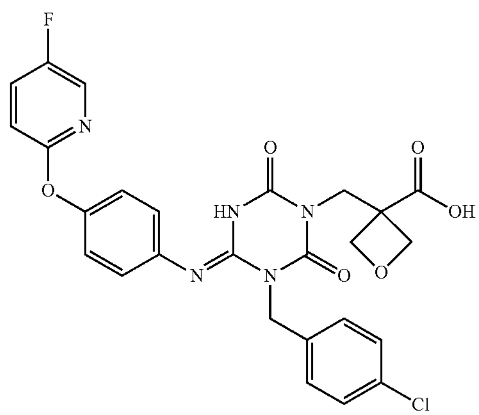 [SMILES: O=C(O)C1(Cn2c(=O)[nH]/c(=N\c3ccc(Oc4ccc(F)cn4)cc3)n(Cc3ccc(Cl)cc3)c2=O)COC1] | 554 | 1.94 | 1 |
| I-060 | 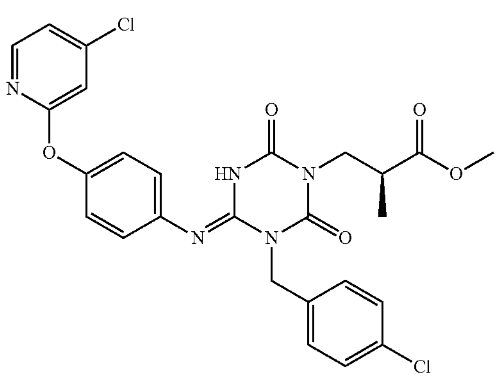 [SMILES: COC(=O)[C@@H](C)Cn1c(=O)[nH]/c(=N\c2ccc(Oc3cc(Cl)ccn3)cc2)n(Cc2ccc(Cl)cc2)c1=O] | 556 | 2.5 | 1 |

TABLE 13

| Compound No | Structure | [M+H]+ | RT | Method |
|---|---|---|---|---|
| I-061 | 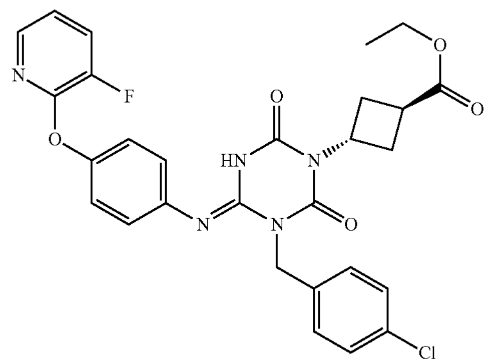 [SMILES: CCOC(=O)[C@H]1C[C@H](n2c(=O)[nH]/c(=N\c3ccc(Oc4ncccc4F)cc3)n(Cc3ccc(Cl)cc3)c2=O)C1] | 566 | 2.52 | 1 |
| I-062 | 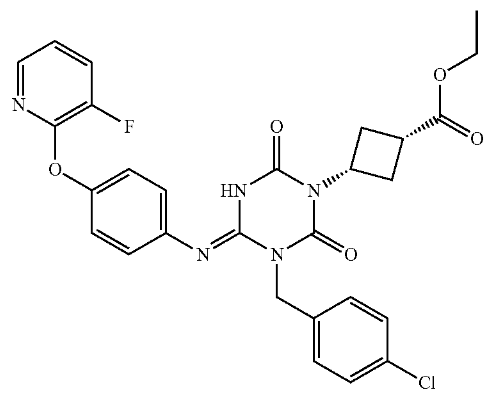 [SMILES: CCOC(=O)[C@H]1C[C@@H](n2c(=O)[nH]/c(=N\c3ccc(Oc4ncccc4F)cc3)n(Cc3ccc(Cl)cc3)c2=O)C1] | 566 | 2.47 | 1 |
| I-063 | 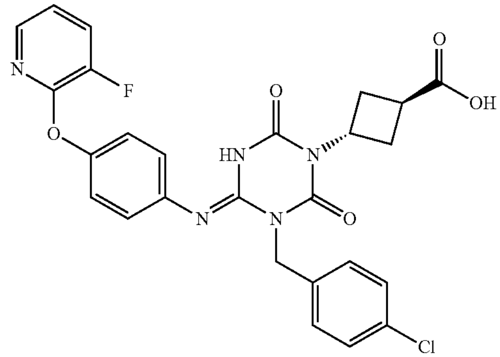 [SMILES: O=c1[nH]/c(=N\c2ccc(Oc3ncccc3F)cc2)n(Cc2ccc(Cl)cc2)c(=O)n1[C@H]1C[C@H](C(=O)O)C1] | 538 | 2.14 | 1 |
| I-064 | 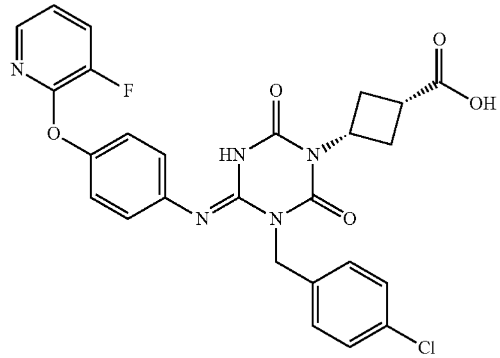 [SMILES: O=c1[nH]/c(=N\c2ccc(Oc3ncccc3F)cc2)n(Cc2ccc(Cl)cc2)c(=O)n1[C@H]1C[C@@H](C(=O)O)C1] | 538 | 2.09 | 1 |

TABLE 13-continued

| Compound No | Structure | [M+H]+ | RT | Method |
|---|---|---|---|---|
| I-065 | 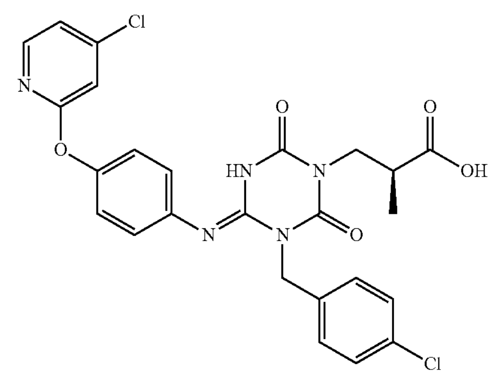 [SMILES: C[C@@H](Cn1c(=O)[nH]/c(=N\c2ccc(Oc3cc(Cl)ccn3)cc2)n(Cc2ccc(Cl)cc2)c1=O)C(=O)O] | 542 | 2.25 | 1 |

TABLE 14

| Compound No | Structure | [M+H]+ | RT | Method |
|---|---|---|---|---|
| I-066 | 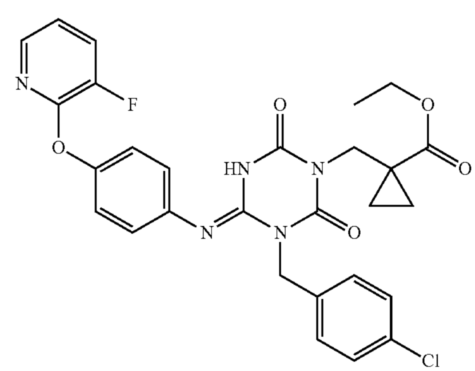 [SMILES: CCOC(=O)C1(Cn2c(=O)[nH]/c(=N\c3ccc(Oc4ncccc4F)cc3)n(Cc3ccc(Cl)cc3)c2=O)CC1] | 566 | 2.49 | 1 |
| I-067 | 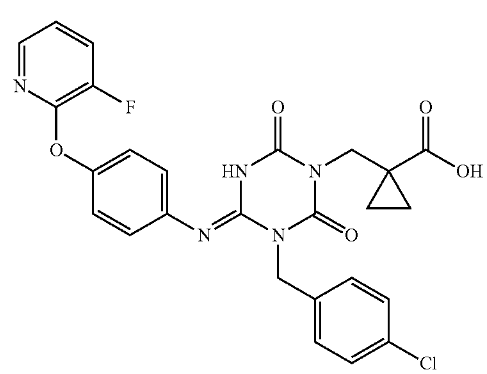 [SMILES: O=C(O)C1(Cn2c(=O)[nH]/c(=N\c3ccc(Oc4ncccc4F)cc3)n(Cc3ccc(Cl)cc3)c2=O)CC1] | 538 | 2.12 | 1 |

TABLE 14-continued

| Compound No | Structure | [M+H]+ | RT | Method |
|---|---|---|---|---|
| I-068 | 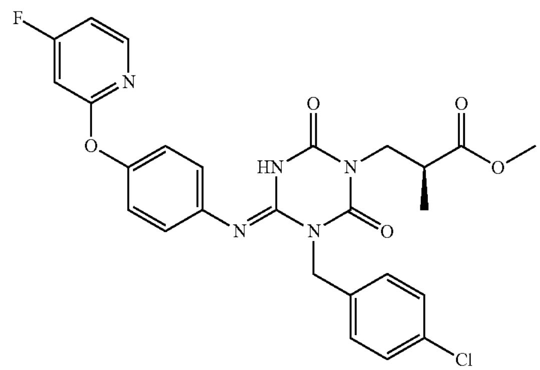 [SMILES: COC(=O)[C@@H](C)Cn1c(=O)[nH]/c(=N\c2ccc(Oc3cc(F)ccn3)cc2)n(Cc2ccc(Cl)cc2)c1=O] | 540 | 2.35 | 1 |
| I-069 | 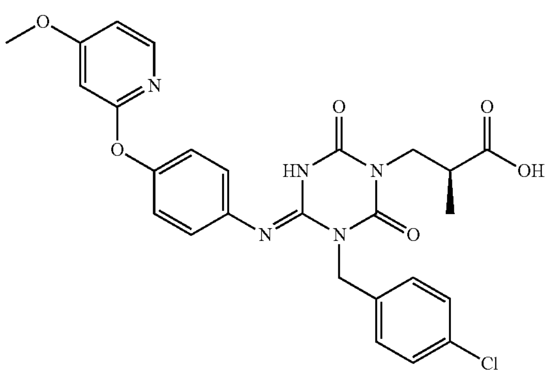 [SMILES: COc1ccnc(Oc2ccc(/N=c3\[nH]c(=O)n(C[C@H](C)C(=O)O)c(=O)n3Cc3ccc(Cl)cc3)cc2)c1] | 538 | 2.02 | 1 |
| I-070 | 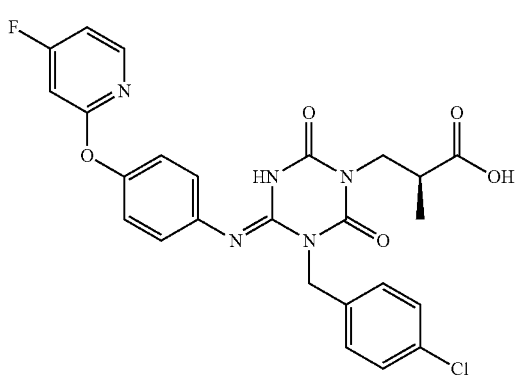 | 526 | 2.11 | 1 |

TABLE 15

| Compound No | Structure | [M + H]+ | RT | Method |
|---|---|---|---|---|
| I-071 | 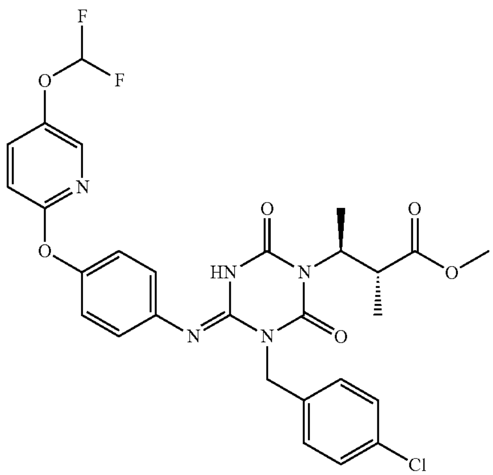 [SMILES: COC(=O)[C@H](C)[C@H](C)n1c(=O)[nH]/c(=N\c2ccc(Oc3ccc(OC(F)F)cn3)cc2)n(Cc2ccc(Cl)cc2)c1=O] | 602 | 2.51 | 1 |
| I-072 | 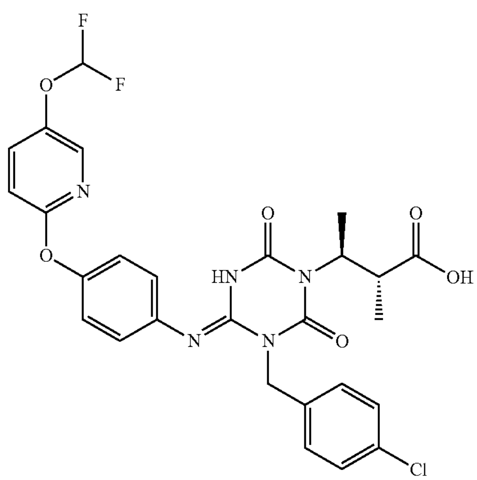 [SMILES: C[C@@H](C(=O)O)[C@H](C)n1c(=O)[nH]/c(=N\c2ccc(Oc3ccc(OC(F)F)cn3)cc2)n(Cc2ccc(Cl)cc2)c1=O] | 588 | 2.25 | 1 |
| I-073 | 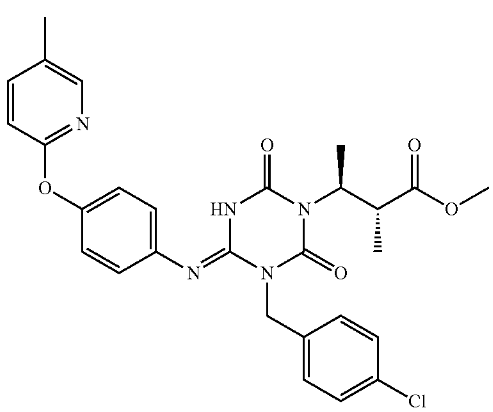 [SMILES: COC(=O)[C@H](C)[C@H](C)n1c(=O)[nH]/c(=N\c2ccc(Oc3ccc(C)cn3)cc2)n(Cc2ccc(Cl)cc2)c1=O] | 550 | 2.52 | 1 |

TABLE 15-continued
| Compound No | Structure | [M + H]+ | RT | Method |
|---|---|---|---|---|
| I-074 | 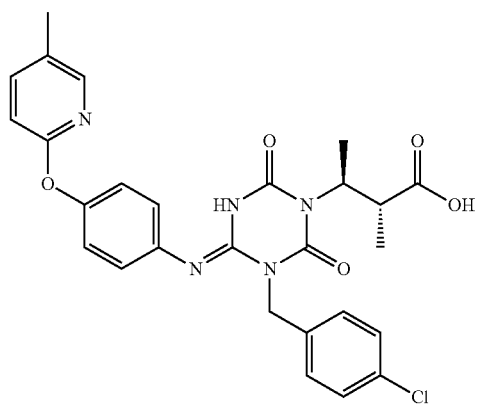 [SMILES: Cc1ccc(Oc2ccc(/N=c3\[nH]c(=O)n([C@@H](C)[C@@H](C)C(=O)O)c(=O)n3Cc3ccc(Cl)cc3)cc2)nc1] | 536 | 2.23 | 1 |
| I-075 | 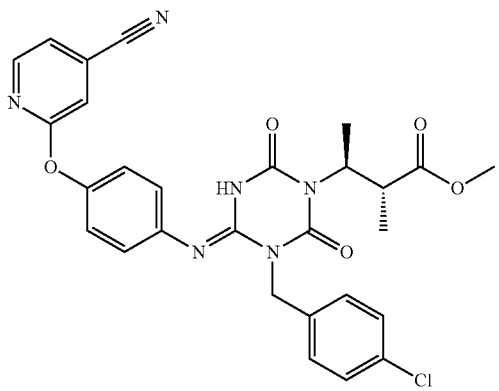 [SMILES: COC(=O)[C@H](C)[C@H](C)n1c(=O)[nH]/c(=N\c2ccc(Oc3cc(C#N)ccn3)cc2)n(Cc2ccc(Cl)cc2)c1=O] | 561 | 2.43 | 1 |
TABLE 16
| Compound No | Structure | [M + H]+ | RT | Method |
|---|---|---|---|---|
| I-076 | 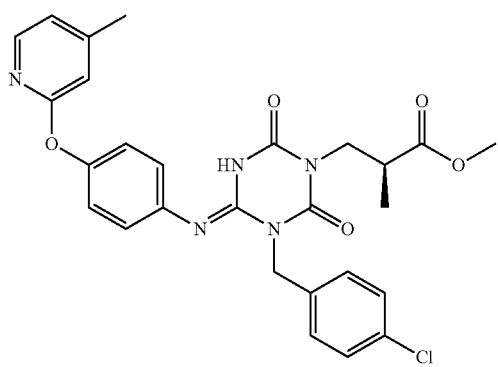 [SMILES: COC(=O)[C@@H](C)Cn1c(=O)[nH]/c(=N\c2ccc(Oc3cc(C)ccn3)cc2)n(Cc2ccc(Cl)cc2)c1=O] | 536 | 2.38 | 1 |

TABLE 16-continued

| Compound No | Structure | [M + H]+ | RT | Method |
|---|---|---|---|---|
| I-077 | 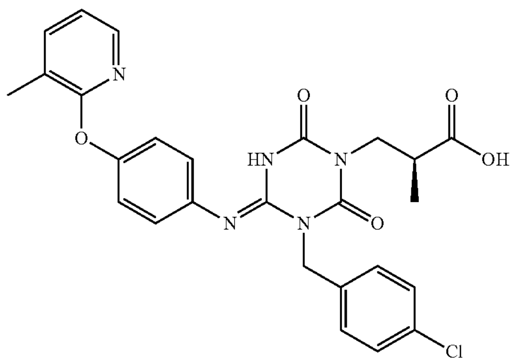 [SMILES: Cc1cccnc1Oc1ccc(/N=c2\[nH]c(=O)n(C[C@H](C)C(=O)O)c(=O)n2Cc2ccc(Cl)cc2)cc1] | 522 | 2.2 | 1 |
| I-078 | 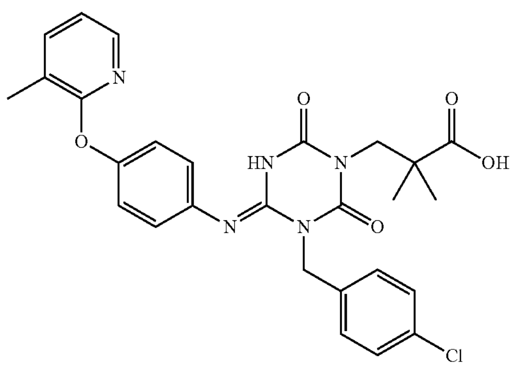 [SMILES: Cc1cccnc1Oc1ccc(/N=c2\[nH]c(=O)n(CC(C)(C)C(=O)O)c(=O)n2Cc2ccc(Cl)cc2)cc1] | 536 | 2.28 | 1 |
| I-079 | 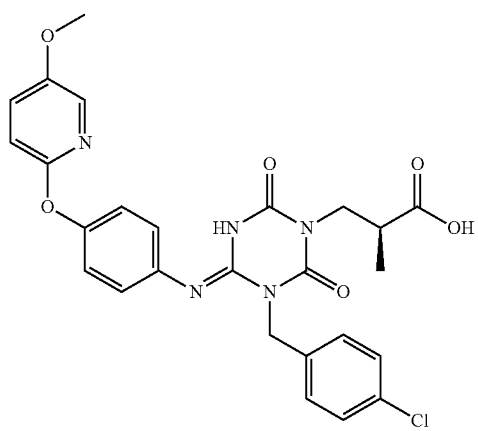 [SMILES: COc1ccc(Oc2ccc(/N=c3\[nH]c(=O)n(C[C@H](C)C(=O)O)c(=O)n3Cc3ccc(Cl)cc3)cc2)nc1] | 538 | 2.04 | 1 |
| I-080 | 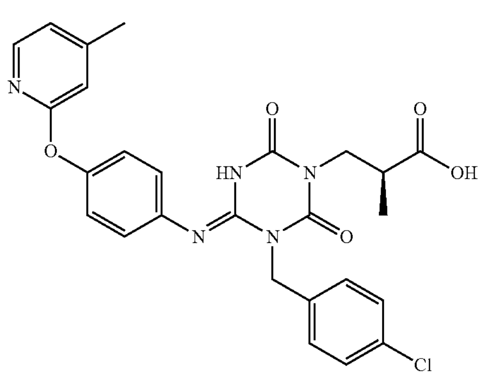 [SMILES: Cc1ccnc(Oc2ccc(/N=c3\[nH]c(=O)n(C[C@H](C)C(=O)O)c(=O)n3Cc3ccc(Cl)cc3)cc2)c1] | 522 | 2.12 | 1 |

TABLE 17

| Compound No | Structure | [M + H]+ | RT | Method |
|---|---|---|---|---|
| I-081 | 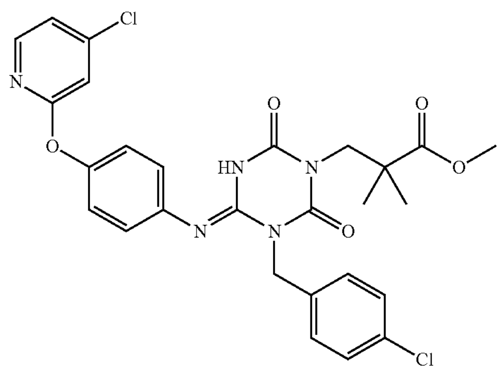 [SMILES: COC(=O)C(C)(C)Cn1c(=O)[nH]/c(=N\c2ccc(Oc3cc(Cl)ccn3)cc2)n(Cc2ccc(Cl)cc2)c1=O] | 570 | 2.6 | 1 |
| I-082 | 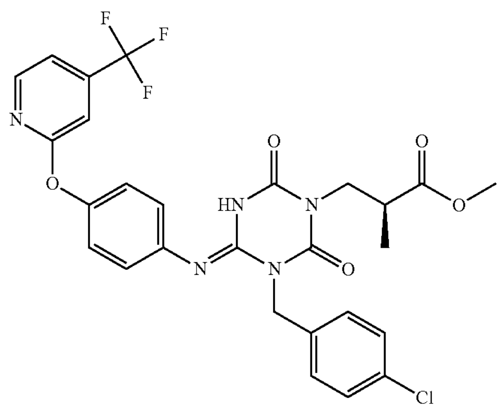 [SMILES: COC(=O)[C@@H](C)Cn1c(=O)[nH]/c(=N\c2ccc(Oc3cc(C(F)(F)F)ccn3)cc2)n(Cc2ccc(Cl)cc2)c1=O] | 590 | 2.56 | 1 |
| I-083 | 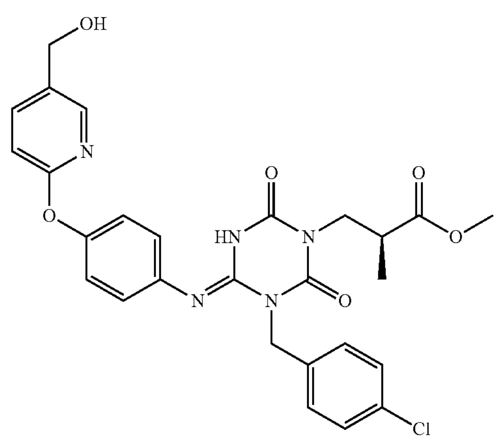 [SMILES: COC(=O)[C@@H](C)Cn1c(=O)[nH]/c(=N\c2ccc(Oc3ccc(CO)cn3)cc2)n(Cc2ccc(Cl)cc2)c1=O] | 552 | 2 | 1 |

TABLE 17-continued
| Compound No | Structure | [M + H]+ | RT | Method |
|---|---|---|---|---|
| I-084 | 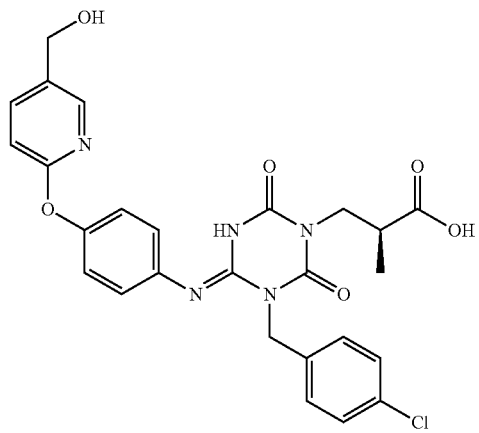 [SMILES: C[C@@H](Cn1c(=O)[nH]/c(=N\c2ccc(Oc3ccc(CO)cn3)cc2)n(Cc2ccc(Cl)cc2)c1=O)C(=O)O] | 538 | 1.77 | 1 |
| I-085 | 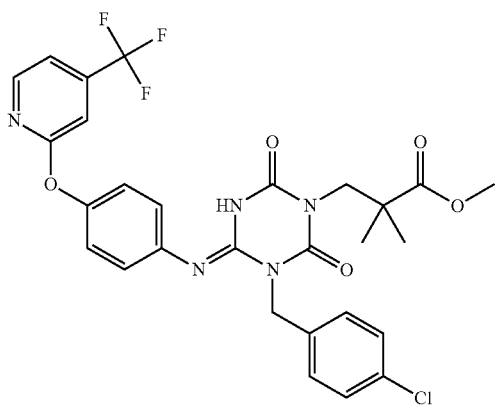 [SMILES: COC(=O)C(C)(C)Cn1c(=O)[nH]/c(=N\c2ccc(Oc3cc(C(F)(F)F)ccn3)cc2)n(Cc2ccc(Cl)cc2)c1=O] | 604 | 2.66 | 1 |
TABLE 18
| Compound No | Structure | [M + H]+ | RT | Method |
|---|---|---|---|---|
| I-086 | 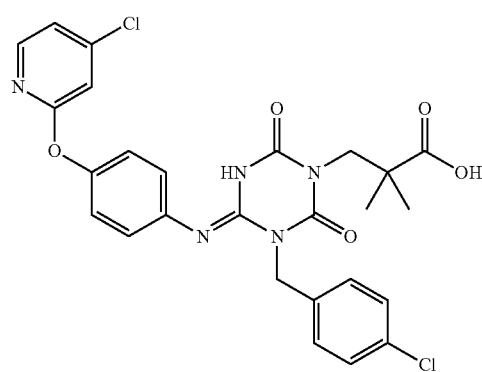 [SMILES: CC(C)(Cn1c(=O)[nH]/c(=N\c2ccc(Oc3cc(Cl)ccn3)cc2)n(Cc2ccc(Cl)cc2)c1=O)C(=O)O] | 556 | 2.33 | 1 |

TABLE 18-continued
| Compound No | Structure | [M + H]+ | RT | Method |
|---|---|---|---|---|
| I-087 | 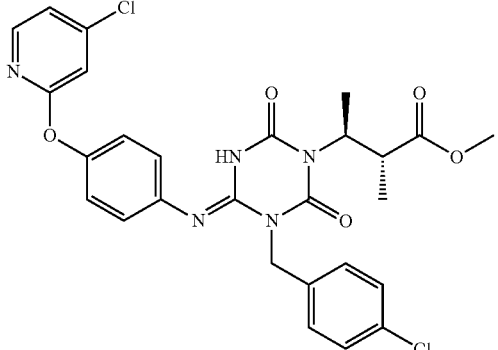 | 570 | 2.64 | 1 |
| I-088 | 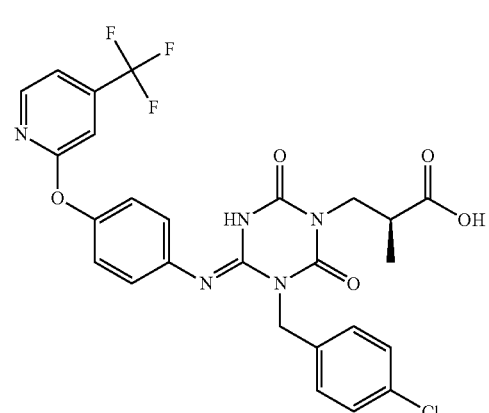 | 576 | 2.33 | 1 |
| I-089 | 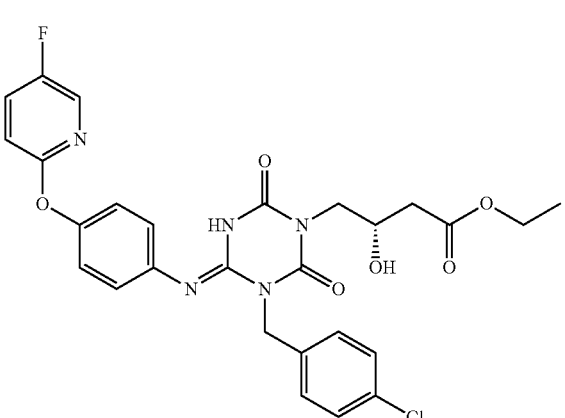 | 570 | 2.17 | 1 |
| I-090 | 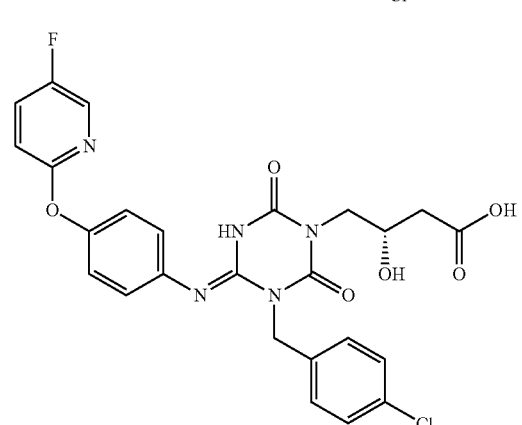 | 542 | 1.88 | 1 |

TABLE 19

| Compound No | Structure | [M + H]+ | RT | Method |
|---|---|---|---|---|
| I-091 | 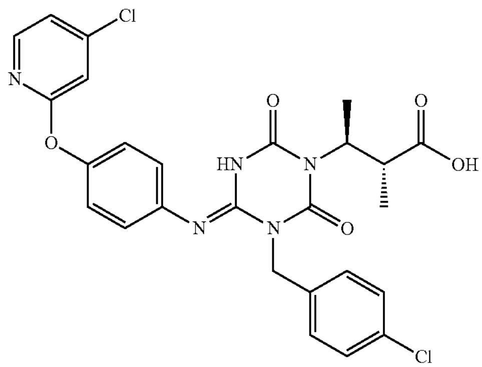 [SMILES: C[C@@H](C(=O)O)[C@H](C)n1c(=O)[nH]/c(=N\c2ccc(Oc3cc(Cl)ccn3)cc2)n(Cc2ccc(Cl)cc2)c1=O] | 556 | 2.37 | 1 |
| I-092 | 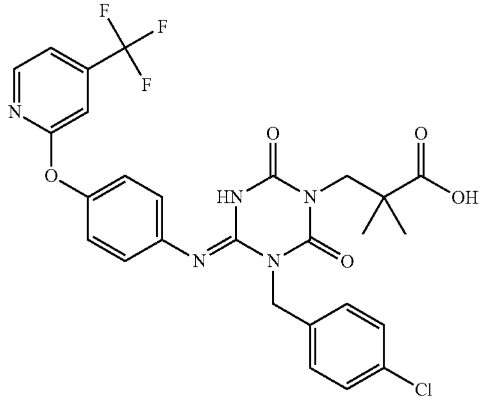 [SMILES: CC(C)(Cn1c(=O)[nH]/c(=N\c2ccc(Oc3cc(C(F)(F)F)ccn3)cc2)n(Cc2ccc(Cl)cc2)c1=O)C(=O)O] | 590 | 2.4 | 1 |
| I-093 | 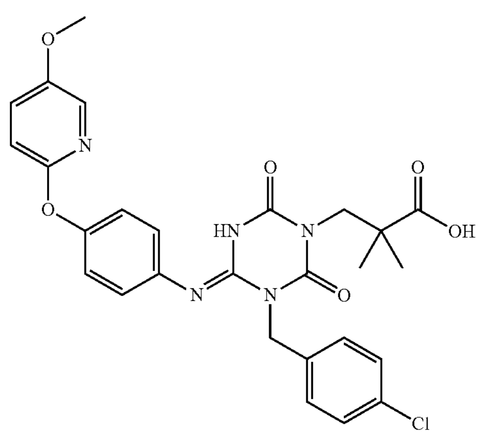 [SMILES: COc1ccc(Oc2ccc(/N=c3\[nH]c(=O)n(CC(C)(C)C(=O)O)c(=O)n3Cc3ccc(Cl)cc3)cc2)nc1] | 552 | 2.23 | 1 |

TABLE 19-continued
| Compound No | Structure | [M + H]+ | RT | Method |
|---|---|---|---|---|
| I-094 | 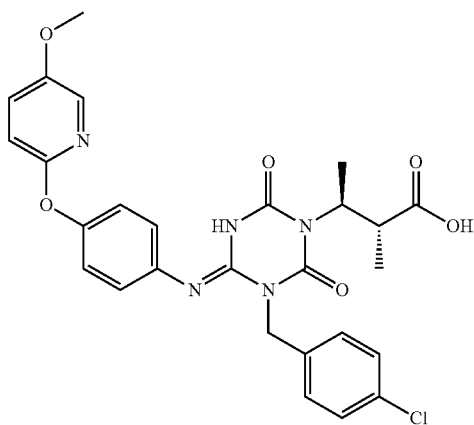 [SMILES: COc1ccc(Oc2ccc(/N=c3\[nH]c(=O)n([C@@H](C)[C@@H](C)C(=O)O)c(=O)n3Cc3ccc(Cl)cc3)cc2)nc1] | 552 | 2.26 | 1 |
| I-095 | 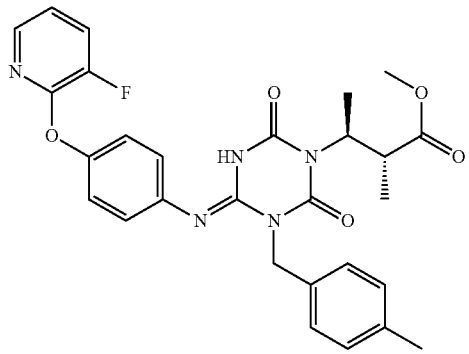 [SMILES: COC(=O)[C@H](C)[C@H](C)n1c(=O)[nH]/c(=N\c2ccc(Oc3ncccc3F)cc2)n(Cc2ccc(C)cc2)c1=O] | 534 | 2.39 | 1 |
TABLE 20
| Compound No | Structure | [M + H]+ | RT | Method |
|---|---|---|---|---|
| I-096 | 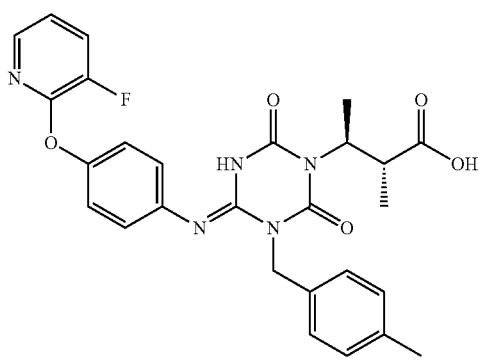 [SMILES: Cc1ccc(Cn2c(=O)n([C@@H](C)[C@@H](C)C(=O)O)c(=O)[nH]/c2=N\c2ccc(Oc3ncccc3F)cc2)cc1] | 520 | 2.11 | 1 |

TABLE 20-continued

| Compound No | Structure | [M + H]+ | RT | Method |
|---|---|---|---|---|
| I-097 | 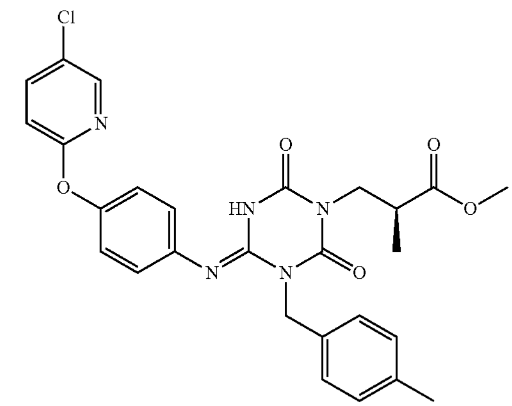 [SMILES: COC(=O)[C@@H](C)Cn1c(=O)[nH]/c(=N\c2ccc(Oc3ccc(Cl)cn3)cc2)n(Cc2ccc(C)cc2)c1=O] | 536 | 2.38 | 1 |
| I-098 | 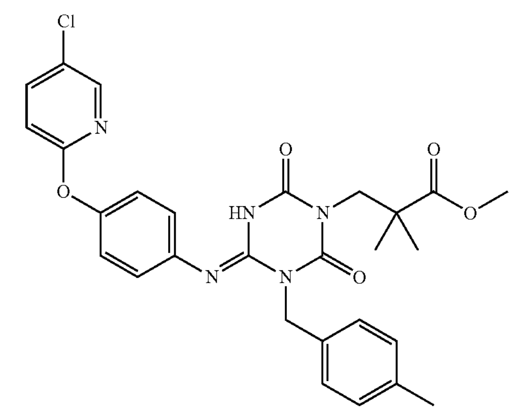 [SMILES: COC(=O)C(C)(C)Cn1c(=O)[nH]/c(=N\c2ccc(Oc3ccc(Cl)cn3)cc2)n(Cc2ccc(C)cc2)c1=O] | 550 | 2.49 | 1 |
| I-099 | 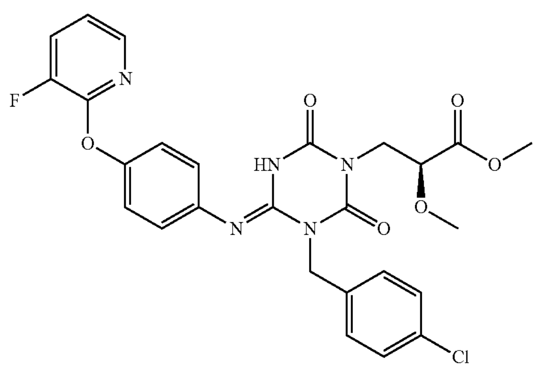 [SMILES: COC(=O)[C@H](Cn1c(=O)[nH]/c(=N\c2ccc(Oc3ncccc3F)cc2)n(Cc2ccc(Cl)cc2)c1=O)OC] | 556 | 2.23 | 1 |
| I-100 | 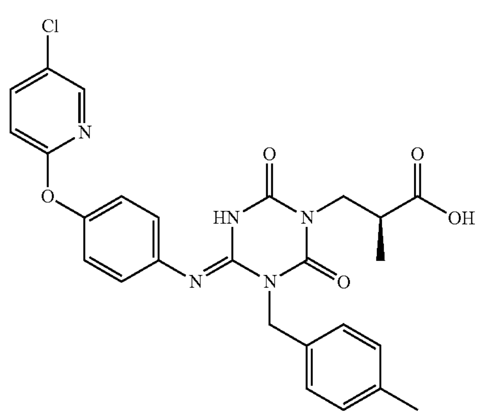 [SMILES: Cc1ccc(Cn2c(=O)n(C[C@H](C)C(=O)O)c(=O)[nH]/c2=N\c2ccc(Oc3ccc(Cl)cn3)cc2)cc1] | 522 | 2.15 | 1 |

TABLE 21

| Compound No | Structure | [M + H]+ | RT | Method |
|---|---|---|---|---|
| I-101 | 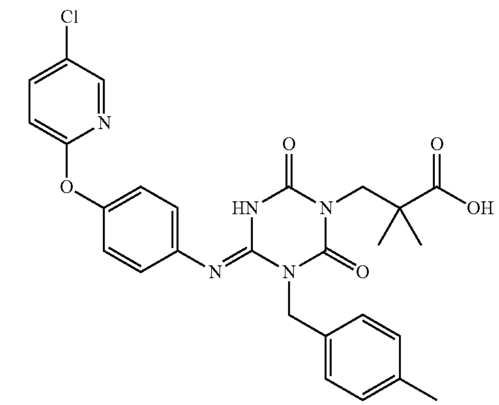 [SMILES: Cc1ccc(Cn2c(=O)n(CC(C)(C)C(=O)O)c(=O)[nH]/c2=N\c2ccc(Oc3ccc(Cl)cn3)cc2)cc1] | 536 | 2.22 | 1 |
| I-102 | 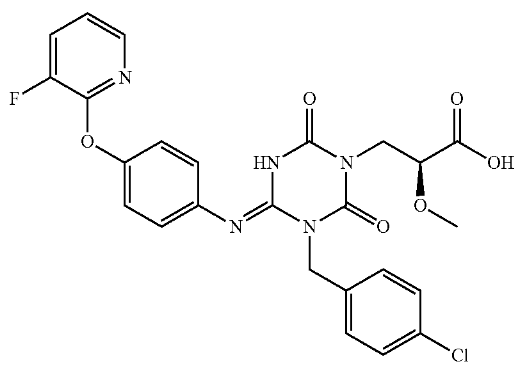 [SMILES: CO[C@@H](Cn1c(=O)[nH]/c(=N\c2ccc(Oc3ncccc3F)cc2)n(Cc2ccc(Cl)cc2)c1=O)C(=O)O] | 542 | 2.01 | 1 |
| I-103 | 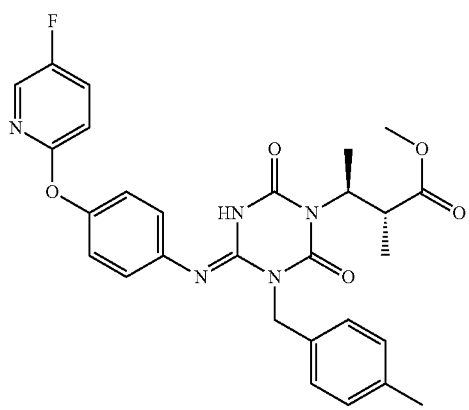 [SMILES: COC(=O)[C@H](C)[C@H](C)n1c(=O)[nH]/c(=N\c2ccc(Oc3ccc(F)cn3)cc2)n(Cc2ccc(C)cc2)c1=O] | 534 | 2.38 | 1 |
| I-104 | 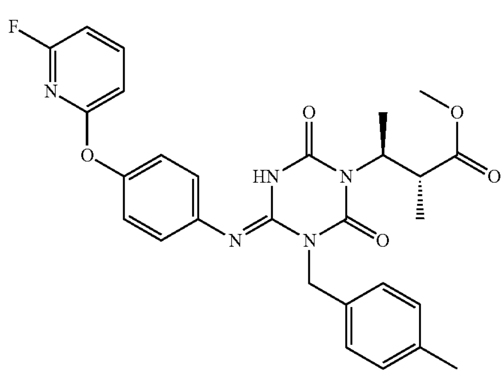 [SMILES: COC(=O)[C@H](C)[C@H](C)n1c(=O)[nH]/c(=N\c2ccc(Oc3cccc(F)n3)cc2)n(Cc2ccc(C)cc2)c1=O] | 534 | 2.41 | 1 |

TABLE 21-continued

| Compound No | Structure | [M + H]+ | RT | Method |
|---|---|---|---|---|
| I-105 | 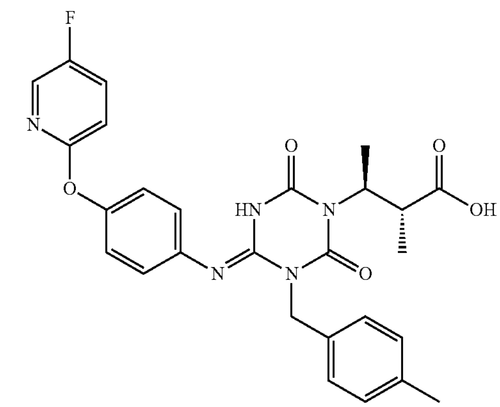 [SMILES: Cc1ccc(Cn2c(=O)n([C@@H](C)[C@@H](C)C(=O)O)c(=O)[nH]/c2=N\c2ccc(Oc3ccc(F)cn3)cc2)cc1] | 520 | 2.1 | 1 |

TABLE 22

| Compound No | Structure | [M + H]+ | RT | Method |
|---|---|---|---|---|
| I-106 | 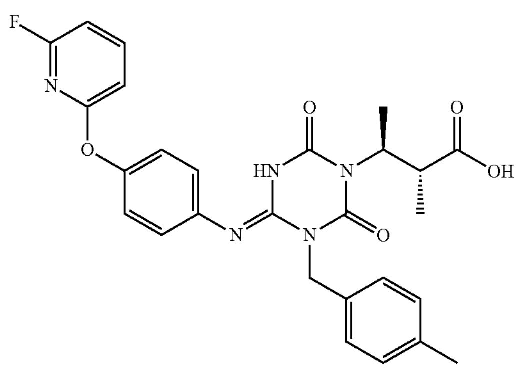 [SMILES: Cc1ccc(Cn2c(=O)n([C@@H](C)[C@@H](C)C(=O)O)c(=O)[nH]/c2=N\c2ccc(Oc3cccc(F)n3)cc2)cc1] | 520 | 2.13 | 1 |
| I-107 | 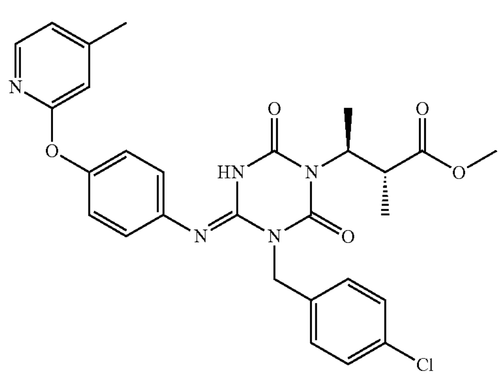 [SMILES: COC(=O)[C@H](C)[C@H](C)n1c(=O)[nH]/c(=N\c2ccc(Oc3cc(C)ccn3)cc2)n(Cc2ccc(Cl)cc2)c1=O] | 550 | 2.52 | 1 |

TABLE 22-continued

| Compound No | Structure | [M + H]+ | RT | Method |
|---|---|---|---|---|
| I-108 | 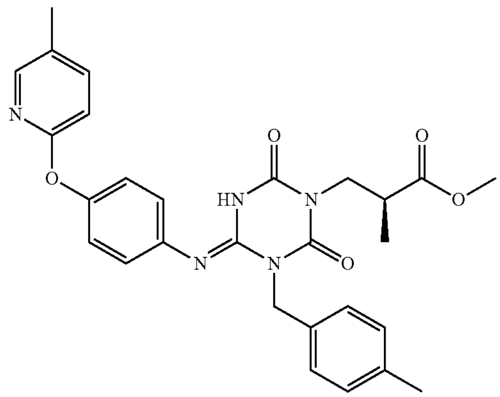 [SMILES: COC(=O)[C@@H](C)Cn1c(=O)[nH]/c(=N\c2ccc(Oc3ccc(C)cn3)cc2)n(Cc2ccc(C)cc2)c1=O] | 516 | 2.29 | 1 |
| I-109 | 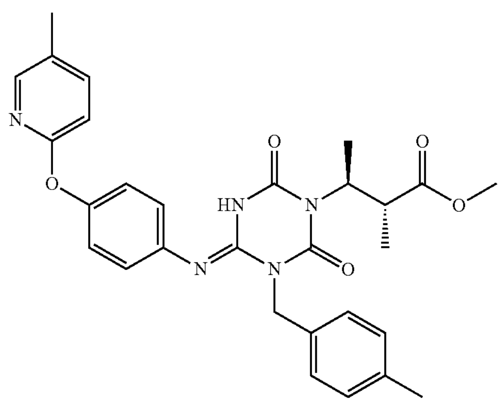 [SMILES: COC(=O)[C@H](C)[C@H](C)n1c(=O)[nH]/c(=N\c2ccc(Oc3ccc(C)cn3)cc2)n(Cc2ccc(C)cc2)c1=O] | 530 | 2.43 | 1 |
| I-110 | 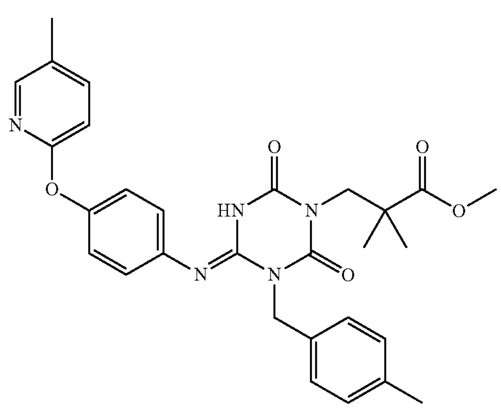 [SMILES: COC(=O)C(C)(C)Cn1c(=O)[nH]/c(=N\c2ccc(Oc3ccc(C)cn3)cc2)n(Cc2ccc(C)cc2)c1=O] | 530 | 2.4 | 1 |

TABLE 23

| Compound No | Structure | [M + H]+ | RT | Method |
|---|---|---|---|---|
| I-111 | 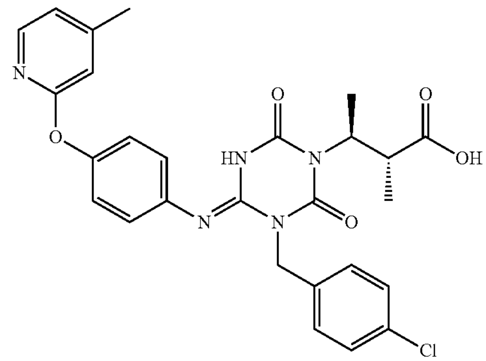 [SMILES: Cc1ccnc(Oc2ccc(/N=c3\[nH]c(=O)n([C@@H](C)[C@@H](C)C(=O)O)c(=O)n3Cc3ccc(Cl)cc3)cc2)c1] | 536 | 2.23 | 1 |
| I-112 | 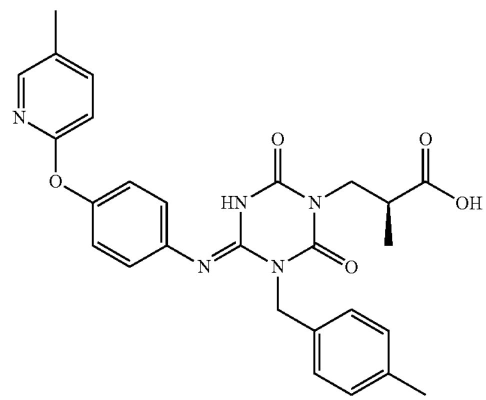 [SMILES: Cc1ccc(Cn2c(=O)n(C[C@H](C)C(=O)O)c(=O)[nH]/c2=N\c2ccc(Oc3ccc(C)cn3)cc2)cc1] | 502 | 2.04 | 1 |
| I-113 | 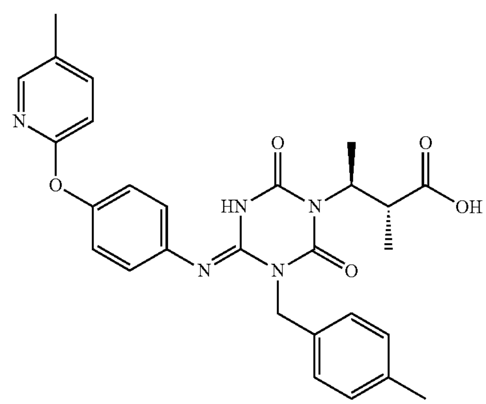 [SMILES: Cc1ccc(Cn2c(=O)n([C@@H](C)[C@@H](C)C(=O)O)c(=O)[nH]/c2=N\c2ccc(Oc3ccc(C)cn3)cc2)cc1] | 516 | 2.14 | 1 |
| I-114 | 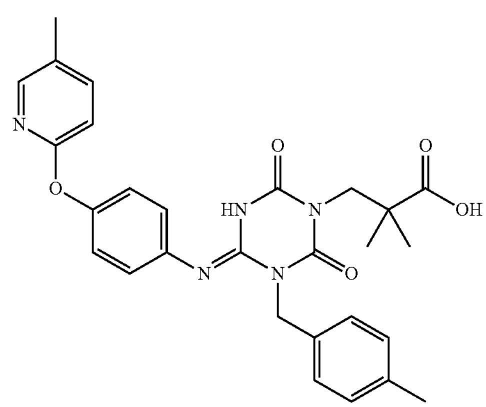 [SMILES: Cc1ccc(Cn2c(=O)n(CC(C)(C)C(=O)O)c(=O)[nH]/c2=N\c2ccc(Oc3ccc(C)cn3)cc2)cc1] | 516 | 2.12 | 1 |

TABLE 23-continued

| Compound No | Structure | [M + H]+ | RT | Method |
|---|---|---|---|---|
| I-115 | 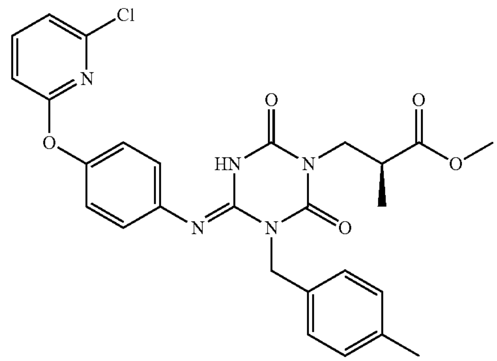 | 536 | 2.36 | 1 |

TABLE 24

| Compound No | Structure | [M + H]+ | RT | Method |
|---|---|---|---|---|
| I-116 | 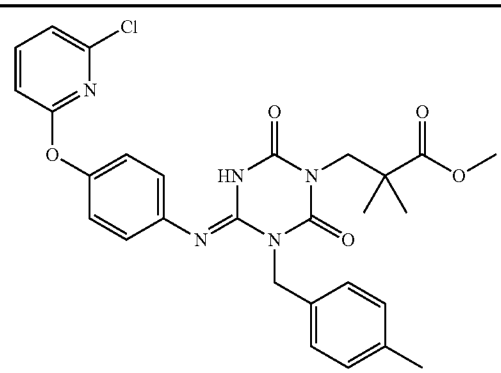 | 550 | 2.46 | 1 |
| I-117 | 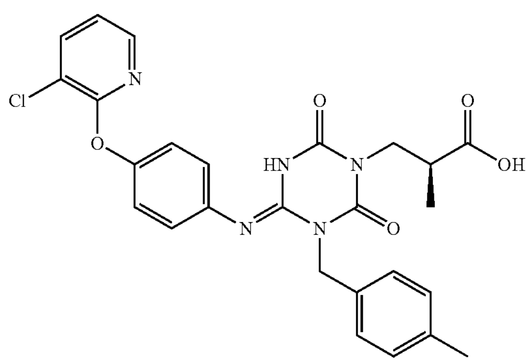 [SMILES: Cc1ccc(Cn2c(=O)n(C[C@H](C)C(=O)O)c(=O)[nH]/c2=N\c2ccc(Oc3ncccc3Cl)cc2)cc1] | 522 | 2.13 | 1 |
| I-118 | 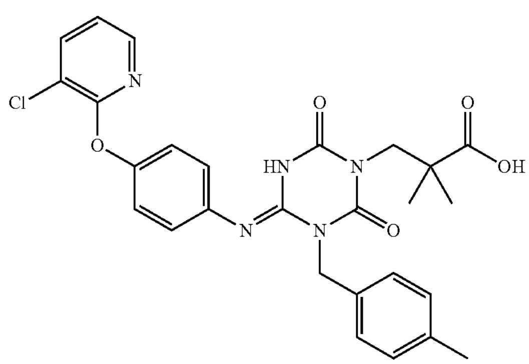 [SMILES: Cc1ccc(Cn2c(=O)n(CC(C)(C)C(=O)O)c(=O)[nH]/c2=N\c2ccc(Oc3ncccc3Cl)cc2)cc1] | 536 | 2.21 | 1 |

TABLE 24-continued
| Compound No | Structure | [M + H]+ | RT | Method |
|---|---|---|---|---|
| I-119 | 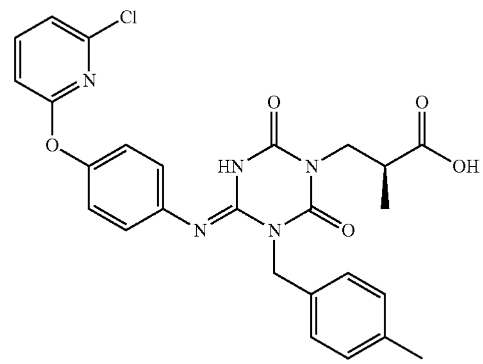 | 522 | 2.11 | 1 |
| I-120 | 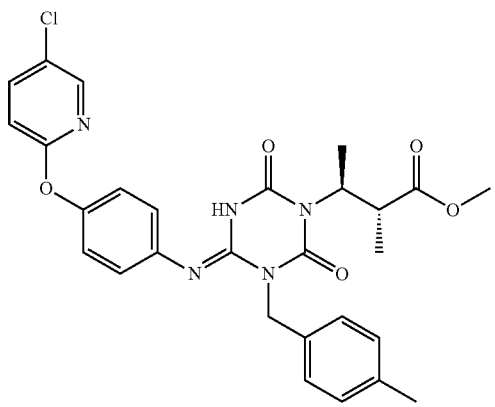 [SMILES: COC(=O)[C@H](C)[C@H](C)n1c(=O)[nH]/c(=N\c2ccc(Oc3ccc(Cl)cn3)cc2)n(Cc2ccc(C)cc2)c1=O] | 550 | 2.52 | 1 |
TABLE 25
| Compound No | Structure | [M + H]+ | RT | Method |
|---|---|---|---|---|
| I-121 | 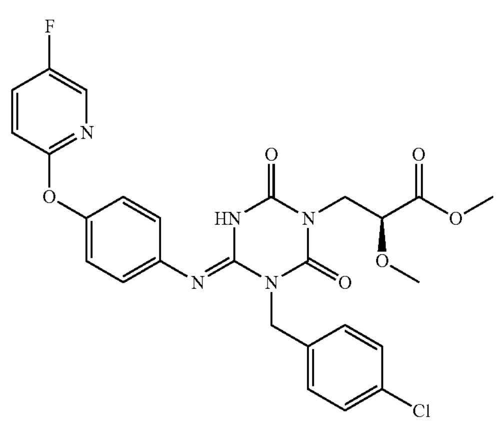 [SMILES: COC(=O)[C@H](Cn1c(=O)[nH]/c(=N\c2ccc(Oc3ccc(F)cn3)cc2)n(Cc2ccc(Cl)cc2)c1=O)OC] | 556 | 2.22 | 1 |

TABLE 25-continued

| Compound No | Structure | [M + H]+ | RT | Method |
|---|---|---|---|---|
| I-122 | 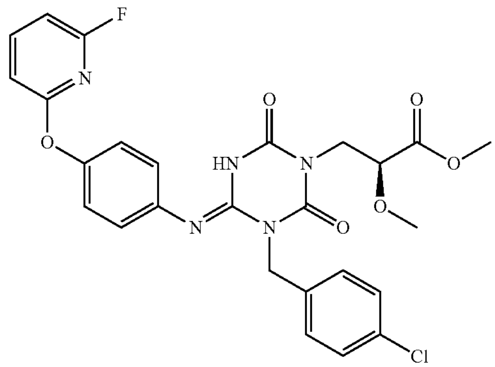 [SMILES: COC(=O)[C@H](Cn1c(=O)[nH]/c(=N\c2ccc(Oc3cccc(F)n3)cc2)n(Cc2ccc(Cl)cc2)c1=O)OC] | 556 | 2.24 | 1 |
| I-123 | 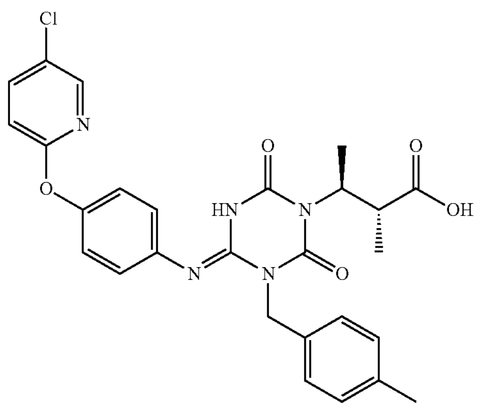 [SMILES: Cc1ccc(Cn2c(=O)n([C@@H](C)[C@@H](C)C(=O)O)c(=O)[nH]/c2=N\c2ccc(Oc3ccc(Cl)cn3)cc2)cc1] | 536 | 2.24 | 1 |
| I-124 | 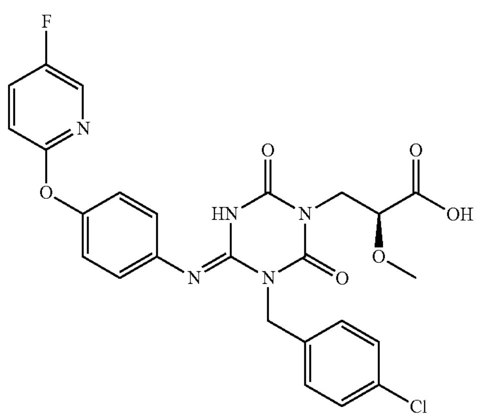 [SMILES: CO[C@@H](Cn1c(=O)[nH]/c(=N\c2ccc(Oc3ccc(F)cn3)cc2)n(Cc2ccc(Cl)cc2)c1=O)C(=O)O] | 542 | 1.99 | 1 |
| I-125 | 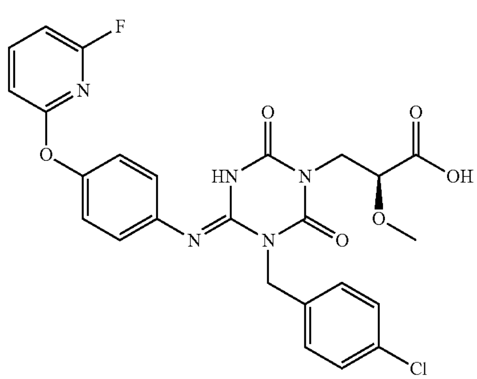 [SMILES: CO[C@@H](Cn1c(=O)[nH]/c(=N\c2ccc(Oc3cccc(F)n3)cc2)n(Cc2ccc(Cl)cc2)c1=O)C(=O)O] | 542 | 2.01 | 1 |

TABLE 26

| Compound No | Structure | [M + H]+ | RT | Method |
|---|---|---|---|---|
| I-126 | 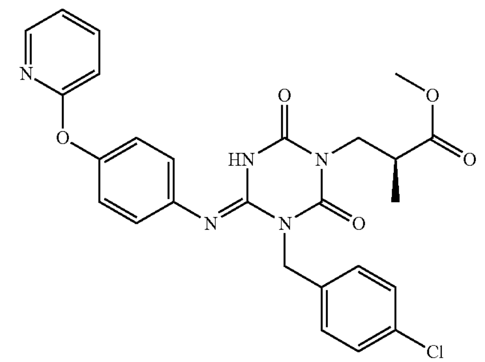 | 522 | 2.28 | 1 |
| I-127 | 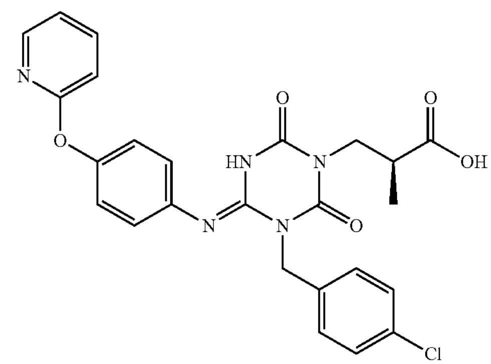 [SMILES: C[C@@H](Cn1c(=O)[nH]/c(=N\c2ccc(Oc3ccccn3)cc2)n(Cc2ccc(Cl)cc2)c1=O)C(=O)O] | 508 | 2.02 | 1 |
| I-128 | 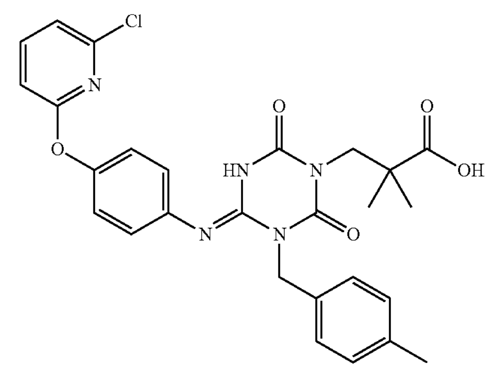 [SMILES: Cc1ccc(Cn2c(=O)n(CC(C)(C)C(=O)O)c(=O)[nH]/c2=N\c2ccc(Oc3cccc(Cl)n3)cc2)cc1] | 536 | 2.2 | 1 |
| I-129 | 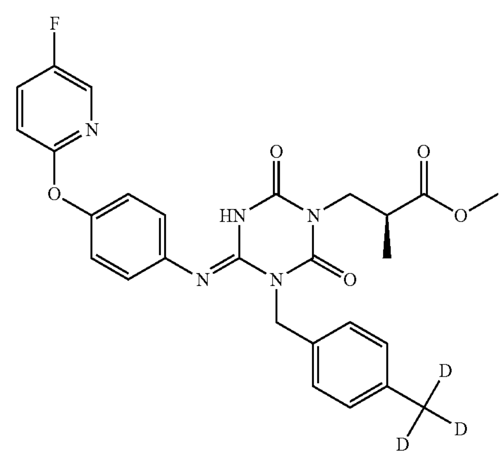 [SMILES: [2H]C([2H])([2H])c1ccc(Cn2c(=O)n(C[C@H](C)C(=O)OC)c(=O)[nH]/c2=N\c2ccc(Oc3ccc(F)cn3)cc2)cc1] | 523 | 2.24 | 1 |

TABLE 26-continued
| Compound No | Structure | [M + H]+ | RT | Method |
|---|---|---|---|---|
| I-130 | 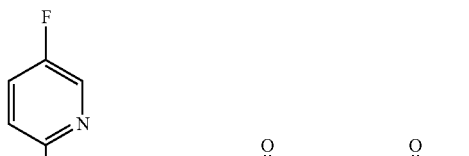 | 509 | 1.99 | 1 |
TABLE 27
| Compound No | Structure | [M + H]+ | RT | Method |
|---|---|---|---|---|
| I-131 | 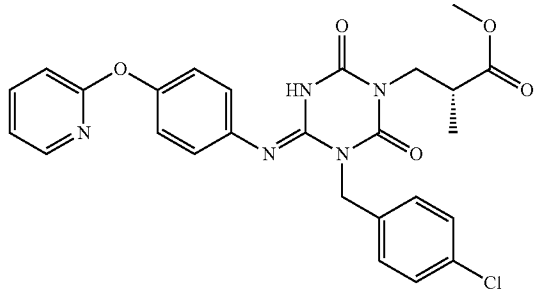 [SMILES: COC(=O)[C@H](C)Cn1c(=O)[nH]/c(=N\c2ccc(Oc3ccccn3)cc2)n(Cc2ccc(Cl)cc2)c1=O] | 522 | 2.27 | 1 |
| I-132 | 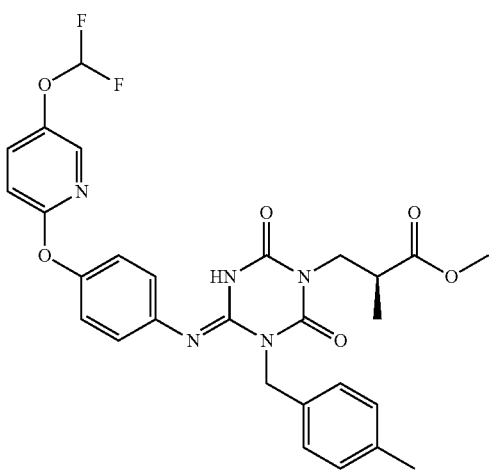 [SMILES: COC(=O)[C@@H](C)Cn1c(=O)[nH]/c(=N\c2ccc(Oc3ccc(OC(F)F)cn3)cc2)n(Cc2ccc(C)cc2)c1=O] | 568 | 2.32 | 1 |

TABLE 27-continued

| Compound No | Structure | [M + H]+ | RT | Method |
|---|---|---|---|---|
| I-133 | 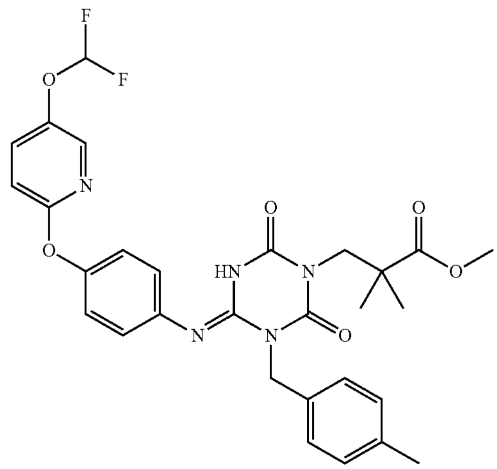 [SMILES: COC(=O)C(C)(C)Cn1c(=O)[nH]/c(=N\c2ccc(Oc3ccc(OC(F)F)cn3)cc2)n(Cc2ccc(C)cc2)c1=O] | 582 | 2.42 | 1 |
| I-134 | 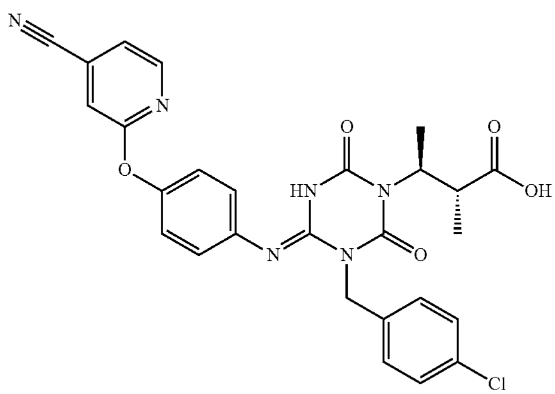 | 547 | 2.16 | 1 |
| I-135 | 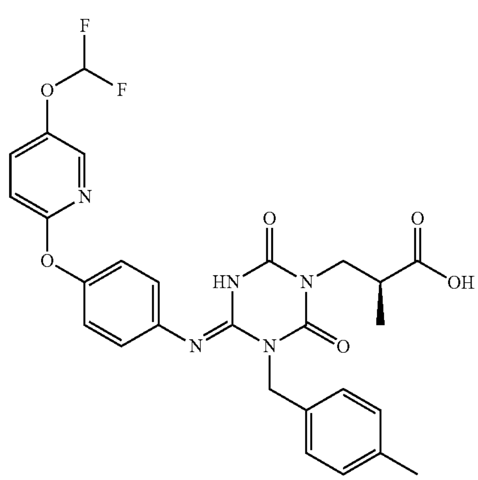 [SMILES: Cc1ccc(Cn2c(=O)n(C[C@H](C)C(=O)O)c(=O)[nH]/c2=N\c2ccc(Oc3ccc(OC(F)F)cn3)cc2)cc1] | 554 | 2.08 | 1 |

TABLE 28

| Compound No | Structure | [M + H]+ | RT | Method |
|---|---|---|---|---|
| I-136 | 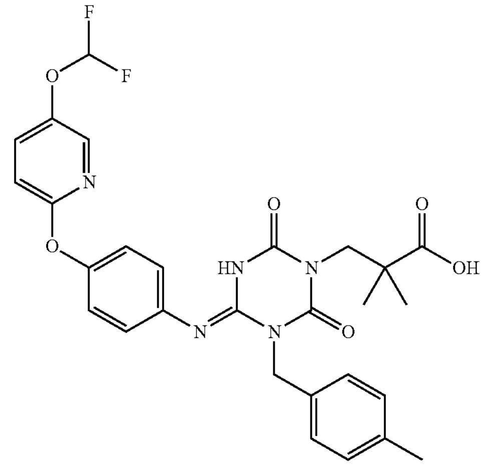 [SMILES: Cc1ccc(Cn2c(=O)n(CC(C)(C)C(=O)O)c(=O)[nH]/c2=N\c2ccc(Oc3ccc(OC(F)F)cn3)cc2)cc1] | 568 | 2.15 | 1 |
| I-137 | 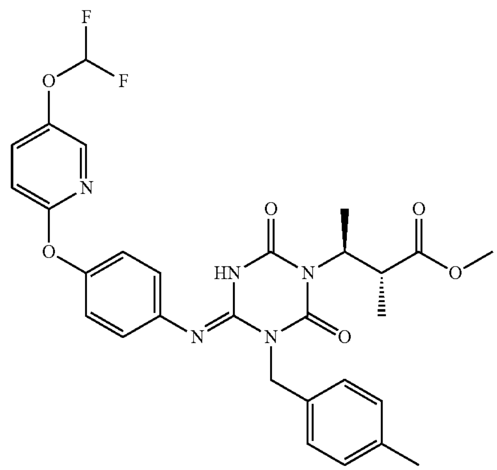 [SMILES: COC(=O)[C@H](C)[C@H](C)n1c(=O)[nH]/c(=N\c2ccc(Oc3ccc(OC(F)F)cn3)cc2)n(Cc2ccc(C)cc2)c1=O] | 582 | 2.43 | 1 |
| I-138 | 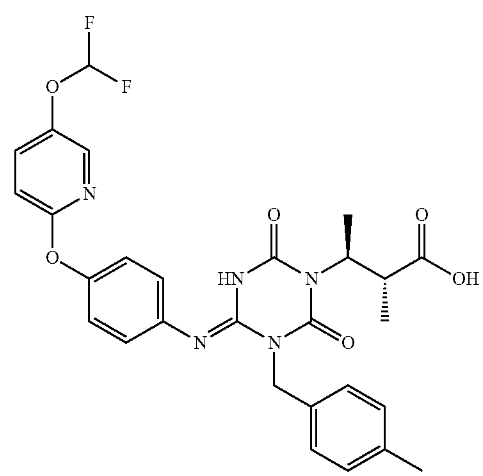 [SMILES: Cc1ccc(Cn2c(=O)n([C@@H](C)[C@@H](C)C(=O)O)c(=O)[nH]/c2=N\c2ccc(Oc3ccc(OC(F)F)cn3)cc2)cc1] | 568 | 2.16 | 1 |

TABLE 28-continued

| Compound No | Structure | [M + H]+ | RT | Method |
|---|---|---|---|---|
| I-139 | 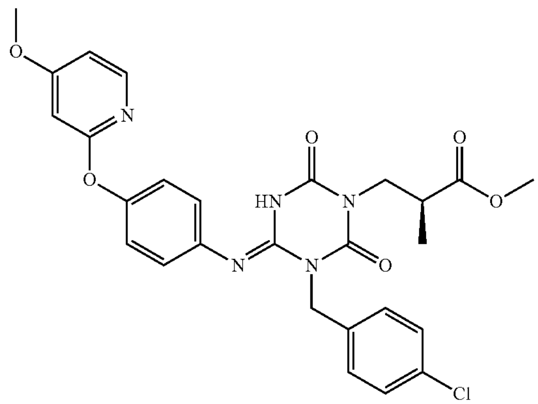 [SMILES: COC(=O)[C@@H](C)Cn1c(=O)[nH]/c(=N\c2ccc(Oc3cc(OC)ccn3)cc2)n(Cc2ccc(Cl)cc2)c1=O] | 552 | 2.29 | 1 |
| I-140 | 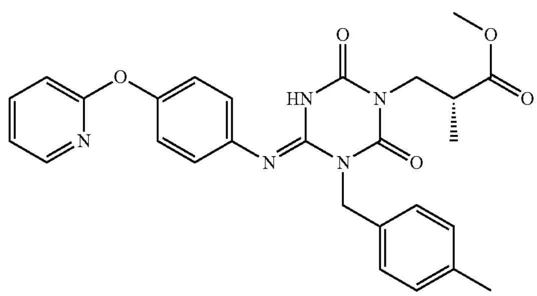 [SMILES: COC(=O)[C@H](C)Cn1c(=O)[nH]/c(=N\c2ccc(Oc3ccccn3)cc2)n(Cc2ccc(C)cc2)c1=O] | 502 | 2.19 | 1 |

TABLE 29

| Compound No | Structure | [M + H]+ | RT | Method |
|---|---|---|---|---|
| I-141 | 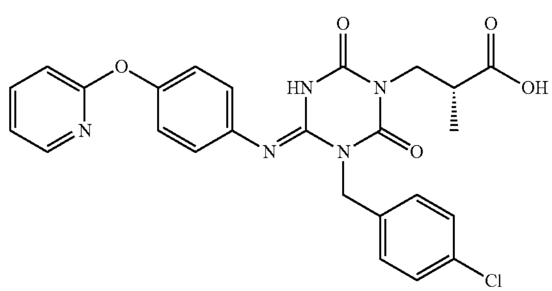 [SMILES: C[C@H](Cn1c(=O)[nH]/c(=N\c2ccc(Oc3ccccn3)cc2)n(Cc2ccc(Cl)cc2)c1=O)C(=O)O] | 508 | 2.02 | 1 |
| I-142 | 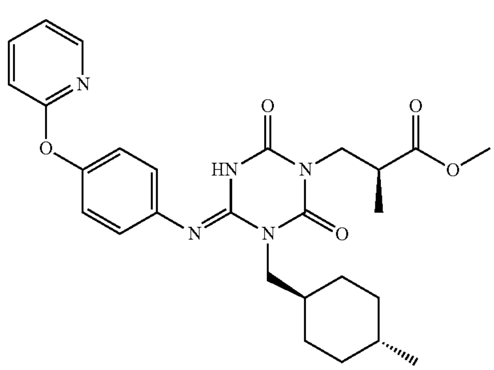 [SMILES: COC(=O)[C@@H](C)Cn1c(=O)[nH]/c(=N\c2ccc(Oc3ccccn3)cc2)n(C[C@H]2CC[C@H](C)CC2)c1=O] | 508 | 2.42 | 1 |

TABLE 29-continued

| Compound No | Structure | [M + H]+ | RT | Method |
|---|---|---|---|---|
| I-143 | 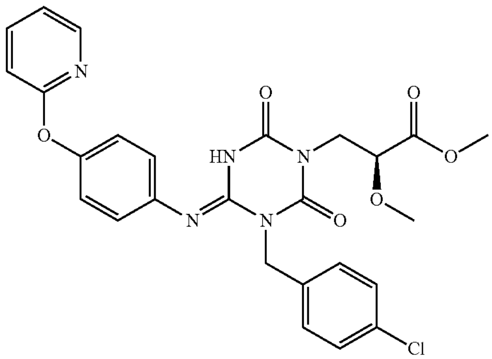 [SMILES: COC(=O)[C@H](Cn1c(=O)[nH]/c(=N\c2ccc(Oc3ccccn3)cc2)n(Cc2ccc(Cl)cc2)c1=O)OC] | 538 | 2.16 | 1 |
| I-144 | 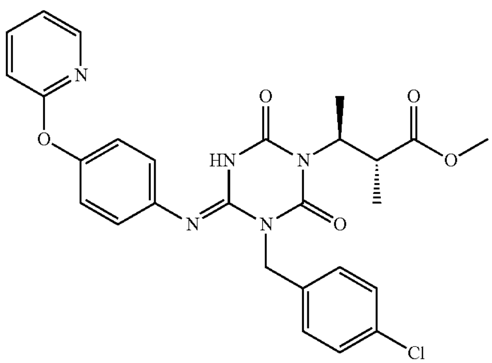 [SMILES: COC(=O)[C@H](C)[C@H](C)n1c(=O)[nH]/c(=N\c2ccc(Oc3ccccn3)cc2)n(Cc2ccc(Cl)cc2)c1=O] | 536 | 2.43 | 1 |
| I-145 | 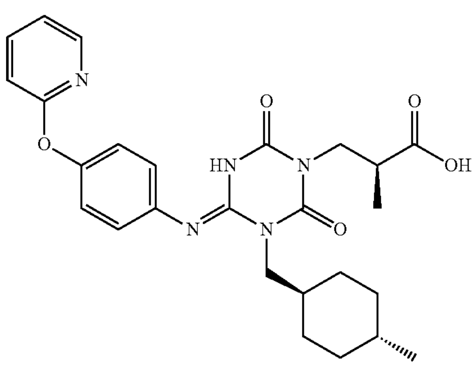 [SMILES: C[C@@H](Cn1c(=O)[nH]/c(=N\c2ccc(Oc3ccccn3)cc2)n(C[C@H]2CC[C@H](C)CC2)c1=O)C(=O)O] | 494 | 2.14 | 1 |

TABLE 30

| Compound No | Structure | [M + H]+ | RT | Method |
|---|---|---|---|---|
| I-146 | 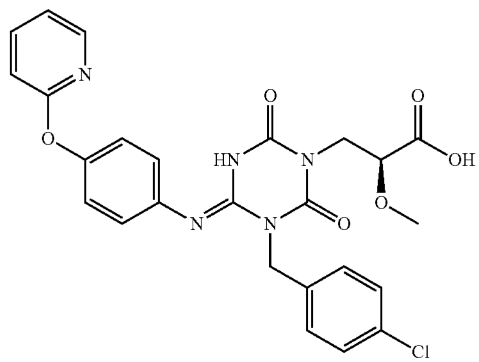 [SMILES: CO[C@@H](Cn1c(=O)[nH]/c(=N\c2ccc(Oc3ccccn3)cc2)n(Cc2ccc(Cl)cc2)c1=O)C(=O)O] | 524 | 1.94 | 1 |
| I-147 | 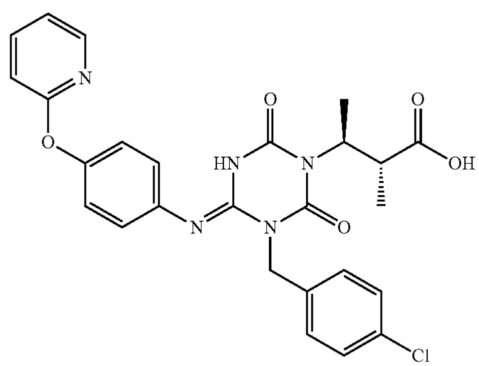 [SMILES: C[C@@H](C(=O)O)[C@H](C)n1c(=O)[nH]/c(=N\c2ccc(Oc3ccccn3)cc2)n(Cc2ccc(Cl)cc2)c1=O] | 522 | 2.12 | 1 |
| I-148 | 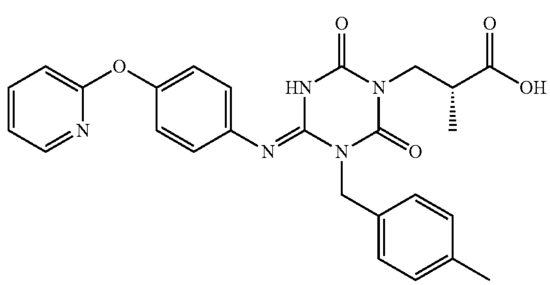 [SMILES: Cc1ccc(Cn2c(=O)n(C[C@@H](C)C(=O)O)c(=O)[nH]/c2=N\c2ccc(Oc3ccccn3)cc2)cc1] | 488 | 1.94 | 1 |
| I-149 | 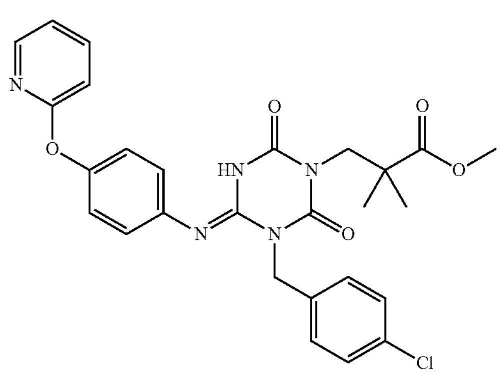 [SMILES: COC(=O)C(C)(C)Cn1c(=O)[nH]/c(=N\c2ccc(Oc3ccccn3)cc2)n(Cc2ccc(Cl)cc2)c1=O] | 536 | 2.39 | 1 |

TABLE 30-continued

| Compound No | Structure | [M + H]+ | RT | Method |
|---|---|---|---|---|
| I-150 | 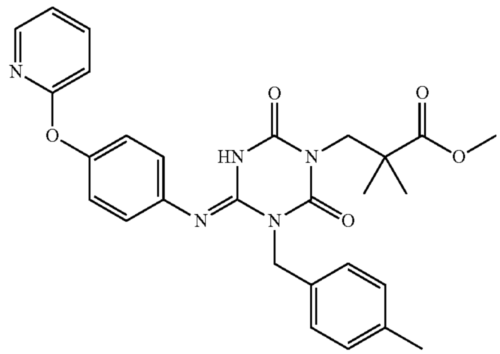 [SMILES: COC(=O)C(C)(C)Cn1c(=O)[nH]/c(=N\c2ccc(Oc3ccccn3)cc2)n(Cc2ccc(C)cc2)c1=O] | 516 | 2.3 | 1 |

TABLE 31

| Compound No | Structure | [M + H]+ | RT | Method |
|---|---|---|---|---|
| I-151 | 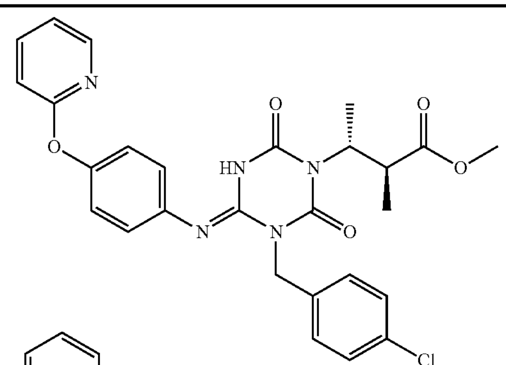 | 536 | 2.42 | 1 |
| I-152 | 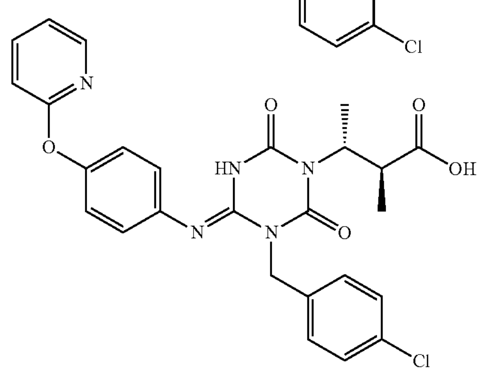 | 522 | 2.14 | 1 |
| I-153 | 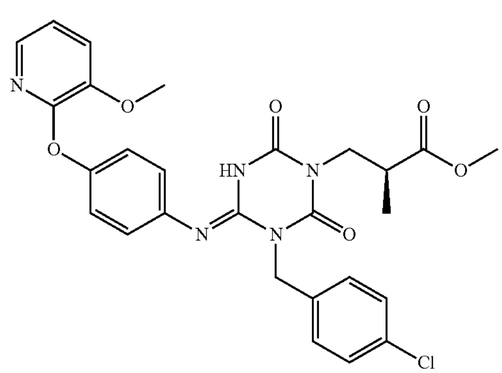 [SMILES: COC(=O)[C@@H](C)Cn1c(=O)[nH]/c(=N\c2ccc(Oc3ncccc3OC)cc2)n(Cc2ccc(Cl)cc2)c1=O] | 552 | 2.22 | 1 |

TABLE 31-continued
| Compound No | Structure | [M + H]+ | RT | Method |
|---|---|---|---|---|
| I-154 | 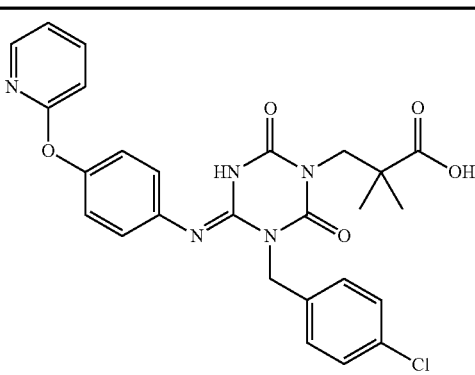 | 522 | 2.11 | 1 |
| I-155 | 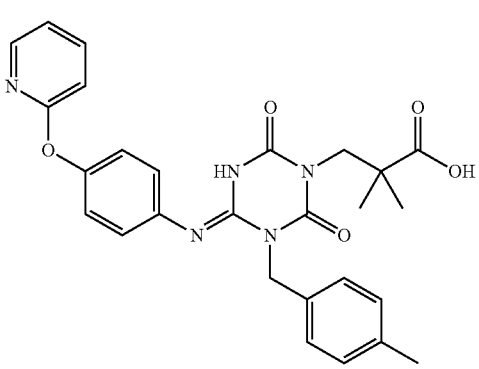 [SMILES: Cc1ccc(Cn2c(=O)n(CC(C)(C)C(=O)O)c(=O)[nH]/c2=N\c2ccc(Oc3ccccn3)cc2)cc1] | 502 | 2.02 | 1 |
TABLE 32
| Compound No | Structure | [M + H]+ | RT | Method |
|---|---|---|---|---|
| I-156 | 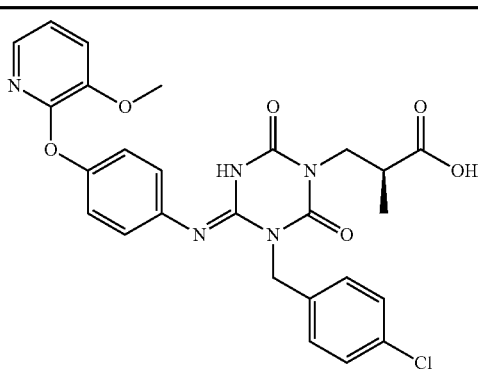 | 538 | 1.98 | 1 |
| I-157 | 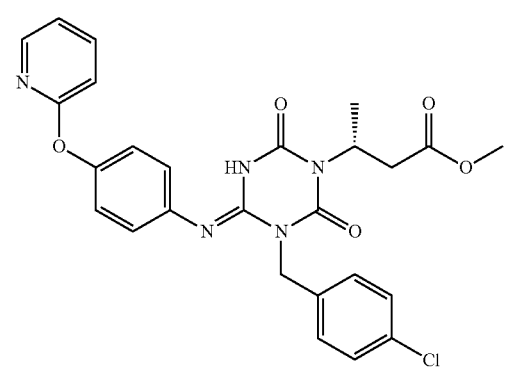 | 522 | 2.32 | 1 |

TABLE 32-continued
| Compound No | Structure | [M + H]+ | RT | Method |
|---|---|---|---|---|
| I-158 | 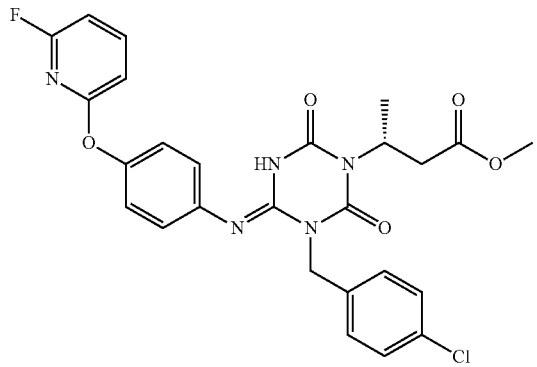 [SMILES: COC(=O)C[C@@H](C)n1c(=O)[nH]/c(=N\c2ccc(Oc3cccc(F)n3)cc2)n(Cc2ccc(Cl)cc2)c1=O] | 540 | 2.4 | 1 |
| I-159 | 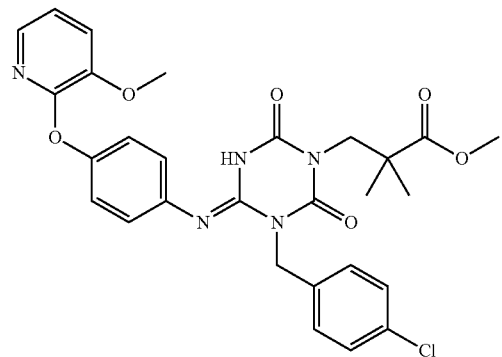 [SMILES: COC(=O)C(C)(C)Cn1c(=O)[nH]/c(=N\c2ccc(Oc3ncccc3OC)cc2)n(Cc2ccc(Cl)cc2)c1=O] | 566 | 2.35 | 1 |
| I-160 | 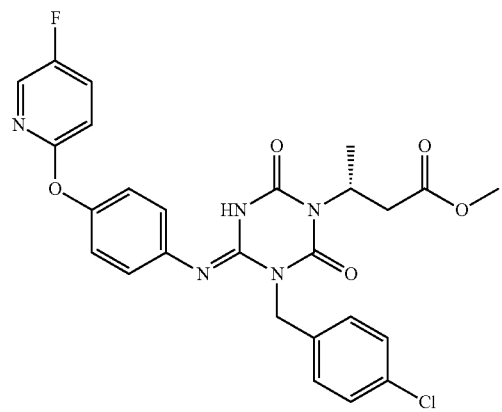 [SMILES: COC(=O)C[C@@H](C)n1c(=O)[nH]/c(=N\c2ccc(Oc3ccc(F)cn3)cc2)n(Cc2ccc(Cl)cc2)c1=O] | 540 | 2.38 | 1 |

TABLE 33
| Compound No | Structure | [M + H]+ | RT | Method |
|---|---|---|---|---|
| I-161 | 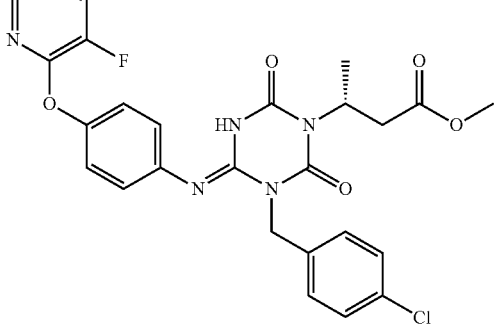 | 540 | 2.39 | 1 |
| I-162 | 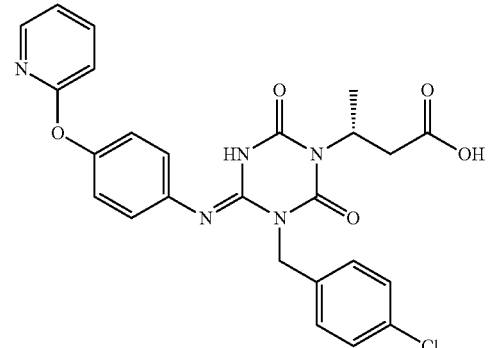 | 506 | 2.06 | 1 |
| I-163 | 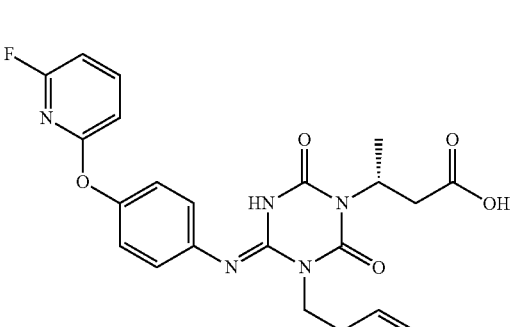 | 526 | 2.14 | 1 |
| I-164 | 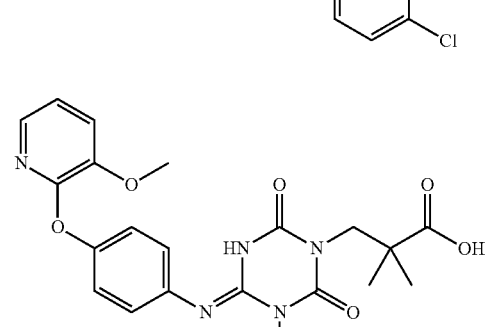 | 552 | 2.07 | 1 |

TABLE 33-continued
| Compound No | Structure | [M + H]+ | RT | Method |
|---|---|---|---|---|
| I-165 | 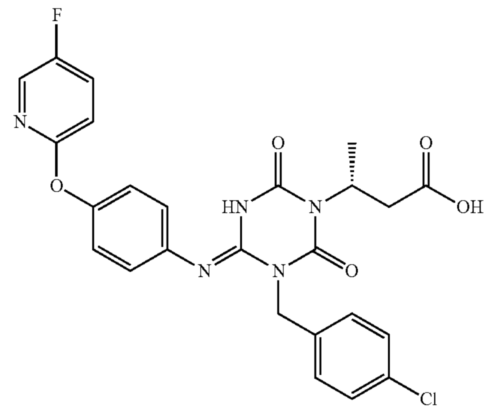 [SMILES: C[C@H](CC(=O)O)n1c(=O)[nH]/c(=N\c2ccc(Oc3ccc(F)cn3)cc2)n(Cc2ccc(Cl)cc2)c1=O] | 526 | 2.12 | 1 |
TABLE 34
| Compound No | Structure | [M + H]+ | RT | Method |
|---|---|---|---|---|
| I-166 | 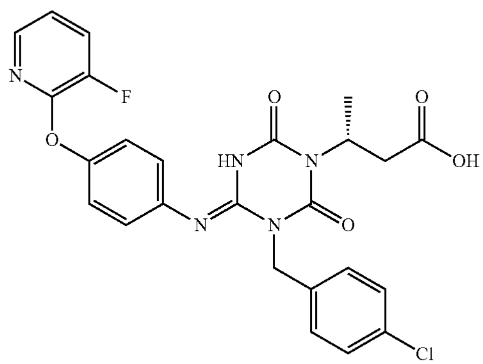 [SMILES: C[C@H](CC(=O)O)n1c(=O)[nH]/c(=N\c2ccc(Oc3ncccc3F)cc2)n(Cc2ccc(Cl)cc2)c1=O] | 526 | 2.13 | 1 |
| I-167 | 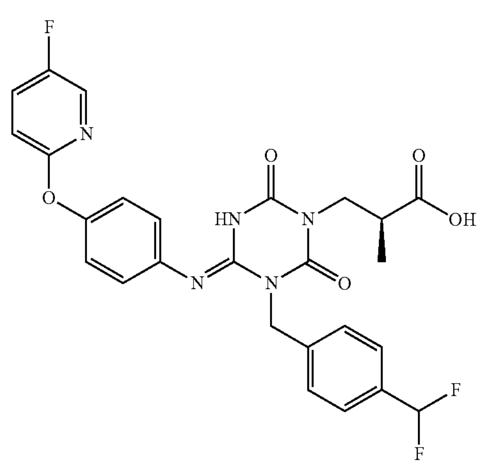 [SMILES: C[C@@H](Cn1c(=O)[nH]/c(=N\c2ccc(Oc3ccc(F)cn3)cc2)n(Cc2ccc(C(F)F)cc2)c1=O)C(=O)O] | 542 | 1.97 | 1 |
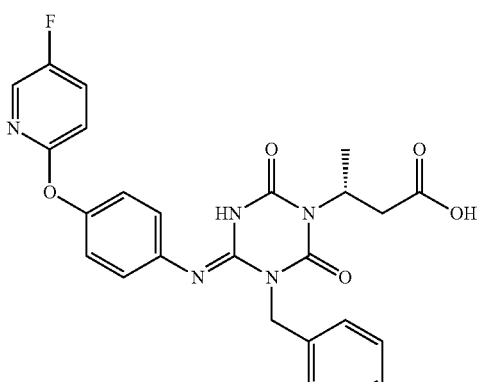

TABLE 34-continued
| Compound No | Structure | [M + H]+ | RT | Method |
|---|---|---|---|---|
| I-168 | 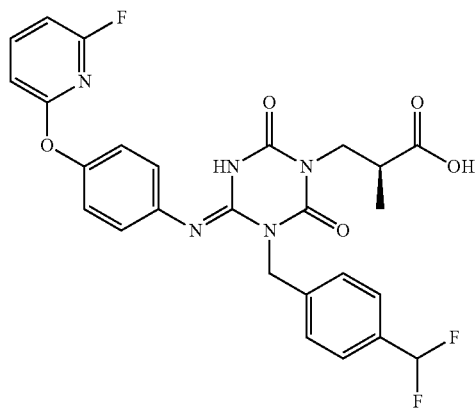 [SMILES: C[C@@H](Cn1c(=O)[nH]/c(=N\c2ccc(Oc3cccc(F)n3)cc2)n(Cc2ccc(C(F)F)cc2)c1=O)C(=O)O] | 542 | 1.99 | 1 |
| I-169 | 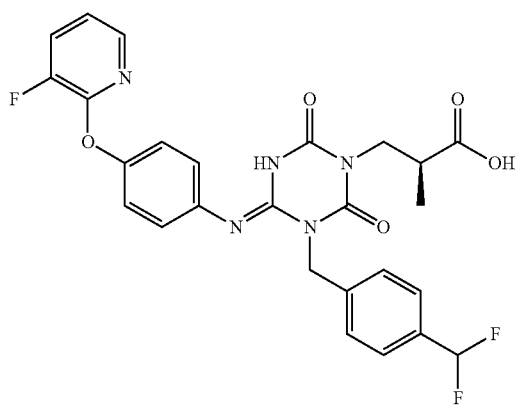 [SMILES: C[C@@H](Cn1c(=O)[nH]/c(=N\c2ccc(Oc3ncccc3F)cc2)n(Cc2ccc(C(F)F)cc2)c1=O)C(=O)O] | 542 | 1.98 | 1 |
| I-170 | 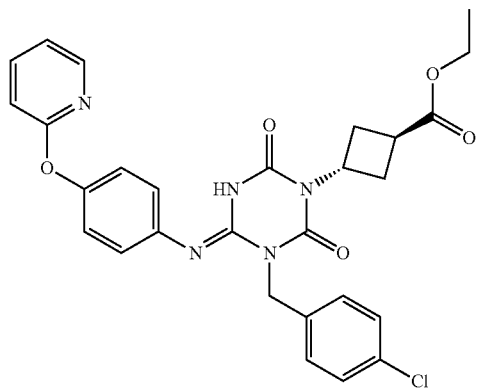 [SMILES: CCOC(=O)[C@H]1C[C@H](n2c(=O)[nH]/c(=N\c3ccc(Oc4ccccn4)cc3)n(Cc3ccc(Cl)cc3)c2=O)C1] | 548 | 2.49 | 1 |

TABLE 35

| Compound No | Structure | [M + H]+ | RT | Method |
|---|---|---|---|---|
| I-171 | 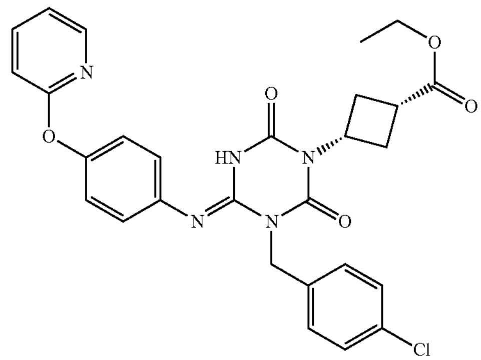 [SMILES: CCOC(=O)[C@H]1C[C@@H](n2c(=O)[nH]/c(=N\c3ccc(Oc4ccccn4)cc3)n(Cc3ccc(Cl)cc3)c2=O)C1] | 548 | 2.43 | 1 |
| I-172 | 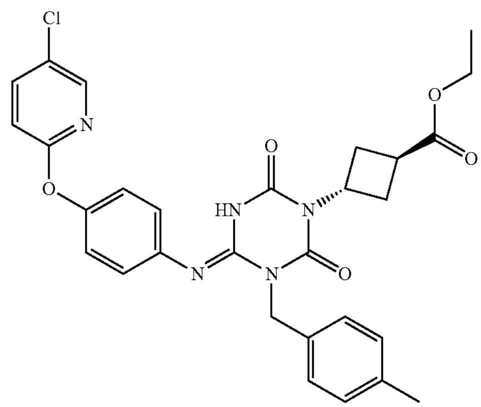 | 562 | 2.6 | 1 |
| I-173 | 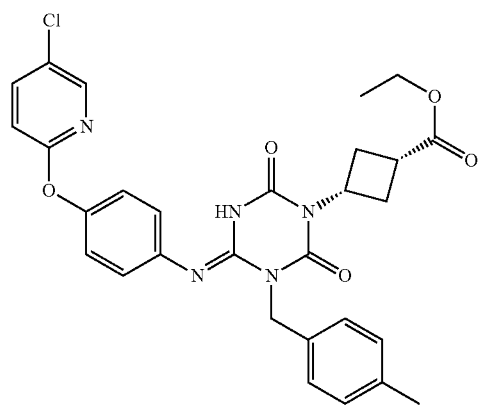 | 562 | 2.54 | 1 |
| I-174 | 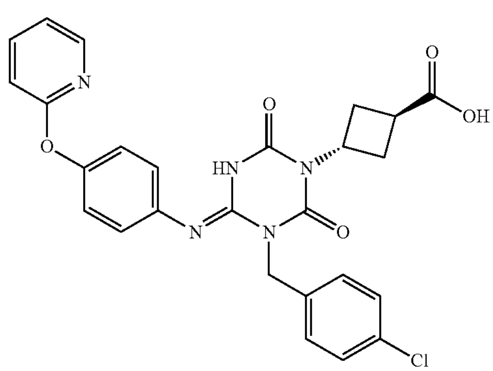 [SMILES: O=c1[nH]/c(=N\c2ccc(Oc3ccccn3)cc2)n(Cc2ccc(Cl)cc2)c(=O)n1[C@H]1C[C@H](C(=O)O)C1] | 520 | 2.1 | 1 |

TABLE 35-continued
| Compound No | Structure | [M + H]+ | RT | Method |
|---|---|---|---|---|
| I-175 | 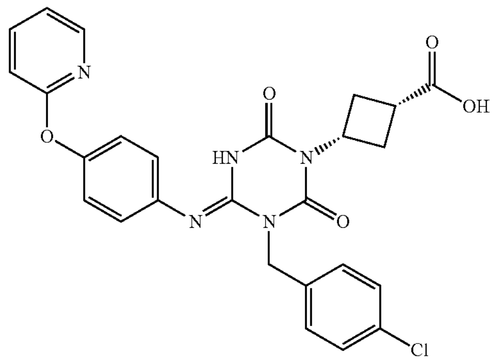 [SMILES: O=c1[nH]/c(=N\c2ccc(Oc3ccccn3)cc2)n(Cc2ccc(Cl)cc2)c(=O)n1[C@H]1C[C@@H](C(=O)O)C1] | 520 | 2.04 | 1 |
TABLE 36
| Compound No | Structure | [M + H]+ | RT | Method |
|---|---|---|---|---|
| I-176 | 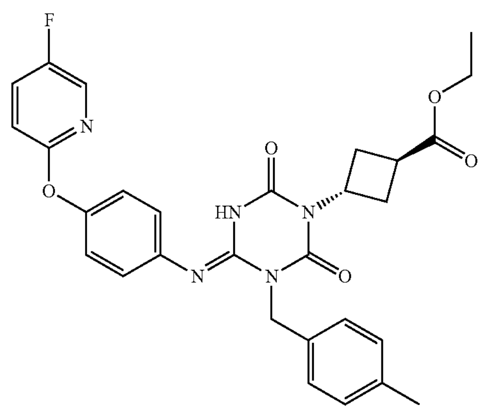 [SMILES: CCOC(=O)[C@H]1C[C@H](n2c(=O)[nH]/c(=N\c3ccc(Oc4ccc(F)cn4)cc3)n(Cc3ccc(C)cc3)c2=O)C1] | 546 | 2.47 | 1 |
| I-177 | 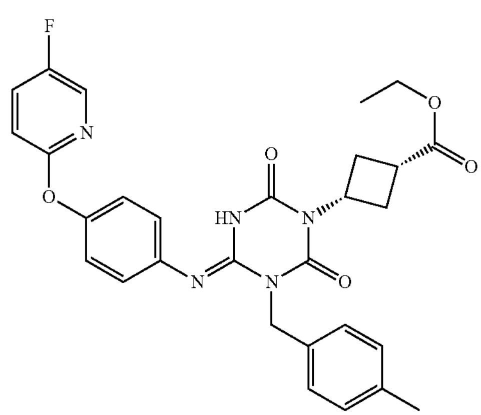 [SMILES: CCOC(=O)[C@H]1C[C@@H](n2c(=O)[nH]/c(=N\c3ccc(Oc4ccc(F)cn4)cc3)n(Cc3ccc(C)cc3)c2=O)C1] | 546 | 2.41 | 1 |
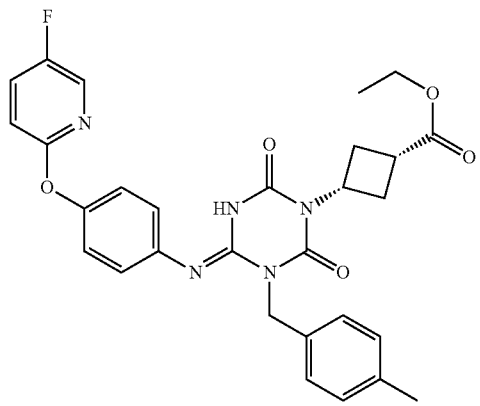

TABLE 36-continued
| Compound No | Structure | [M + H]+ | RT | Method |
|---|---|---|---|---|
| I-178 | 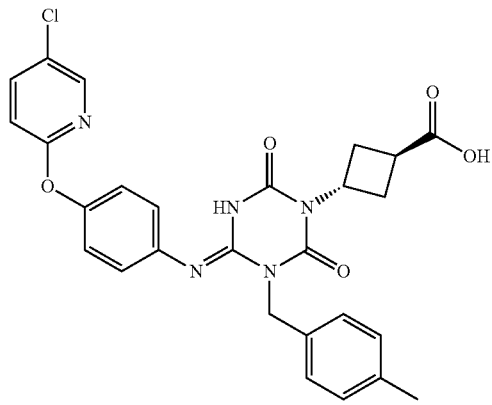 [SMILES: Cc1ccc(Cn2c(=O)n([C@H]3C[C@H](C(=O)O)C3)c(=O)[nH]/c2=N\c2ccc(Oc3ccc(Cl)cn3)cc2)cc1] | 534 | 2.22 | 1 |
| I-179 | 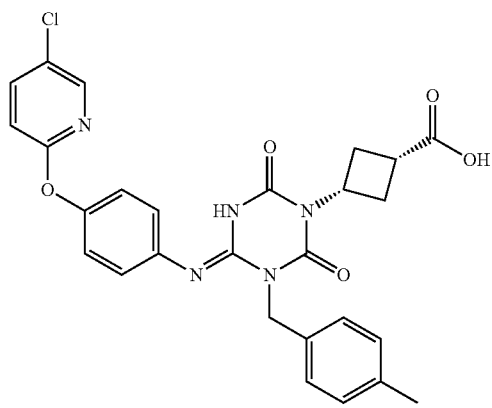 [SMILES: Cc1ccc(Cn2c(=O)n([C@H]3C[C@@H](C(=O)O)C3)c(=O)[nH]/c2=N\c2ccc(Oc3ccc(Cl)cn3)cc2)cc1] | 534 | 2.17 | 1 |
| I-180 | 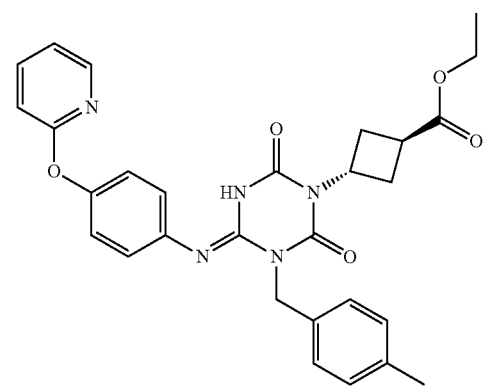 [SMILES: CCOC(=O)[C@H]1C[C@H](n2c(=O)[nH]/c(=N\c3ccc(Oc4ccccn4)cc3)n(Cc3ccc(C)cc3)c2=O)C1] | 528 | 2.42 | 1 |

TABLE 37

| Compound No | Structure | [M + H]+ | RT | Method |
|---|---|---|---|---|
| I-181 | 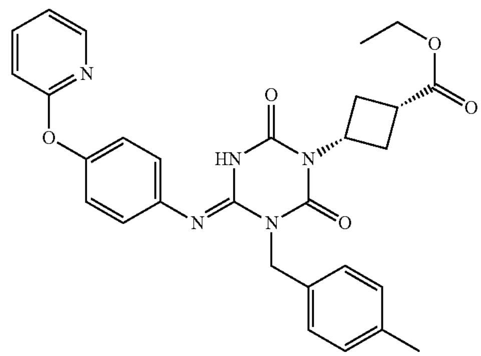 [SMILES: CCOC(=O)[C@H]1C[C@@H](n2c(=O)[nH]/c(=N\c3ccc(Oc4ccccn4)cc3)n(Cc3ccc(C)cc3)c2=O)C1] | 528 | 2.35 | 1 |
| I-182 | 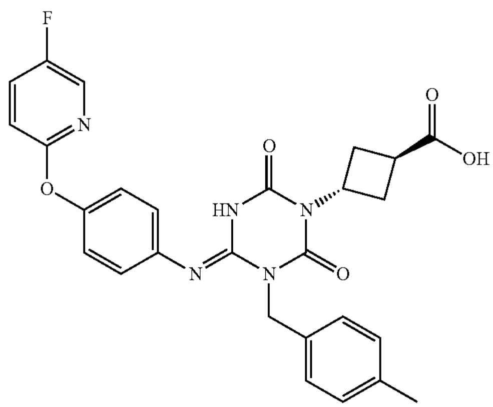 [SMILES: Cc1ccc(Cn2c(=O)n([C@H]3C[C@H](C(=O)O)C3)c(=O)[nH]/c2=N\c2ccc(Oc3ccc(F)cn3)cc2)cc1] | 518 | 2.07 | 1 |
| I-183 | 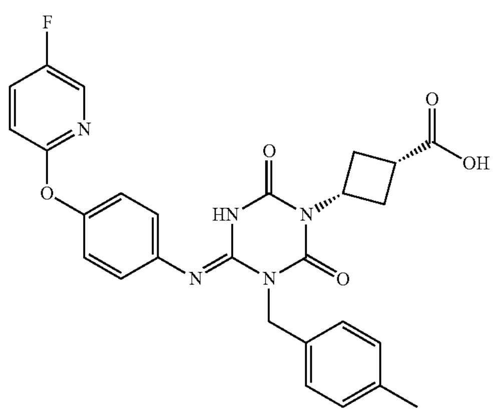 [SMILES: Cc1ccc(Cn2c(=O)n([C@H]3C[C@@H](C(=O)O)C3)c(=O)[nH]/c2=N\c2ccc(Oc3ccc(F)cn3)cc2)cc1] | 518 | 2.02 | 1 |
| I-184 | 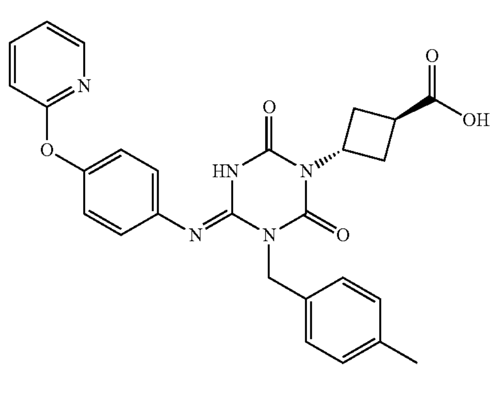 [SMILES: Cc1ccc(Cn2c(=O)n([C@H]3C[C@H](C(=O)O)C3)c(=O)[nH]/c2=N\c2ccc(Oc3ccccn3)cc2)cc1] | 500 | 2.01 | 1 |

TABLE 37-continued
| Compound No | Structure | [M + H]+ | RT | Method |
|---|---|---|---|---|
| I-185 | 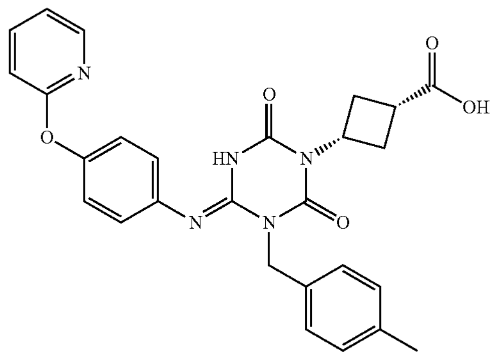 [SMILES: Cc1ccc(Cn2c(=O)n([C@H]3C[C@@H](C(=O)O)C3)c(=O)[nH]/c2=N\c2ccc(Oc3ccccn3)cc2)cc1] | 500 | 1.96 | 1 |
TABLE 38
| Compound No | Structure | [M + H]+ | RT | Method |
|---|---|---|---|---|
| I-186 | 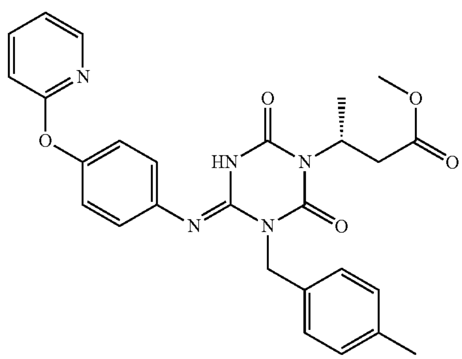 [SMILES: COC(=O)C[C@@H](C)n1c(=O)[nH]/c(=N\c2ccc(Oc3ccccn3)cc2)n(Cc2ccc(C)cc2)c1=O] | 502 | 2.23 | 1 |
| I-187 | 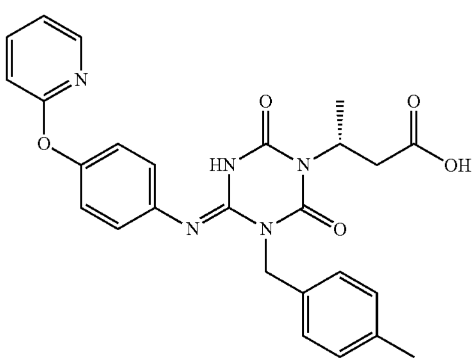 [SMILES: Cc1ccc(Cn2c(=O)n([C@H](C)CC(=O)O)c(=O)[nH]/c2=N\c2ccc(Oc3ccccn3)cc2)cc1] | 488 | 1.97 | 1 |
| I-188 | 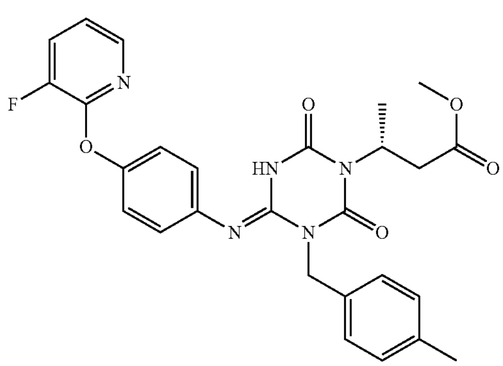 [SMILES: COC(=O)C[C@@H](C)n1c(=O)[nH]/c(=N\c2ccc(Oc3ncccc3F)cc2)n(Cc2ccc(C)cc2)c1=O] | 520 | 2.3 | 1 |

TABLE 38-continued
| Compound No | Structure | [M + H]+ | RT | Method |
|---|---|---|---|---|
| I-189 | 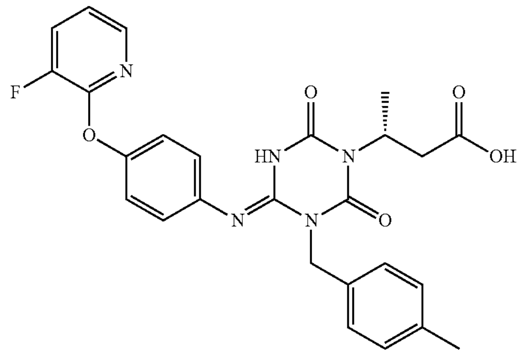 [SMILES: Cc1ccc(Cn2c(=O)n([C@H](C)CC(=O)O)c(=O)[nH]/c2=N\c2ccc(Oc3ncccc3F)cc2)cc1] | 506 | 2.05 | 1 |
| I-190 | 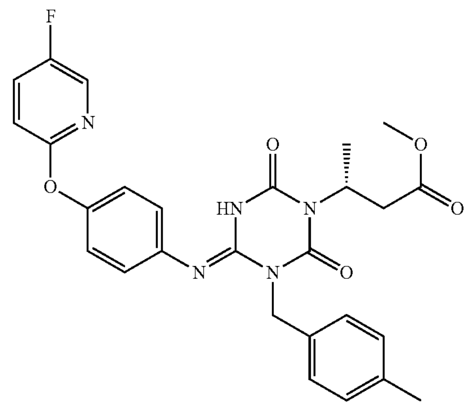 [SMILES: COC(=O)C[C@@H](C)n1c(=O)[nH]/c(=N\c2ccc(Oc3ccc(F)cn3)cc2)n(Cc2ccc(C)cc2)c1=O] | 520 | 2.29 | 1 |
TABLE 39
| Compound No | Structure | [M + H]+ | RT | Method |
|---|---|---|---|---|
| I-191 | 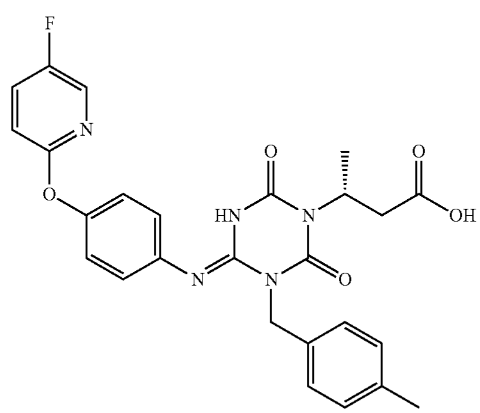 [SMILES: Cc1ccc(Cn2c(=O)n([C@H](C)CC(=O)O)c(=O)[nH]/c2=N\c2ccc(Oc3ccc(F)cn3)cc2)cc1] | 506 | 2.05 | 1 |

TABLE 39-continued

| No | Structure | [M + H]+ | RT | Method |
|---|---|---|---|---|
| I-192 | 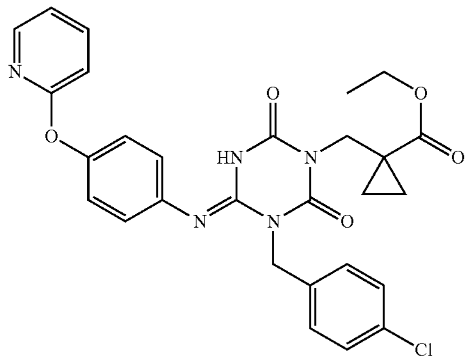 | 548 | 2.46 | 1 |
| I-193 | 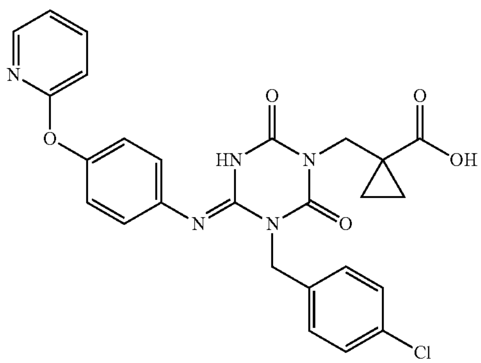 [SMILES: O=C(O)C1(Cn2c(=O)[nH]/c(=N\c3ccc(Oc4ccccn4)cc3)n(Cc3ccc(Cl)cc3)c2=O)CC1] | 520 | 2.08 | 1 |
| I-194 | 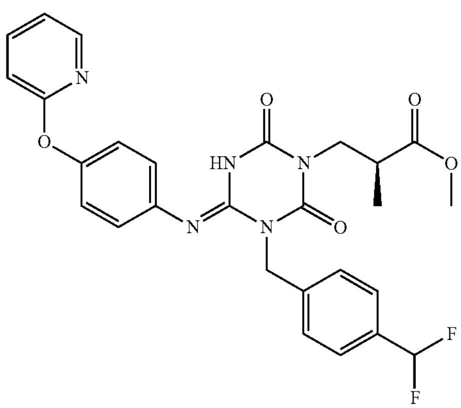 [SMILES: COC(=O)[C@@H](C)Cn1c(=O)[nH]/c(=N\c2ccc(Oc3ccccn3)cc2)n(Cc2ccc(C(F)F)cc2)c1=O] | 538 | 2.14 | 1 |
| I-195 | 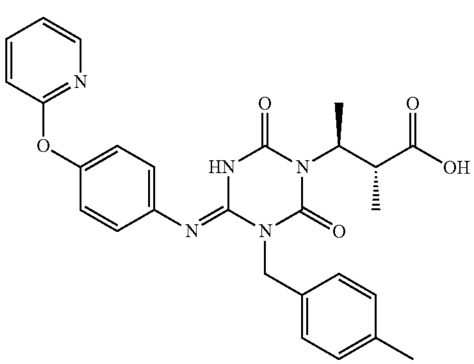 [SMILES: Cc1ccc(Cn2c(=O)n([C@@H](C)[C@@H](C)C(=O)O)c(=O)[nH]/c2=N\c2ccc(Oc3ccccn3)cc2)cc1] | 502 | 2.06 | 1 |

TABLE 40

| Compound No | Structure | [M + H]+ | RT | Method |
|---|---|---|---|---|
| I-196 | 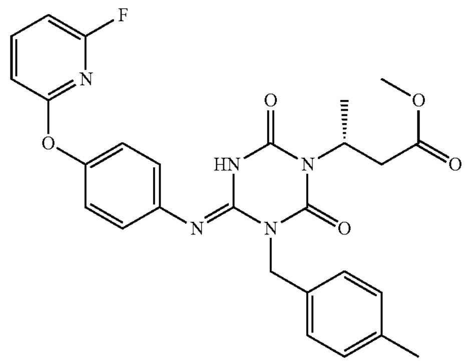 [SMILES: COC(=O)C[C@@H](C)n1c(=O)[nH]/c(=N\c2ccc(Oc3cccc(F)n3)cc2)n(Cc2ccc(C)cc2)c1=O] | 520 | 2.33 | 1 |
| I-197 | 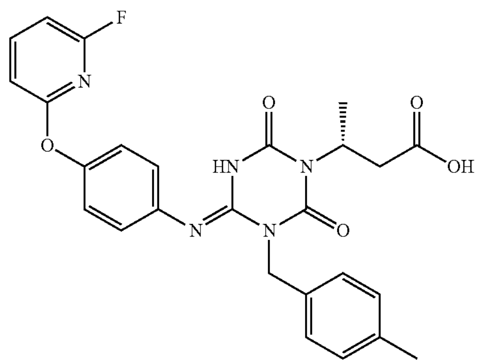 [SMILES: Cc1ccc(Cn2c(=O)n([C@H](C)CC(=O)O)c(=O)[nH]/c2=N\c2ccc(Oc3cccc(F)n3)cc2)cc1] | 506 | 2.07 | 1 |
| I-198 | 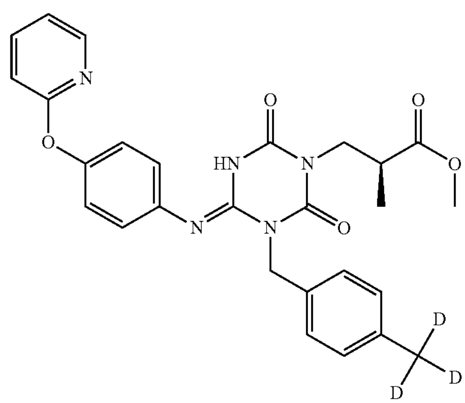 [SMILES: [2H]C([2H])([2H])c1ccc(Cn2c(=O)n(C[C@H](C)C(=O)OC)c(=O)[nH]/c2=N\c2ccc(Oc3ccccn3)cc2)cc1] | 505 | 2.18 | 1 |
| I-199 | 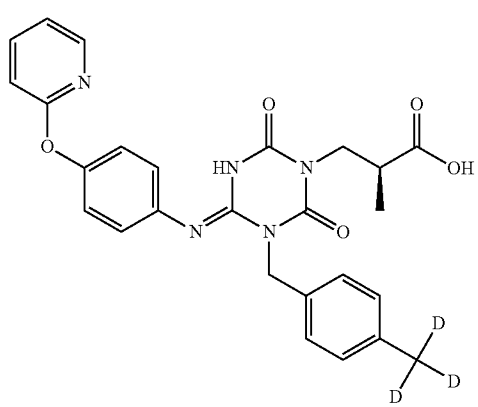 [SMILES: [2H]C([2H])([2H])c1ccc(Cn2c(=O)n(C[C@H](C)C(=O)O)c(=O)[nH]/c2=N\c2ccc(Oc3ccccn3)cc2)cc1] | 491 | 1.93 | 1 |

TABLE 41

| Compound No | Structure | [M + H]+ | RT | Method |
|---|---|---|---|---|
| 1-200 | 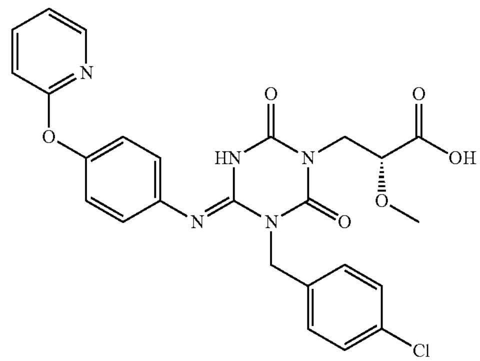 [SMILES: CO[C@H](Cn1c(=O)[nH]/c(=N\c2ccc(Oc3ccccn3)cc2)n(Cc2ccc(Cl)cc2)c1=O)C(=O)O] | 524 | 1.94 | 1 |
| 1-201 | 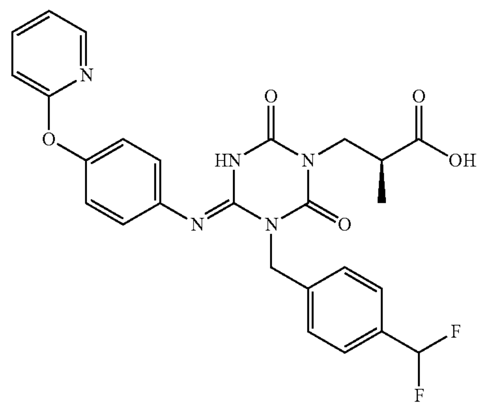 [SMILES: C[C@@H](Cn1c(=O)[nH]/c(=N\c2ccc(Oc3ccccn3)cc2)n(Cc2ccc(C(F)F)cc2)c1=O)C(=O)O] | 524 | 1.9 | 1 |
| 1-202 | 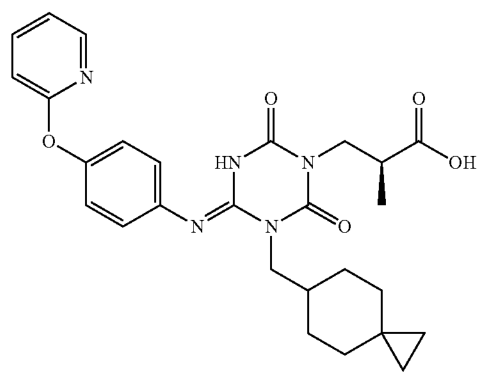 [SMILES: C[C@@H](Cn1c(=O)[nH]/c(=N\c2ccc(Oc3ccccn3)cc2)n(CC2CCC3(CC2)CC3)c1=O)C(=O)O] | 506 | 2.15 | 1 |
| 1-203 | 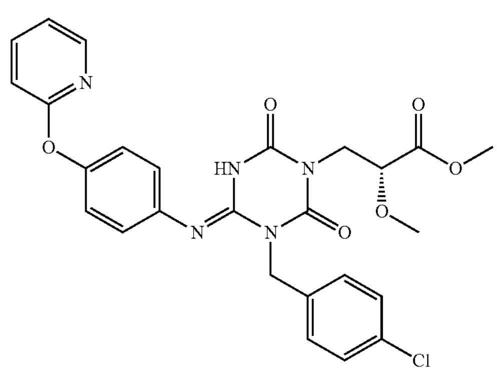 [SMILES: COC(=O)[C@@H](Cn1c(=O)[nH]/c(=N\c2ccc(Oc3ccccn3)cc2)n(Cc2ccc(Cl)cc2)c1=O)OC] | 538 | 2.16 | 1 |

TABLE 41-continued
| Compound No | Structure | [M + H]+ | RT | Method |
|---|---|---|---|---|
| 1-204 | 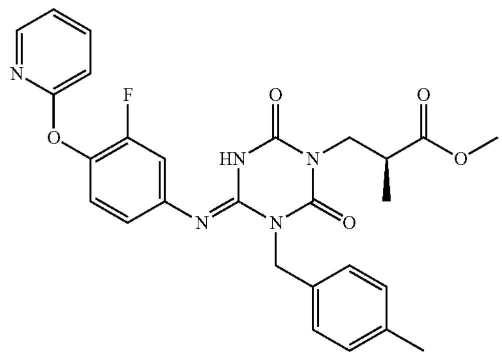 | 520 | 2.36 | 1 |
TABLE 42
| Compound No | Structure | [M + H]+ | RT | Method |
|---|---|---|---|---|
| I-205 | 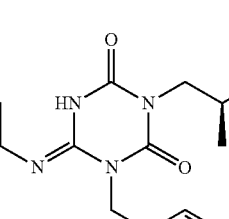 | 540 | 2.47 | 1 |
| I-206 | 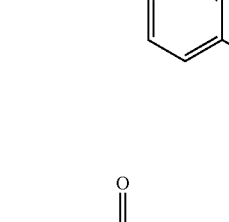 | 520 | 2.05 | 1 |
| I-207 | 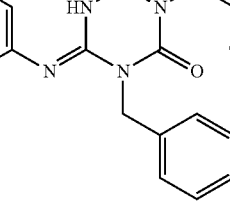 | 538 | 2.14 | 1 |

TABLE 42-continued

| Compound No | Structure | [M + H]+ | RT | Method |
|---|---|---|---|---|
| I-208 | 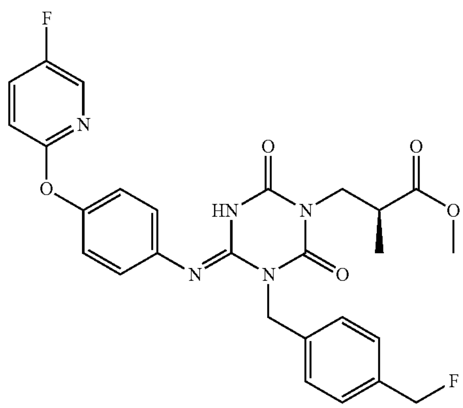 [SMILES: COC(=O)[C@@H](C)Cn1c(=O)[nH]/c(=N\c2ccc(Oc3ccc(F)cn3)cc2)n(Cc2ccc(CF)cc2)c1=O] | 538 | 2.11 | 1 |
| I-209 | 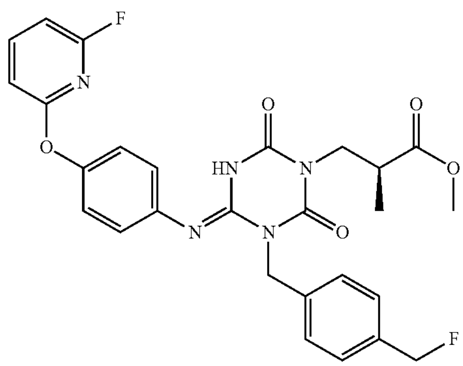 [SMILES: COC(=O)[C@@H](C)Cn1c(=O)[nH]/c(=N\c2ccc(Oc3cccc(F)n3)cc2)n(Cc2ccc(CF)cc2)c1=O] | 538 | 2.16 | 1 |

TABLE 43

| Compound No | Structure | [M + H]+ | RT | Method |
|---|---|---|---|---|
| I-210 | 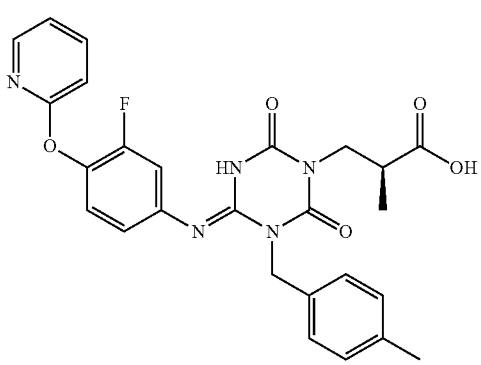 [SMILES: Cc1ccc(Cn2c(=O)n(C[C@H](C)C(=O)O)c(=O)[nH]/c2=N\c2ccc(Oc3ccccn3)c(F)c2)cc1] | 506 | 2.11 | 1 |

TABLE 43-continued
| Compound No | Structure | [M + H]+ | RT | Method |
|---|---|---|---|---|
| I-211 | 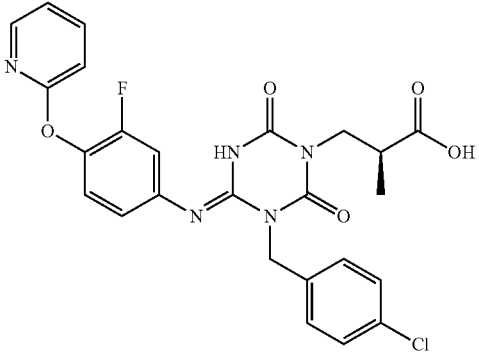 | 526 | 2.19 | 1 |
| I-212 | 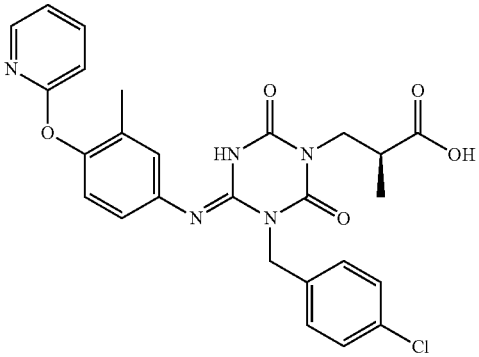 | 522 | 2.14 | 1 |
| I-213 | 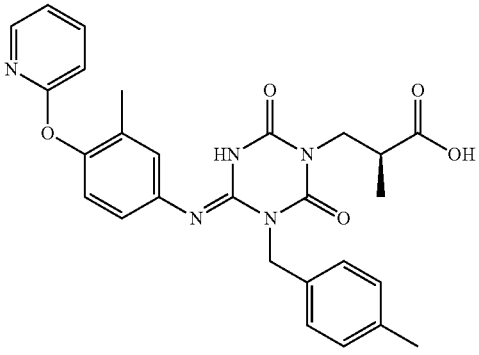 [SMILES: Cc1ccc(Cn2c(=O)n(C[C@H](C)C(=O)O)c(=O)[nH]/c2=N\c2ccc(Oc3ccccn3)c(C)c2)cc1] | 502 | 2.06 | 1 |
| I-214 | 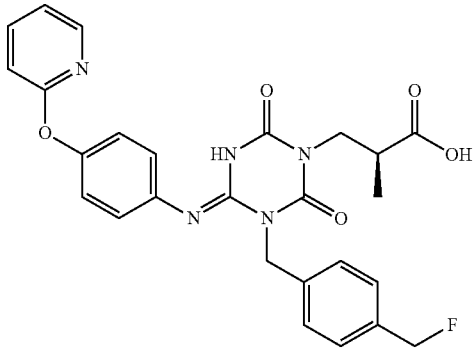 [SMILES: C[C@@H](Cn1c(=O)[nH]/c(=N\c2ccc(Oc3ccccn3)cc2)n(Cc2ccc(CF)cc2)c1=O)C(=O)O] | 506 | 1.82 | 1 |

TABLE 44

| Compound No | Structure | [M + H]+ | RT | Method |
|---|---|---|---|---|
| I-215 | 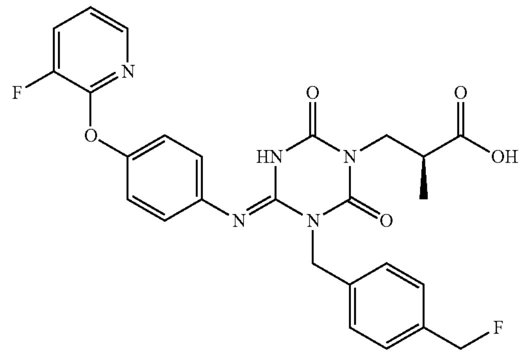 [SMILES: C[C@@H](Cn1c(=O)[nH]/c(=N\c2ccc(Oc3ncccc3F)cc2)n(Cc2ccc(CF)cc2)c1=O)C(=O)O] | 524 | 1.89 | 1 |
| I-216 | 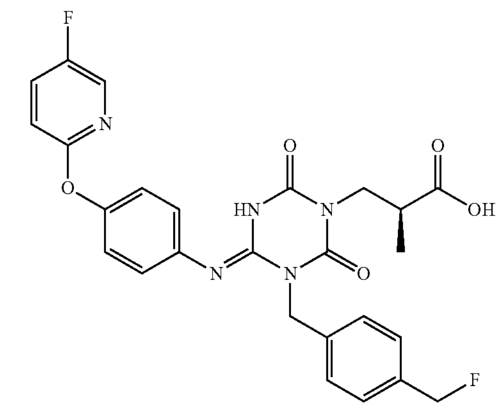 [SMILES: C[C@@H](Cn1c(=O)[nH]/c(=N\c2ccc(Oc3ccc(F)cn3)cc2)n(Cc2ccc(CF)cc2)c1=O)C(=O)O] | 524 | 1.88 | 1 |
| I-217 | 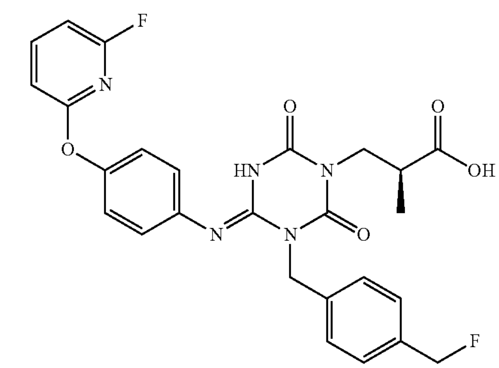 [SMILES: C[C@@H](Cn1c(=O)[nH]/c(=N\c2ccc(Oc3cccc(F)n3)cc2)n(Cc2ccc(CF)cc2)c1=O)C(=O)O] | 524 | 1.91 | 1 |
| I-218 | 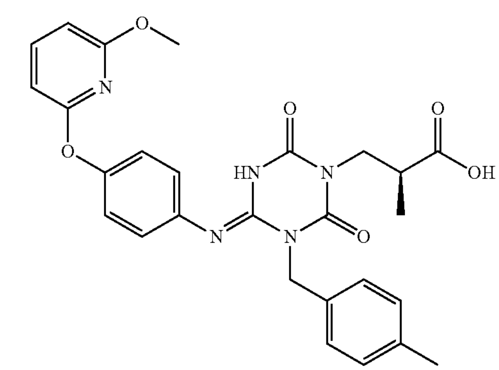 [SMILES: COc1cccc(Oc2ccc(/N=c3\[nH]c(=O)n(C[C@H](C)C(=O)O)c(=O)n3Cc3ccc(C)cc3)cc2)n1] | 518 | 2.08 | 1 |

TABLE 44-continued
| Compound No | Structure | [M + H]+ | RT | Method |
|---|---|---|---|---|
| I-219 | 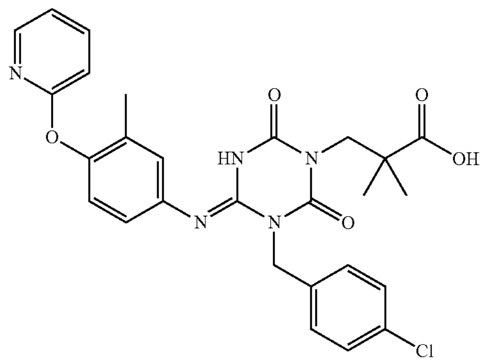 | 536 | 2.22 | 1 |
TABLE 45
| Compound No | Structure | [M + H]+ | RT | Method |
|---|---|---|---|---|
| I-220 | 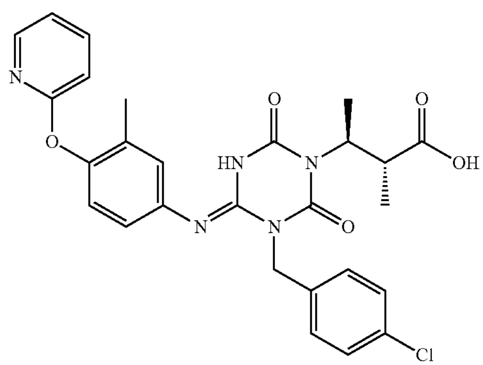 [SMILES: Cc1cc(/N=c2\[nH]c(=O)n([C@@H](C)[C@@H](C)C(=O)O)c(=O)n2Cc2ccc(Cl)cc2)ccc1Oc1ccccn1] | 536 | 2.26 | 1 |
| I-221 | 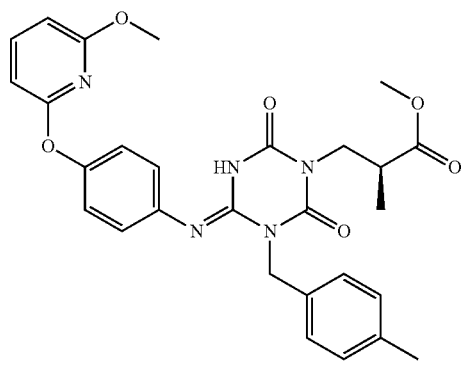 [SMILES: COC(=O)[C@@H](C)Cn1c(=O)[nH]/c(=N\c2ccc(Oc3cccc(OC)n3)cc2)n(Cc2ccc(C)cc2)c1=O] | 532 | 2.34 | 1 |

TABLE 45-continued
| Compound No | Structure | [M + H]+ | RT | Method |
|---|---|---|---|---|
| I-222 | 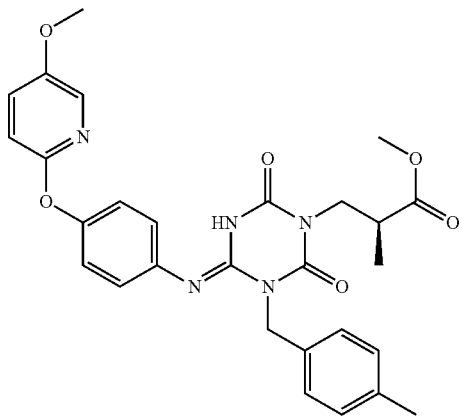 [SMILES: COC(=O)[C@@H](C)Cn1c(=O)[nH]/c(=N\c2ccc(Oc3ccc(OC)cn3)cc2)n(Cc2ccc(C)cc2)c1=O] | 532 | 2.2 | 1 |
| I-223 | 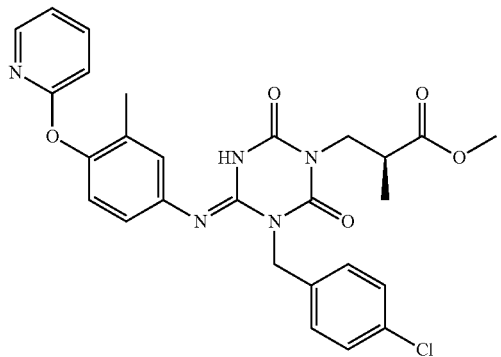 [SMILES: COC(=O)[C@@H](C)Cn1c(=O)[nH]/c(=N\c2ccc(Oc3ccccn3)c(C)c2)n(Cc2ccc(Cl)cc2)c1=O] | 536 | 2.4 | 1 |
| I-224 | 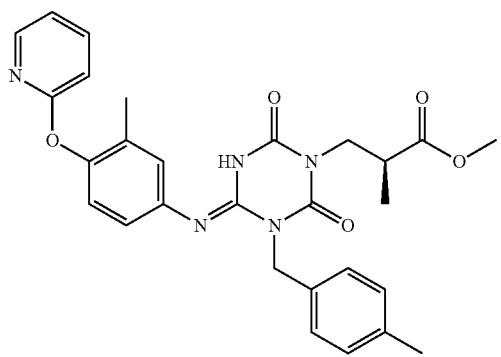 [SMILES: COC(=O)[C@@H](C)Cn1c(=O)[nH]/c(=N\c2ccc(Oc3ccccn3)c(C)c2)n(Cc2ccc(C)cc2)c1=O] | | | |

TABLE 46

| Compound No | Structure | [M + H]+ | RT | Method |
|---|---|---|---|---|
| I-225 | 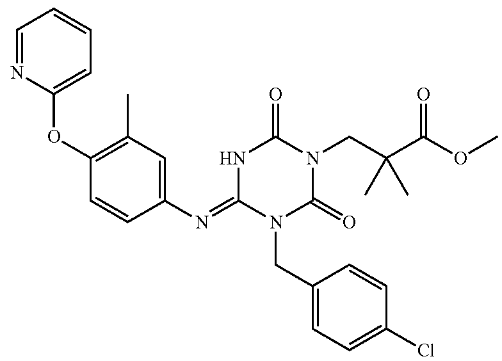 [SMILES: COC(=O)C(C)(C)Cn1c(=O)[nH]/c(=N\c2ccc(Oc3ccccn3)c(C)c2)n(Cc2ccc(Cl)cc2)c1=O] | 550 | 2.51 | 1 |
| I-226 | 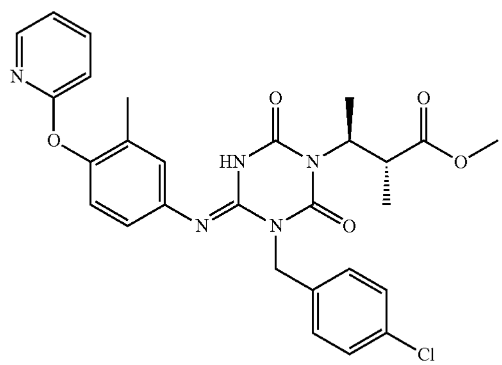 [SMILES: COC(=O)[C@H](C)[C@H](C)n1c(=O)[nH]/c(=N\c2ccc(Oc3ccccn3)c(C)c2)n(Cc2ccc(Cl)cc2)c1=O] | 550 | 2.55 | 1 |
| I-227 | 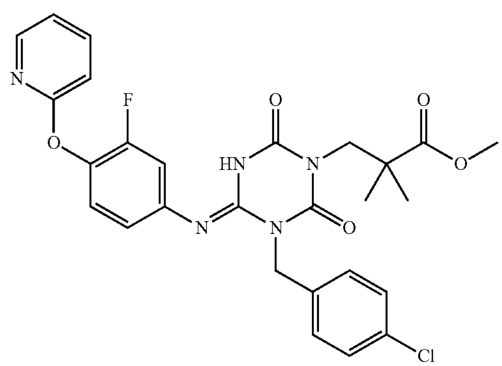 | 554 | 2.54 | 1 |
| I-228 | 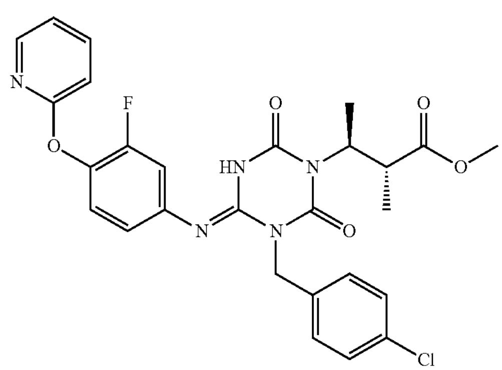 | 554 | 2.57 | 1 |

TABLE 46-continued

| Compound No | Structure | [M + H]+ | RT | Method |
|---|---|---|---|---|
| I-229 | 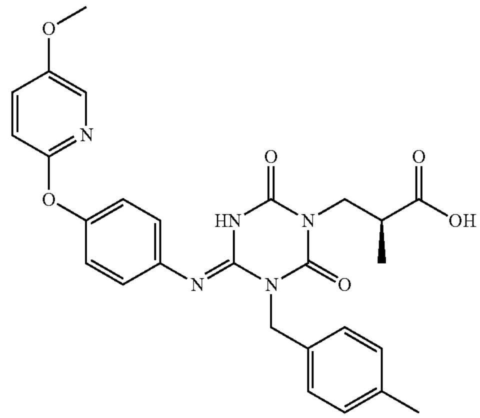 [SMILES: COc1ccc(Oc2ccc(/N=c3\[nH]c(=O)n(C[C@H](C)C(=O)O)c(=O)n3Cc3ccc(C)cc3)cc2)nc1] | 518 | 1.96 | 1 |

TABLE 47

| Compound No | Structure | [M + H]+ | RT | Method |
|---|---|---|---|---|
| I-230 | 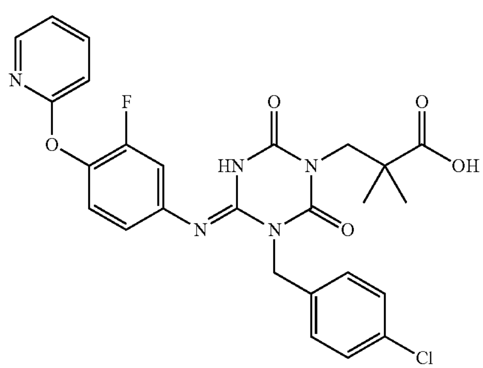 | 540 | 2.26 | 1 |
| I-231 | 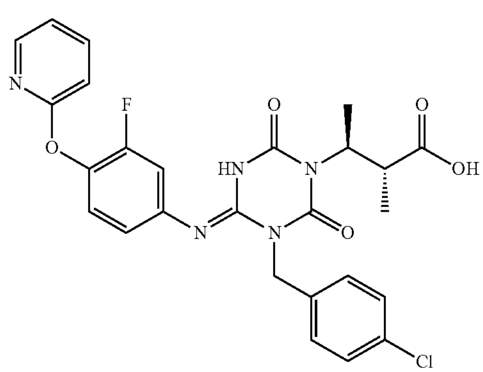 | 540 | 2.29 | 1 |

TABLE 47-continued

| Compound No | Structure | [M + H]+ | RT | Method |
|---|---|---|---|---|
| I-232 | 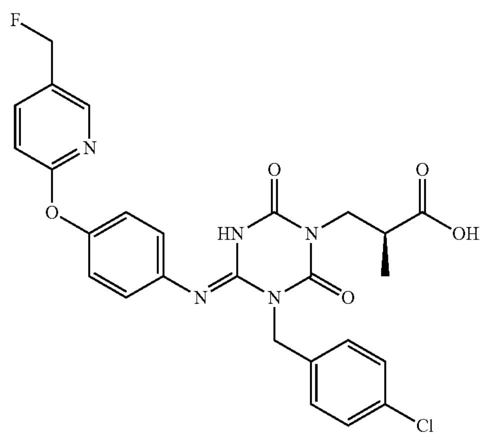 [SMILES: C[C@@H](Cn1c(=O)[nH]/c(=N\c2ccc(Oc3ccc(CF)cn3)cc2)n(Cc2ccc(Cl)cc2)c1=O)C(=O)O] | 540 | 2.05 | 1 |
| I-233 | 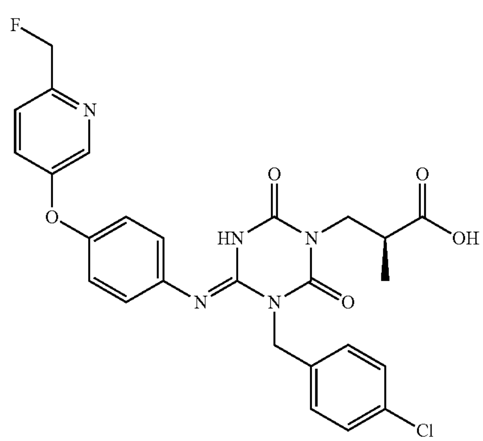 [SMILES: C[C@@H](Cn1c(=O)[nH]/c(=N\c2ccc(Oc3ccc(CF)nc3)cc2)n(Cc2ccc(Cl)cc2)c1=O)C(=O)O] | 540 | 1.95 | 1 |
| I-234 | 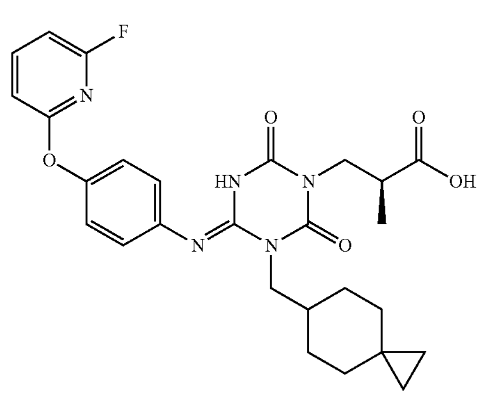 [SMILES: C[C@@H](Cn1c(=O)[nH]/c(=N\c2ccc(Oc3cccc(F)n3)cc2)n(CC2CCC3(CC2)CC3)c1=O)C(=O)O] | 524 | 2.22 | 1 |

TABLE 48
| Compound No | Structure | [M + H]+ | RT | Method |
|---|---|---|---|---|
| I-235 | 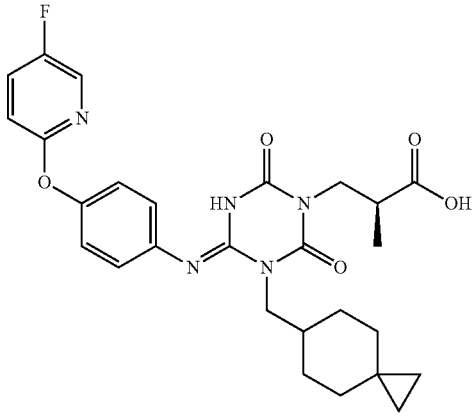 [SMILES: C[C@@H](Cn1c(=O)[nH]/c(=N\c2ccc(Oc3ccc(F)cn3)cc2)n(CC2CCC3(CC2)CC3)c1=O)C(=O)O] | 524 | 2.19 | 1 |
| I-236 | 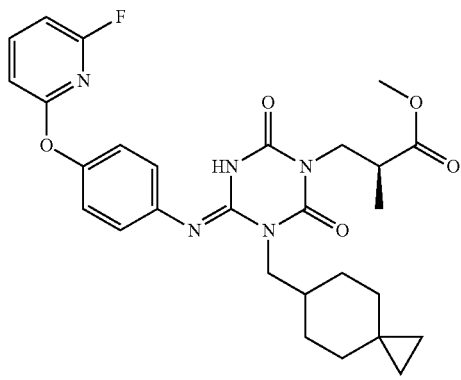 [SMILES: COC(=O)[C@@H](C)Cn1c(=O)[nH]/c(=N\c2ccc(Oc3cccc(F)n3)cc2)n(CC2CCC3(CC2)CC3)c1=O] | 538 | 2.49 | 1 |
| I-237 | 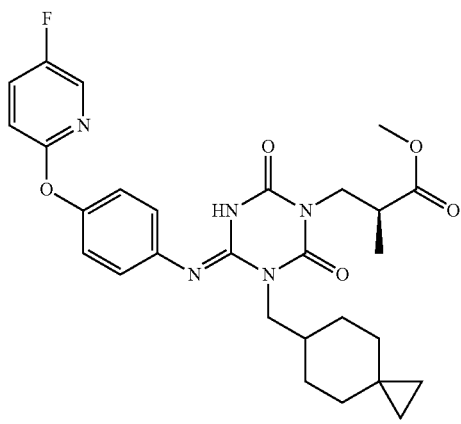 [SMILES: COC(=O)[C@@H](C)Cn1c(=O)[nH]/c(=N\c2ccc(Oc3ccc(F)cn3)cc2)n(CC2CCC3(CC2)CC3)c1=O] | 538 | 2.46 | 1 |

TABLE 48-continued
| Compound No | Structure | [M + H]+ | RT | Method |
|---|---|---|---|---|
| I-238 | 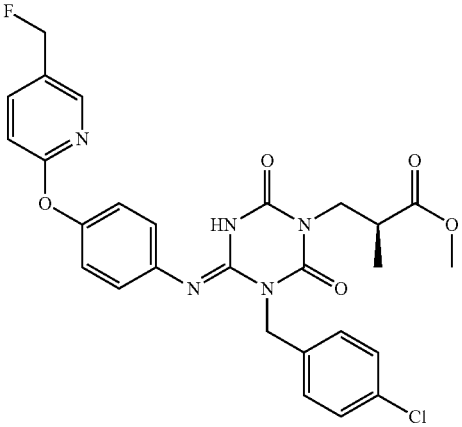 [SMILES: COC(=O)[C@@H](C)Cn1c(=O)[nH]/c(=N\c2ccc(Oc3ccc(CF)cn3)cc2)n(Cc2ccc(Cl)cc2)c1=O] | 554 | 2.33 | 1 |
| I-239 | 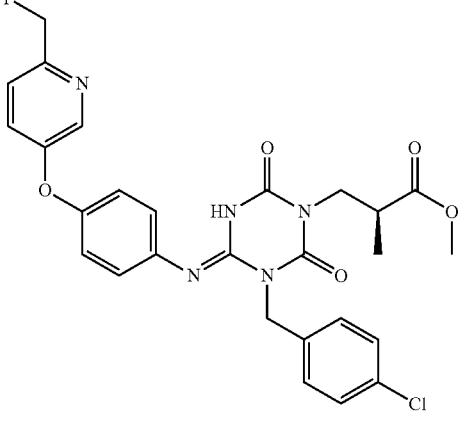 | 554 | 2.23 | 1 |
TABLE 49
| Compound No | Structure | [M + H]+ | RT | Method |
|---|---|---|---|---|
| I-240 | 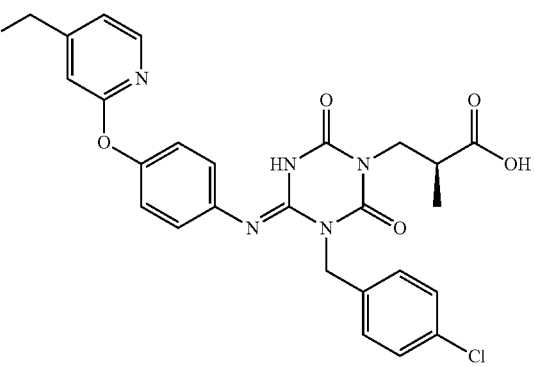 | 537.952 | 1.5 | 1 |

TABLE 49-continued
| Compound No | Structure | [M + H]+ | RT | Method |
|---|---|---|---|---|
| I-241 | 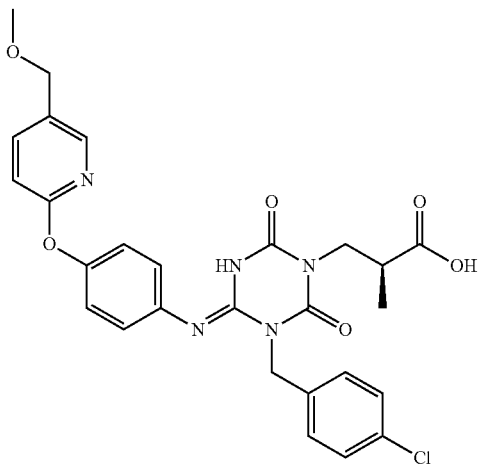 [SMILES: COCc1ccc(Oc2ccc(/N=c3\[nH]c(=O)n(C[C@H](C)C(=O)O)c(=O)n3Cc3ccc(Cl)cc3)cc2)nc1] | 552 | 2.04 | 1 |
| I-242 | 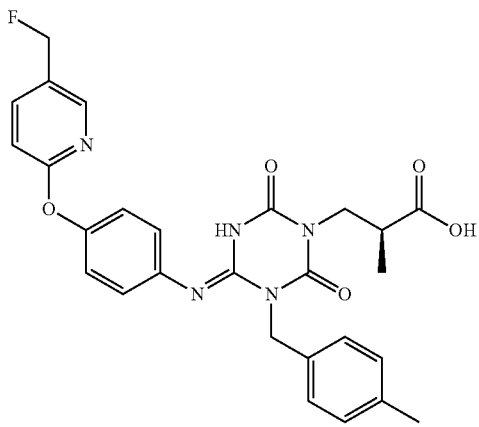 [SMILES: Cc1ccc(Cn2c(=O)n(C[C@H](C)C(=O)O)c(=O)[nH]/c2=N\c2ccc(Oc3ccc(CF)cn3)cc2)cc1] | 520 | 1.98 | 1 |
| I-243 | 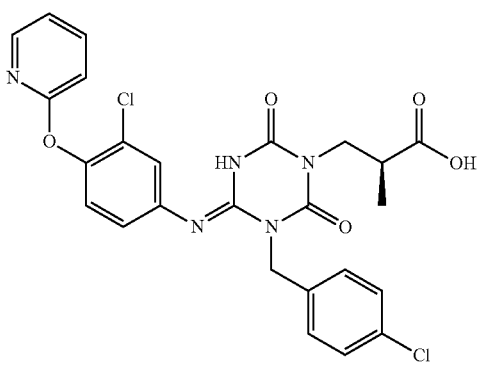 [SMILES: C[C@@H](Cn1c(=O)[nH]/c(=N\c2ccc(Oc3ccccn3)c(Cl)c2)n(Cc2ccc(Cl)cc2)c1=O)C(=O)O] | 542 | 2.29 | 1 |

TABLE 49-continued
| Compound No | Structure | [M + H]+ | RT | Method |
|---|---|---|---|---|
| I-244 | 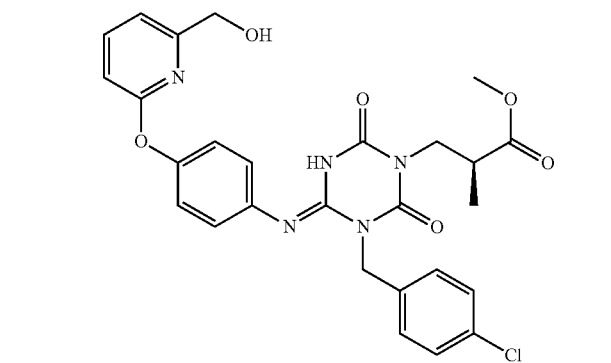 [SMILES: COC(=O)[C@@H](C)Cn1c(=O)[nH]/c(=N\c2ccc(Oc3cccc(CO)n3)cc2)n(Cc2ccc(Cl)cc2)c1=O] | 512 | 2.33 | 1 |
TABLE 50
| Compound No | Structure | [M + H]+ | RT | Method |
|---|---|---|---|---|
| I-245 | 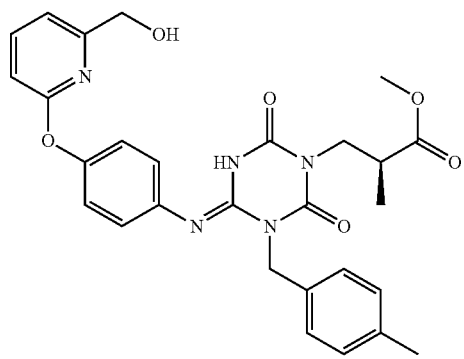 [SMILES: COC(=O)[C@@H](C)Cn1c(=O)[nH]/c(=N\c2ccc(Oc3cccc(CO)n3)cc2)n(Cc2ccc(C)cc2)c1=O] | 552 | 2.06 | 1 |
| I-246 | 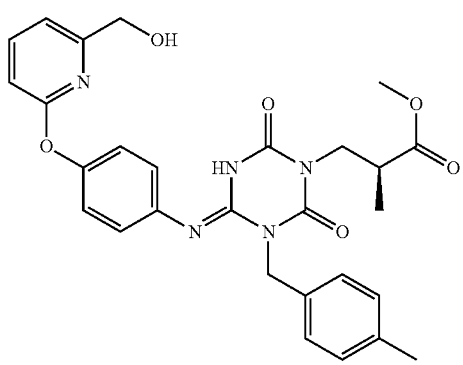 | 532 | 1.97 | 1 |

TABLE 50-continued
| Compound No | Structure | [M + H]+ | RT | Method |
|---|---|---|---|---|
| I-247 | 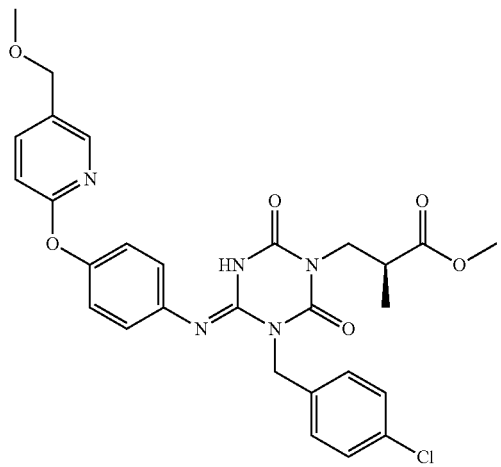 [SMILES: COCc1ccc(Oc2ccc(/N=c3\[nH]c(=O)n(C[C@H](C)C(=O)OC)c(=O)n3Cc3ccc(Cl)cc3)cc2)nc1] | 566 | 2.28 | 1 |
| I-248 | 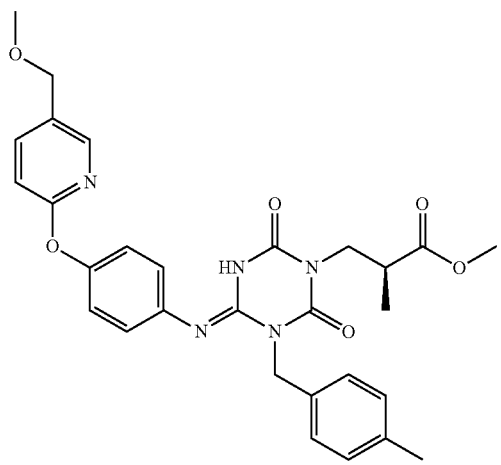 [SMILES: COCc1ccc(Oc2ccc(/N=c3\[nH]c(=O)n(C[C@H](C)C(=O)OC)c(=O)n3Cc3ccc(C)cc3)cc2)nc1] | 548 | 2.19 | 1 |
| I-249 | 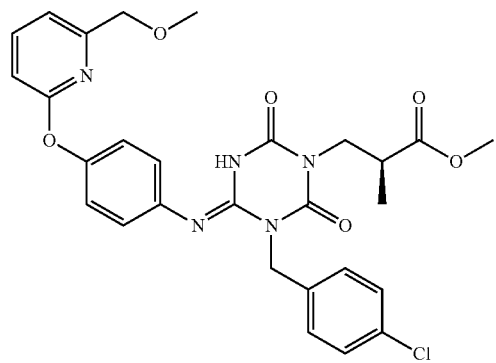 [SMILES: COCc1cccc(Oc2ccc(/N=c3\[nH]c(=O)n(C[C@H](C)C(=O)OC)c(=O)n3Cc3ccc(Cl)cc3)cc2)n1] | 566 | 2.32 | 1 |

TABLE 51

| Compound No | Structure | [M + H]+ | RT | Method |
|---|---|---|---|---|
| I-250 | 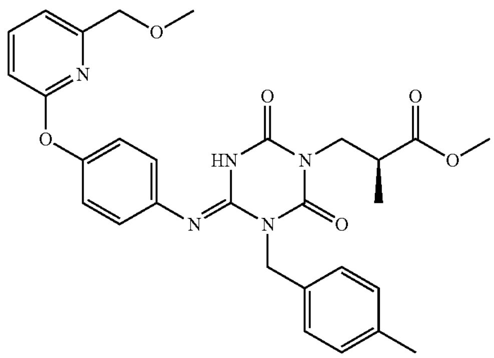 [SMILES: COCc1cccc(Oc2ccc(/N=c3\[nH]c(=O)n(C[C@H](C)C(=O)OC)c(=O)n3Cc3ccc(C)cc3)cc2)n1] | 546 | 2.23 | 1 |
| I-251 | 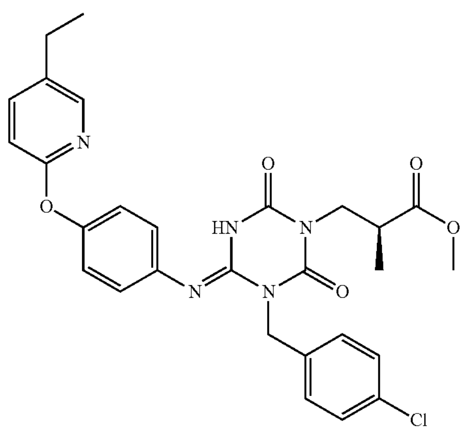 [SMILES: CCc1ccc(Oc2ccc(/N=c3\[nH]c(=O)n(C[C@H](C)C(=O)OC)c(=O)n3Cc3ccc(Cl)cc3)cc2)nc1] | 550 | 2.5 | 1 |
| I-252 | 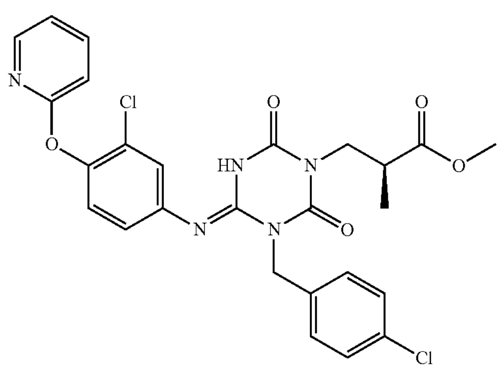 [SMILES: COC(=O)[C@@H](C)Cn1c(=O)[nH]/c(=N\c2ccc(Oc3ccccn3)c(Cl)c2)n(Cc2ccc(Cl)cc2)c1=O] | 556 | 2.54 | 1 |
| I-253 | 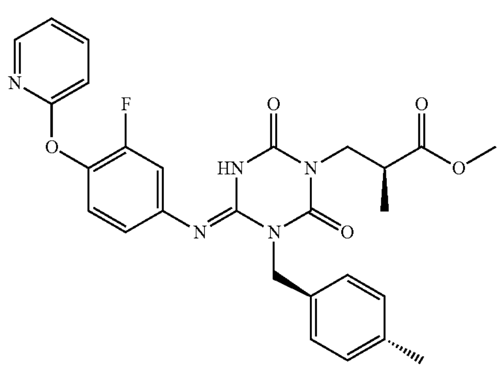 | 526 | 2.6 | 1 |

TABLE 51-continued

| Compound No | Structure | [M + H]+ | RT | Method |
|---|---|---|---|---|
| I-254 | 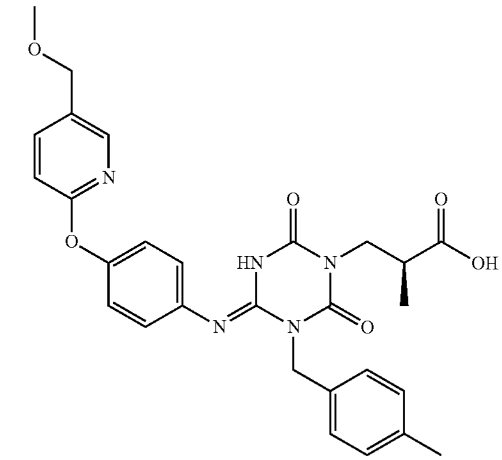 [SMILES: COCc1ccc(Oc2ccc(/N=c3\[nH]c(=O)n(C[C@H](C)C(=O)O)c(=O)n3Cc3ccc(C)cc3)cc2)nc1] | 532 | 1.95 | 1 |

TABLE 52

| Compound No | Structure | [M + H]+ | RT | Method |
|---|---|---|---|---|
| I-255 | 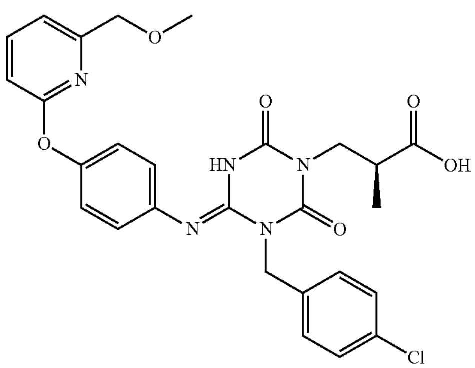 [SMILES: COCc1cccc(Oc2ccc(/N=c3\[nH]c(=O)n(C[C@H](C)C(=O)O)c(=O)n3Cc3ccc(Cl)cc3)cc2)n1] | 552 | 2.07 | 1 |
| I-256 | 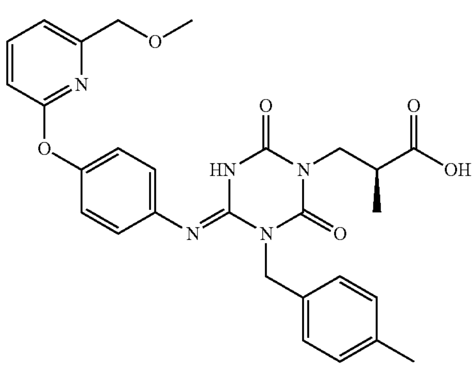 [SMILES: COCc1cccc(Oc2ccc(/N=c3\[nH]c(=O)n(C[C@H](C)C(=O)O)c(=O)n3Cc3ccc(C)cc3)cc2)n1] | 532 | 1.99 | 1 |

| Compound No | Structure | [M + H]+ | RT | Method |
|---|---|---|---|---|
| I-257 | 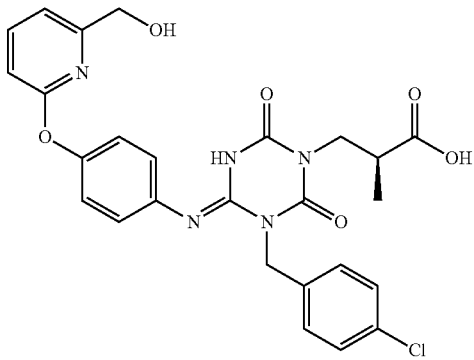 [SMILES: C[C@@H](Cn1c(=O)[nH]/c(=N\c2ccc(Oc3cccc(CO)n3)cc2)n(Cc2ccc(Cl)cc2)c1=O)C(=O)O] | 538 | 1.83 | 1 |
| I-258 | 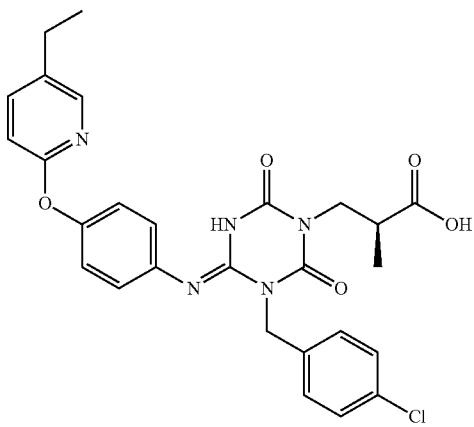 [SMILES: CCc1ccc(Oc2ccc(/N=c3\[nH]c(=O)n(C[C@H](C)C(=O)O)c(=O)n3Cc3ccc(Cl)cc3)cc2)nc1] | 536 | 2.24 | 1 |
| I-259 | 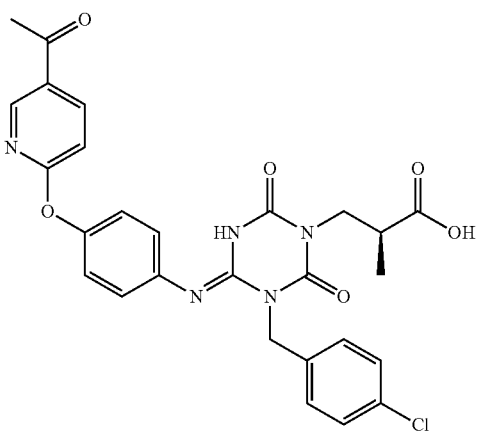 [SMILES: CC(=O)c1ccc(Oc2ccc(/N=c3\[nH]c(=O)n(C[C@H](C)C(=O)O)c(=O)n3Cc3ccc(Cl)cc3)cc2)nc1] | 550 | 2.01 | 1 |

TABLE 53

| Compound No | Structure | [M + H]+ | RT | Method |
|---|---|---|---|---|
| I-260 | 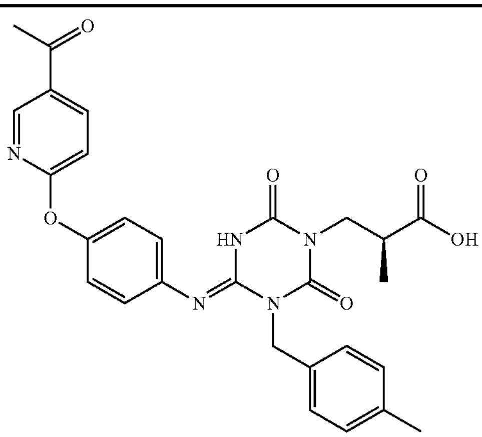 | 530 | 1.93 | 1 |
| I-261 | 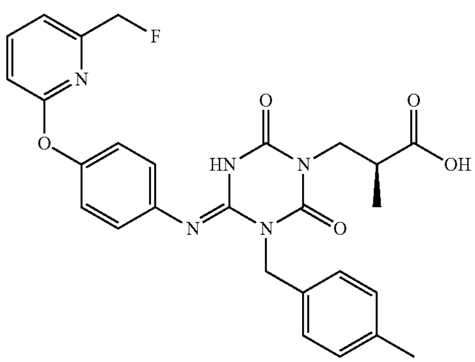 [SMILES: Cc1ccc(Cn2c(=O)n(C[C@H](C)C(=O)O)c(=O)[nH]/c2=N\c2ccc(Oc3cccc(CF)n3)cc2)cc1] | 520 | 2.01 | 1 |
| I-262 | 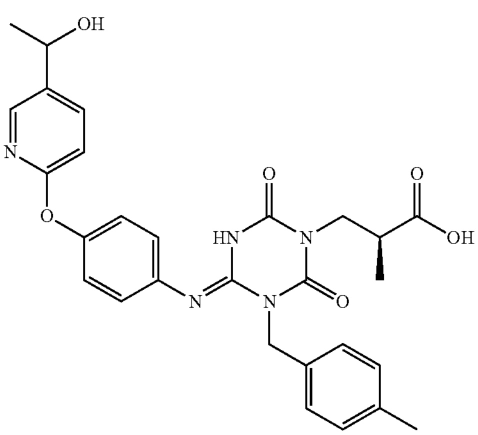 [SMILES: Cc1ccc(Cn2c(=O)n(C[C@H](C)C(=O)O)c(=O)[nH]/c2=N\c2ccc(Oc3ccc(C(C)O)cn3)cc2)cc1] | 532 | 1.77 | 1 |
| I-263 | 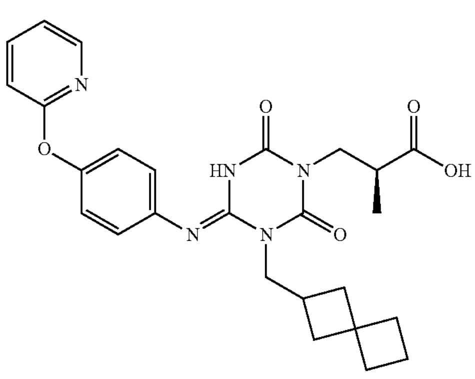 [SMILES: C[C@@H](Cn1c(=O)[nH]/c(=N\c2ccc(Oc3ccccn3)cc2)n(CC2CC3(CCC3)C2)c1=O)C(=O)O] | 492 | 2.11 | 1 |

TABLE 53-continued
| Compound No | Structure | [M + H]+ | RT | Method |
|---|---|---|---|---|
| I-264 | 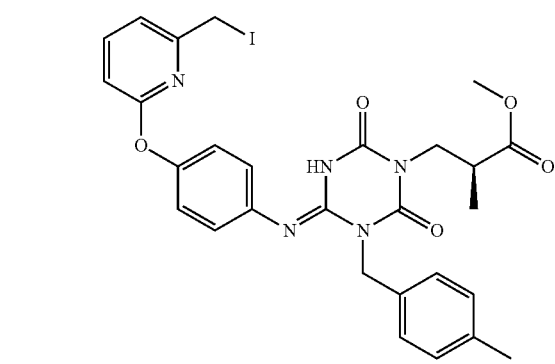 | 510 | 2.18 | 1 |
TABLE 54
| Compound No | Structure | [M + H]+ | RT | Method |
|---|---|---|---|---|
| I-265 | 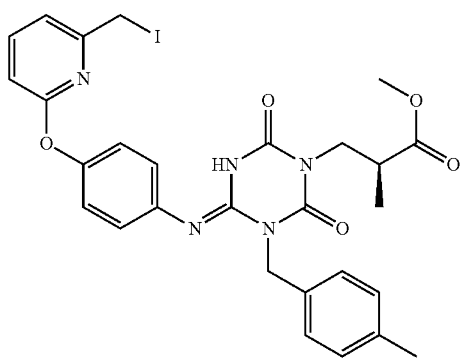 [SMILES: COC(=O)[C@@H](C)Cn1c(=O)[nH]/c(=N\c2ccc(Oc3cccc(CI)n3)cc2)n(Cc2ccc(C)cc2)c1=O] | 642 | 2.42 | 1 |
| I-266 | 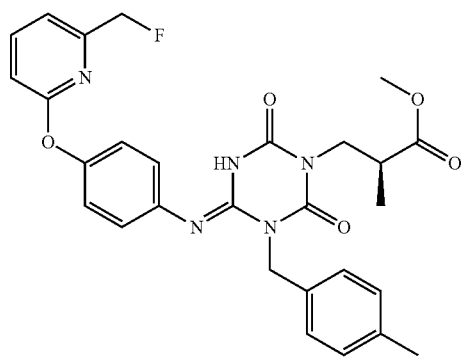 | 534 | 2.26 | 1 |

TABLE 54-continued
| Compound No | Structure | [M + H]+ | RT | Method |
|---|---|---|---|---|
| I-267 | 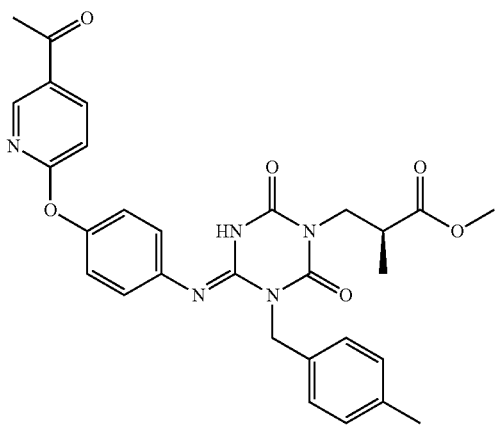 [SMILES: COC(=O)[C@@H](C)Cn1c(=O)[nH]/c(=N\c2ccc(Oc3ccc(C(C)=O)cn3)cc2)n(Cc2ccc(C)cc2)c1=O] | 544 | 2.17 | 1 |
| I-268 | 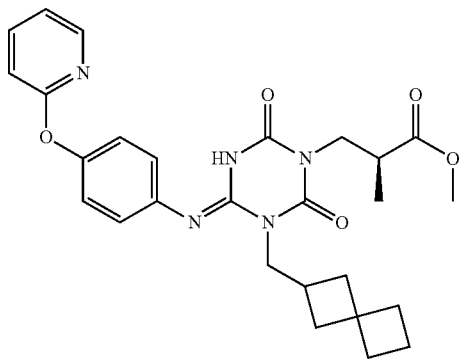 [SMILES: COC(=O)[C@@H](C)Cn1c(=O)[nH]/c(=N\c2ccc(Oc3ccccn3)cc2)n(CC2CC3(CCC3)C2)c1=O] | 506 | 2.37 | 1 |
| I-269 | 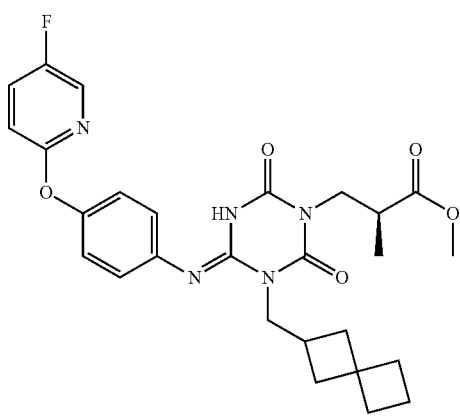 [SMILES: COC(=O)[C@@H](C)Cn1c(=O)[nH]/c(=N\c2ccc(Oc3ccc(F)cn3)cc2)n(CC2CC3(CCC3)C2)c1=O] | 524 | 2.43 | 1 |

TABLE 55

| Compound No | Structure | [M + H]+ | RT | Method |
|---|---|---|---|---|
| I-270 | 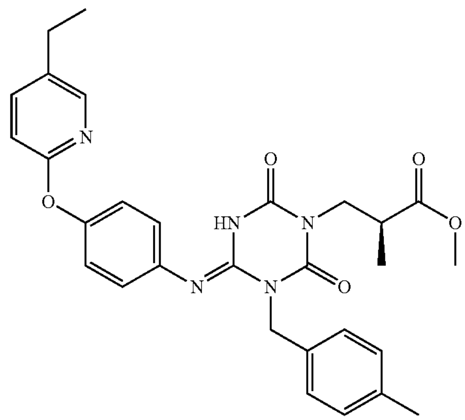 [SMILES: CCc1ccc(Oc2ccc(/N=c3\[nH]c(=O)n(C[C@H](C)C(=O)OC)c(=O)n3Cc3ccc(C)cc3)cc2)nc1] | 530 | 2.43 | 1 |
| I-271 | 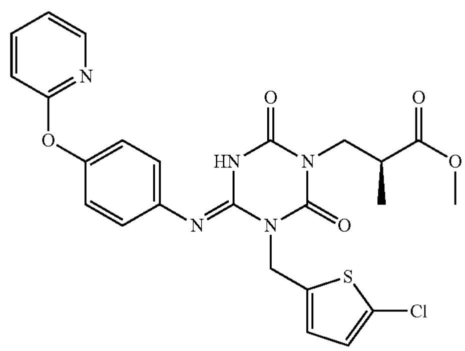 [SMILES: COC(=O)[C@@H](C)Cn1c(=O)[nH]/c(=N\c2ccc(Oc3ccccn3)cc2)n(Cc2ccc(Cl)s2)c1=O] | 527.98 | 2.43 | 1 |
| I-272 | 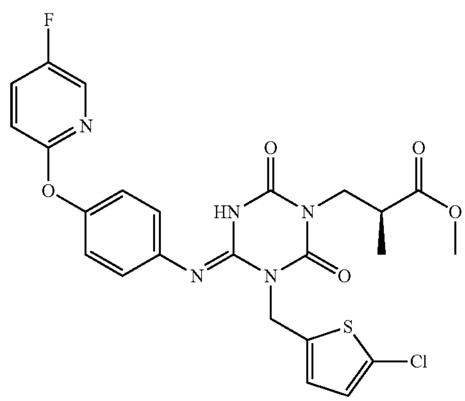 [SMILES: COC(=O)[C@@H](C)Cn1c(=O)[nH]/c(=N\c2ccc(Oc3ccc(F)cn3)cc2)n(Cc2ccc(Cl)s2)c1=O] | 545.97 | 2.47 | 1 |
| I-273 | 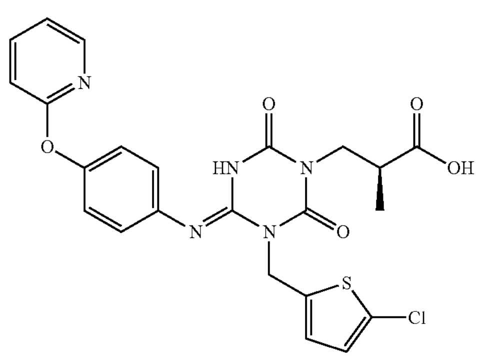 [SMILES: C[C@@H](Cn1c(=O)[nH]/c(=N\c2ccc(Oc3ccccn3)cc2)n(Cc2ccc(Cl)s2)c1=O)C(=O)O] | 513.953 | 2.14 | 1 |

TABLE 55-continued
| Compound No | Structure | [M + H]+ | RT | Method |
|---|---|---|---|---|
| I-274 | 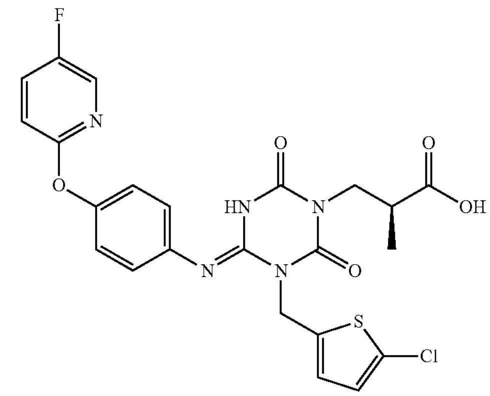 [SMILES: C[C@@H](Cn1c(=O)[nH]/c(=N\c2ccc(Oc3ccc(F)cn3)cc2)n(Cc2ccc(Cl)s2)c1=O)C(=O)O] | 532 | 2.19 | 1 |
TABLE 56
| Compound No | Structure | [M + H]+ | RT | Method |
|---|---|---|---|---|
| I-275 | 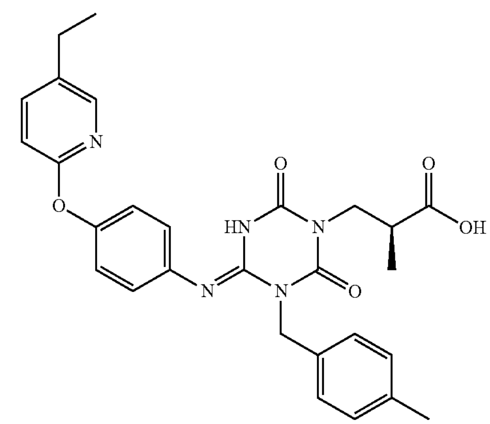 [SMILES: CCc1ccc(Oc2ccc(/N=c3\[nH]c(=O)n(C[C@H](C)C(=O)O)c(=O)n3Cc3ccc(C)cc3)cc2)nc1] | 516 | 2.18 | 1 |
| I-276 | 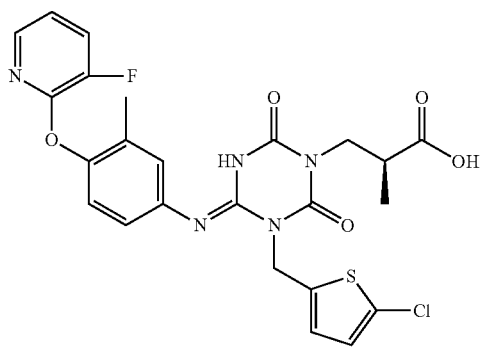 [SMILES: Cc1cc(/N=c2\[nH]c(=O)n(C[C@H](C)C(=O)O)c(=O)n2Cc2ccc(Cl)s2)ccc1Oc1ncccc1F] | 546 | 2.32 | 1 |

TABLE 56-continued
| Compound No | Structure | [M + H]+ | RT | Method |
|---|---|---|---|---|
| I-277 | 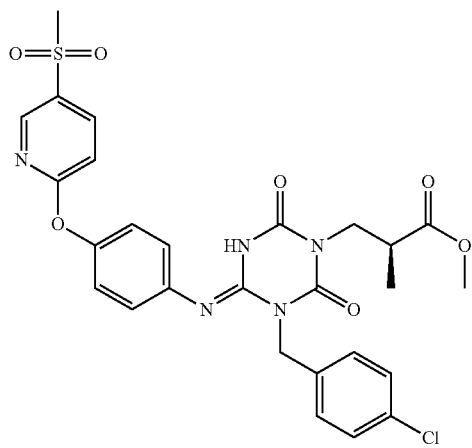 [SMILES: COC(=O)[C@@H](C)Cn1c(=O)[nH]/c(=N\c2ccc(Oc3ccc(S(C)(=O)=O)cn3)cc2)n(Cc2ccc(Cl)cc2)c1=O] | 601 | 2.15 | 1 |
| I-278 | 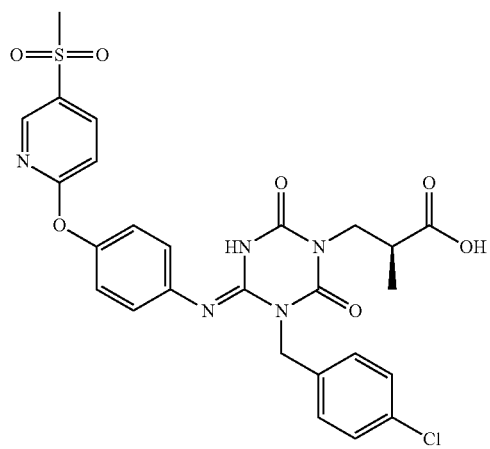 [SMILES: C[C@@H](Cn1c(=O)[nH]/c(=N\c2ccc(Oc3ccc(S(C)(=O)=O)cn3)cc2)n(Cc2ccc(Cl)cc2)c1=O)C(=O)O] | 587 | 1.89 | 1 |
The following compounds of the Reference Examples were synthesized in a similar manner to those described in the above general procedures for the synthesis of the compound of the invention and Reference Examples, with reference to the contents described in WO2010/092966 and WO2012/020749 as needed.

REFERENCE EXAMPLES

TABLE 57

| Compound No | Structure | [M + H]+ | RT | Method |
|---|---|---|---|---|
| R-001 | 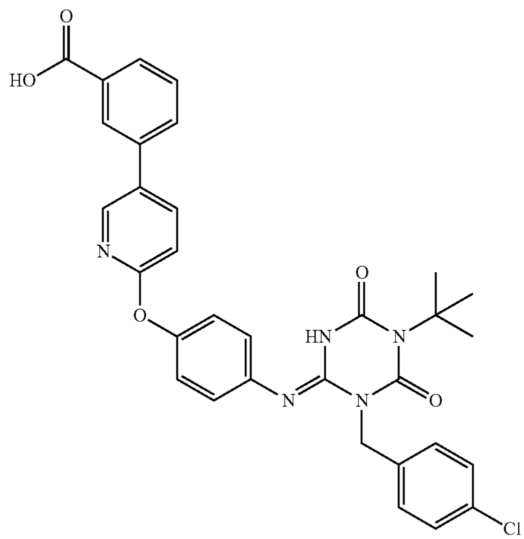 [SMILES: CC(C)(C)n1c(=O)[nH]/c(=N\c2ccc(Oc3ccc(-c4cccc(C(=O)O)c4)cn3)cc2)n(Cc2ccc(Cl)cc2)c1=O] | 598 | 2.55 | 1 |
| R-002 | 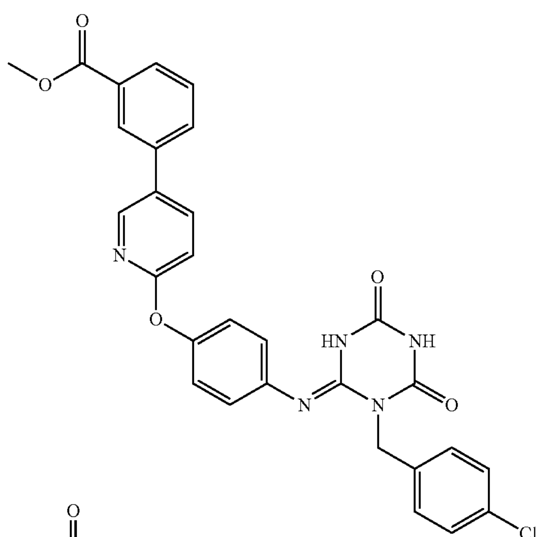 [SMILES: COC(=O)c1cccc(-c2ccc(Oc3ccc(/N=c4\[nH]c(=O)[nH]c(=O)n4Cc4ccc(Cl)cc4)cc3)nc2)c1] | 556 | 2.38 | 1 |
| R-003 | 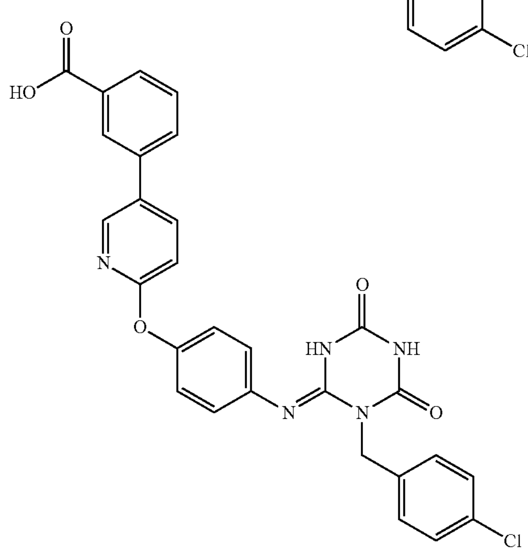 | 542 | 2.07 | 1 |

TABLE 57-continued

| Compound No | Structure | [M + H]+ | RT | Method |
|---|---|---|---|---|
| R-004 | 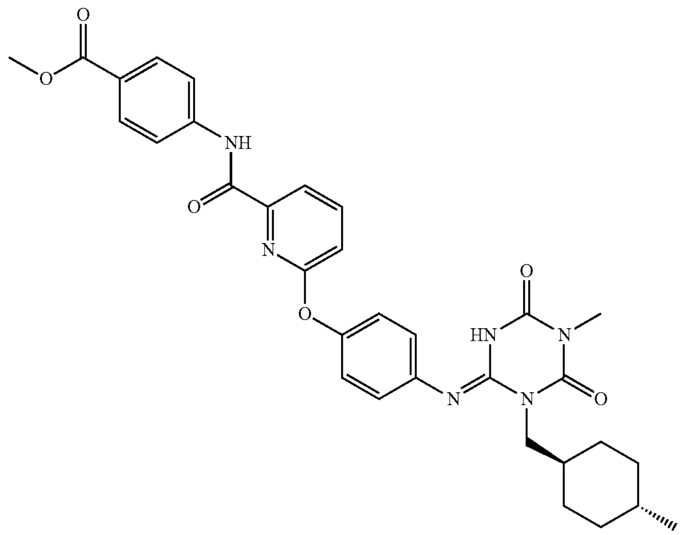 | 599 | 2.59 | 1 |

TABLE 58

| Compound No | Structure | [M + H]+ | RT | Method |
|---|---|---|---|---|
| R-005 | 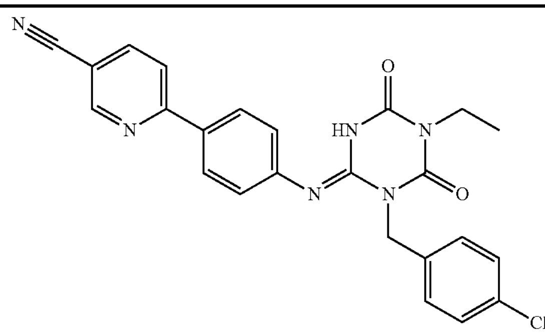 | 459 | 2.28 | 1 |
| R-006 | 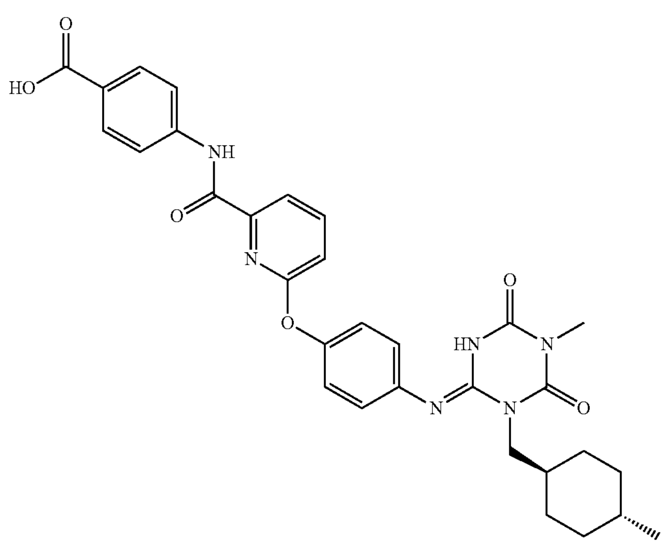 [SMILES: Cn1c(=O)[nH]/c(=N\c2ccc(Oc3cccc(C(=O)Nc4ccc(C(=O)O)cc4)n3)cc2)n(C[C@H]2CC[C@H](C)CC2)c1=O] | 585 | 2.24 | 1 |

TABLE 58-continued

| Compound No | Structure | [M + H]+ | RT | Method |
|---|---|---|---|---|
| R-007 | 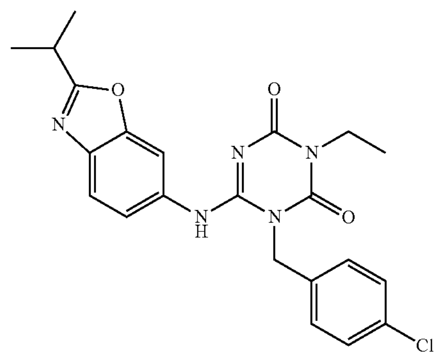 [SMILES: CCn1c(=O)nc(Nc2ccc3nc(C(C)C)oc3c2)n(Cc2ccc(Cl)cc2)c1=O] | 440 | 2.3 | 1 |
| R-008 | 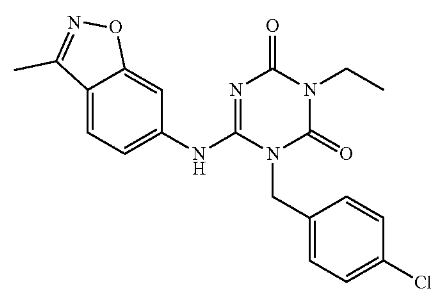 [SMILES: CCn1c(=O)nc(Nc2ccc3c(C)noc3c2)n(Cc2ccc(Cl)cc2)c1=O] | 412 | 2.21 | 1 |
| R-009 | 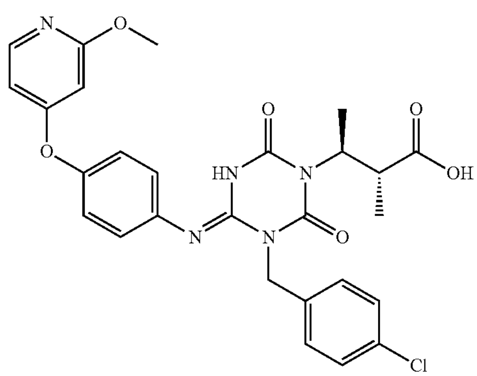 | 552 | 2.11 | 1 |
| R-010 | 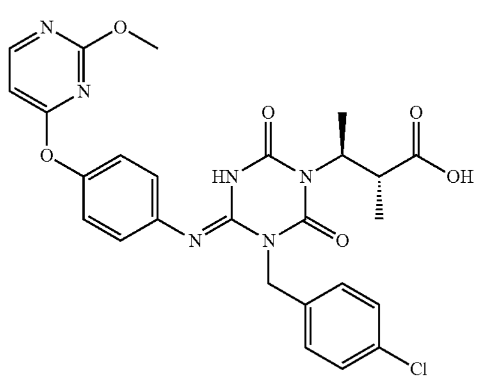 [SMILES: COc1nccc(Oc2ccc(/N=c3\[nH]c(=O)n([C@@H](C)[C@@H](C)C(=O)O)c(=O)n3Cc3ccc(Cl)cc3)cc2)n1] | 553 | 2.05 | 1 |

TABLE 59
| Compound No | Structure | [M + H]+ | RT | Method |
|---|---|---|---|---|
| R-011 | 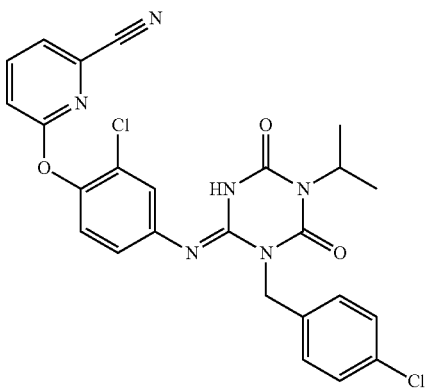 [SMILES: CC(C)n1c(=O)[nH]/c(=N\c2ccc(Oc3cccc(C#N)n3)c(Cl)c2)n(Cc2ccc(Cl)cc2)c1=O] | 523 | 2.61 | 1 |
| R-012 | 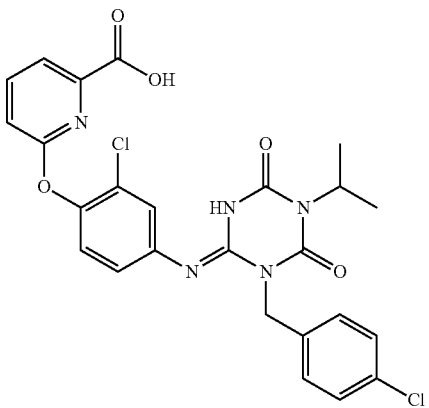 [SMILES: CC(C)n1c(=O)[nH]/c(=N\c2ccc(Oc3cccc(C(=O)O)n3)c(Cl)c2)n(Cc2ccc(Cl)cc2)c1=O] | 542 | 2.47 | 1 |
| R-013 | 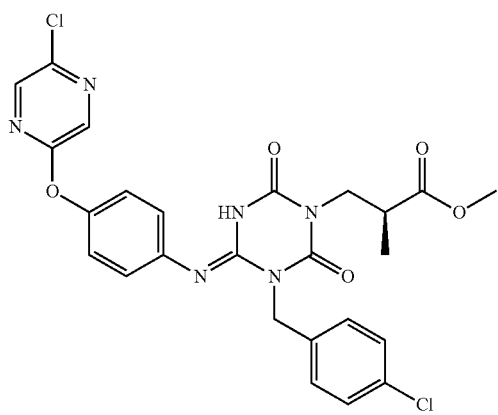 [SMILES: COC(=O)[C@@H](C)Cn1c(=O)[nH]/c(=N\c2ccc(Oc3cnc(Cl)cn3)cc2)n(Cc2ccc(Cl)cc2)c1=O] | 557 | 2.37 | 1 |

TABLE 59-continued

| Compound No | Structure | [M + H]+ | RT | Method |
|---|---|---|---|---|
| R-014 | 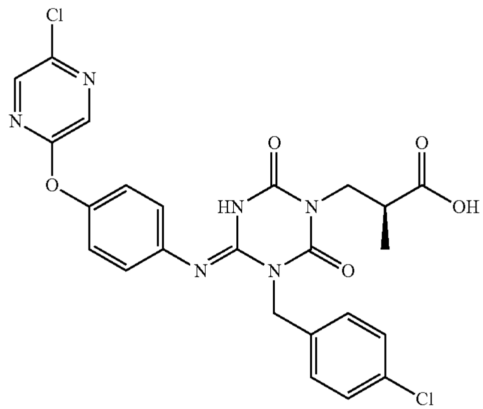 [SMILES: C[C@@H](Cn1c(=O)[nH]/c(=N\c2ccc(Oc3cnc(Cl)cn3)cc2)n(Cc2ccc(Cl)cc2)c1=O)C(=O)O] | 543 | 2.12 | 1 |
| R-015 | 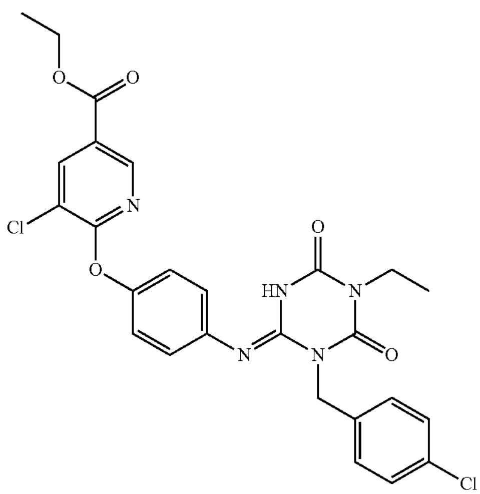 [SMILES: CCOC(=O)c1cnc(Oc2ccc(/N=c3\[nH]c(=O)n(CC)c(=O)n3Cc3ccc(Cl)cc3)cc2)c(Cl)c1] | 556 | 2.7 | 1 |

TABLE 60

| Compound No | Structure | [M + H]+ | RT | Method |
|---|---|---|---|---|
| R-016 | 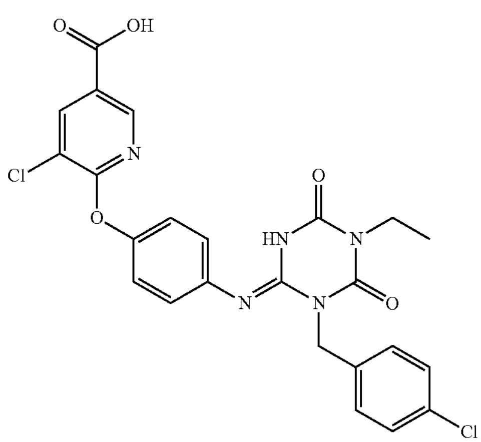 [SMILES: CCn1c(=O)[nH]/c(=N\c2ccc(Oc3ncc(C(=O)O)cc3Cl)cc2)n(Cc2ccc(Cl)cc2)c1=O] | 528 | 2.27 | 1 |

TABLE 60-continued
| Compound No | Structure | [M + H]+ | RT | Method |
|---|---|---|---|---|
| R-017 | 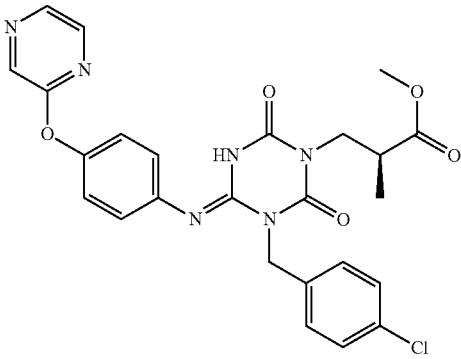 | 523 | 2.12 | 1 |
| R-018 | 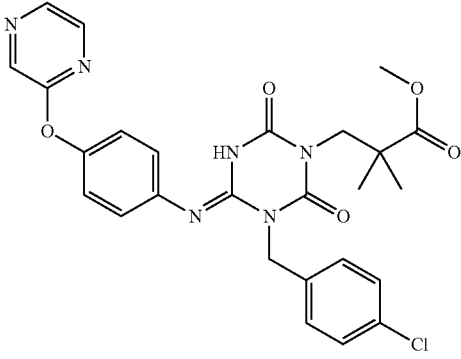 [SMILES: COC(=O)C(C)(C)Cn1c(=O)[nH]/c(=N\c2ccc(Oc3cnccn3)cc2)n(Cc2ccc(Cl)cc2)c1=O] | 527 | 2.23 | 1 |
| R-019 | 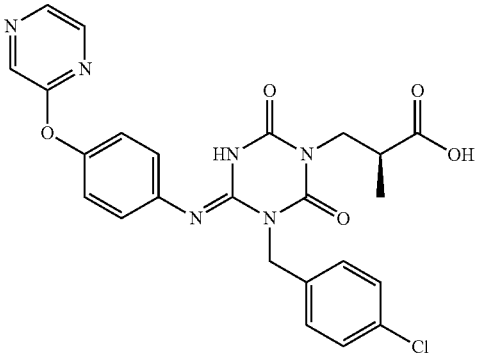 [SMILES: C[C@@H](Cn1c(=O)[nH]/c(=N\c2ccc(Oc3cnccn3)cc2)n(Cc2ccc(Cl)cc2)c1=O)C(=O)O] | 509 | 1.86 | 1 |
| R-020 | 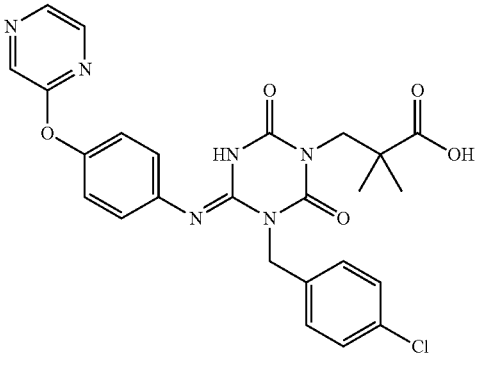 [SMILES: CC(C)(Cn1c(=O)[nH]/c(=N\c2ccc(Oc3cnccn3)cc2)n(Cc2ccc(Cl)cc2)c1=O)C(=O)O] | 523 | 1.94 | 1 |

TABLE 61

| Compound No | Structure | [M + H]+ | RT | Method |
|---|---|---|---|---|
| R-021 | 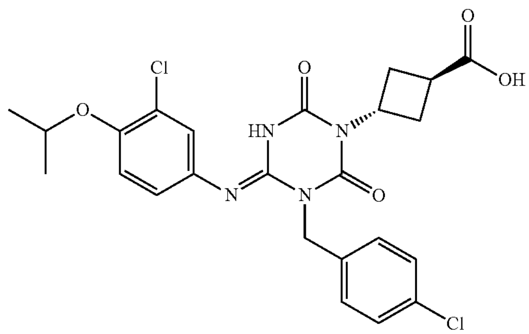 [SMILES: CC(C)Oc1ccc(/N=c2\[nH]c(=O)n([C@H]3C[C@H](C(=O)O)C3)c(=O)n2Cc2ccc(Cl)cc2)cc1Cl] | 519 | 2.31 | 1 |
| R-022 | 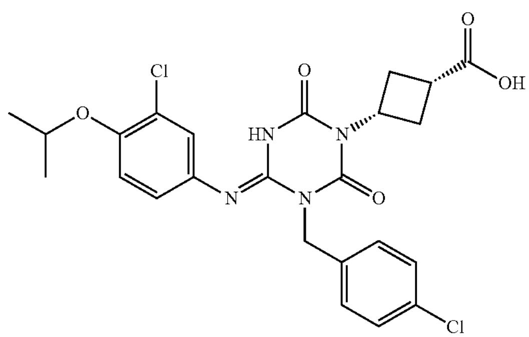 [SMILES: CC(C)Oc1ccc(/N=c2\[nH]c(=O)n([C@H]3C[C@@H](C(=O)O)C3)c(=O)n2Cc2ccc(Cl)cc2)cc1Cl] | 519 | 2.26 | 1 |
| R-023 | 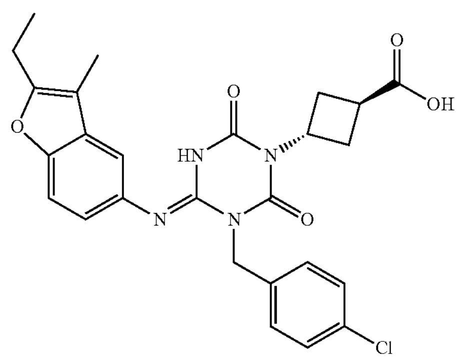 [SMILES: CCc1oc2ccc(/N=c3\[nH]c(=O)n([C@H]4C[C@H](C(=O)O)C4)c(=O)n3Cc3ccc(Cl)cc3)cc2c1C] | 509 | 2.32 | 1 |
| R-024 | 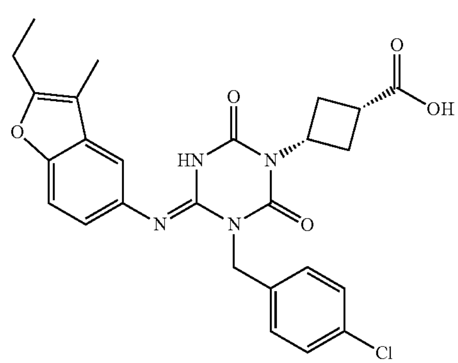 [SMILES: CCc1oc2ccc(/N=c3\[nH]c(=O)n([C@H]4C[C@@H](C(=O)O)C4)c(=O)n3Cc3ccc(Cl)cc3)cc2c1C] | 509 | 2.27 | 1 |

TABLE 61-continued
| Compound No | Structure | [M + H]+ | RT | Method |
|---|---|---|---|---|
| R-025 | 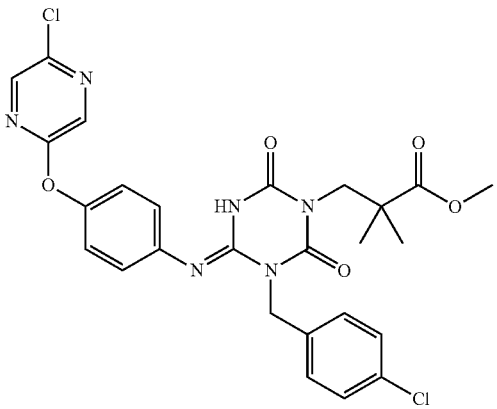 [SMILES: COC(=O)C(C)(C)Cn1c(=O)[nH]/c(=N\c2ccc(Oc3cnc(Cl)cn3)cc2)n(Cc2ccc(Cl)cc2)c1=O] | 571 | 2.48 | 1 |
TABLE 62
| Compound No | Structure | [M + H]+ | RT | Method |
|---|---|---|---|---|
| R-026 | 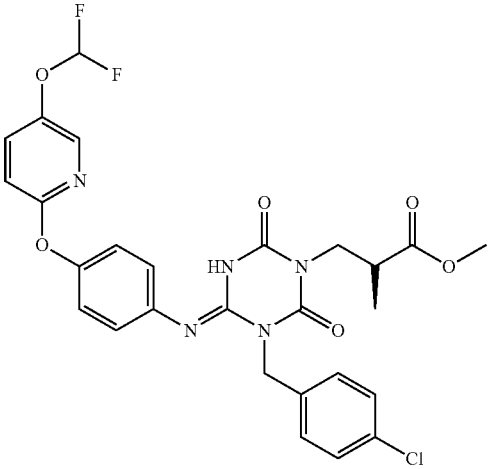 | 588 | 2.39 | 1 |
| R-027 | 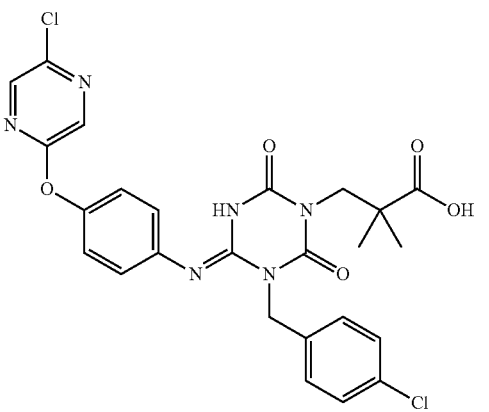 [SMILES: CC(C)(Cn1c(=O)[nH]/c(=N\c2ccc(Oc3cnc(Cl)cn3)cc2)n(Cc2ccc(Cl)cc2)c1=O)C(=O)O] | 557 | 2.19 | 1 |

TABLE 62-continued
| Compound No | Structure | [M + H]+ | RT | Method |
|---|---|---|---|---|
| R-028 | 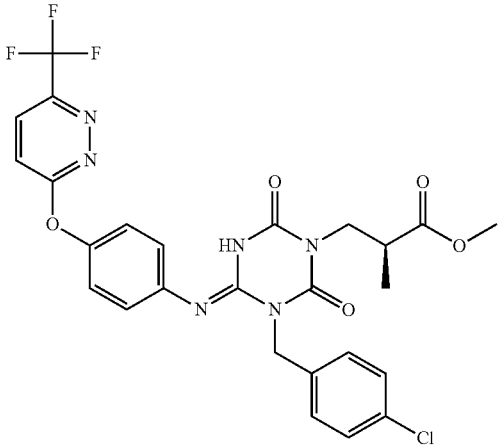 [SMILES: COC(=O)[C@@H](C)Cn1c(=O)[nH]/c(=N\c2ccc(Oc3ccc(C(F)(F)F)nn3)cc2)n(Cc2ccc(Cl)cc2)c1=O] | 591 | 2.32 | 1 |
| R-029 | 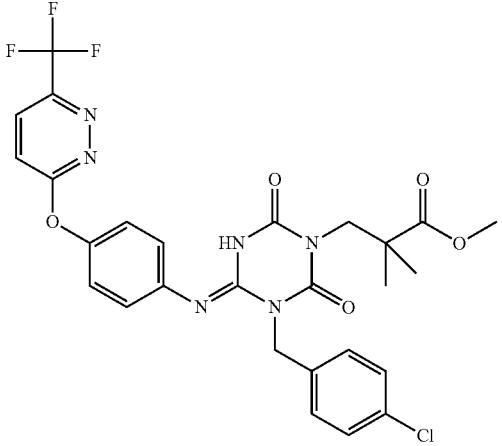 [SMILES: COC(=O)C(C)(C)Cn1c(=O)[nH]/c(=N\c2ccc(Oc3ccc(C(F)(F)F)nn3)cc2)n(Cc2ccc(Cl)cc2)c1=O] | 605 | 2.42 | 1 |
| R-030 | 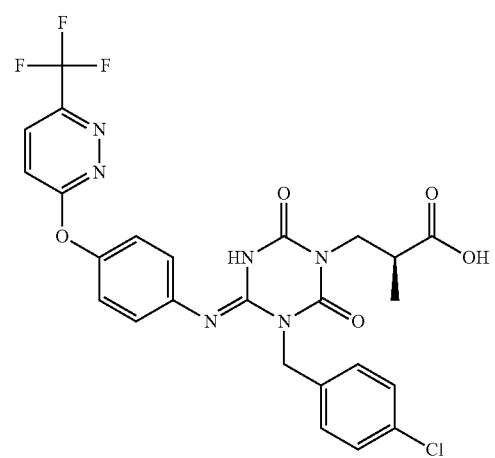 | 577 | 2.08 | 1 |

TABLE 63

| Compound No | Structure | [M + H]+ | RT | Method |
|---|---|---|---|---|
| R-031 | 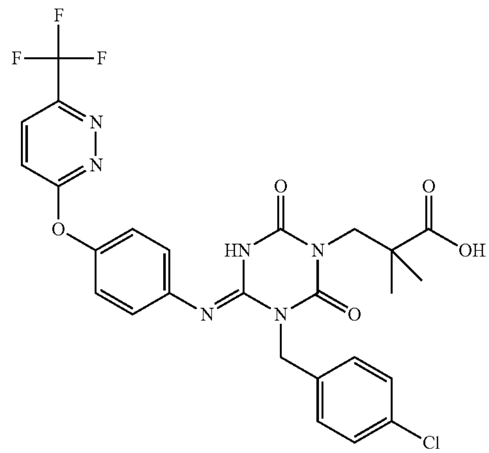 [SMILES: CC(C)(Cn1c(=O)[nH]/c(=N\c2ccc(Oc3ccc(C(F)(F)F)nn3)cc2)n(Cc2ccc(Cl)cc2)c1=O)C(=O)O] | 591 | 2.15 | 1 |
| R-032 | 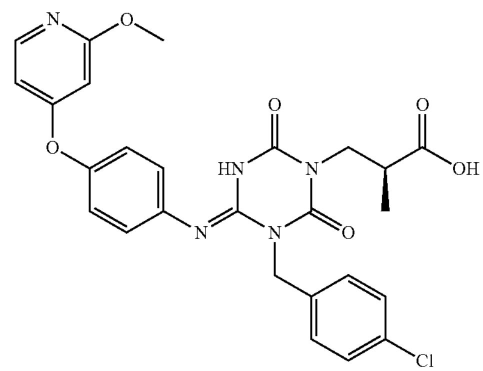 | 538 | 2 | 1 |
| R-033 | 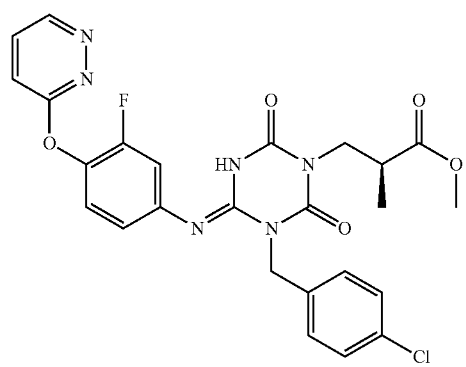 [SMILES: COC(=O)[C@@H](C)Cn1c(=O)[nH]/c(=N\c2ccc(Oc3cccnn3)c(F)c2)n(Cc2ccc(Cl)cc2)c1=O] | 541 | 2.17 | 1 |
| R-034 | 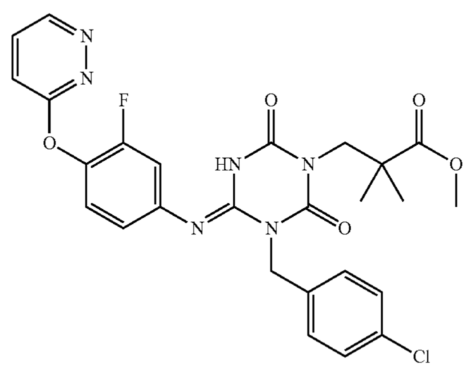 [SMILES: COC(=O)C(C)(C)Cn1c(=O)[nH]/c(=N\c2ccc(Oc3cccnn3)c(F)c2)n(Cc2ccc(Cl)cc2)c1=O] | 555 | 2.27 | 1 |

TABLE 63-continued
| Compound No | Structure | [M + H]+ | RT | Method |
|---|---|---|---|---|
| R-035 | 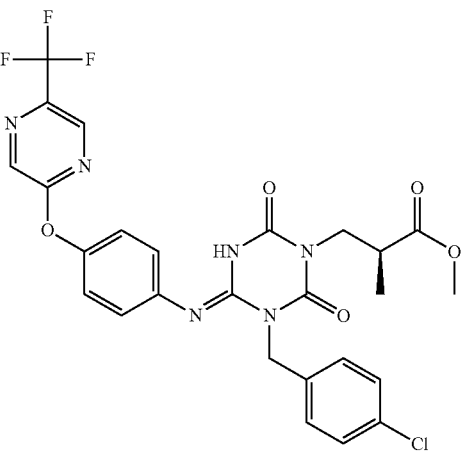 [SMILES: COC(=O)[C@@H](C)Cn1c(=O)[nH]/c(=N\c2ccc(Oc3cnc(C(F)(F)F)cn3)cc2)n(Cc2ccc(Cl)cc2)c1=O] | 591 | 2.46 | 1 |
TABLE 64
| Compound No | Structure | [M + H]+ | RT | Method |
|---|---|---|---|---|
| R-036 | 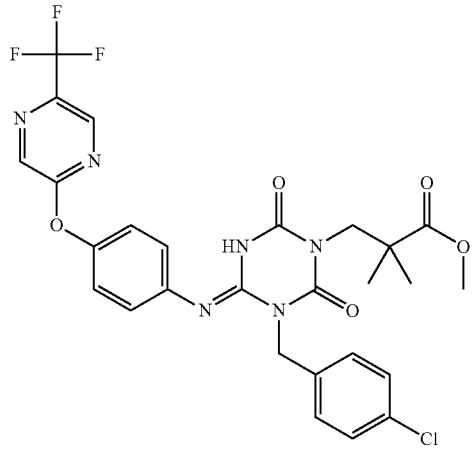 [SMILES: COC(=O)C(C)(C)Cn1c(=O)[nH]/c(=N\c2ccc(Oc3cnc(C(F)(F)F)cn3)cc2)n(Cc2ccc(Cl)cc2)c1=O] | 605 | 2.56 | 1 |
| R-037 | 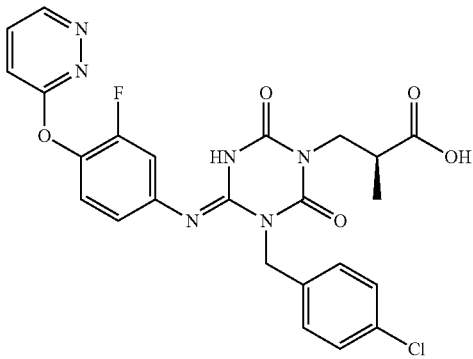 [SMILES: C[C@@H](Cn1c(=O)[nH]/c(=N\c2ccc(Oc3cccnn3)c(F)c2)n(Cc2ccc(Cl)cc2)c1=O)C(=O)O] | 527 | 1.93 | 1 |

TABLE 64-continued

| Compound No | Structure | [M + H]+ | RT | Method |
|---|---|---|---|---|
| R-038 | 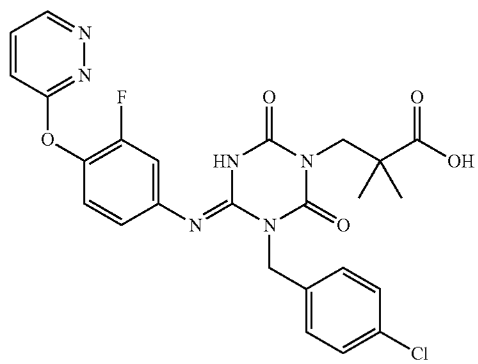 [SMILES: CC(C)(Cn1c(=O)[nH]/c(=N\c2ccc(Oc3cccnn3)c(F)c2)n(Cc2ccc(Cl)cc2)c1=O)C(=O)O] | 543 | 2.01 | 1 |
| R-039 | 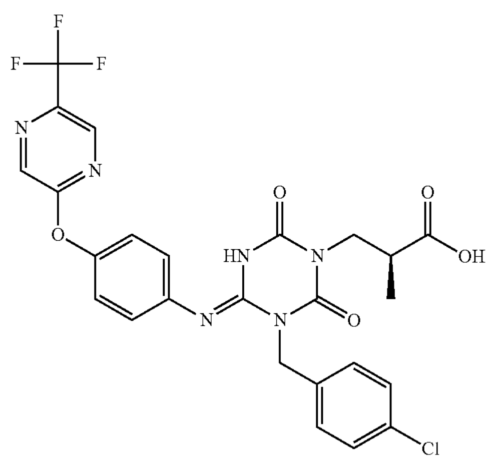 [SMILES: C[C@@H](Cn1c(=O)[nH]/c(=N\c2ccc(Oc3cnc(C(F)(F)F)cn3)cc2)n(Cc2ccc(Cl)cc2)c1=O)C(=O)O] | 577 | 2.22 | 1 |
| R-040 | 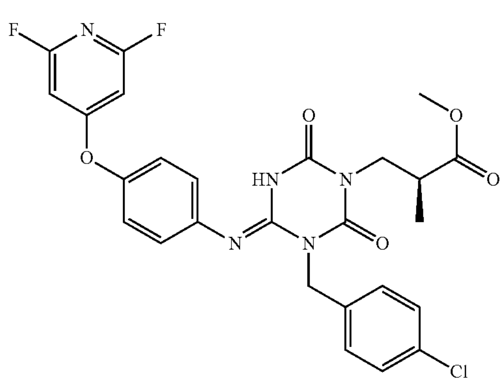 [SMILES: COC(=O)[C@@H](C)Cn1c(=O)[nH]/c(=N\c2ccc(Oc3cc(F)nc(F)c3)cc2)n(Cc2ccc(Cl)cc2)c1=O] | 558 | 2.47 | 1 |

TABLE 65

| Compound No | Structure | [M + H]+ | RT | Method |
|---|---|---|---|---|
| R-041 | 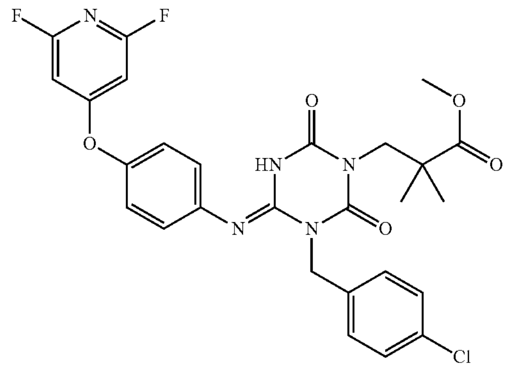 [SMILES: COC(=O)C(C)(C)Cn1c(=O)[nH]/c(=N\c2ccc(Oc3cc(F)nc(F)c3)cc2)n(Cc2ccc(Cl)cc2)c1=O] | 572 | 2.57 | 1 |
| R-042 | 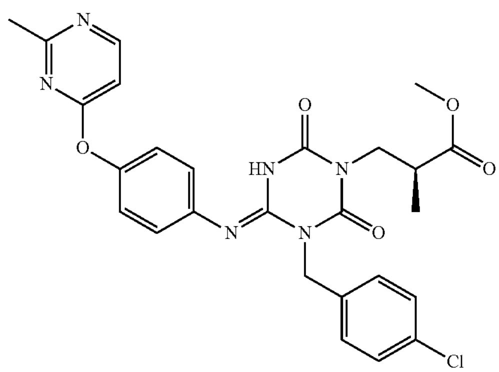 [SMILES: COC(=O)[C@@H](C)Cn1c(=O)[nH]/c(=N\c2ccc(Oc3ccnc(C)n3)cc2)n(Cc2ccc(Cl)cc2)c1=O] | 537 | 2.03 | 1 |
| R-043 | 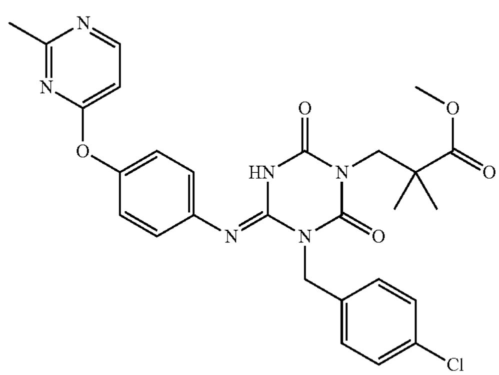 [SMILES: COC(=O)C(C)(C)Cn1c(=O)[nH]/c(=N\c2ccc(Oc3ccnc(C)n3)cc2)n(Cc2ccc(Cl)cc2)c1=O] | 551 | 2.15 | 1 |
| R-044 | 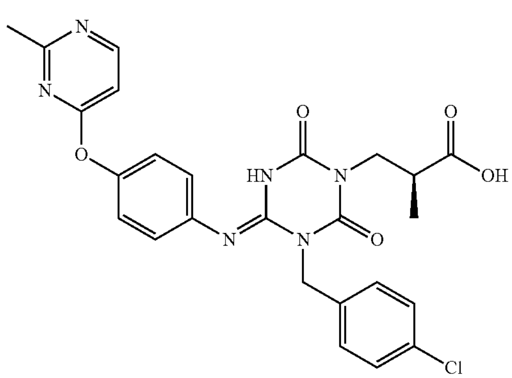 [SMILES: Cc1nccc(Oc2ccc(/N=c3\[nH]c(=O)n(C[C@H](C)C(=O)O)c(=O)n3Cc3ccc(Cl)cc3)cc2)n1] | 523 | 1.78 | 1 |

TABLE 65-continued

| Compound No | Structure | [M + H]+ | RT | Method |
|---|---|---|---|---|
| R-045 | 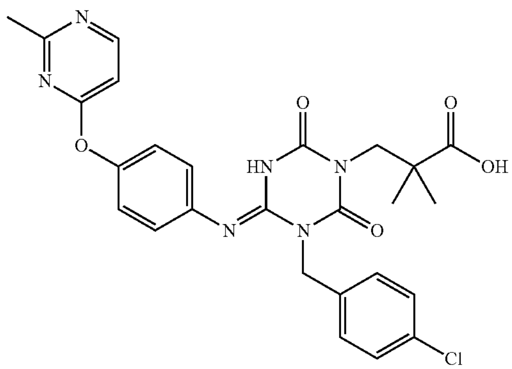 [SMILES: Cc1nccc(Oc2ccc(/N=c3\[nH]c(=O)n(CC(C)(C)C(=O)O)c(=O)n3Cc3ccc(Cl)cc3)cc2)n1] | 537 | 1.87 | 1 |

TABLE 66

| Compound No | Structure | [M + H]+ | RT | Method |
|---|---|---|---|---|
| R-046 | 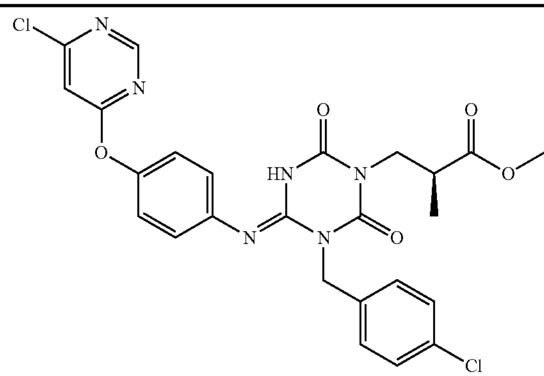 | 557 | 2.32 | 1 |
| R-047 | 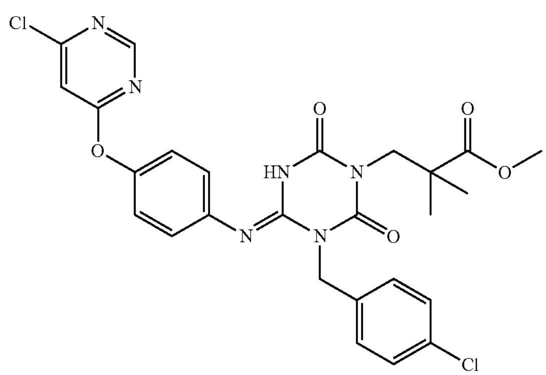 [SMILES: COC(=O)C(C)(C)Cn1c(=O)[nH]/c(=N\c2ccc(Oc3cc(Cl)ncn3)cc2)n(Cc2ccc(Cl)cc2)c1=O] | 571 | 2.42 | 1 |
| R-048 | 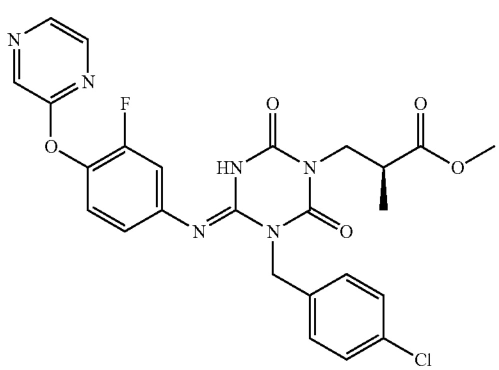 | 541 | 2.27 | 1 |

TABLE 66-continued
| Compound No | Structure | [M + H]+ | RT | Method |
|---|---|---|---|---|
| R-049 | 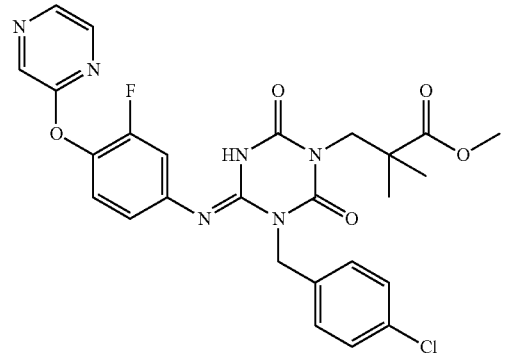 [SMILES: COC(=O)C(C)(C)Cn1c(=O)[nH]/c(=N\c2ccc(Oc3cnccn3)c(F)c2)n(Cc2ccc(Cl)cc2)c1=O] | 555 | 2.37 | 1 |
| R-050 | 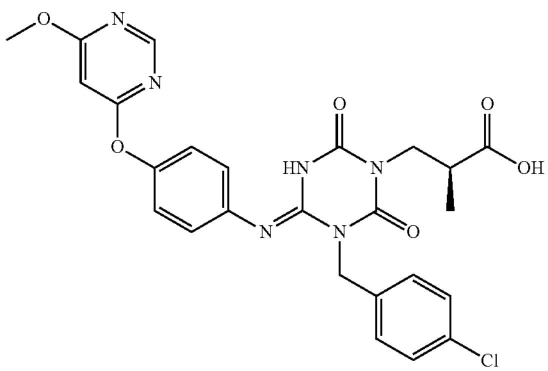 [SMILES: COc1cc(Oc2ccc(/N=c3\[nH]c(=O)n(C[C@H](C)C(=O)O)c(=O)n3Cc3ccc(Cl)cc3)cc2)ncn1] | 539 | 2.02 | 1 |
TABLE 67
| Compound No | Structure | [M + H]+ | RT | Method |
|---|---|---|---|---|
| R-051 | 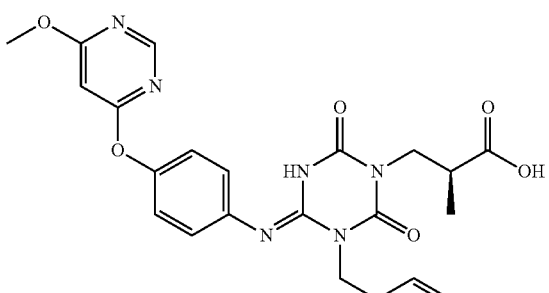 | 556 | 2.49 | 1 |
| R-052 | 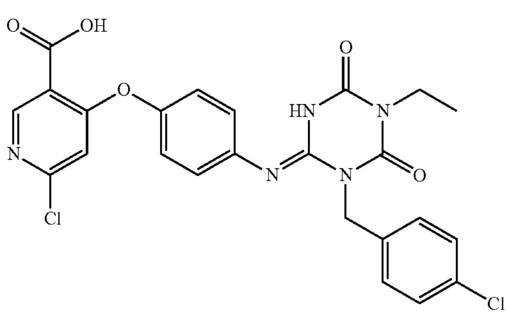 [SMILES: CCn1c(=O)[nH]/c(=N\c2ccc(Oc3cc(Cl)ncc3C(=O)O)cc2)n(Cc2ccc(Cl)cc2)c1=O] | 528 | 2.08 | 1 |

TABLE 67-continued

| Compound No | Structure | [M + H]+ | RT | Method |
|---|---|---|---|---|
| R-053 | 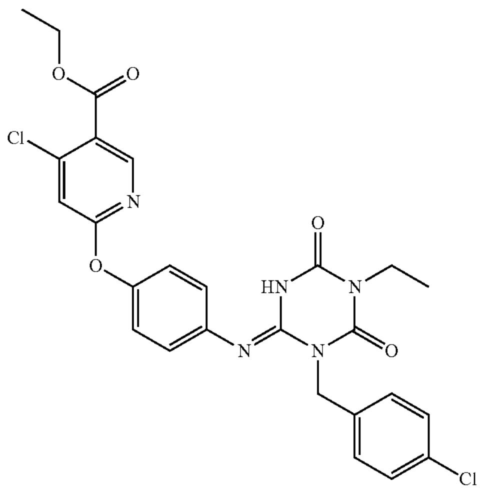 [SMILES: CCOC(=O)c1cnc(Oc2ccc(/N=c3\[nH]c(=O)n(CC)c(=O)n3Cc3ccc(Cl)cc3)cc2)cc1Cl] | 556 | 2.61 | 1 |
| R-054 | 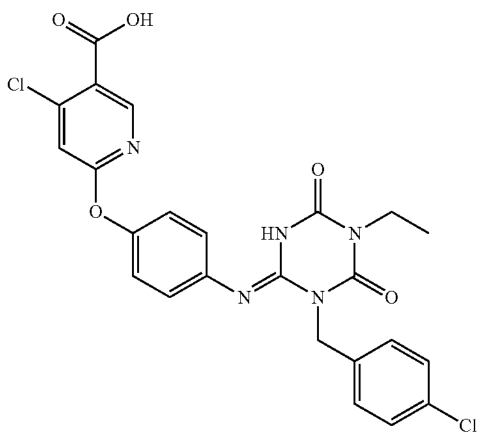 [SMILES: CCn1c(=O)[nH]/c(=N\c2ccc(Oc3cc(Cl)c(C(=O)O)cn3)cc2)n(Cc2ccc(Cl)cc2)c1=O] | 528 | 2.19 | 1 |
| R-055 | 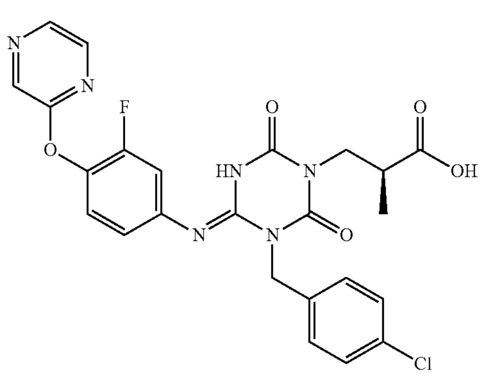 | 527 | 2.01 | 1 |

TABLE 68

| Compound No | Structure | [M + H]+ | RT | Method |
|---|---|---|---|---|
| R-056 | 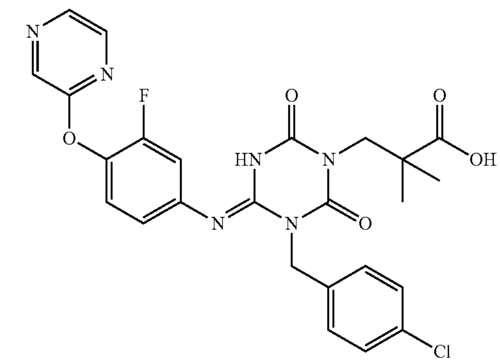 [SMILES: CC(C)(Cn1c(=O)[nH]/c(=N\c2ccc(Oc3cnccn3)c(F)c2)n(Cc2ccc(Cl)cc2)c1=O)C(=O)O] | 541 | 2.1 | 1 |
| R-057 | 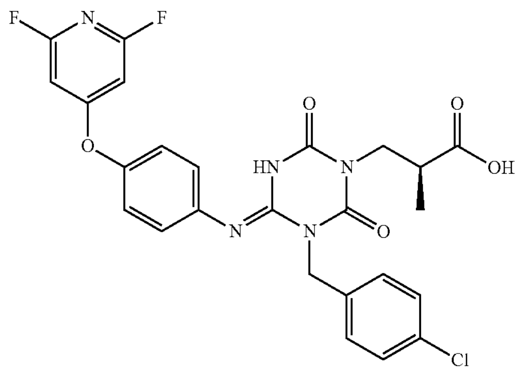 [SMILES: C[C@@H](Cn1c(=O)[nH]/c(=N\c2ccc(Oc3cc(F)nc(F)c3)cc2)n(Cc2ccc(Cl)cc2)c1=O)C(=O)O] | 544 | 2.21 | 1 |
| R-058 | 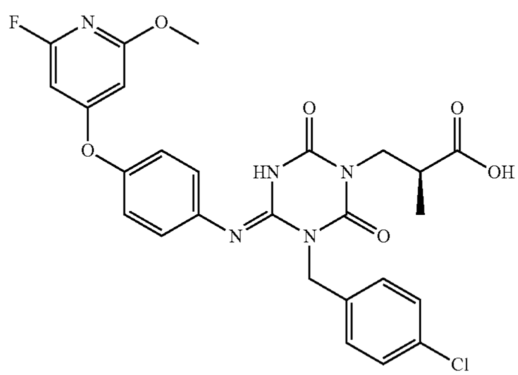 [SMILES: COc1cc(Oc2ccc(/N=c3\[nH]c(=O)n(C[C@H](C)C(=O)O)c(=O)n3Cc3ccc(Cl)cc3)cc2)cc(F)n1] | 556 | 2.27 | 1 |
| R-059 | 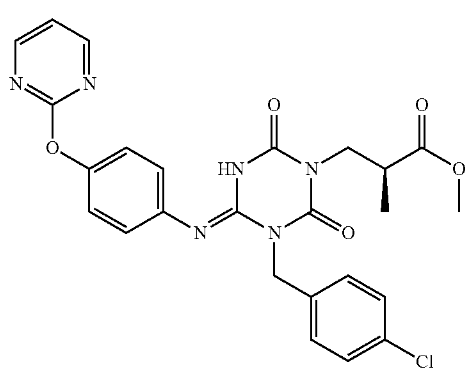 [SMILES: COC(=O)[C@@H](C)Cn1c(=O)[nH]/c(=N\c2ccc(Oc3ncccn3)cc2)n(Cc2ccc(Cl)cc2)c1=O] | 523 | 2.03 | 1 |

TABLE 68-continued
| Compound No | Structure | [M + H]+ | RT | Method |
|---|---|---|---|---|
| R-060 | 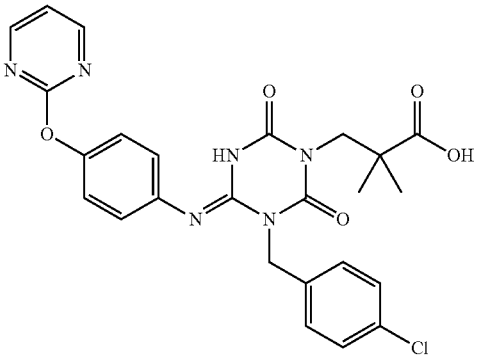 [SMILES: CC(C)(Cn1c(=O)[nH]/c(=N\c2ccc(Oc3ncccn3)cc2)n(Cc2ccc(Cl)cc2)c1=O)C(=O)O] | 523 | 1.86 | 1 |
TABLE 69
| Compound No | Structure | [M + H]+ | RT | Method |
|---|---|---|---|---|
| R-061 | 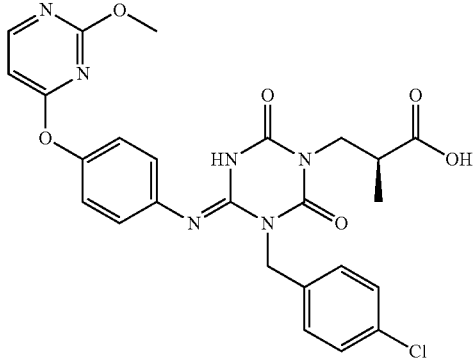 | 539 | 1.94 | 1 |
| R-062 | 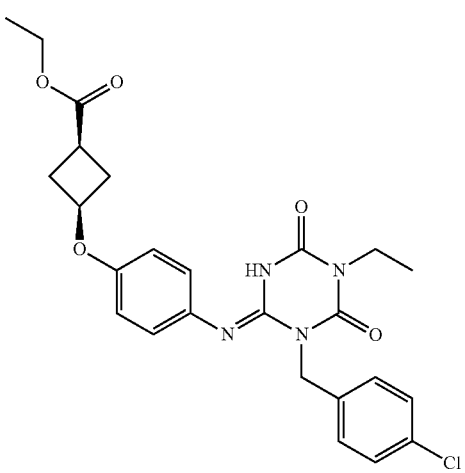 [SMILES: CCOC(=O)[C@H]1C[C@@H](Oc2ccc(/N=c3\[nH]c(=O)n(CC)c(=O)n3Cc3ccc(Cl)cc3)cc2)C1] | 499 | 2.28 | 1 |

TABLE 69-continued

| Compound No | Structure | [M + H]+ | RT | Method |
|---|---|---|---|---|
| R-063 | 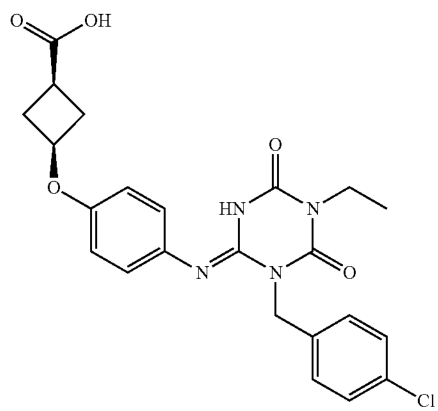 [SMILES: CCn1c(=O)[nH]/c(=N\c2ccc(O[C@H]3C[C@@H](C(=O)O)C3)cc2)n(Cc2ccc(Cl)cc2)c1=O] | 471 | 1.87 | 1 |
| R-064 | 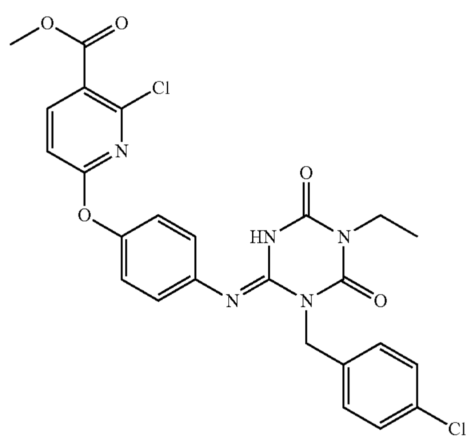 [SMILES: CCn1c(=O)[nH]/c(=N\c2ccc(Oc3ccc(C(=O)OC)c(Cl)n3)cc2)n(Cc2ccc(Cl)cc2)c1=O] | 542 | 2.41 | 1 |
| R-065 | 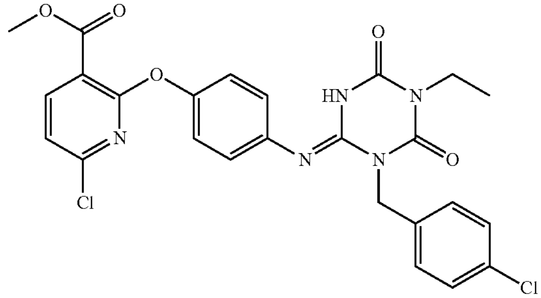 [SMILES: CCn1c(=O)[nH]/c(=N\c2ccc(Oc3nc(Cl)ccc3C(=O)OC)cc2)n(Cc2ccc(Cl)cc2)c1=O] | 542 | 2.4 | 1 |

TABLE 70

| Compound No | Structure | [M + H]+ | RT | Method |
|---|---|---|---|---|
| R-066 | 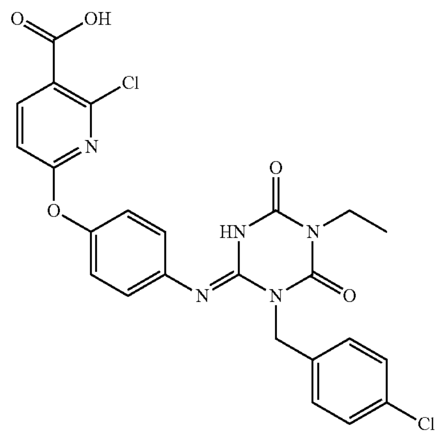 [SMILES: CCn1c(=O)[nH]/c(=N\c2ccc(Oc3ccc(C(=O)O)c(Cl)n3)cc2)n(Cc2ccc(Cl)cc2)c1=O] | 528 | 2.11 | 1 |
| R-067 | 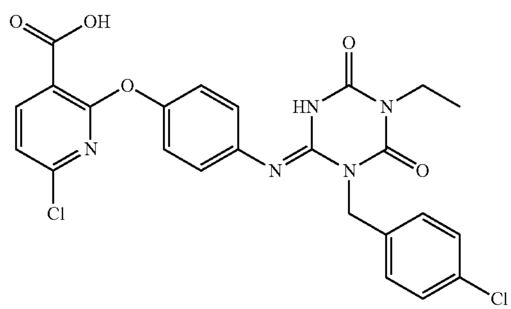 [SMILES: CCn1c(=O)[nH]/c(=N\c2ccc(Oc3nc(Cl)ccc3C(=O)O)cc2)n(Cc2ccc(Cl)cc2)c1=O] | 528 | 2.12 | 1 |
| R-068 | 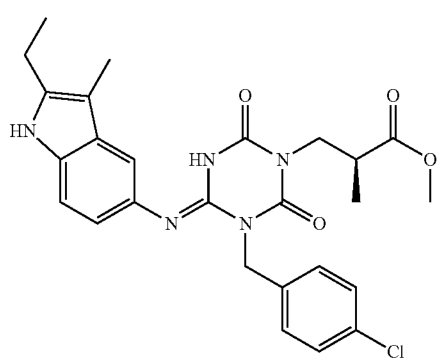 [SMILES: CCc1[nH]c2ccc(/N=c3\[nH]c(=O)n(C[C@H](C)C(=O)OC)c(=O)n3Cc3ccc(Cl)cc3)cc2c1C] | 510 | 2.25 | 1 |
| R-069 | 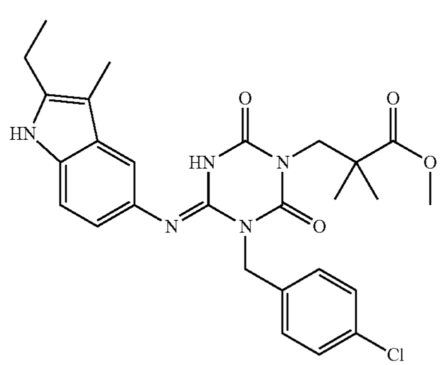 [SMILES: CCc1[nH]c2ccc(/N=c3\[nH]c(=O)n(CC(C)(C)C(=O)OC)c(=O)n3Cc3ccc(Cl)cc3)cc2c1C] | 524 | 2.36 | 1 |

TABLE 70-continued
| Compound No | Structure | [M + H]+ | RT | Method |
|---|---|---|---|---|
| R-070 | 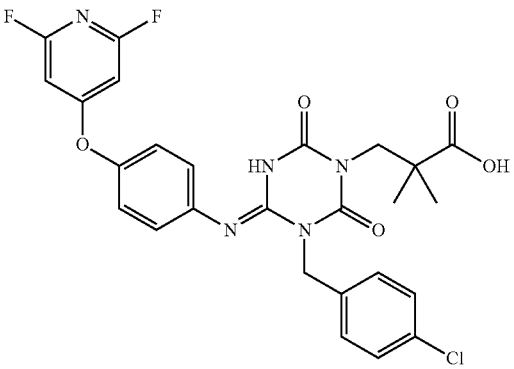 [SMILES: CC(C)(Cn1c(=O)[nH]/c(=N\c2ccc(Oc3cc(F)nc(F)c3)cc2)n(Cc2ccc(Cl)cc2)c1=O)C(=O)O] | 558 | 2.29 | 1 |
TABLE 71
| Compound No | Structure | [M + H]+ | RT | Method |
|---|---|---|---|---|
| R-071 | 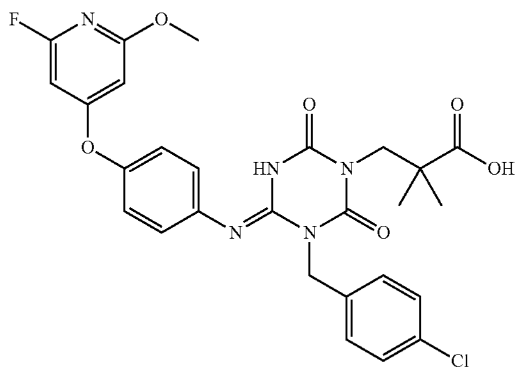 [SMILES: COc1cc(Oc2ccc(/N=c3\[nH]c(=O)n(CC(C)(C)C(=O)O)c(=O)n3Cc3ccc(Cl)cc3)cc2)cc(F)n1] | 570 | 2.35 | 1 |
| R-072 | 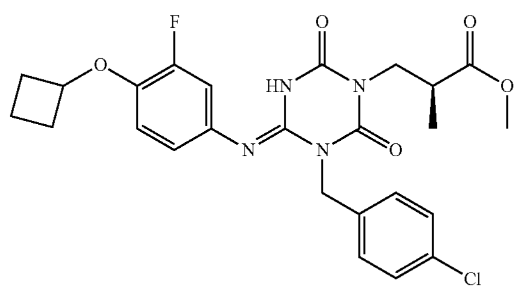 [SMILES: COC(=O)[C@@H](C)Cn1c(=O)[nH]/c(=N\c2ccc(OC3CCC3)c(F)c2)n(Cc2ccc(Cl)cc2)c1=O] | 517 | 2.45 | 1 |
| R-073 | 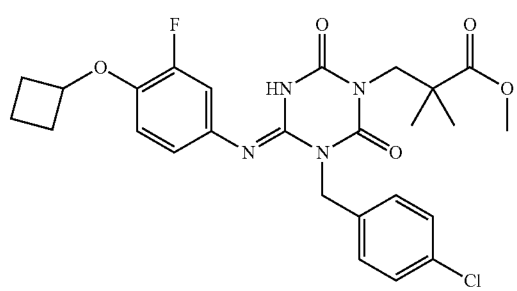 [SMILES: COC(=O)C(C)(C)Cn1c(=O)[nH]/c(=N\c2ccc(OC3CCC3)c(F)c2)n(Cc2ccc(Cl)cc2)c1=O] | 531 | 2.55 | 1 |

TABLE 71-continued

| Compound No | Structure | [M + H]+ | RT | Method |
|---|---|---|---|---|
| R-074 | 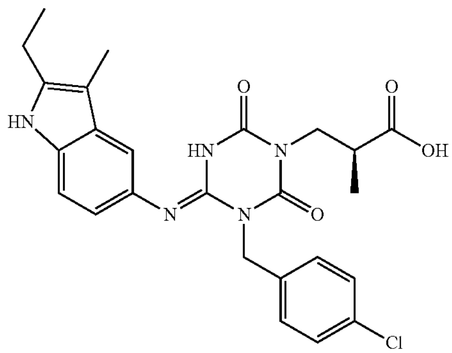 [SMILES: CCc1[nH]c2ccc(/N=c3\[nH]c(=O)n(C[C@H](C)C(=O)O)c(=O)n3Cc3ccc(Cl)cc3)cc2c1C] | 496 | 2 | 1 |
| R-075 | 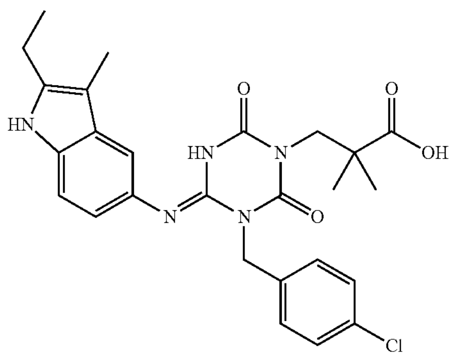 [SMILES: CCc1[nH]c2ccc(/N=c3\[nH]c(=O)n(CC(C)(C)C(=O)O)c(=O)n3Cc3ccc(Cl)cc3)cc2c1C] | 510 | 2.09 | 1 |

TABLE 72

| Compound No | Structure | [M + H]+ | RT | Method |
|---|---|---|---|---|
| R-076 | 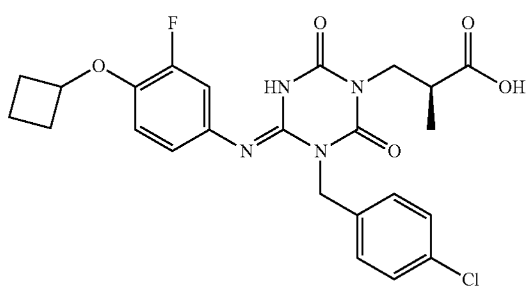 [SMILES: C[C@@H](Cn1c(=O)[nH]/c(=N\c2ccc(OC3CCC3)c(F)c2)n(Cc2ccc(Cl)cc2)c1=O)C(=O)O] | 503 | 2.19 | 1 |
| R-077 | 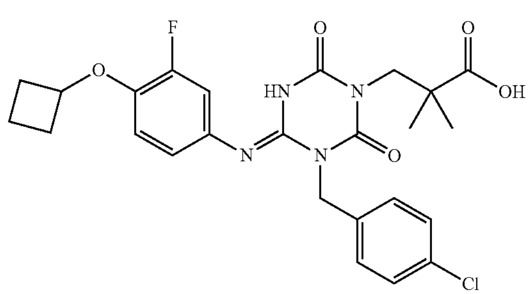 [SMILES: CC(C)(Cn1c(=O)[nH]/c(=N\c2ccc(OC3CCC3)c(F)c2)n(Cc2ccc(Cl)cc2)c1=O)C(=O)O] | 517 | 2.27 | 1 |

TABLE 72-continued

| Compound No | Structure | [M + H]+ | RT | Method |
|---|---|---|---|---|
| R-078 | 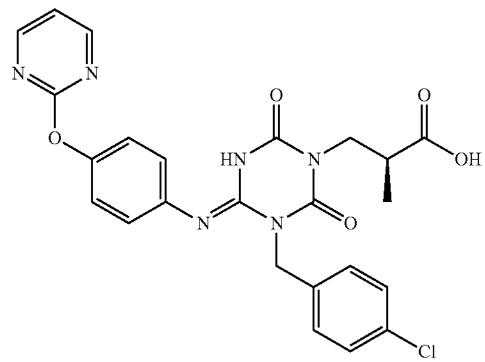 | 509 | 1.77 | 1 |
| R-079 | 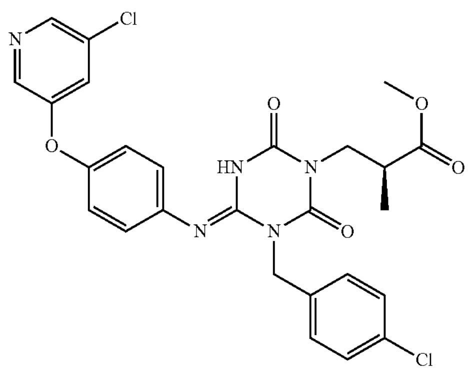 | 556 | 2.37 | 1 |
| R-080 | 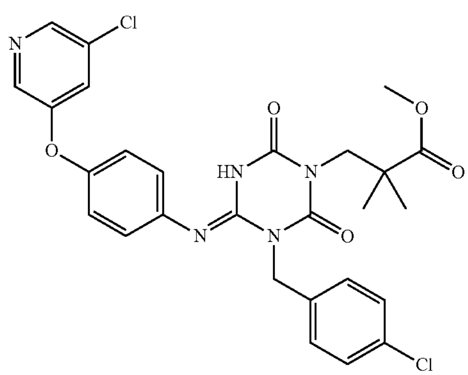 [SMILES: COC(=O)C(C)(C)Cn1c(=O)[nH]/c(=N\c2ccc(Oc3cncc(Cl)c3)cc2)n(Cc2ccc(Cl)cc2)c1=O] | 570 | 2.48 | 1 |

TABLE 73

| Compound No | Structure | [M + H]+ | RT | Method |
|---|---|---|---|---|
| R-081 | 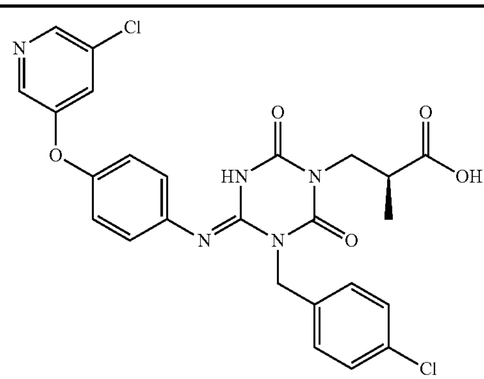 | 542 | 2.17 | 1 |

TABLE 73-continued

| Compound No | Structure | [M + H]+ | RT | Method |
|---|---|---|---|---|
| R-082 | 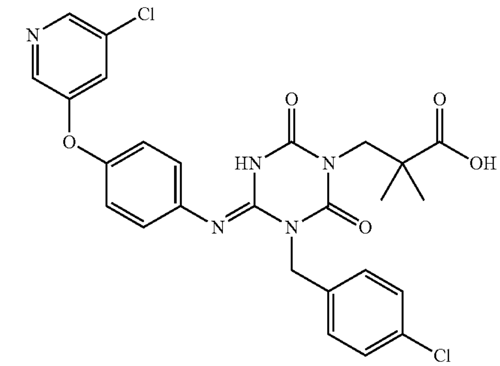 | 556 | 2.2 | 1 |
| R-083 | 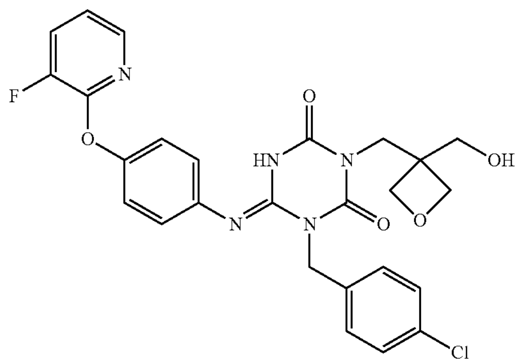 [SMILES: O=c1[nH]/c(=N\c2ccc(Oc3ncccc3F)cc2)n(Cc2ccc(Cl)cc2)c(=O)n1CC1(CO)COC1] | 540 | 1.98 | 1 |
| R-084 | 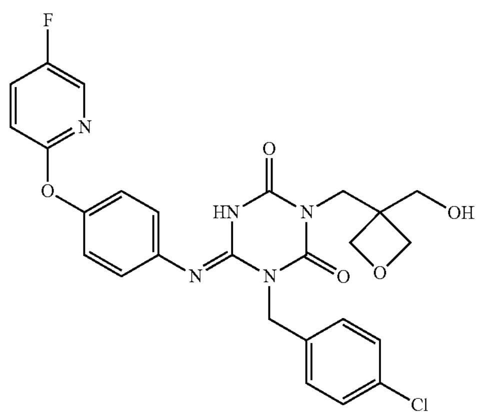 [SMILES: O=c1[nH]/c(=N\c2ccc(Oc3ccc(F)cn3)cc2)n(Cc2ccc(Cl)cc2)c(=O)n1CC1(CO)COC1] | 540 | 1.97 | 1 |
| R-085 | 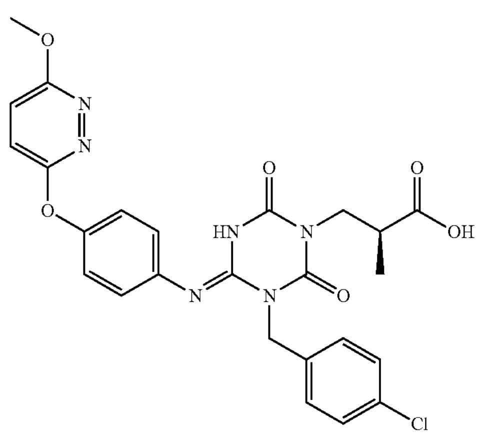 [SMILES: COc1ccc(Oc2ccc(/N=c3\[nH]c(=O)n(C[C@H](C)C(=O)O)c(=O)n3Cc3ccc(Cl)cc3)cc2)nn1] | 539 | 1.93 | 1 |

TABLE 74
| Compound No | Structure | [M + H]+ | RT | Method |
|---|---|---|---|---|
| R-086 | 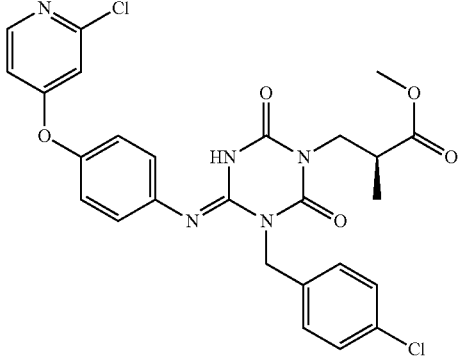 [SMILES: COC(=O)[C@@H](C)Cn1c(=O)[nH]/c(=N\c2ccc(Oc3ccnc(Cl)c3)cc2)n(Cc2ccc(Cl)cc2)c1=O] | 556 | 2.38 | 1 |
| R-087 | 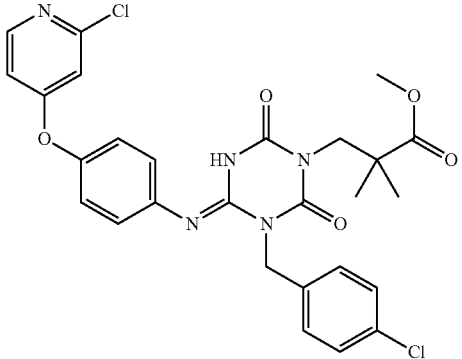 [SMILES: COC(=O)C(C)(C)Cn1c(=O)[nH]/c(=N\c2ccc(Oc3ccnc(Cl)c3)cc2)n(Cc2ccc(Cl)cc2)c1=O] | 570 | 2.47 | 1 |
| R-088 | 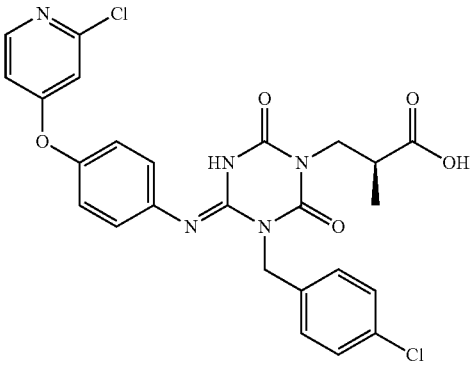 | 542 | 2.09 | 1 |
| R-089 | 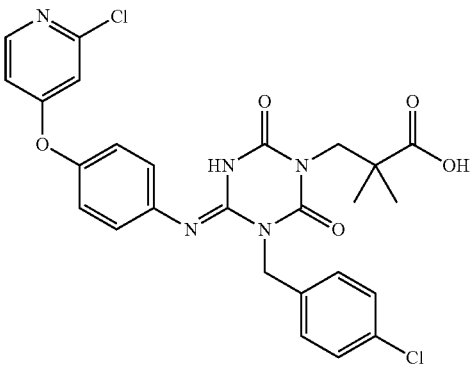 [SMILES: CC(C)(Cn1c(=O)[nH]/c(=N\c2ccc(Oc3ccnc(Cl)c3)cc2)n(Cc2ccc(Cl)cc2)c1=O)C(=O)O] | 556 | 2.17 | 1 |

TABLE 74-continued

| Compound No | Structure | [M + H]+ | RT | Method |
|---|---|---|---|---|
| R-090 | 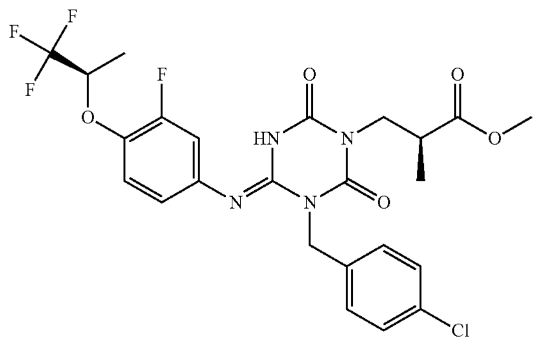 [SMILES: COC(=O)[C@@H](C)Cn1c(=O)[nH]/c(=N\c2ccc(O[C@H](C)C(F)(F)F)c(F)c2)n(Cc2ccc(Cl)cc2)c1=O] | 559 | 2.55 | 1 |

TABLE 75

| Compound No | Structure | [M + H]+ | RT | Method |
|---|---|---|---|---|
| R-091 | 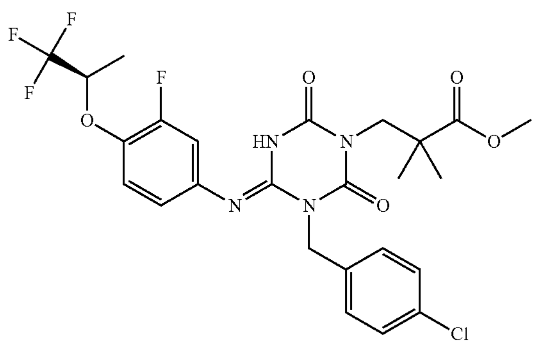 [SMILES: COC(=O)C(C)(C)Cn1c(=O)[nH]/c(=N\c2ccc(O[C@H](C)C(F)(F)F)c(F)c2)n(Cc2ccc(Cl)cc2)c1=O] | 573 | 2.58 | 1 |
| R-092 | 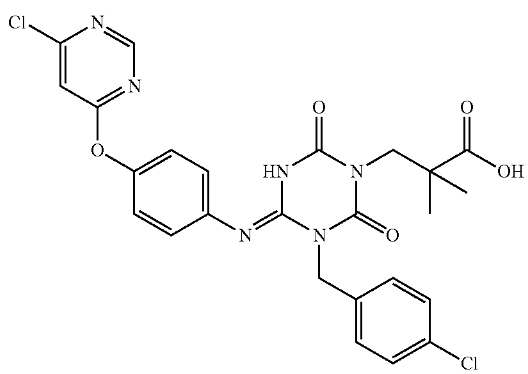 [SMILES: CC(C)(Cn1c(=O)[nH]/c(=N\c2ccc(Oc3cc(Cl)ncn3)cc2)n(Cc2ccc(Cl)cc2)c1=O)C(=O)O] | 557 | 2.15 | 1 |
| R-093 | 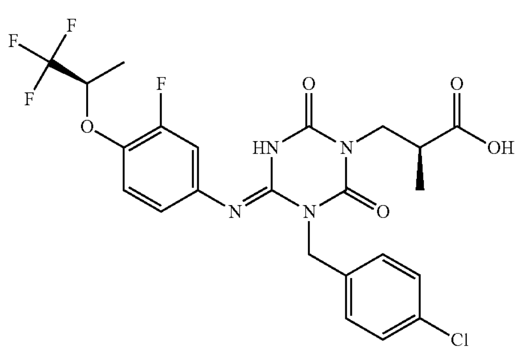 [SMILES: C[C@@H](Cn1c(=O)[nH]/c(=N\c2ccc(O[C@H](C)C(F)(F)F)c(F)c2)n(Cc2ccc(Cl)cc2)c1=O)C(=O)O] | 545 | 2.26 | 1 |

TABLE 75-continued
| Compound No | Structure | [M + H]+ | RT | Method |
|---|---|---|---|---|
| R-094 | 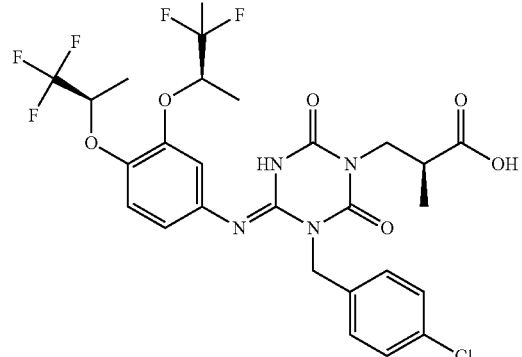 | 639 | 2.46 | 1 |
| R-095 | 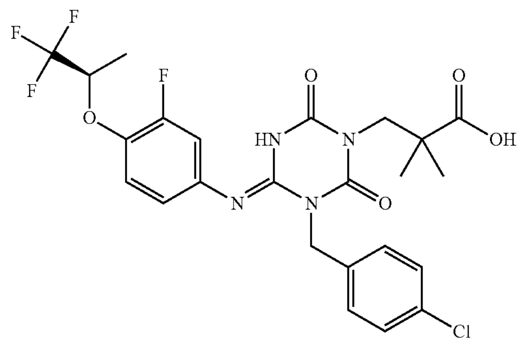 [SMILES: C[C@@H](Oc1ccc(/N=c2\[nH]c(=O)n(CC(C)(C)C(=O)O)c(=O)n2Cc2ccc(Cl)cc2)cc1F)C(F)(F)F] | 559 | 2.33 | 1 |
TABLE 76
| Compound No | Structure | [M + H]+ | RT | Method |
|---|---|---|---|---|
| R-096 | 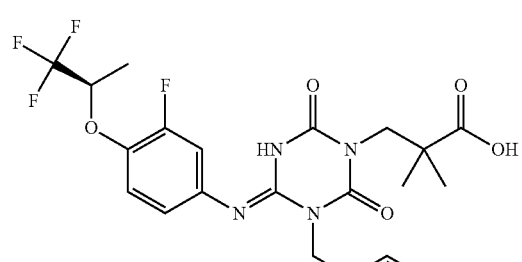 | 653 | 2.51 | 1 |
| R-097 | 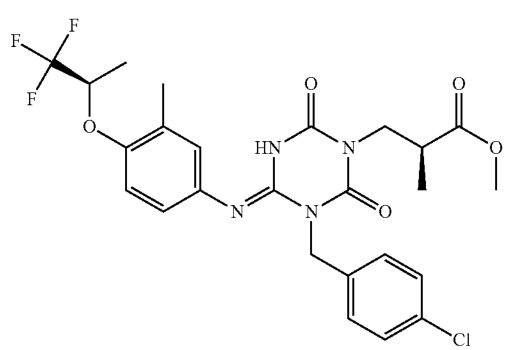 [SMILES: COC(=O)[C@@H](C)Cn1c(=O)[nH]/c(=N\c2ccc(O[C@H](C)C(F)(F)F)c(C)c2)n(Cc2ccc(Cl)cc2)c1=O] | 555 | 2.49 | 1 |

TABLE 76-continued
| Compound No | Structure | [M + H]+ | RT | Method |
|---|---|---|---|---|
| R-098 | 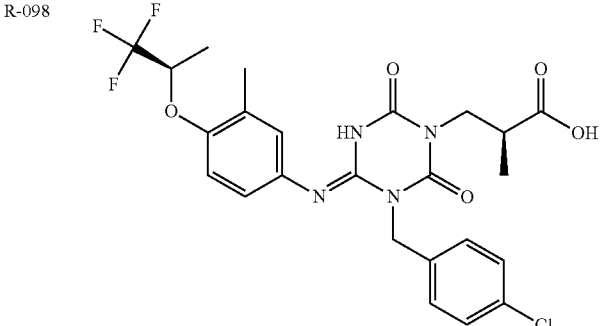 | 541 | 2.25 | 1 |
| R-099 | 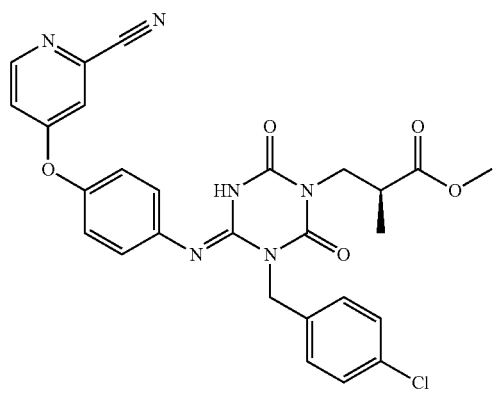 [SMILES: COC(=O)[C@@H](C)Cn1c(=O)[nH]/c(=N\c2ccc(Oc3ccnc(C#N)c3)cc2)n(Cc2ccc(Cl)cc2)c1=O] | 547 | 2.25 | 1 |
| R-100 | 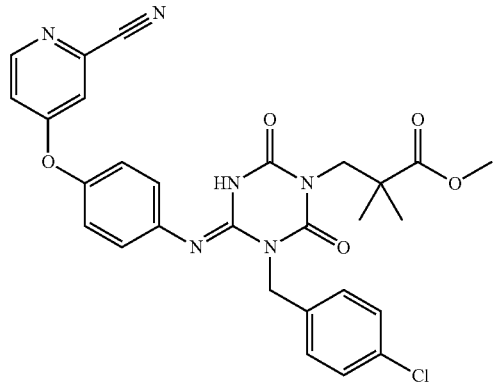 [SMILES: COC(=O)C(C)(C)Cn1c(=O)[nH]/c(=N\c2ccc(Oc3ccnc(C#N)c3)cc2)n(Cc2ccc(Cl)cc2)c1=O] | 561 | 2.36 | 1 |
TABLE 77
| Compound No | Structure | [M + H]+ | RT | Method |
|---|---|---|---|---|
| R-101 | 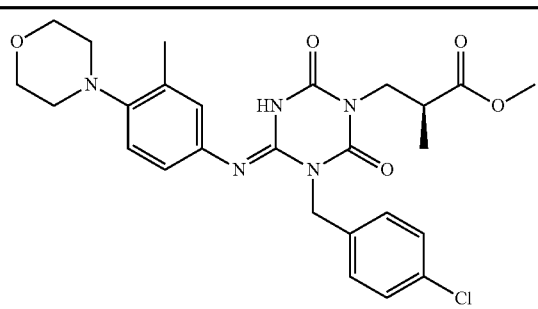 | 528 | 2.2 | 1 |

TABLE 77-continued
| Compound No | Structure | [M + H]+ | RT | Method |
|---|---|---|---|---|
| R-102 | 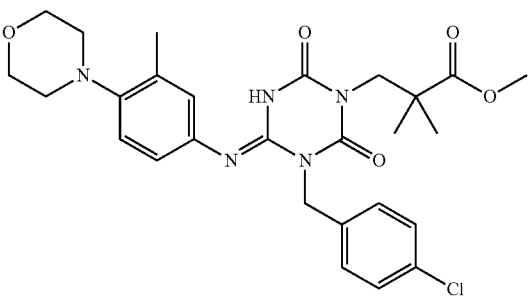 [SMILES: COC(=O)C(C)(C)Cn1c(=O)[nH]/c(=N\c2ccc(N3CCOCC3)c(C)c2)n(Cc2ccc(Cl)cc2)c1=O] | 542 | 2.32 | 1 |
| R-103 | 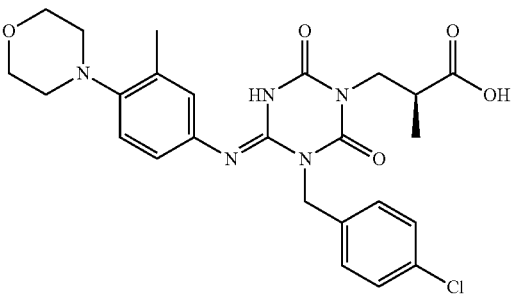 [SMILES: Cc1cc(/N=c2\[nH]c(=O)n(C[C@H](C)C(=O)O)c(=O)n2Cc2ccc(Cl)cc2)ccc1N1CCOCC1] | 514 | 1.91 | 1 |
| R-104 | 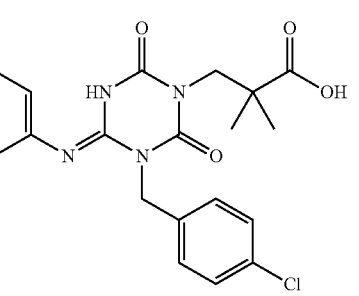 | 528 | 2 | 1 |
| R-105 | 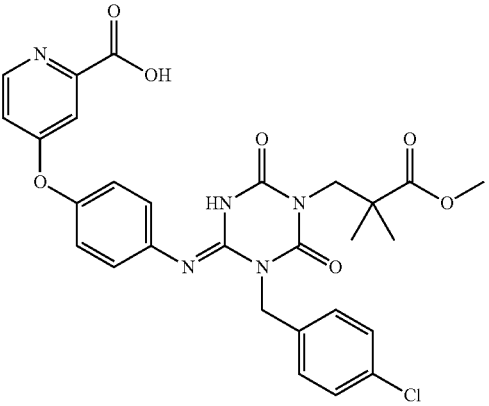 [SMILES: COC(=O)C(C)(C)Cn1c(=O)[nH]/c(=N\c2ccc(Oc3ccnc(C(=O)O)c3)cc2)n(Cc2ccc(Cl)cc2)c1=O] | 580 | 1.94 | 1 |

TABLE 78

| Compound No | Structure | [M + H]+ | RT | Method |
|---|---|---|---|---|
| R-106 | 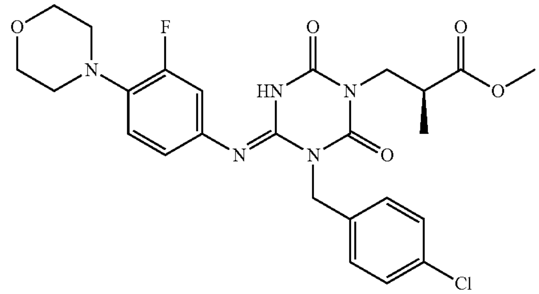 [SMILES: COC(=O)[C@@H](C)Cn1c(=O)[nH]/c(=N\c2ccc(N3CCOCC3)c(F)c2)n(Cc2ccc(Cl)cc2)c1=O] | 532 | 2.14 | 1 |
| R-107 | 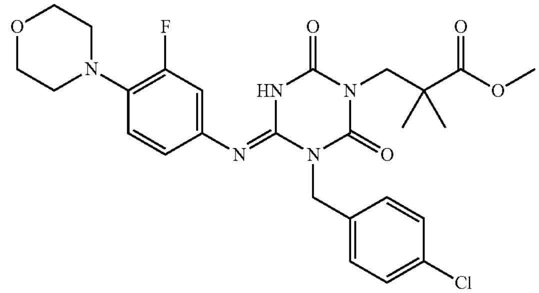 [SMILES: COC(=O)C(C)(C)Cn1c(=O)[nH]/c(=N\c2ccc(N3CCOCC3)c(F)c2)n(Cc2ccc(Cl)cc2)c1=O] | 546 | 2.26 | 1 |
| R-108 | 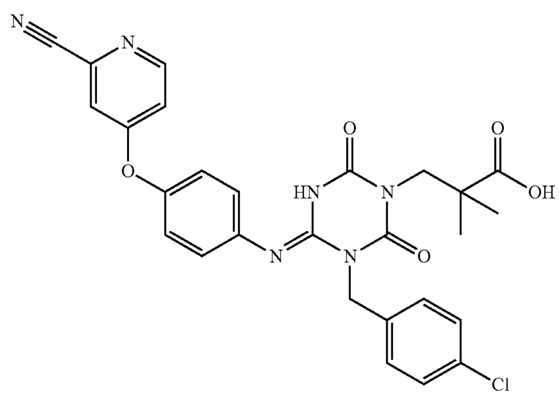 [SMILES: CC(C)(Cn1c(=O)[nH]/c(=N\c2ccc(Oc3ccnc(C#N)c3)cc2)n(Cc2ccc(Cl)cc2)c1=O)C(=O)O] | 547 | 2.18 | 1 |
| R-109 | 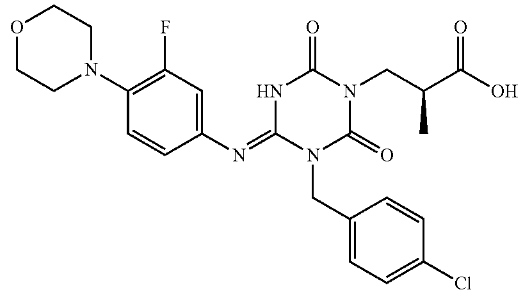 [SMILES: C[C@@H](Cn1c(=O)[nH]/c(=N\c2ccc(N3CCOCC3)c(F)c2)n(Cc2ccc(Cl)cc2)c1=O)C(=O)O] | 518 | 1.88 | 1 |
| R-110 | 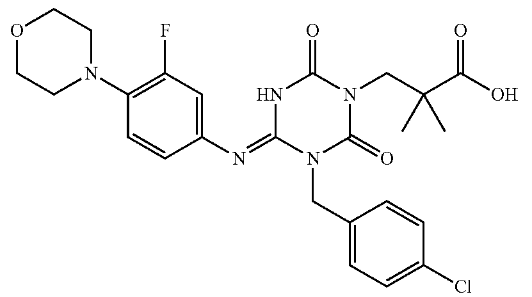 [SMILES: CC(C)(Cn1c(=O)[nH]/c(=N\c2ccc(N3CCOCC3)c(F)c2)n(Cc2ccc(Cl)cc2)c1=O)C(=O)O] | 532 | 1.97 | 1 |

TABLE 79

| Compound No | Structure | [M + H]+ | RT | Method |
|---|---|---|---|---|
| R-111 | 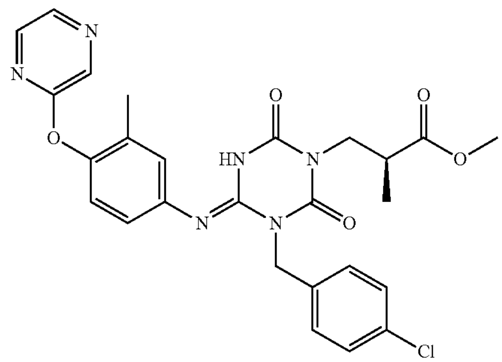 [SMILES: COC(=O)[C@@H](C)Cn1c(=O)[nH]/c(=N\c2ccc(Oc3cnccn3)c(C)c2)n(Cc2ccc(Cl)cc2)c1=O] | 537 | 2.22 | 1 |
| R-112 | 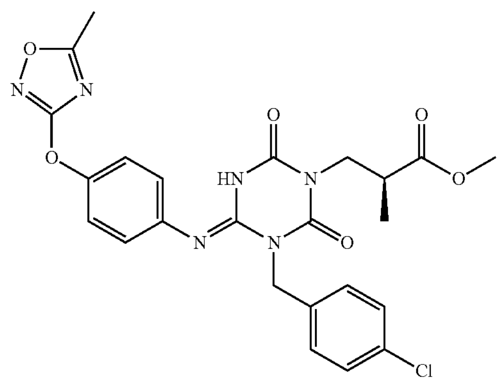 [SMILES: COC(=O)[C@@H](C)Cn1c(=O)[nH]/c(=N\c2ccc(Oc3noc(C)n3)cc2)n(Cc2ccc(Cl)cc2)c1=O] | 527 | 2.15 | 1 |
| R-113 | 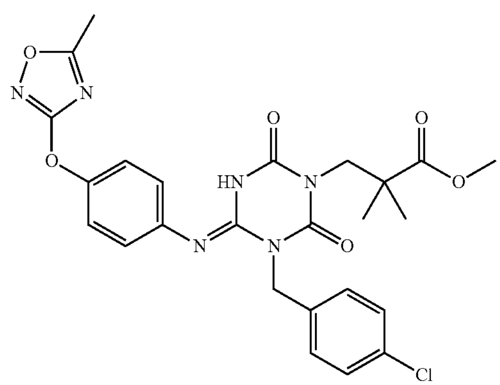 [SMILES: COC(=O)C(C)(C)Cn1c(=O)[nH]/c(=N\c2ccc(Oc3noc(C)n3)cc2)n(Cc2ccc(Cl)cc2)c1=O] | 541 | 2.27 | 1 |
| R-114 | 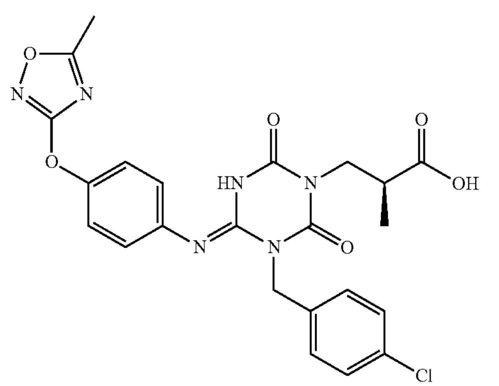 [SMILES: Cc1nc(Oc2ccc(/N=c3\[nH]c(=O)n(C[C@H](C)C(=O)O)c(=O)n3Cc3ccc(Cl)cc3)cc2)no1] | 513 | 1.9 | 1 |

TABLE 79-continued

| Compound No | Structure | [M + H]+ | RT | Method |
|---|---|---|---|---|
| R-115 | 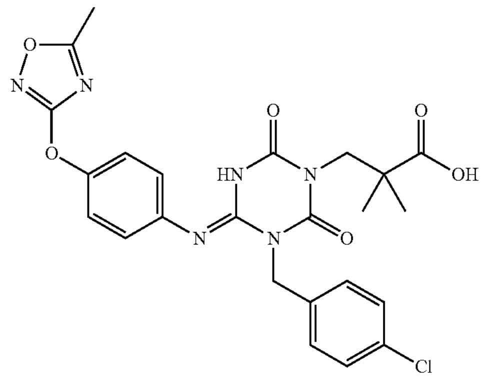 [SMILES: Cc1nc(Oc2ccc(/N=c3\[nH]c(=O)n(CC(C)(C)C(=O)O)c(=O)n3Cc3ccc(Cl)cc3)cc2)no1] | 527 | 1.99 | 1 |

TABLE 80

| Compound No | Structure | [M + H]+ | RT | Method |
|---|---|---|---|---|
| R-116 | 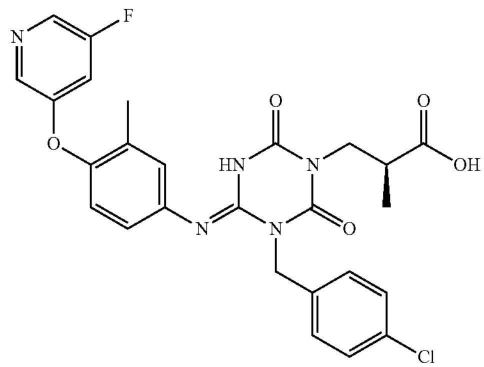 [SMILES: Cc1cc(/N=c2\[nH]c(=O)n(C[C@H](C)C(=O)O)c(=O)n2Cc2ccc(Cl)cc2)ccc1Oc1cncc(F)c1] | 540 | 208 | 1 |
| R-117 | 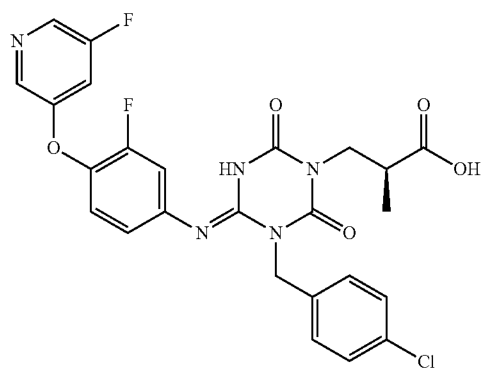 [SMILES: C[C@@H](Cn1c(=O)[nH]/c(=N\c2ccc(Oc3cncc(F)c3)c(F)c2)n(Cc2ccc(Cl)cc2)c1=O)C(=O)O] | 544 | 2.12 | 1 |
| R-118 | 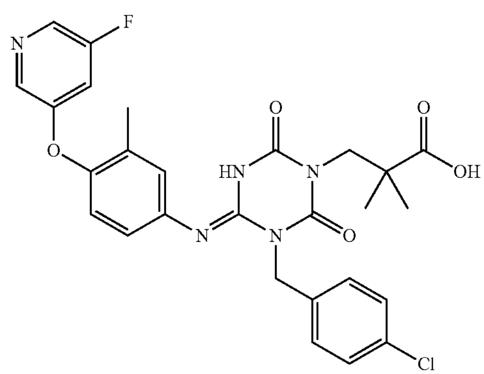 [SMILES: Cc1cc(/N=c2\[nH]c(=O)n(CC(C)(C)C(=O)O)c(=O)n2Cc2ccc(Cl)cc2)ccc1Oc1cncc(F)c1] | 554 | 2.16 | 1 |

TABLE 80-continued

| Compound No | Structure | [M + H]+ | RT | Method |
|---|---|---|---|---|
| R-119 | 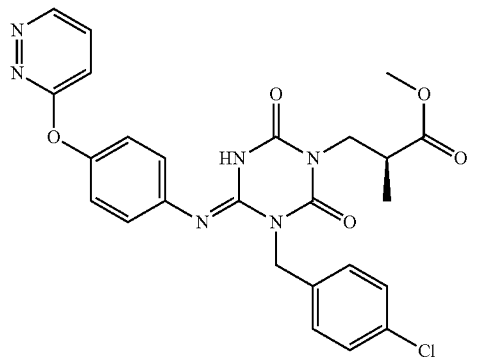 | 523 | 2.01 | 1 |
| R-120 | 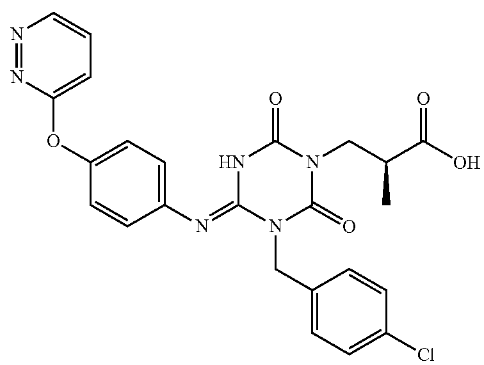 | 509 | 1.77 | 1 |

TABLE 81

| Compound No | Structure | [M + H]+ | RT | Method |
|---|---|---|---|---|
| R-121 | 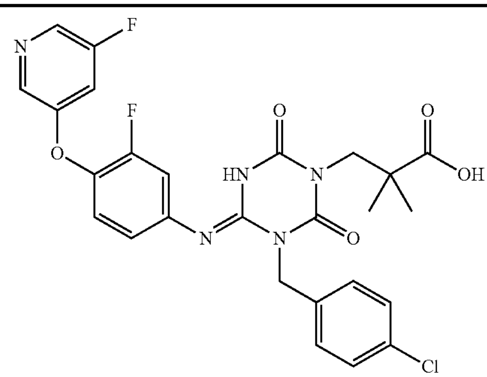 | 558 | 2.2 | 1 |
| R-122 | 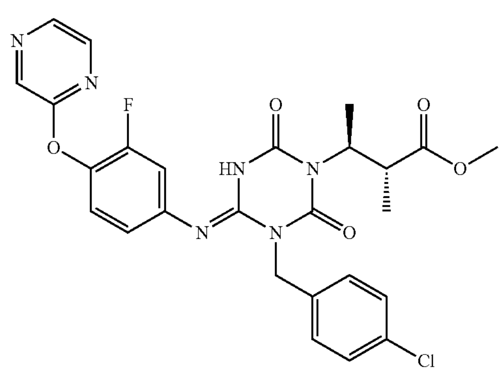 [SMILES: COC(=O)[C@H](C)[C@H](C)n1c(=O)[nH]/c(=N\c2ccc(Oc3cnccn3)c(F)c2)n(Cc2ccc(Cl)cc2)c1=O] | 555 | 2.42 | 1 |

TABLE 81-continued

| Compound No | Structure | [M + H]+ | RT | Method |
|---|---|---|---|---|
| R-123 | 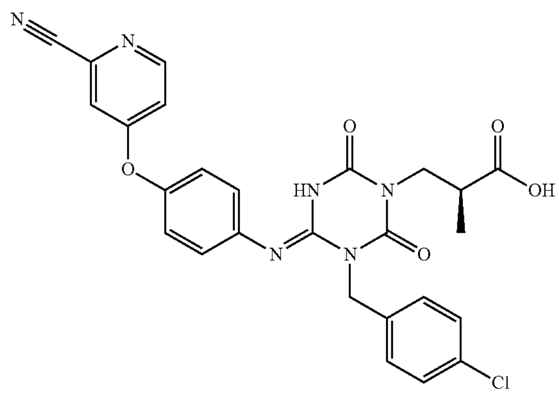 [SMILES: C[C@@H](Cn1c(=O)[nH]/c(=N\c2ccc(Oc3ccnc(C#N)c3)cc2)n(Cc2ccc(Cl)cc2)c1=O)C(=O)O] | 533 | 2 | 1 |
| R-124 | 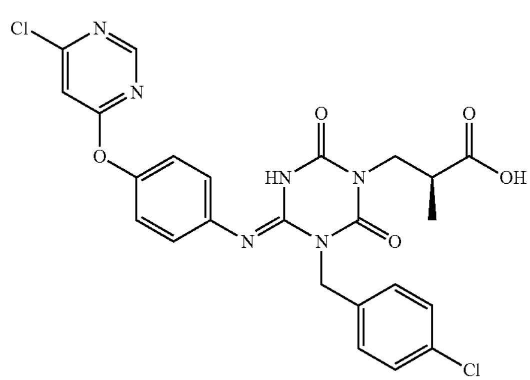 [SMILES: C[C@@H](Cn1c(=O)[nH]/c(=N\c2ccc(Oc3cc(Cl)ncn3)cc2)n(Cc2ccc(Cl)cc2)c1=O)C(=O)O] | 543 | 2.07 | 1 |
| R-125 | 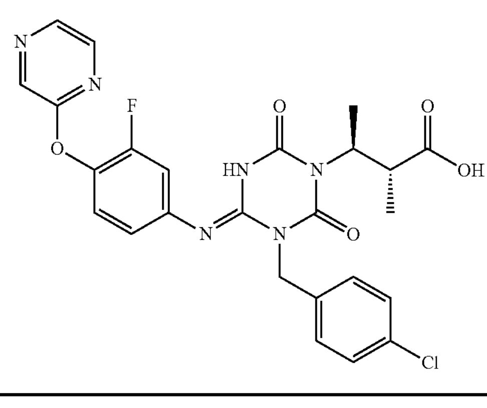 | 541 | 2.13 | 1 |

TABLE 82

| Compound No | Structure | [M + H]+ | RT | Method |
|---|---|---|---|---|
| R-126 | 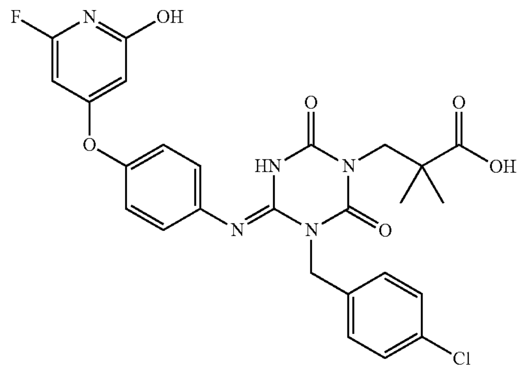 [SMILES: CC(C)(Cn1c(=O)[nH]/c(=N\c2ccc(Oc3cc(O)nc(F)c3)cc2)n(Cc2ccc(Cl)cc2)c1=O)C(=O)O] | 556 | 1.99 | 1 |
| R-127 | 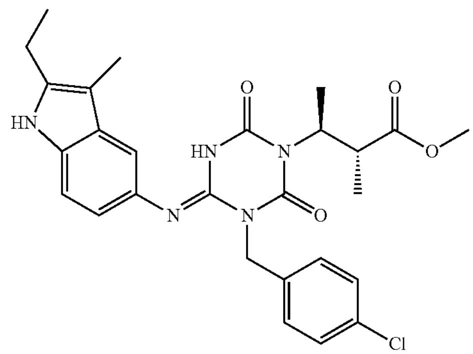 [SMILES: CCc1[nH]c2ccc(/N=c3\[nH]c(=O)n([C@@H](C)[C@@H](C)C(=O)OC)c(=O)n3Cc3ccc(Cl)cc3)cc2c1C] | 524 | 2.39 | 1 |
| R-128 | 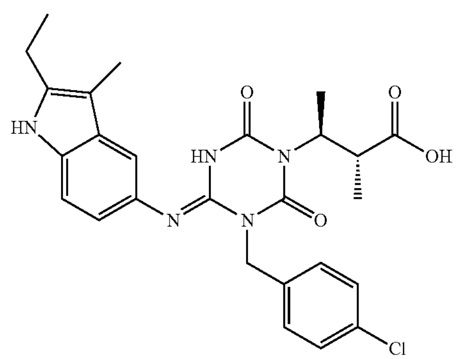 [SMILES: CCc1[nH]c2ccc(/N=c3\[nH]c(=O)n([C@@H](C)[C@@H](C)C(=O)O)c(=O)n3Cc3ccc(Cl)cc3)cc2c1C] | 510 | 2.1 | 1 |
| R-129 | 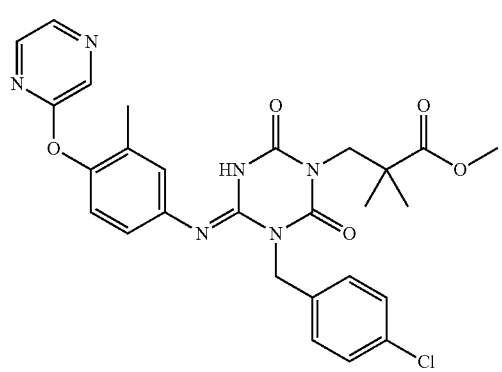 [SMILES: COC(=O)C(C)(C)Cn1c(=O)[nH]/c(=N\c2ccc(Oc3cnccn3)c(C)c2)n(Cc2ccc(Cl)cc2)c1=O] | 551 | 2.33 | 1 |

TABLE 82-continued

| Compound No | Structure | [M + H]+ | RT | Method |
|---|---|---|---|---|
| R-130 | 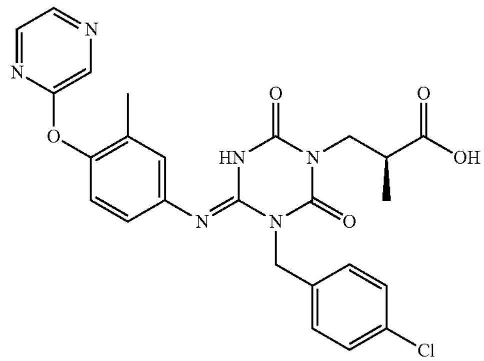 [SMILES: Cc1cc(/N=c2\[nH]c(=O)n(C[C@H](C)C(=O)O)c(=O)n2Cc2ccc(Cl)cc2)ccc1Oc1cnccn1] | 523 | 1.97 | 1 |

TABLE 83

| Compound No | Structure | [M + H]+ | RT | Method |
|---|---|---|---|---|
| R-131 | 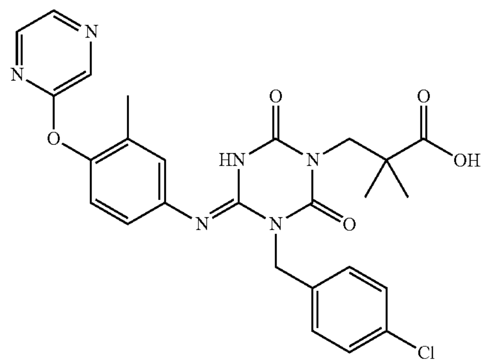 [SMILES: Cc1cc(/N=c2\[nH]c(=O)n(CC(C)(C)C(=O)O)c(=O)n2Cc2ccc(Cl)cc2)ccc1Oc1cnccn1] | 537 | 2.06 | 1 |
| R-132 | 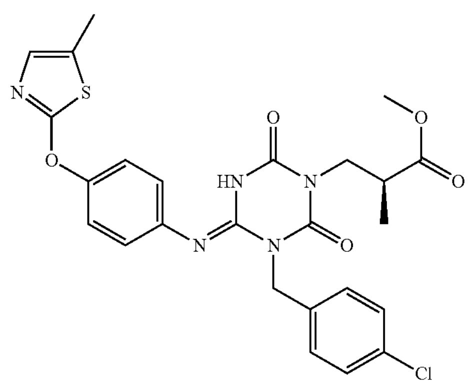 [SMILES: COC(=O)[C@@H](C)Cn1c(=O)[nH]/c(=N\c2ccc(Oc3ncc(C)s3)cc2)n(Cc2ccc(Cl)cc2)c1=O] | 542 | 2.38 | 1 |
| R-133 | 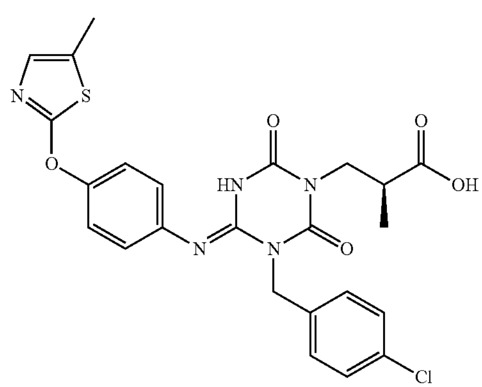 [SMILES: Cc1cnc(Oc2ccc(/N=c3\[nH]c(=O)n(C[C@H](C)C(=O)O)c(=O)n3Cc3ccc(Cl)cc3)cc2)s1] | 528 | 2.13 | 1 |

TABLE 83-continued

| Compound No | Structure | [M + H]+ | RT | Method |
|---|---|---|---|---|
| R-134 | 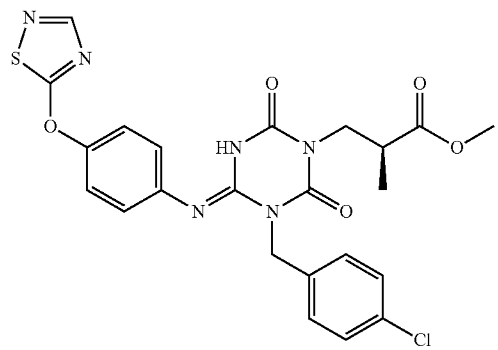 [SMILES: COC(=O)[C@@H](C)Cn1c(=O)[nH]/c(=N\c2ccc(Oc3ncns3)cc2)n(Cc2ccc(Cl)cc2)c1=O] | 529 | 2.2 | 1 |
| R-135 | 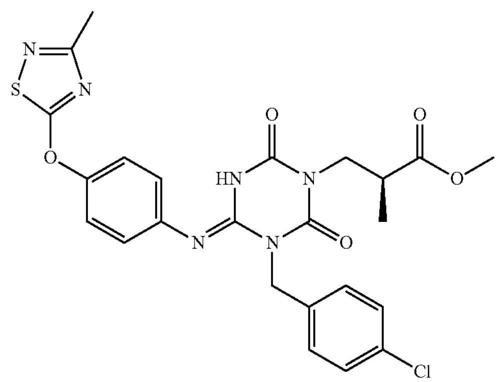 [SMILES: COC(=O)[C@@H](C)Cn1c(=O)[nH]/c(=N\c2ccc(Oc3nc(C)ns3)cc2)n(Cc2ccc(Cl)cc2)c1=O] | 543 | 2.27 | 1 |

TABLE 84

| Compound No | Structure | [M + H]+ | RT | Method |
|---|---|---|---|---|
| R-136 | 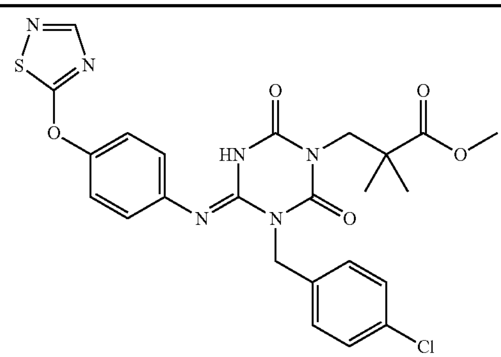 | 543 | 2.31 | 1 |
| R-137 | 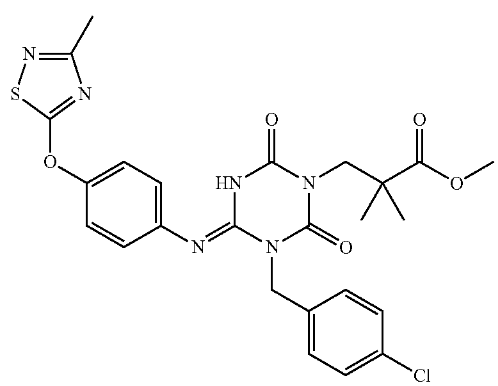 [SMILES: COC(=O)C(C)(C)Cn1c(=O)[nH]/c(=N\c2ccc(Oc3nc(C)ns3)cc2)n(Cc2ccc(Cl)cc2)c1=O] | 557 | 2.38 | 1 |

TABLE 84-continued

| Compound No | Structure | [M + H]+ | RT | Method |
|---|---|---|---|---|
| R-138 | 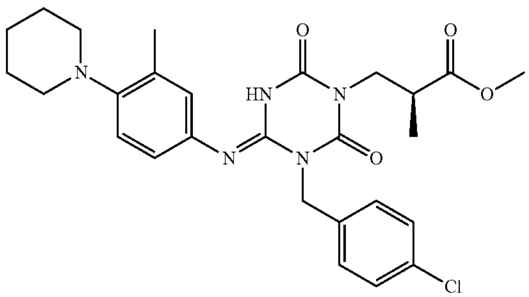 [SMILES: COC(=O)[C@@H](C)Cn1c(=O)[nH]/c(=N\c2ccc(N3CCCCC3)c(C)c2)n(Cc2ccc(Cl)cc2)c1=O] | 526 | 1.98 | 1 |
| R-139 | 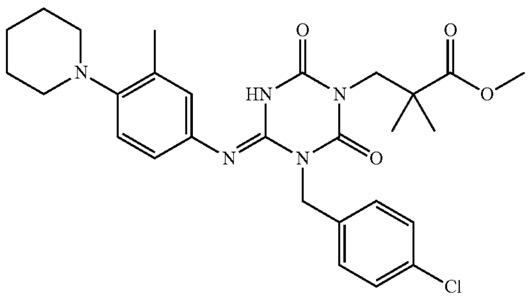 [SMILES: COC(=O)C(C)(C)Cn1c(=O)[nH]/c(=N\c2ccc(N3CCCCC3)c(C)c2)n(Cc2ccc(Cl)cc2)c1=O] | 540 | 2.12 | 1 |
| R-140 | 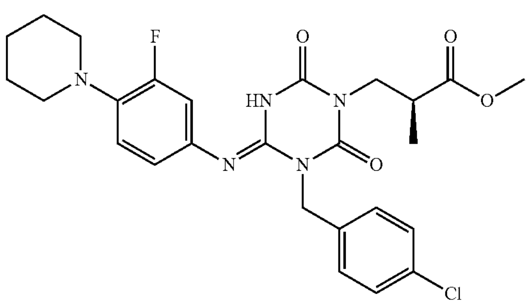 [SMILES: COC(=O)[C@@H](C)Cn1c(=O)[nH]/c(=N\c2ccc(N3CCCCC3)c(F)c2)n(Cc2ccc(Cl)cc2)c1=O] | 530 | 2.43 | 1 |

TABLE 85

| Compound No | Structure | [M + H]+ | RT | Method |
|---|---|---|---|---|
| R-141 | 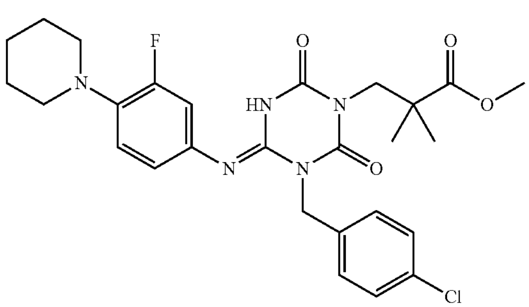 | 544 | 2.54 | 1 |

TABLE 85-continued

| Compound No | Structure | [M + H]+ | RT | Method |
|---|---|---|---|---|
| R-142 | 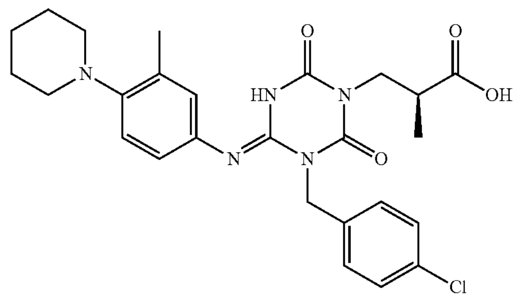 [SMILES: Cc1cc(/N=c2\[nH]c(=O)n(C[C@H](C)C(=O)O)c(=O)n2Cc2ccc(Cl)cc2)ccc1N1CCCCC1] | 512 | 2.17 | 2 |
| R-143 | 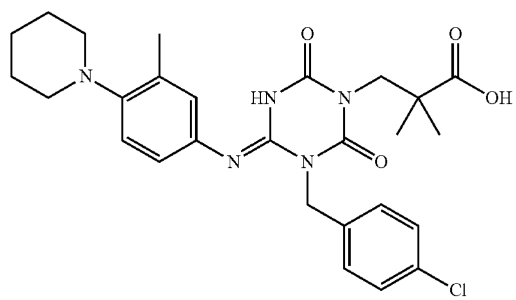 [SMILES: Cc1cc(/N=c2\[nH]c(=O)n(CC(C)(C)C(=O)O)c(=O)n2Cc2ccc(Cl)cc2)ccc1N1CCCCC1] | 526 | 1.77 | 1 |
| R-144 | 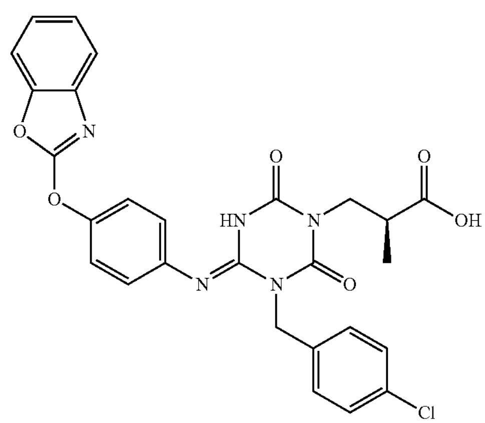 | 548 | 2.26 | 1 |
| R-145 | 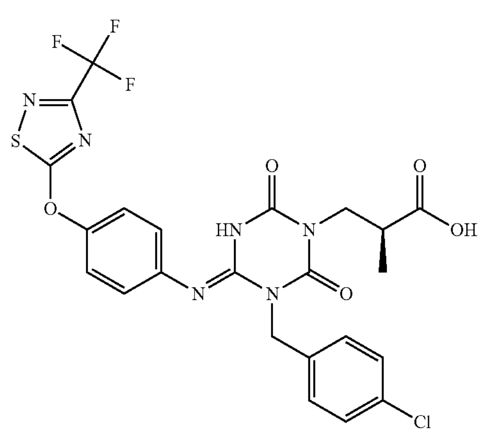 [SMILES: C[C@@H](Cn1c(=O)[nH]/c(=N\c2ccc(Oc3nc(C(F)(F)F)ns3)cc2)n(Cc2ccc(Cl)cc2)c1=O)C(=O)O] | 583 | 2.8 | 1 |

TABLE 86
| Compound No | Structure | [M + H]+ | RT | Method |
|---|---|---|---|---|
| R-146 | 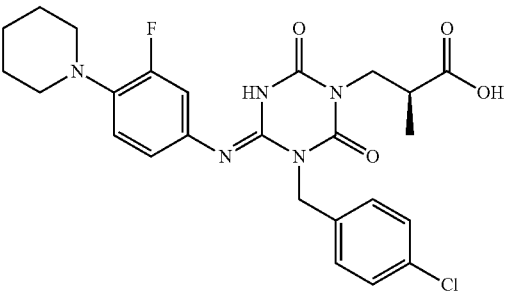 | 516 | 2.14 | 1 |
| R-147 | 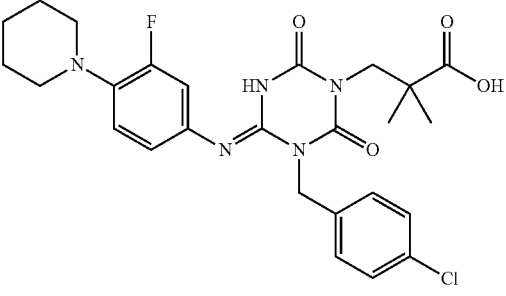 [SMILES: CC(C)(Cn1c(=O)[nH]/c(=N\c2ccc(N3CCCCC3)c(F)c2)n(Cc2ccc(Cl)cc2)c1=O)C(=O)O] | 530 | 2.23 | 1 |
| R-148 | 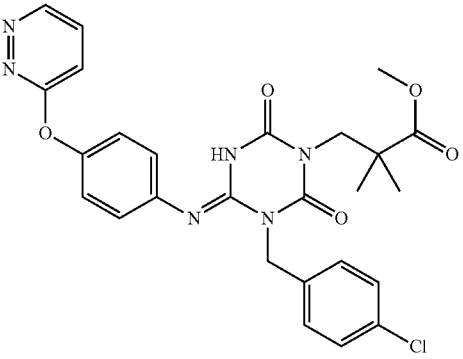 [SMILES: COC(=O)C(C)(C)Cn1c(=O)[nH]/c(=N\c2ccc(Oc3cccnn3)cc2)n(Cc2ccc(Cl)cc2)c1=O] | 537 | 2.12 | 1 |
| R-149 | 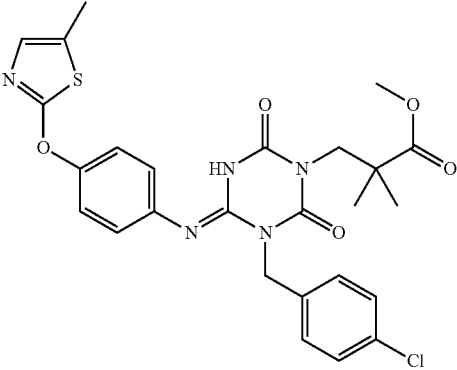 [SMILES: COC(=O)C(C)(C)Cn1c(=O)[nH]/c(=N\c2ccc(Oc3ncc(C)s3)cc2)n(Cc2ccc(Cl)cc2)c1=O] | 556 | 2.49 | 1 |

TABLE 86-continued

| Compound No | Structure | [M + H]+ | RT | Method |
|---|---|---|---|---|
| R-150 | 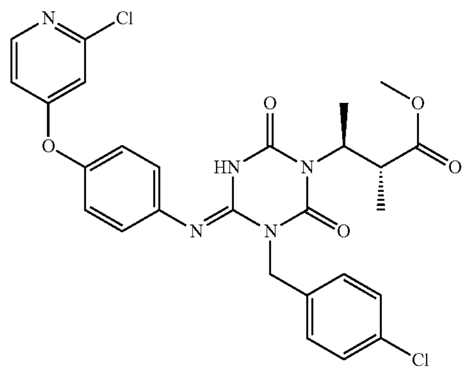 [SMILES: COC(=O)[C@H](C)[C@H](C)n1c(=O)[nH]/c(=N\c2ccc(Oc3ccnc(Cl)c3)cc2)n(Cc2ccc(Cl)cc2)c1=O] | 570 | 2.49 | 1 |

TABLE 87

| Compound No | Structure | [M + H]+ | RT | Method |
|---|---|---|---|---|
| R-151 | 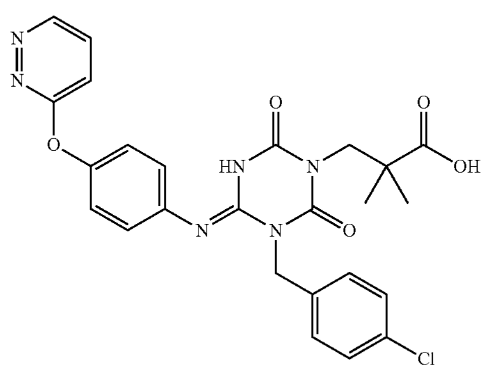 [SMILES: CC(C)(Cn1c(=O)[nH]/c(=N\c2ccc(Oc3cccnn3)cc2)n(Cc2ccc(Cl)cc2)c1=O)C(=O)O] | 523 | 1.87 | 1 |
| R-152 | 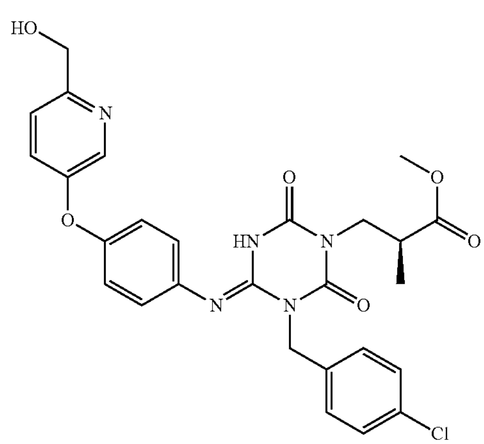 [SMILES: COC(=O)[C@@H](C)Cn1c(=O)[nH]/c(=N\c2ccc(Oc3ccc(CO)nc3)cc2)n(Cc2ccc(Cl)cc2)c1=O] | 552 | 1.8 | 1 |

TABLE 87-continued

| Compound No | Structure | [M + H]+ | RT | Method |
|---|---|---|---|---|
| R-153 | 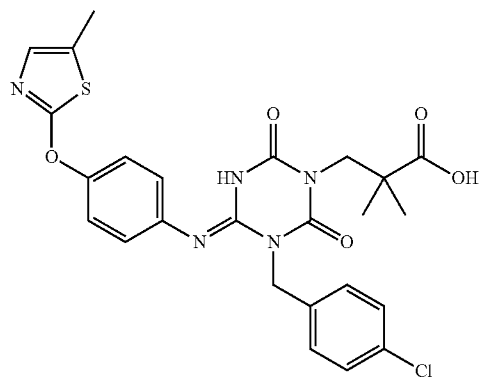 [SMILES: Cc1cnc(Oc2ccc(/N=c3\[nH]c(=O)n(CC(C)(C)C(=O)O)c(=O)n3Cc3ccc(Cl)cc3)cc2)s1] | 542 | 2.22 | 1 |
| R-154 | 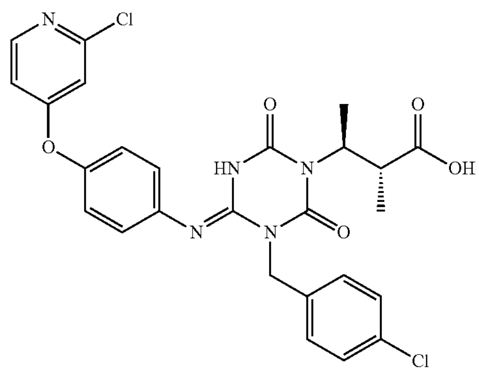 [SMILES: C[C@@H](C(=O)O)[C@H](C)n1c(=O)[nH]/c(=N\c2ccc(Oc3ccnc(Cl)c3)cc2)n(Cc2ccc(Cl)cc2)c1=O] | 555 | 2.21 | 1 |
| R-155 | 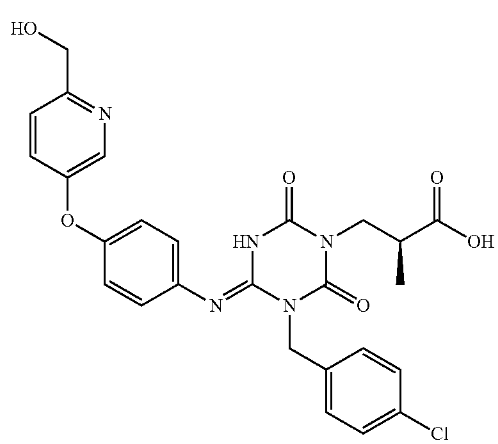 [SMILES: C[C@@H](Cn1c(=O)[nH]/c(=N\c2ccc(Oc3ccc(CO)nc3)cc2)n(Cc2ccc(Cl)cc2)c1=O)C(=O)O] | 538 | 1.55 | 1 |

TABLE 88

| Compound No | Structure | [M + H]+ | RT | Method |
|---|---|---|---|---|
| R-156 | 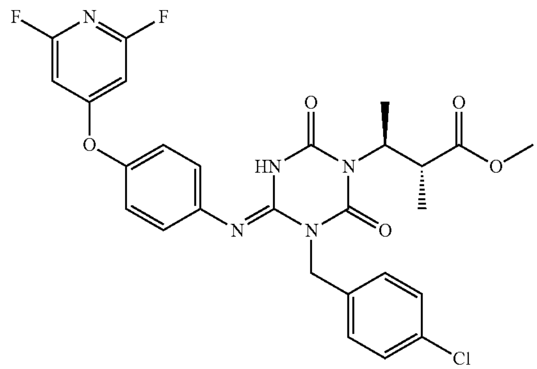 [SMILES: COC(=O)[C@H](C)[C@H](C)n1c(=O)[nH]/c(=N\c2ccc(Oc3cc(F)nc(F)c3)cc2)n(Cc2ccc(Cl)cc2)c1=O] | 572 | 2.6 | 1 |
| R-157 | 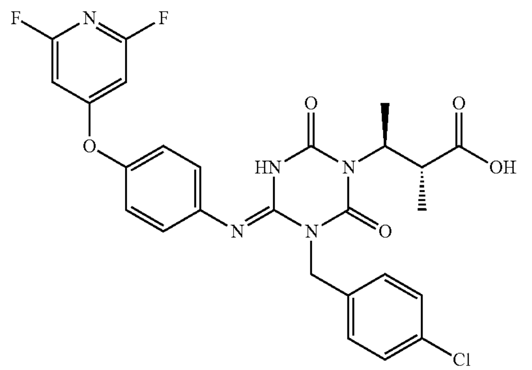 | 558 | 2.33 | 1 |
| R-158 | 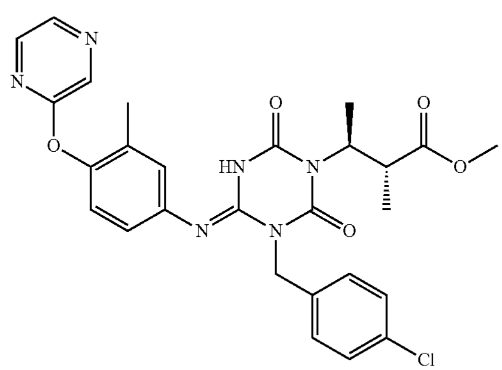 [SMILES: COC(=O)[C@H](C)[C@H](C)n1c(=O)[nH]/c(=N\c2ccc(Oc3cnccn3)c(C)c2)n(Cc2ccc(Cl)cc2)c1=O] | 551 | 2.38 | 1 |
| R-159 | 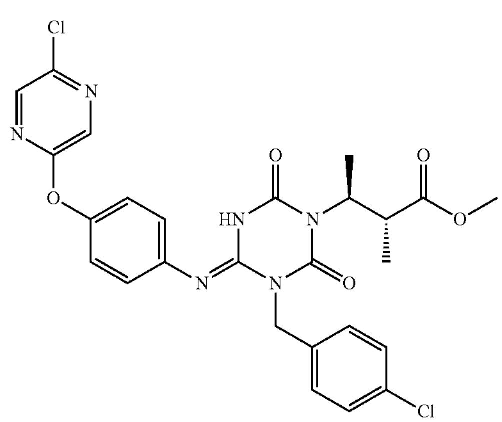 [SMILES: COC(=O)[C@H](C)[C@H](C)n1c(=O)[nH]/c(=N\c2ccc(Oc3cnc(Cl)cn3)cc2)n(Cc2ccc(Cl)cc2)c1=O] | 571 | 2.5 | 1 |

TABLE 88-continued
| Compound No | Structure | [M + H]+ | RT | Method |
|---|---|---|---|---|
| R-160 | 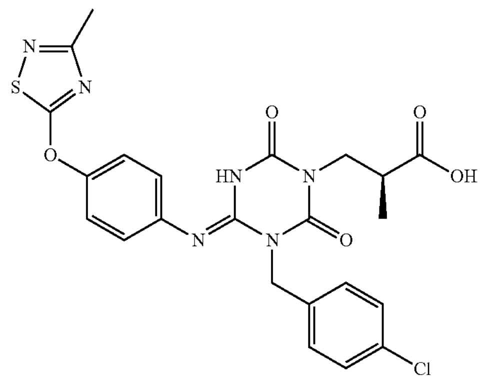 [SMILES: Cc1nsc(Oc2ccc(/N=c3\[nH]c(=O)n(C[C@H](C)C(=O)O)c(=O)n3Cc3ccc(Cl)cc3)cc2)n1] | 529 | 2.02 | 1 |
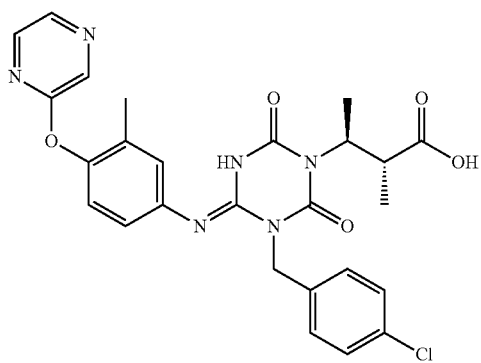
TABLE 89
| Compound No | Structure | [M + H]+ | RT | Method |
|---|---|---|---|---|
| R-161 | 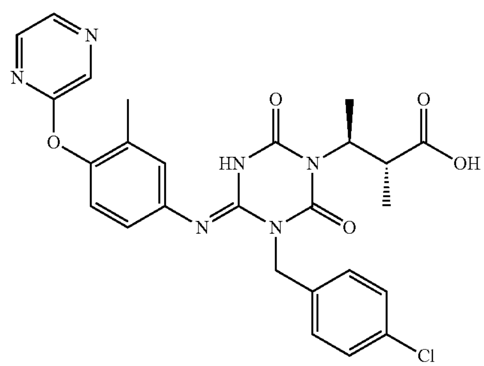 [SMILES: Cc1cc(/N=c2\[nH]c(=O)n([C@@H](C)[C@@H](C)C(=O)O)c(=O)n2Cc2ccc(Cl)cc2)ccc1Oc1cnccn1] | 537 | 2.08 | 1 |
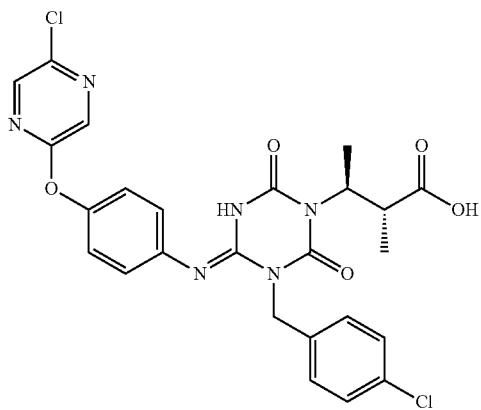 [SMILES: C[C@@H](C(=O)O)[C@H](C)n1c(=O)[nH]/c(=N\c2ccc(Oc3cnc(Cl)cn3)cc2)n(Cc2ccc(Cl)cc2)c1=O]
| R-162 | | 557 | 2.23 | 1 |

TABLE 89-continued

| Compound No | Structure | [M + H]+ | RT | Method |
|---|---|---|---|---|
| R-163 | 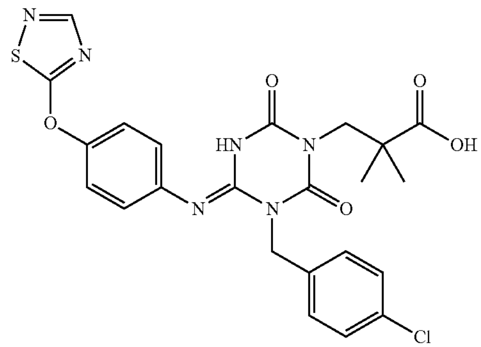 [SMILES: CC(C)(Cn1c(=O)[nH]/c(=N\c2ccc(Oc3ncns3)cc2)n(Cc2ccc(Cl)cc2)c1=O)C(=O)O] | 529 | 2.03 | 1 |
| R-164 | 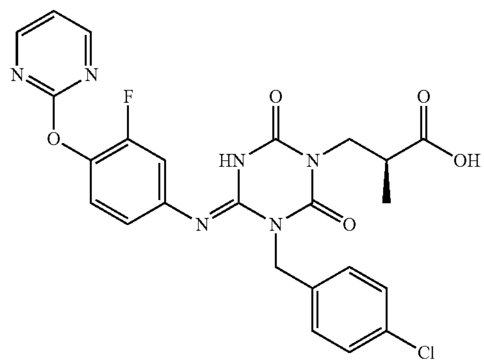 [SMILES: C[C@@H](Cn1c(=O)[nH]/c(=N\c2ccc(Oc3ncccn3)c(F)c2)n(Cc2ccc(Cl)cc2)c1=O)C(=O)O] | 527 | 1.93 | 1 |
| R-165 | 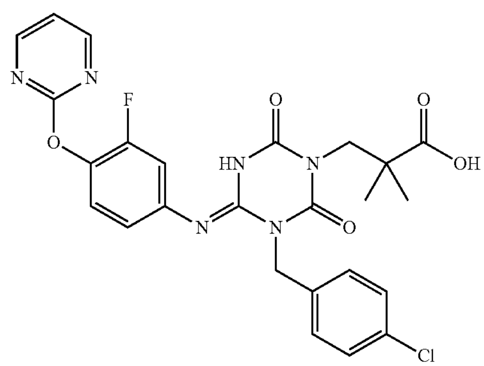 [SMILES: CC(C)(Cn1c(=O)[nH]/c(=N\c2ccc(Oc3ncccn3)c(F)c2)n(Cc2ccc(Cl)cc2)c1=O)C(=O)O] | 541 | 2.01 | 1 |

TABLE 90

| Compound No | Structure | [M + H]+ | RT | Method |
|---|---|---|---|---|
| R-166 | 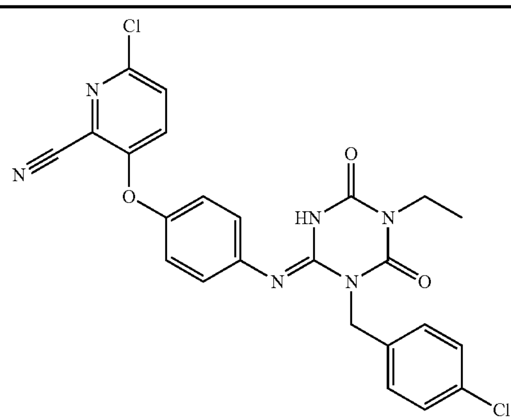 | 509 | 2.42 | 1 |

TABLE 90-continued

| Compound No | Structure | [M + H]+ | RT | Method |
|---|---|---|---|---|
| R-167 | 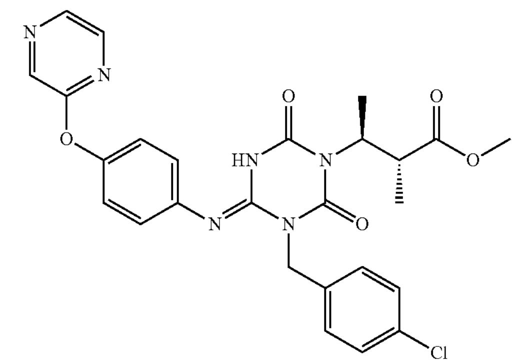 [SMILES: COC(=O)[C@H](C)[C@H](C)n1c(=O)[nH]/c(=N\c2ccc(Oc3cnccn3)cc2)n(Cc2ccc(Cl)cc2)c1=O] | 537 | 2.27 | 1 |
| R-168 | 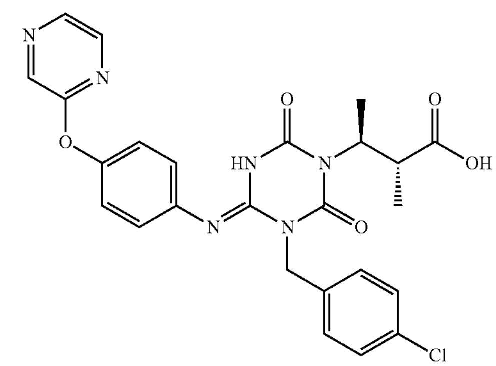 [SMILES: C[C@@H](C(=O)O)[C@H](C)n1c(=O)[nH]/c(=N\c2ccc(Oc3cnccn3)cc2)n(Cc2ccc(Cl)cc2)c1=O] | 523 | 1.97 | 1 |
| R-169 | 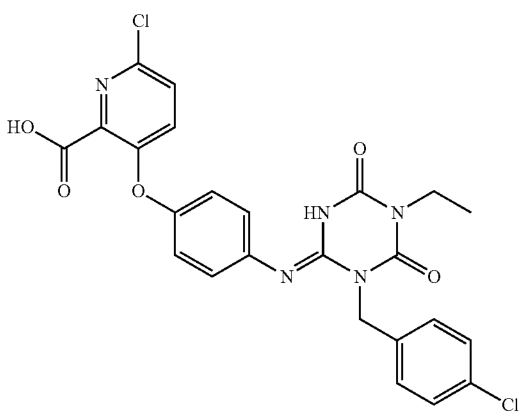 [SMILES: CCn1c(=O)[nH]/c(=N\c2ccc(Oc3ccc(Cl)nc3C(=O)O)cc2)n(Cc2ccc(Cl)cc2)c1=O] | 528 | 2.05 | 1 |
| R-170 | 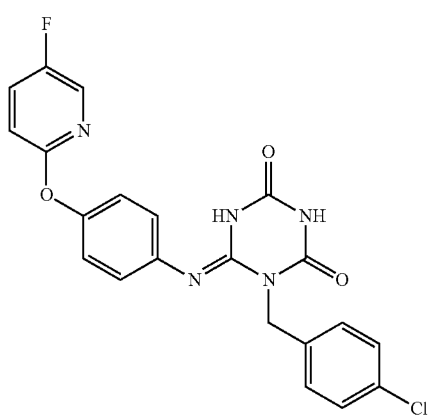 [SMILES: O=c1[nH]c(=O)n(Cc2ccc(Cl)cc2)/c(=N/c2ccc(Oc3ccc(F)cn3)cc2)[nH]1] | 440 | 2.02 | 1 |

TABLE 91

| Compound No | Structure | [M + H]+ | RT | Method |
|---|---|---|---|---|
| R-171 | 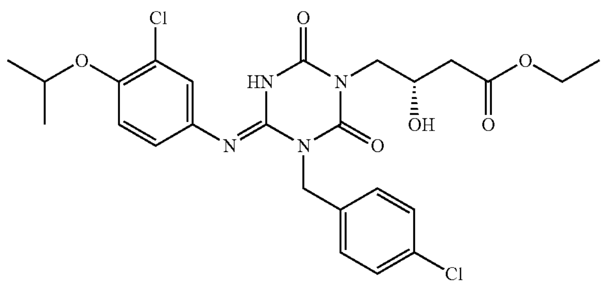 [SMILES: CCOC(=O)C[C@H](O)Cn1c(=O)[nH]/c(=N\c2ccc(OC(C)C)c(Cl)c2)n(Cc2ccc(Cl)cc2)c1=O] | 551 | 2.35 | 1 |
| R-172 | 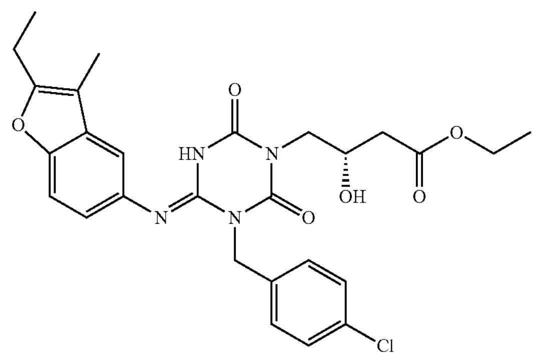 [SMILES: CCOC(=O)C[C@H](O)Cn1c(=O)[nH]/c(=N\c2ccc3oc(CC)c(C)c3c2)n(Cc2ccc(Cl)cc2)c1=O] | 541 | 2.35 | 1 |
| R-173 | 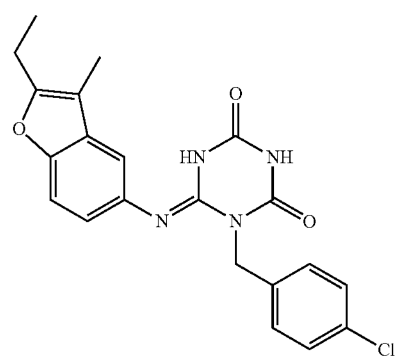 [SMILES: CCc1oc2ccc(/N=c3\[nH]c(=O)[nH]c(=O)n3Cc3ccc(Cl)cc3)cc2c1C] | 411 | 2.23 | 1 |
| R-174 | 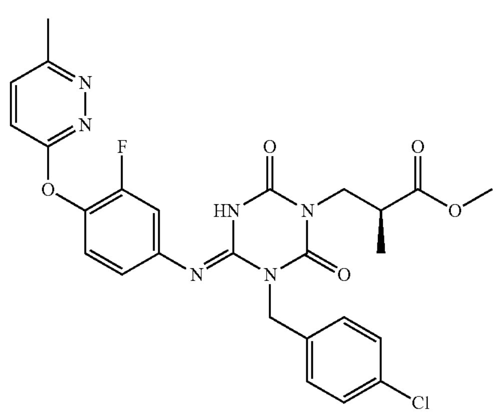 [SMILES: COC(=O)[C@@H](C)Cn1c(=O)[nH]/c(=N\c2ccc(Oc3ccc(C)nn3)c(F)c2)n(Cc2ccc(Cl)cc2)c1=O] | 555 | 2.24 | 1 |

TABLE 91-continued
| Compound No | Structure | [M + H]+ | RT | Method |
|---|---|---|---|---|
| R-175 | 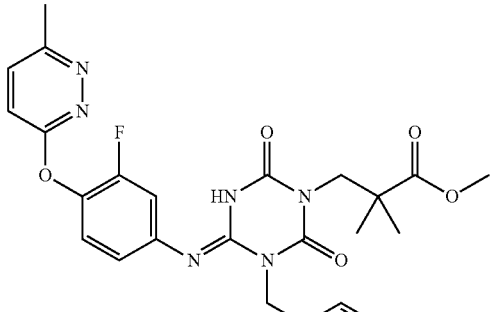 | 569 | 2.34 | 1 |
TABLE 92
| Compound No | Structure | [M + H]+ | RT | Method |
|---|---|---|---|---|
| R-176 | 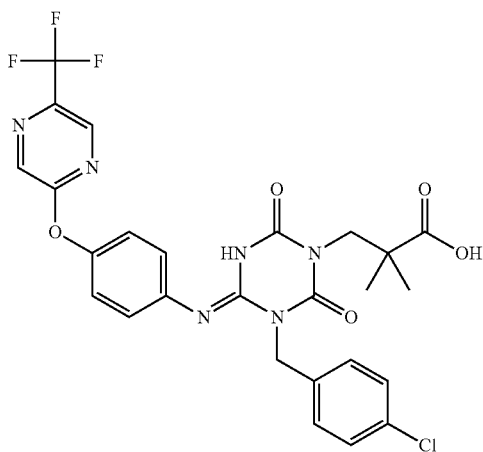 [SMILES: CC(C)(Cn1c(=O)[nH]/c(=N\c2ccc(Oc3cnc(C(F)(F)F)cn3)cc2)n(Cc2ccc(Cl)cc2)c1=O)C(=O)O] | 591 | 2.3 | 1 |
| R-177 | 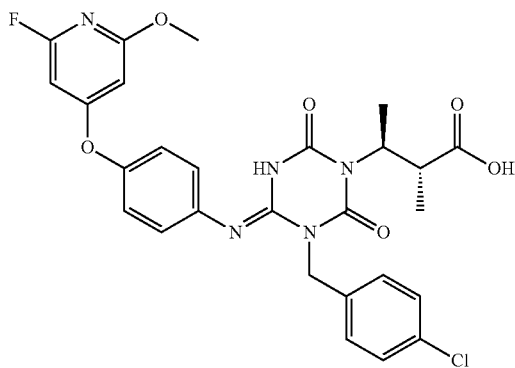 [SMILES: COc1cc(Oc2ccc(/N=c3\[nH]c(=O)n([C@@H](C)[C@@H](C)C(=O)O)c(=O)n3Cc3ccc(Cl)cc3)cc2)cc(F)n1] | 570 | 2.4 | 1 |

TABLE 92-continued

| Compound No | Structure | [M + H]+ | RT | Method |
|---|---|---|---|---|
| R-178 | 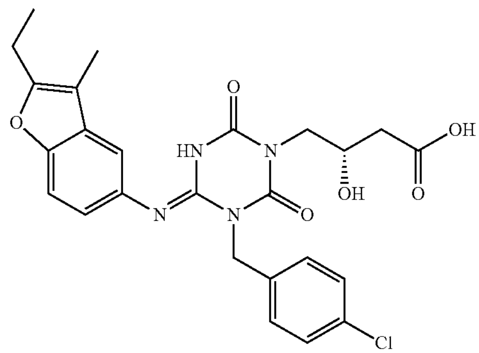 [SMILES: CCc1oc2ccc(/N=c3\[nH]c(=O)n(C[C@@H](O)CC(=O)O)c(=O)n3Cc3ccc(Cl)cc3)cc2c1C] | 513 | 2.06 | 1 |
| R-179 | 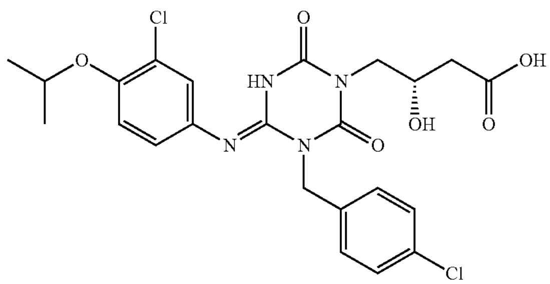 [SMILES: CC(C)Oc1ccc(/N=c2\[nH]c(=O)n(C[C@@H](O)CC(=O)O)c(=O)n2Cc2ccc(Cl)cc2)cc1Cl] | 523 | 2.05 | 1 |
| R-180 | 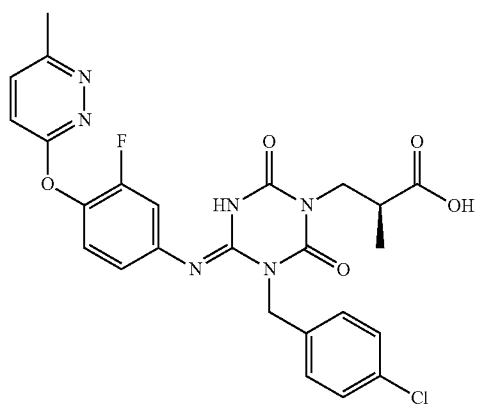 [SMILES: Cc1ccc(Oc2ccc(/N=c3\[nH]c(=O)n(C[C@H](C)C(=O)O)c(=O)n3Cc3ccc(Cl)cc3)cc2F)nn1] | 541 | 1.99 | 1 |

TABLE 93

| Compound No | Structure | [M + H]+ | RT | Method |
|---|---|---|---|---|
| R-181 | 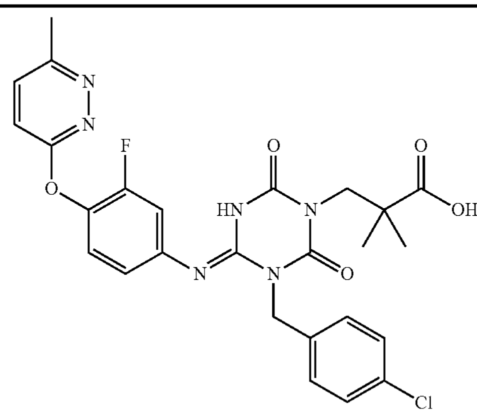 | 555 | 2.08 | 1 |

TABLE 93-continued
| Compound No | Structure | [M + H]+ | RT | Method |
|---|---|---|---|---|
| R-182 | 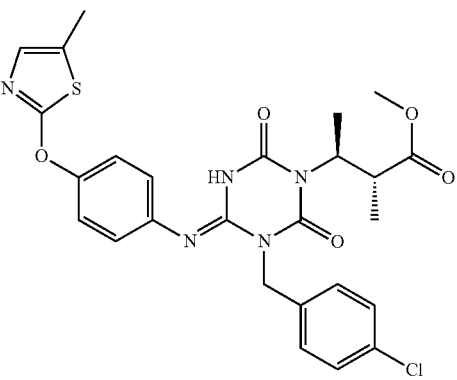 [SMILES: COC(=O)[C@H](C)[C@H](C)n1c(=O)[nH]/c(=N\c2ccc(Oc3ncc(C)s3)cc2)n(Cc2ccc(Cl)cc2)c1=O] | 556 | 2.53 | 1 |
| R-183 | 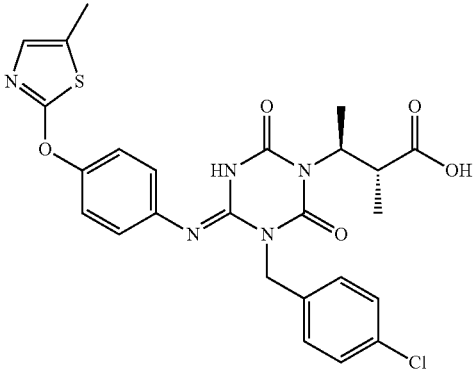 [SMILES: Cc1cnc(Oc2ccc(/N=c3\[nH]c(=O)n([C@@H](C)[C@@H](C)C(=O)O)c(=O)n3Cc3ccc(Cl)cc3)cc2)s1] | 542 | 2.25 | 1 |
| R-184 | 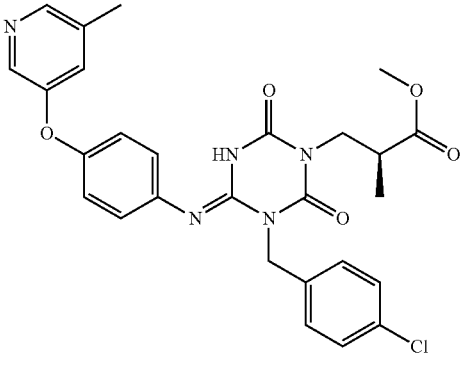 [SMILES: COC(=O)[C@@H](C)Cn1c(=O)[nH]/c(=N\c2ccc(Oc3cncc(C)c3)cc2)n(Cc2ccc(Cl)cc2)c1=O] | 536 | 1.92 | 1 |
| R-185 | 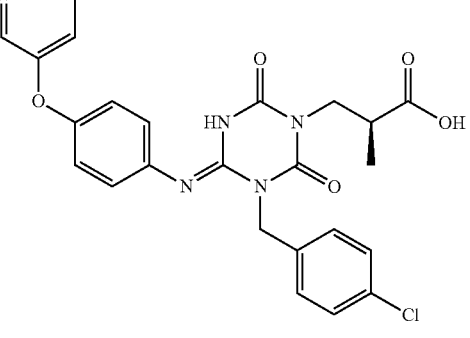 | 522 | 1.66 | 1 |

TABLE 94

| Compound No | Structure | [M + H]+ | RT | Method |
|---|---|---|---|---|
| R-186 | 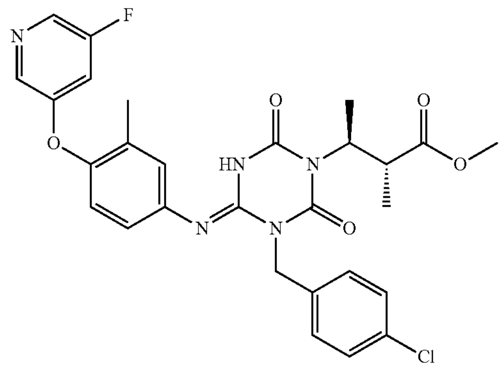 [SMILES: COC(=O)[C@H](C)[C@H](C)n1c(=O)[nH]/c(=N\c2ccc(Oc3cncc(F)c3)c(C)c2)n(Cc2ccc(Cl)cc2)c1=O] | 568 | 2.51 | 1 |
| R-187 | 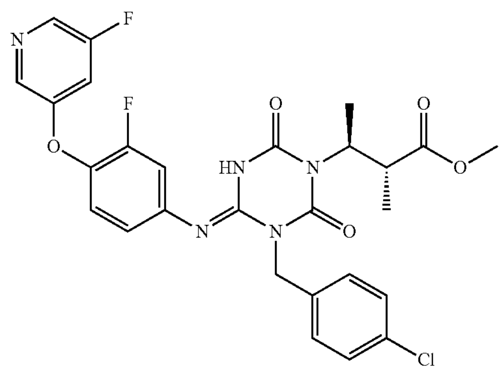 [SMILES: COC(=O)[C@H](C)[C@H](C)n1c(=O)[nH]/c(=N\c2ccc(Oc3cncc(F)c3)c(F)c2)n(Cc2ccc(Cl)cc2)c1=O] | 572 | 2.54 | 1 |
| R-188 | 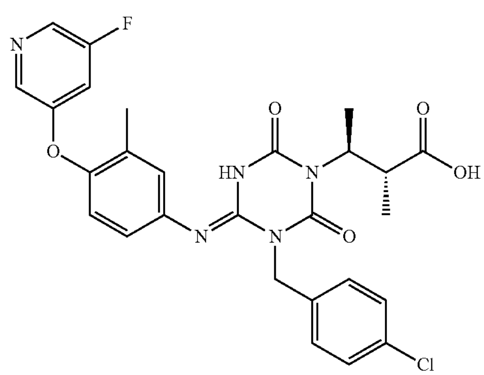 [SMILES: Cc1cc(/N=c2\[nH]c(=O)n([C@@H](C)[C@@H](C)C(=O)O)c(=O)n2Cc2ccc(Cl)cc2)ccc1Oc1cncc(F)c1] | 554 | 2.21 | 1 |
| R-189 | 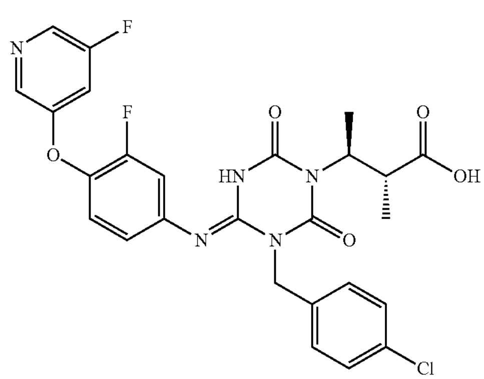 [SMILES: C[C@@H](C(=O)O)[C@H](C)n1c(=O)[nH]/c(=N\c2ccc(Oc3cncc(F)c3)c(F)c2)n(Cc2ccc(Cl)cc2)c1=O] | 558 | 2.25 | 1 |

TABLE 94-continued

| Compound No | Structure | [M + H]+ | RT | Method |
|---|---|---|---|---|
| R-190 | 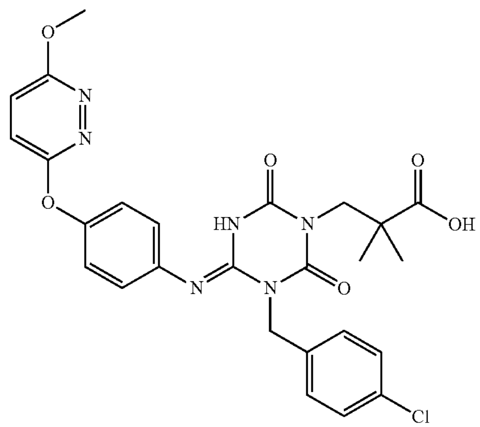 | 553 | 2.02 | 1 |

TABLE 95

| Compound No | Structure | [M + H]+ | RT | Method |
|---|---|---|---|---|
| R-191 | 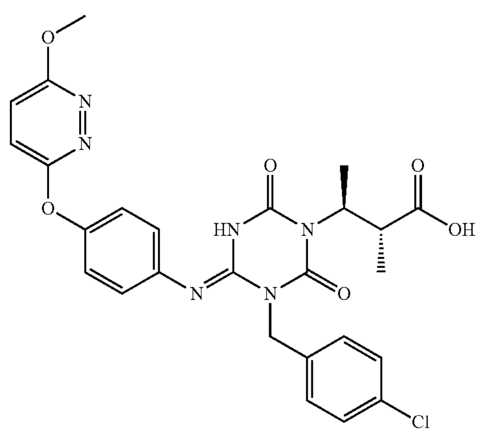 | 553 | 2.04 | 1 |
| R-192 | 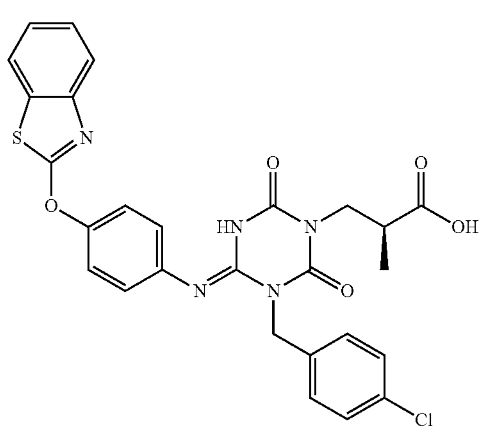 [SMILES: C[C@@H](Cn1c(=O)[nH]/c(=N\c2ccc(Oc3nc4ccccc4s3)cc2)n(Cc2ccc(Cl)cc2)c1=O)C(=O)O] | 564 | 2.37 | 1 |

TABLE 95-continued

| Compound No | Structure | [M + H]+ | RT | Method |
| --- | --- | --- | --- | --- |
| R-193 | 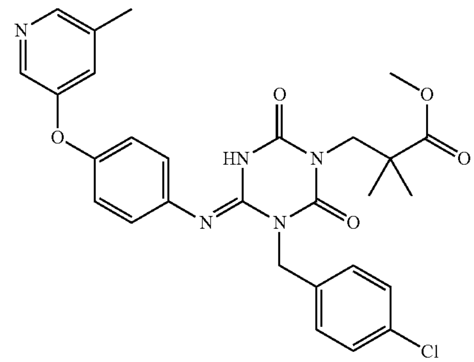 [SMILES: COC(=O)C(C)(C)Cn1c(=O)[nH]/c(=N\c2ccc(Oc3cncc(C)c3)cc2)n(Cc2ccc(Cl)cc2)c1=O] | 550 | 2.04 | 1 |
| R-194 | 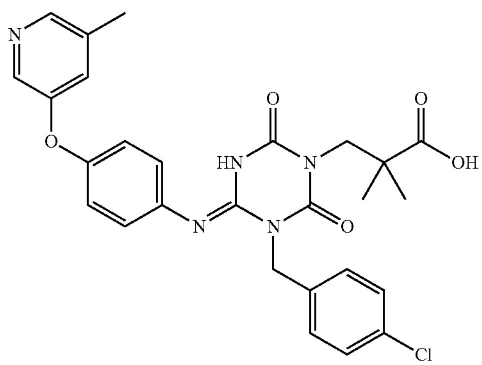 [SMILES: Cc1cncc(Oc2ccc(/N=c3\[nH]c(=O)n(CC(C)(C)C(=O)O)c(=O)n3Cc3ccc(Cl)cc3)cc2)c1] | 536 | 1.75 | 1 |
| R-195 | 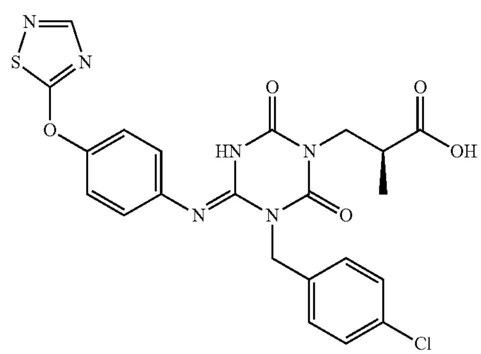 [SMILES: C[C@@H](Cn1c(=O)[nH]/c(=N\c2ccc(Oc3ncns3)cc2)n(Cc2ccc(Cl)cc2)c1=O)C(=O)O] | 515 | 1.95 | 1 |

TABLE 96

| Compound No | Structure | [M + H]+ | RT | Method |
| --- | --- | --- | --- | --- |
| R-196 | 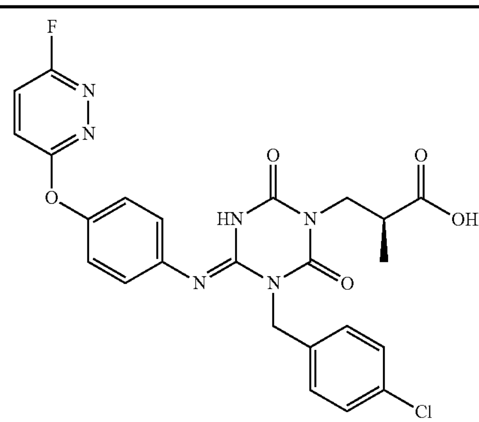 | 527 | 1.88 | 1 |

TABLE 96-continued

| Compound No | Structure | [M + H]+ | RT | Method |
|---|---|---|---|---|
| R-197 | (6-chloropyridazin-3-yl)oxy-phenyl / triazinedione / (4-chlorobenzyl) / CH(CH3)COOH | 543 | 1.96 | 1 |
| R-198 | (6-fluoropyrimidin-4-yl)oxy-phenyl / triazinedione / (4-chlorobenzyl) / CH(CH3)COOH | 527 | 2 | 1 |
| R-199 | (5-methoxypyridin-3-yl)oxy-phenyl / triazinedione / (4-chlorobenzyl) / CH(CH3)COOCH3 | 552 | 2.11 | 1 |
| R-200 | (5-methoxypyridin-3-yl)oxy-phenyl / triazinedione / (4-chlorobenzyl) / C(CH3)2COOCH3 | 566 | 2.22 | 1 |

TABLE 97
| Compound No | Structure | [M + H]+ | RT | Method |
|---|---|---|---|---|
| R-201 | 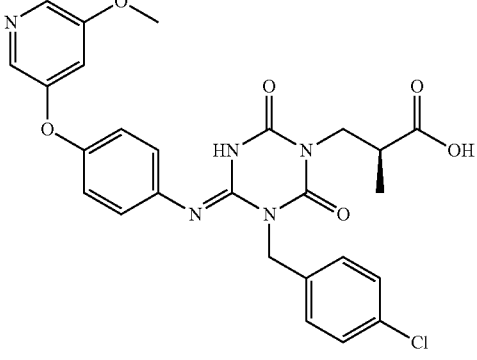 | 538 | 1.85 | 1 |
| R-202 | 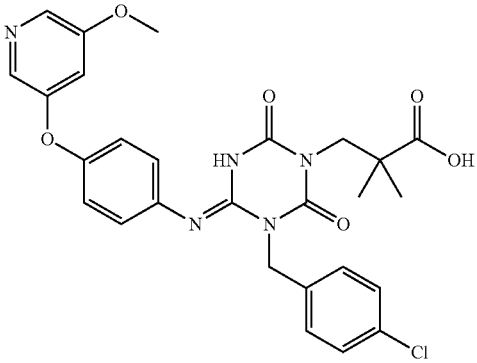 [SMILES: COc1cncc(Oc2ccc(/N=c3\[nH]c(=O)n(CC(C)(C)C(=O)O)c(=O)n3Cc3ccc(Cl)cc3)cc2)c1] | 552 | 1.94 | 1 |
| R-203 | 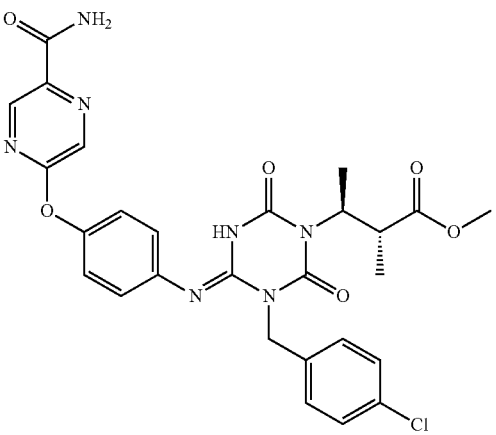 [SMILES: COC(=O)[C@H](C)[C@H](C)n1c(=O)[nH]/c(=N\c2ccc(Oc3cnc(C(N)=O)cn3)cc2)n(Cc2ccc(Cl)cc2)c1=O] | 581 | 2.12 | 1 |
| R-204 | 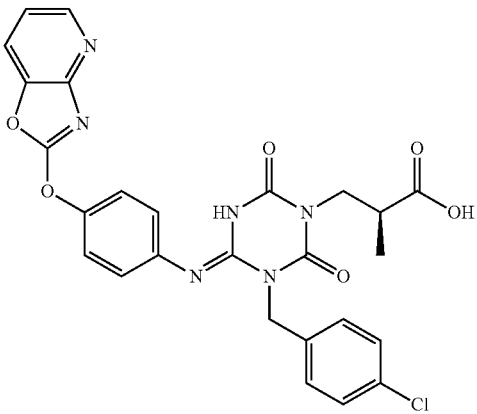 [SMILES: C[C@@H](Cn1c(=O)[nH]/c(=N\c2ccc(Oc3nc4ncccc4o3)cc2)n(Cc2ccc(Cl)cc2)c1=O)C(=O)O] | 549 | 1.97 | 1 |

TABLE 97-continued

| Compound No | Structure | [M + H]+ | RT | Method |
|---|---|---|---|---|
| R-205 | 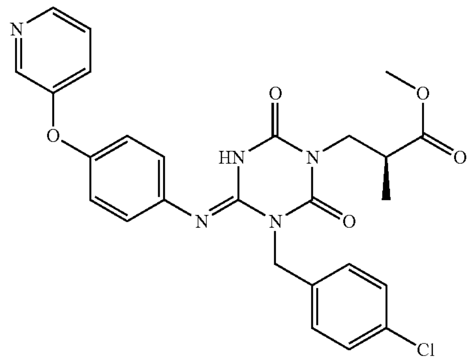 [SMILES: COC(=O)[C@@H](C)Cn1c(=O)[nH]/c(=N\c2ccc(Oc3cccnc3)cc2)n(Cc2ccc(Cl)cc2)c1=O] | 522 | 1.94 | 1 |

TABLE 98

| Compound No | Structure | [M + H]+ | RT | Method |
|---|---|---|---|---|
| R-206 | 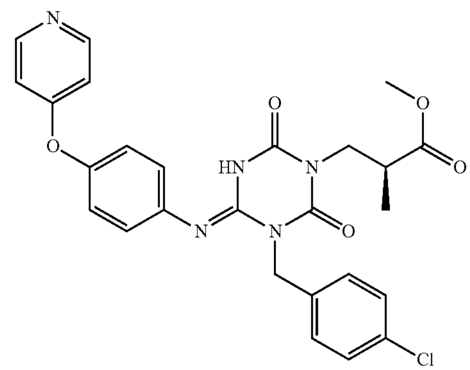 [SMILES: COC(=O)[C@@H](C)Cn1c(=O)[nH]/c(=N\c2ccc(Oc3ccncc3)cc2)n(Cc2ccc(Cl)cc2)c1=O] | 522 | 1.5 | 1 |
| R-207 | 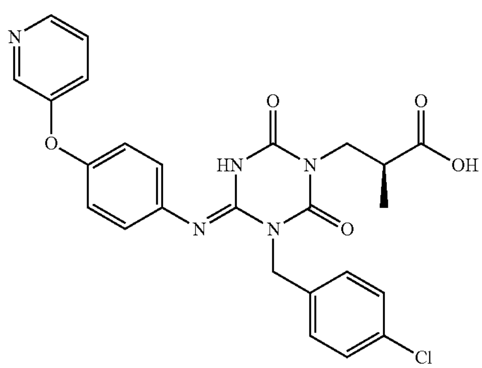 [SMILES: C[C@@H](Cn1c(=O)[nH]/c(=N\c2ccc(Oc3cccnc3)cc2)n(Cc2ccc(Cl)cc2)c1=O)C(=O)O] | 508 | 1.69 | 1 |
| R-208 | 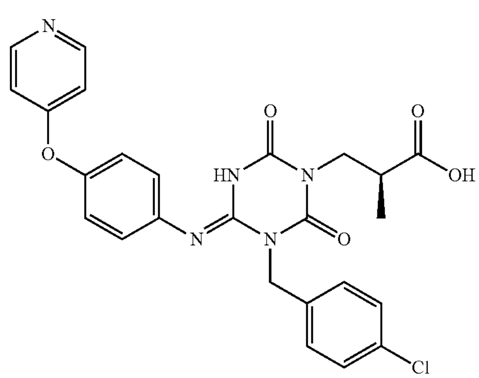 [SMILES: C[C@@H](Cn1c(=O)[nH]/c(=N\c2ccc(Oc3ccncc3)cc2)n(Cc2ccc(Cl)cc2)c1=O)C(=O)O] | 508 | 1.39 | 1 |

TABLE 98-continued

| Compound No | Structure | [M + H]+ | RT | Method |
|---|---|---|---|---|
| R-209 | 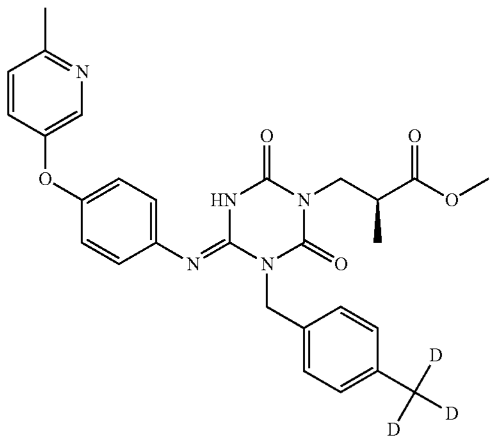 [SMILES: [2H]C([2H])([2H])c1ccc(Cn2c(=O)n(C[C@H](C)C(=O)OC)c(=O)[nH]/c2=N\c2ccc(Oc3ccc(C)nc3)cc2)cc1] | 519 | 1.7 | 1 |
| R-210 | 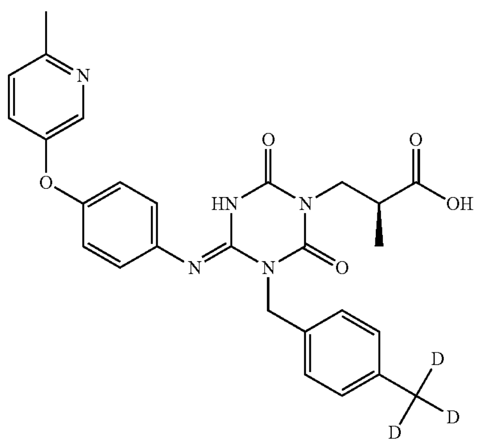 [SMILES: [2H]C([2H])([2H])c1ccc(Cn2c(=O)n(C[C@H](C)C(=O)O)c(=O)[nH]/c2=N\c2ccc(Oc3ccc(C)nc3)cc2)cc1] | 505 | 1.51 | 1 |

TABLE 99

| Compound No | Structure | [M + H]+ | RT | Method |
|---|---|---|---|---|
| R-211 | 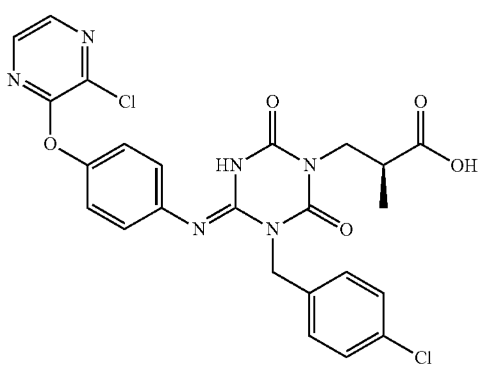 [SMILES: C[C@@H](Cn1c(=O)[nH]/c(=N\c2ccc(Oc3nccnc3Cl)cc2)n(Cc2ccc(Cl)cc2)c1=O)C(=O)O] | 543 | 2.1 | 1 |

TABLE 99-continued
| Compound No | Structure | [M + H]+ | RT | Method |
|---|---|---|---|---|
| R-212 | 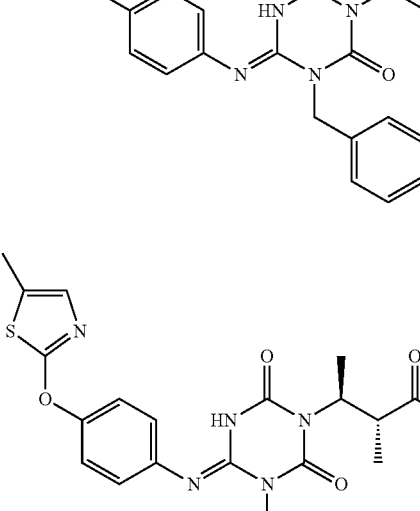 | 547 | 2.11 | 1 |
| R-213 | 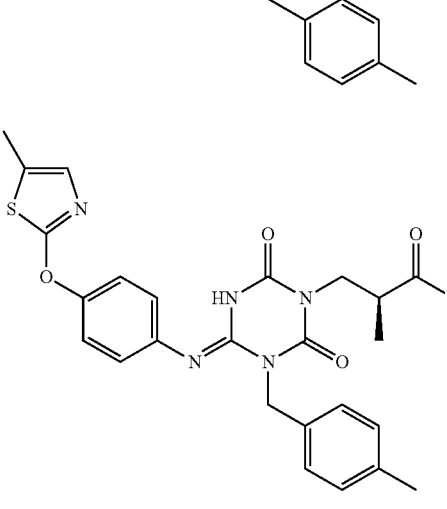 | 536 | 2.44 | 1 |
| R-214 | 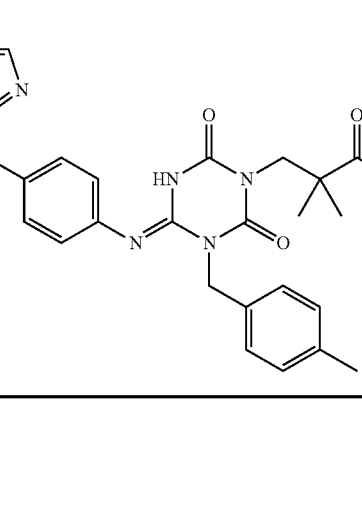 | 522 | 2.3 | 1 |
| R-215 | 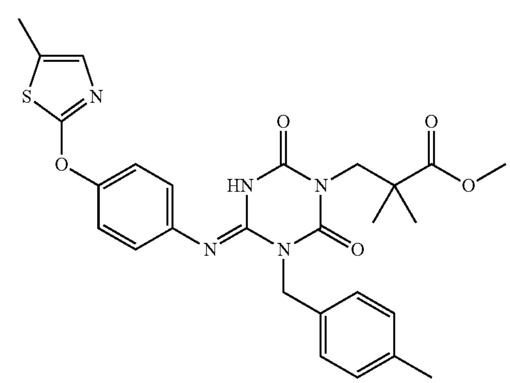 | 536 | 2.4 | 1 |

TABLE 100

| Compound No | Structure | [M + H]+ | RT | Method |
|---|---|---|---|---|
| R-216 | 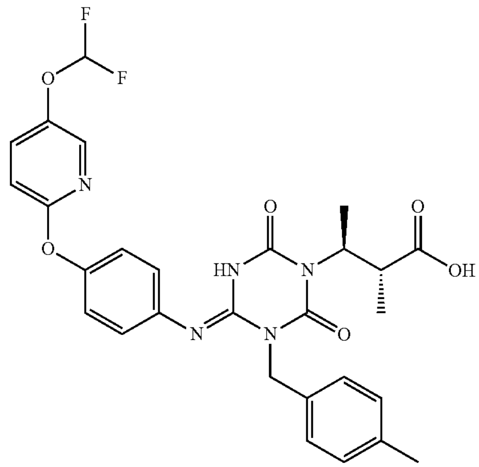 [SMILES: Cc1ccc(Cn2c(=O)n([C@@H](C)[C@@H](C)C(=O)O)c(=O)[nH]/c2=N\c2ccc(Oc3ccc(OC(F)F)cn3)cc2)cc1] | 568 | 2.16 | 1 |
| R-217 | 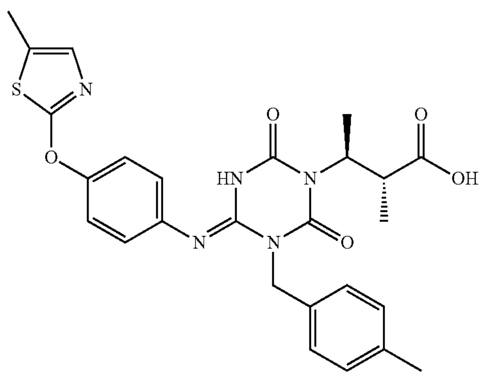 [SMILES: Cc1ccc(Cn2c(=O)n([C@@H](C)[C@@H](C)C(=O)O)c(=O)[nH]/c2=N\c2ccc(Oc3ncc(C)s3)cc2)cc1] | 522 | 2.16 | 1 |
| R-218 | 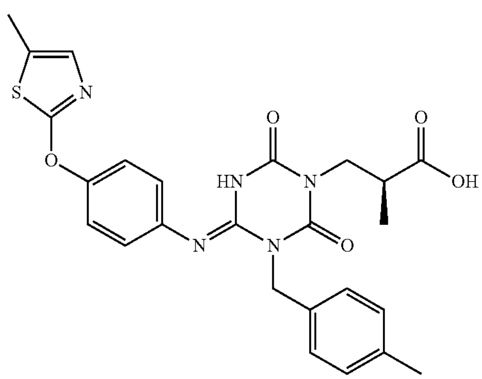 [SMILES: Cc1ccc(Cn2c(=O)n(C[C@H](C)C(=O)O)c(=O)[nH]/c2=N\c2ccc(Oc3ncc(C)s3)cc2)cc1] | 508 | 2.05 | 1 |
| R-219 | 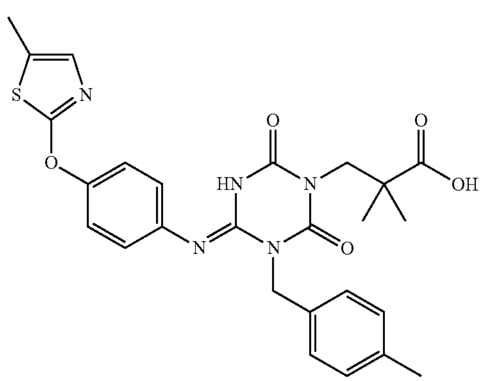 [SMILES: Cc1ccc(Cn2c(=O)n(CC(C)(C)C(=O)O)c(=O)[nH]/c2=N\c2ccc(Oc3ncc(C)s3)cc2)cc1] | 522 | 2.13 | 1 |

TABLE 100-continued

| Compound No | Structure | [M + H]+ | RT | Method |
|---|---|---|---|---|
| R-220 | 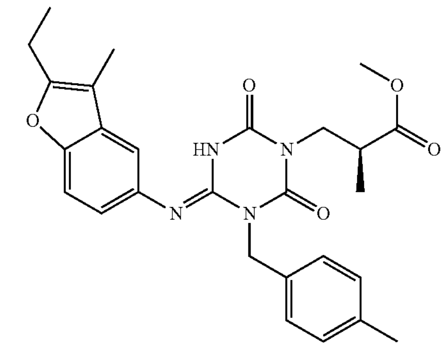 [SMILES: CCc1oc2ccc(/N=c3\[nH]c(=O)n(C[C@H](C)C(=O)OC)c(=O)n3Cc3ccc(C)cc3)cc2c1C] | 491 | 2.44 | 1 |

TABLE 101

| Compound No | Structure | [M + H]+ | RT | Method |
|---|---|---|---|---|
| R-221 | 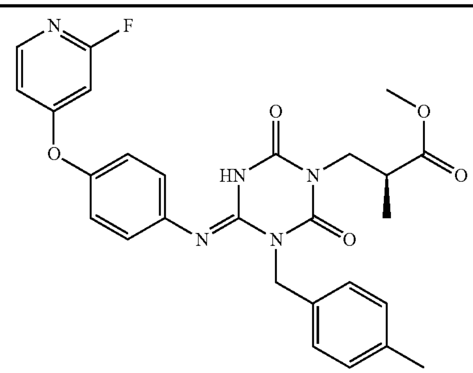 | 520 | 2.21 | 1 |
| R-222 | 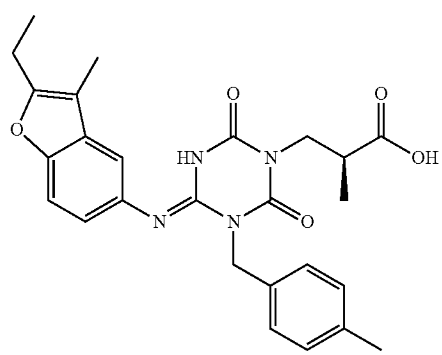 [SMILES: CCc1oc2ccc(/N=c3\[nH]c(=O)n(C[C@H](C)C(=O)O)c(=O)n3Cc3ccc(C)cc3)cc2c1C] | 477 | 2.19 | 1 |
| R-223 | 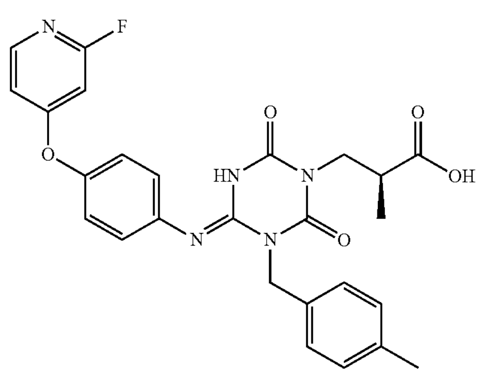 [SMILES: Cc1ccc(Cn2c(=O)n(C[C@H](C)C(=O)O)c(=O)[nH]/c2=N\c2ccc(Oc3ccnc(F)c3)cc2)cc1] | 506 | 1.95 | 1 |

TABLE 101-continued

| Compound No | Structure | [M + H]+ | RT | Method |
|---|---|---|---|---|
| R-224 | 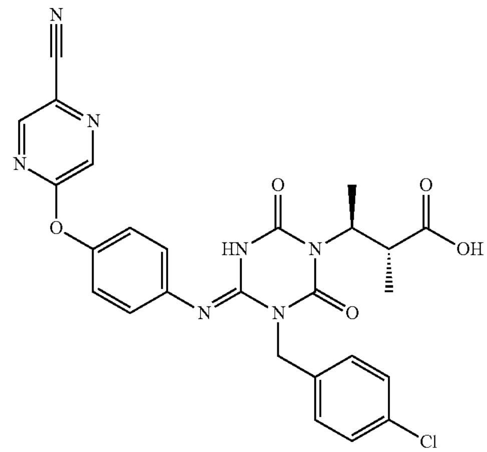 [SMILES: C[C@@H](C(=O)O)[C@H](C)n1c(=O)[nH]/c(=N\c2ccc(Oc3cnc(C#N)cn3)cc2)n(Cc2ccc(Cl)cc2)c1=O] | 548 | 2.1 | 1 |
| R-225 | 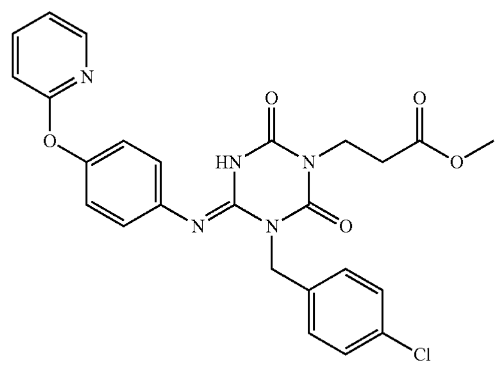 [SMILES: COC(=O)CCn1c(=O)[nH]/c(=N\c2ccc(Oc3ccccn3)cc2)n(Cc2ccc(Cl)cc2)c1=O] | 508 | 2.19 | 1 |

TABLE 102

| Compound No | Structure | [M + H]+ | RT | Method |
|---|---|---|---|---|
| R-226 | 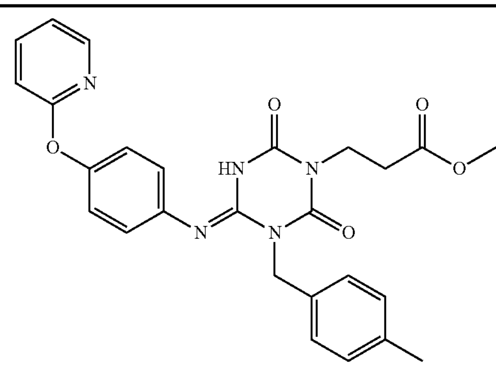 | 488 | 2.1 | 1 |
| R-227 | 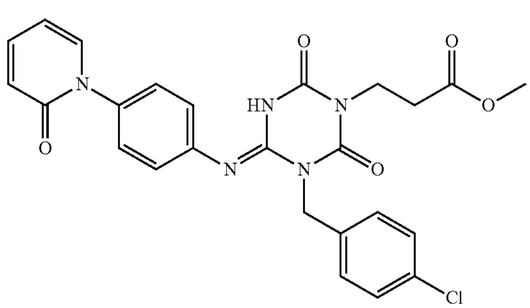 [SMILES: COC(=O)CCn1c(=O)[nH]/c(=N\c2ccc(-n3ccccc3=O)cc2)n(Cc2ccc(Cl)cc2)c1=O] | 508 | 1.88 | 1 |

TABLE 102-continued

| Compound No | Structure | [M + H]+ | RT | Method |
|---|---|---|---|---|
| R-228 | 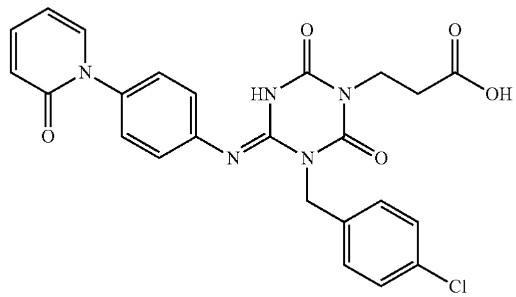 [SMILES: O=C(O)CCn1c(=O)[nH]/c(=N\c2ccc(-n3ccccc3=O)cc2)n(Cc2ccc(Cl)cc2)c1=O] | 494 | 1.66 | 1 |
| R-229 | 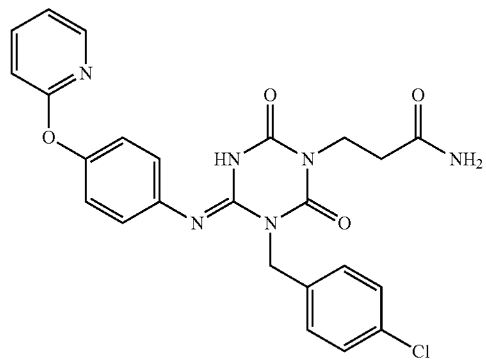 [SMILES: NC(=O)CCn1c(=O)[nH]/c(=N\c2ccc(Oc3ccccn3)cc2)n(Cc2ccc(Cl)cc2)c1=O] | 493 | 1.82 | 1 |
| R-230 | 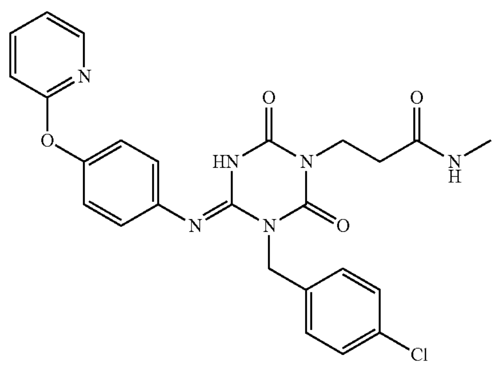 [SMILES: CNC(=O)CCn1c(=O)[nH]/c(=N\c2ccc(Oc3ccccn3)cc2)n(Cc2ccc(Cl)cc2)c1=O] | 507 | 1.88 | 1 |

TABLE 103

| Compound No | Structure | [M + H]+ | RT | Method |
|---|---|---|---|---|
| R-231 | 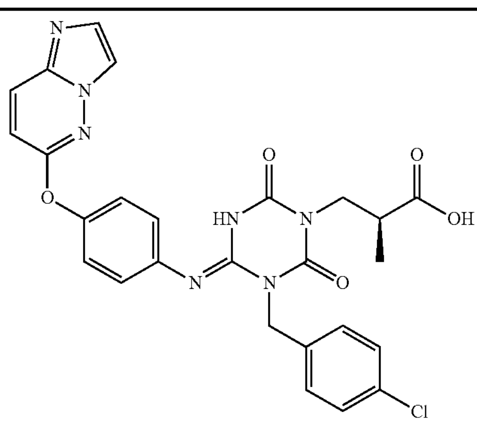 | 548 | 1.52 | 1 |

TABLE 103-continued
| Compound No | Structure | [M + H]+ | RT | Method |
|---|---|---|---|---|
| R-232 | 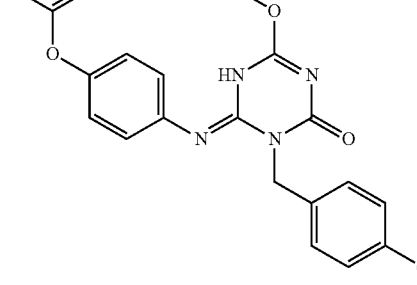 | 461 | 1.9 | 1 |
| R-233 | 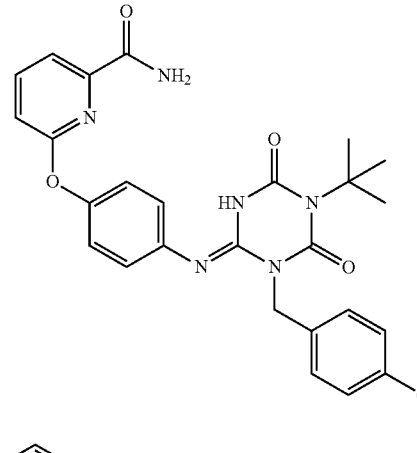 | 521 | 2.07 | 1 |
| R-234 | 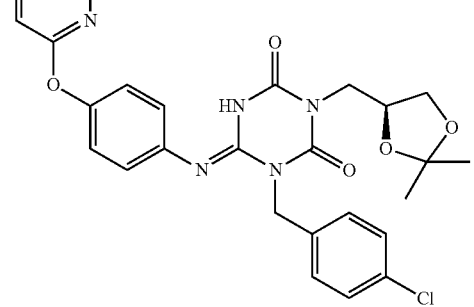 | 536 | 2.32 | 1 |
| R-235 | 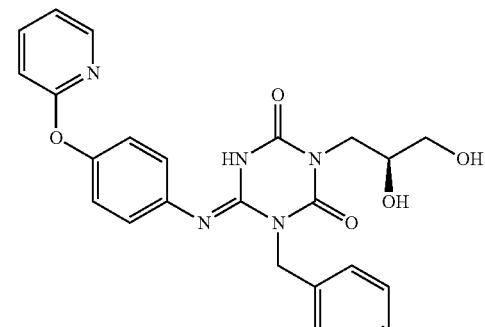 | 496 | 1.8 | 1 |

TABLE 104
| Compound No | Structure | [M + H]+ | RT | Method |
|---|---|---|---|---|
| R-236 | 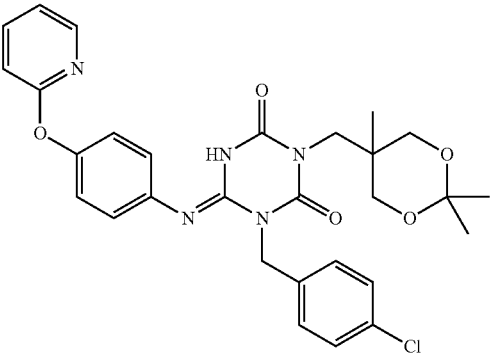 [SMILES: CC1(Cn2c(=O)[nH]/c(=N\c3ccc(Oc4ccccn4)cc3)n(Cc3ccc(Cl)cc3)c2=O)COC(C)(C)OC1] | 564 | 2.43 | 1 |
| R-237 | 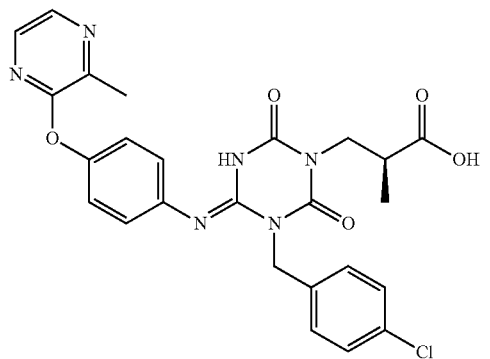 [SMILES: Cc1nccnc1Oc1ccc(/N=c2\[nH]c(=O)n(C[C@H](C)C(=O)O)c(=O)n2Cc2ccc(Cl)cc2)cc1] | 523 | 1.98 | 1 |
| R-238 | 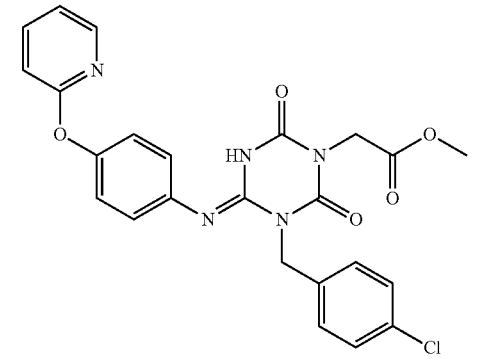 [SMILES: COC(=O)Cn1c(=O)[nH]/c(=N\c2ccc(Oc3ccccn3)cc2)n(Cc2ccc(Cl)cc2)c1=O] | 494 | 2.13 | 1 |
| R-239 | 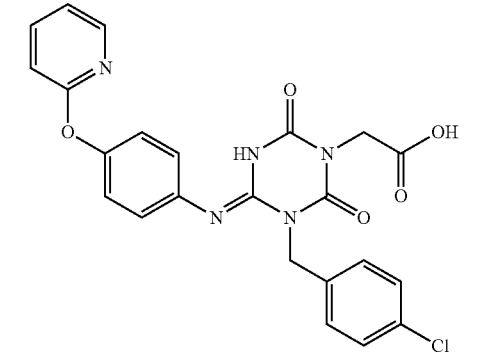 [SMILES: O=C(O)Cn1c(=O)[nH]/c(=N\c2ccc(Oc3ccccn3)cc2)n(Cc2ccc(Cl)cc2)c1=O] | 480 | 1.93 | 1 |

TABLE 104-continued

| Compound No | Structure | [M + H]+ | RT | Method |
|---|---|---|---|---|
| R-240 | 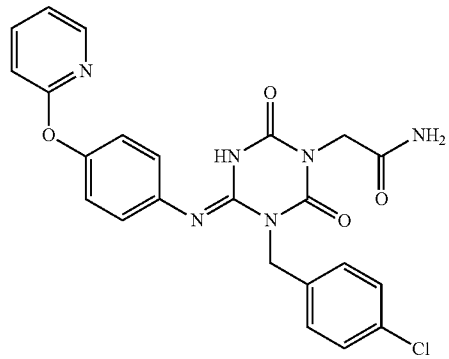 [SMILES: NC(=O)Cn1c(=O)[nH]/c(=N\c2ccc(Oc3ccccn3)cc2)n(Cc2ccc(Cl)cc2)c1=O] | 479 | 1.8 | 1 |

TABLE 105

| Compound No | Structure | [M + H]+ | RT | Method |
|---|---|---|---|---|
| R-241 | 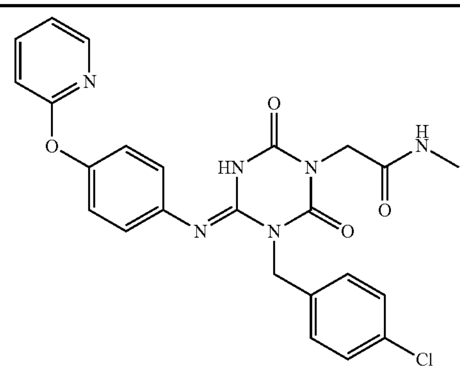 | 493 | 1.87 | 1 |
| R-242 | 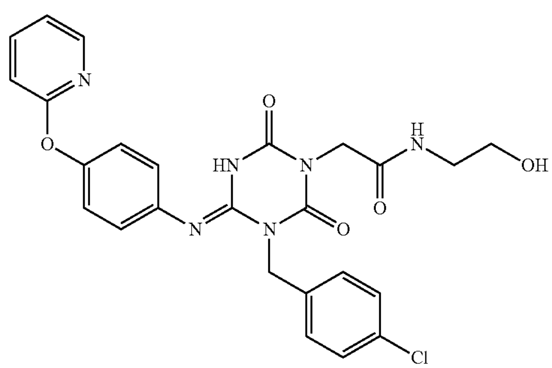 [SMILES: O=C(Cn1c(=O)[nH]/c(=N\c2ccc(Oc3ccccn3)cc2)n(Cc2ccc(Cl)cc2)c1=O)NCCO] | 523 | 1.75 | 1 |
| R-243 | 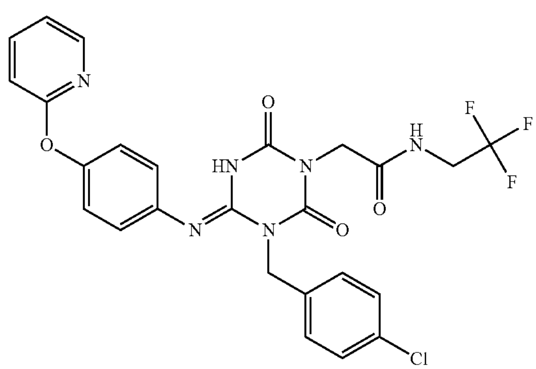 [SMILES: O=C(Cn1c(=O)[nH]/c(=N\c2ccc(Oc3ccccn3)cc2)n(Cc2ccc(Cl)cc2)c1=O)NCC(F)(F)F] | 561 | 2.12 | 1 |

TABLE 105-continued

| Compound No | Structure | [M + H]+ | RT | Method |
|---|---|---|---|---|
| R-244 | 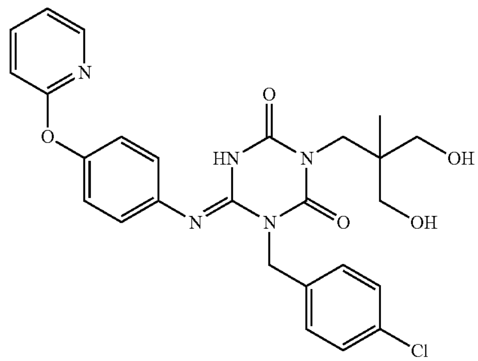 [SMILES: CC(CO)(CO)Cn1c(=O)[nH]/c(=N\c2ccc(Oc3ccccn3)cc2)n(Cc2ccc(Cl)cc2)c1=O] | 524 | 1.94 | 1 |
| R-245 | 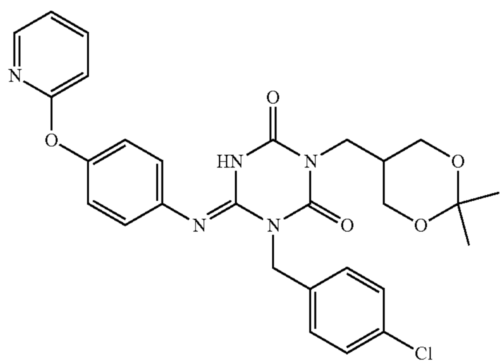 [SMILES: CC1(C)OCC(Cn2c(=O)[nH]/c(=N\c3ccc(Oc4ccccn4)cc3)n(Cc3ccc(Cl)cc3)c2=O)CO1] | 550 | 2.3 | 1 |

TABLE 106

| Compound No | Structure | [M + H]+ | RT | Method |
|---|---|---|---|---|
| R-246 | 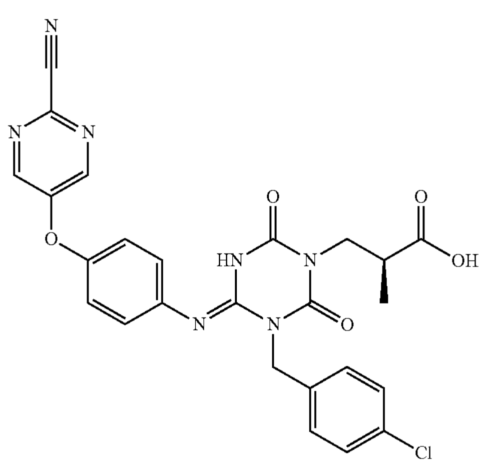 [SMILES: C[C@@H](Cn1c(=O)[nH]/c(=N\c2ccc(Oc3cnc(C#N)nc3)cc2)n(Cc2ccc(Cl)cc2)c1=O)C(=O)O] | 534 | 2.02 | 1 |

TABLE 106-continued

| Compound No | Structure | [M + H]+ | RT | Method |
|---|---|---|---|---|
| R-247 | 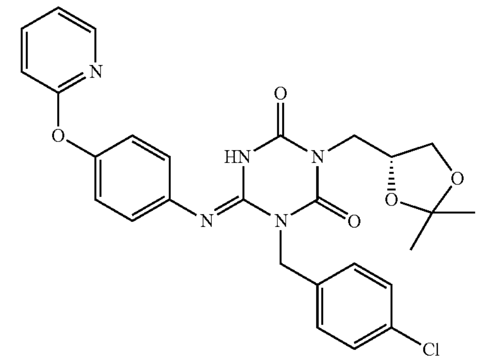 [SMILES: CC1(C)OC[C@@H](Cn2c(=O)[nH]/c(=N\c3ccc(Oc4ccccn4)cc3)n(Cc3ccc(Cl)cc3)c2=O)O1] | 536 | 2.33 | 1 |
| R-248 | 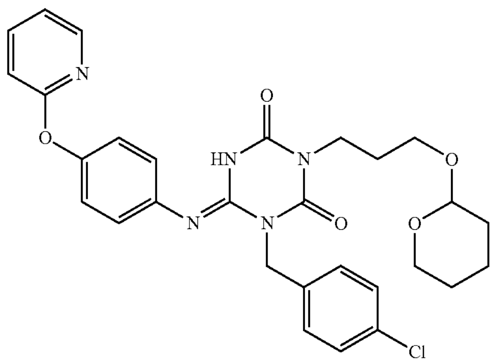 [SMILES: O=c1[nH]/c(=N\c2ccc(Oc3ccccn3)cc2)n(Cc2ccc(Cl)cc2)c(=O)n1CCCOC1CCCCO1] | 564 | 2.5 | 1 |
| R-249 | 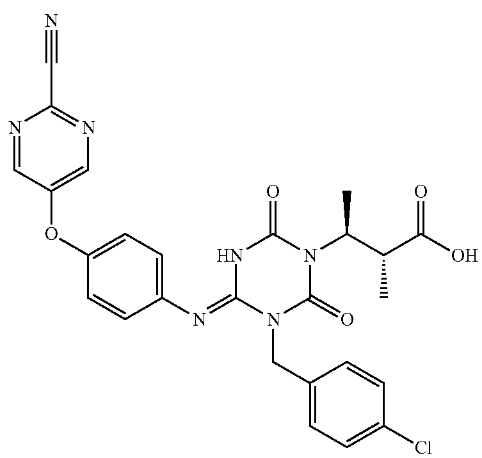 [SMILES: C[C@@H](C(=O)O)[C@H](C)n1c(=O)[nH]/c(=N\c2ccc(Oc3cnc(C#N)nc3)cc2)n(Cc2ccc(Cl)cc2)c1=O] | 548 | 2.13 | 1 |
| R-250 | 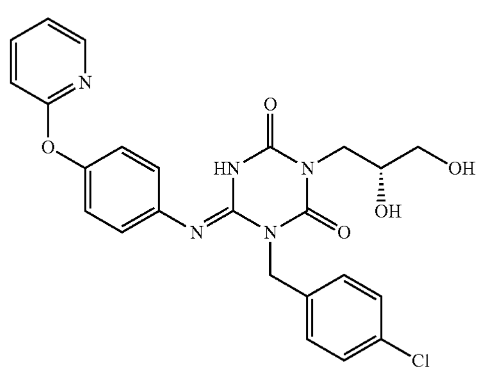 [SMILES: O=c1[nH]/c(=N\c2ccc(Oc3ccccn3)cc2)n(Cc2ccc(Cl)cc2)c(=O)n1C[C@@H](O)CO] | 496 | 1.8 | 1 |

TABLE 107

| Compound No | Structure | [M + H]+ | RT | Method |
|---|---|---|---|---|
| R-251 | 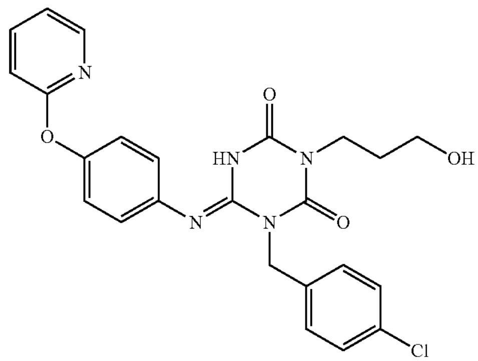 [SMILES: O=c1[nH]/c(=N\c2ccc(Oc3ccccn3)cc2)n(Cc2ccc(Cl)cc2)c(=O)n1CCCO] | 480 | 1.97 | 1 |
| R-252 | 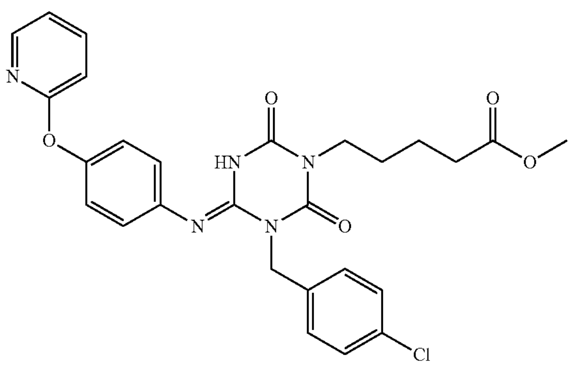 [SMILES: COC(=O)CCCCn1c(=O)[nH]/c(=N\c2ccc(Oc3ccccn3)cc2)n(Cc2ccc(Cl)cc2)c1=O] | 536 | 2.35 | 1 |
| R-253 | 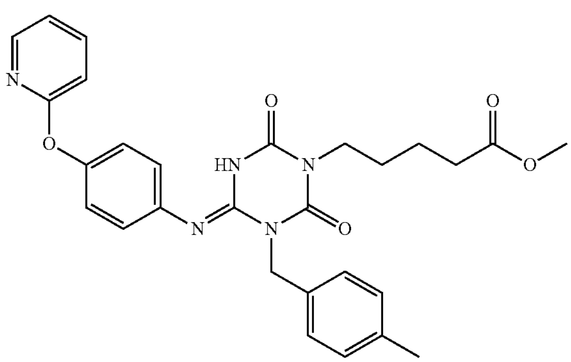 [SMILES: COC(=O)CCCCn1c(=O)[nH]/c(=N\c2ccc(Oc3ccccn3)cc2)n(Cc2ccc(C)cc2)c1=O] | 516 | 2.25 | 1 |
| R-254 | 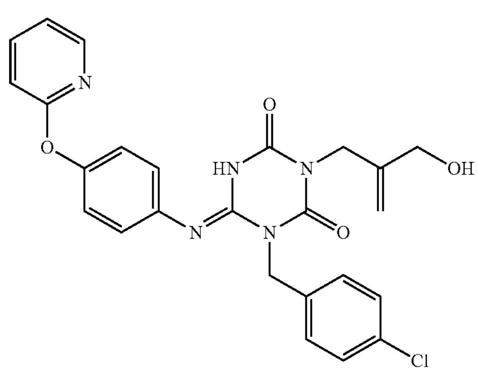 [SMILES: C=C(CO)Cn1c(=O)[nH]/c(=N\c2ccc(Oc3ccccn3)cc2)n(Cc2ccc(Cl)cc2)c1=O] | 492 | 2.02 | 1 |

TABLE 107-continued
| Compound No | Structure | [M + H]+ | RT | Method |
|---|---|---|---|---|
| R-255 | 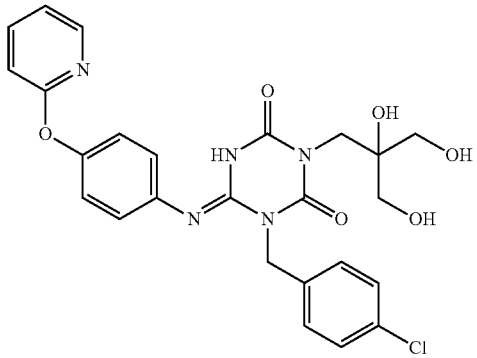 [SMILES: O=c1[nH]/c(=N\c2ccc(Oc3ccccn3)cc2)n(Cc2ccc(Cl)cc2)c(=O)n1CC(O)(CO)CO] | 526 | 1.77 | 1 |
TABLE 108
| Compound No | Structure | [M + H]+ | RT | Method |
|---|---|---|---|---|
| R-256 | 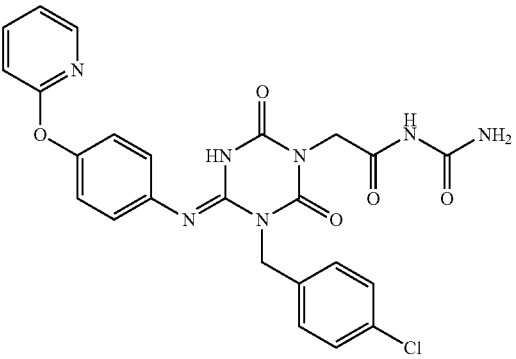 [SMILES: NC(=O)NC(=O)Cn1c(=O)[nH]/c(=N\c2ccc(Oc3ccccn3)cc2)n(Cc2ccc(Cl)cc2)c1=O] | 522 | 1.86 | 1 |
| R-257 | 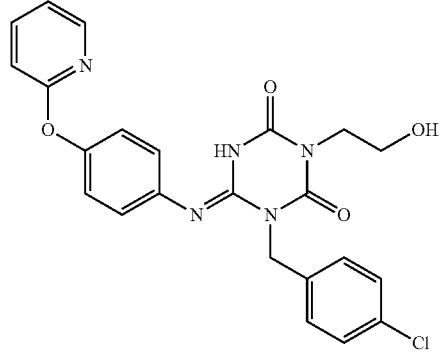 [SMILES: O=c1[nH]/c(=N\c2ccc(Oc3ccccn3)cc2)n(Cc2ccc(Cl)cc2)c(=O)n1CCO] | 466 | 1.93 | 1 |
| R-258 | 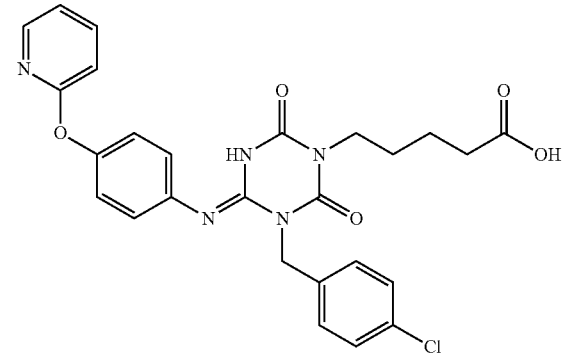 [SMILES: O=C(O)CCCCn1c(=O)[nH]/c(=N\c2ccc(Oc3ccccn3)cc2)n(Cc2ccc(Cl)cc2)c1=O] | 522 | 2.05 | 1 |

TABLE 108-continued

| Compound No | Structure | [M + H]+ | RT | Method |
|---|---|---|---|---|
| R-259 | 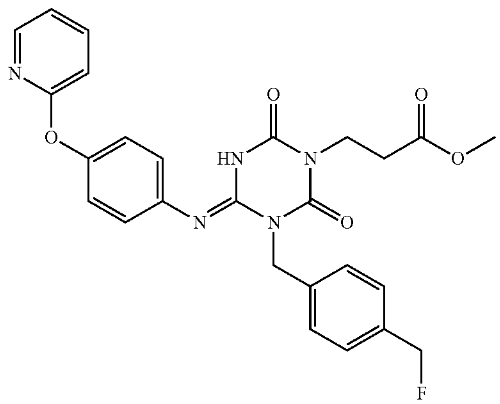 [SMILES: COC(=O)CCn1c(=O)[nH]/c(=N\c2ccc(Oc3ccccn3)cc2)n(Cc2ccc(CF)cc2)c1=O] | 506 | 1.96 | 1 |
| R-260 | 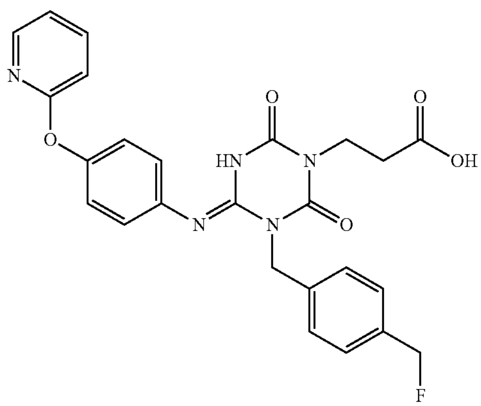 [SMILES: O=C(O)CCn1c(=O)[nH]/c(=N\c2ccc(Oc3ccccn3)cc2)n(Cc2ccc(CF)cc2)c1=O] | 492 | 1.75 | 1 |

TABLE 109

| Compound No | Structure | [M + H]+ | RT | Method |
|---|---|---|---|---|
| R-261 | 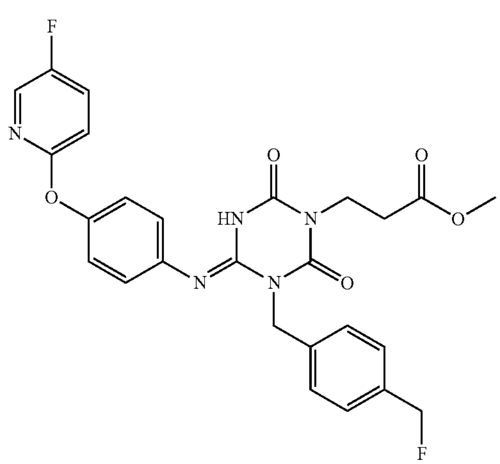 [SMILES: COC(=O)CCn1c(=O)[nH]/c(=N\c2ccc(Oc3ccc(F)cn3)cc2)n(Cc2ccc(CF)cc2)c1=O] | 524 | 2.03 | 1 |

TABLE 109-continued

| Compound No | Structure | [M + H]+ | RT | Method |
|---|---|---|---|---|
| R-262 | 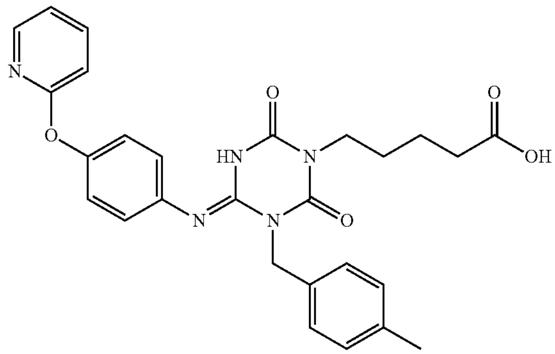 [SMILES: Cc1ccc(Cn2c(=O)n(CCCCC(=O)O)c(=O)[nH]/c2=N\c2ccc(Oc3ccccn3)cc2)cc1] | 502 | 1.96 | 1 |
| R-263 | 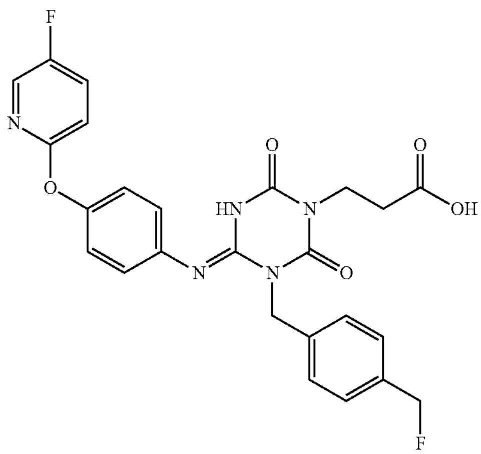 [SMILES: O=C(O)CCn1c(=O)[nH]/c(=N\c2ccc(Oc3ccc(F)cn3)cc2)n(Cc2ccc(CF)cc2)c1=O] | 510 | 1.81 | 1 |
| R-264 | 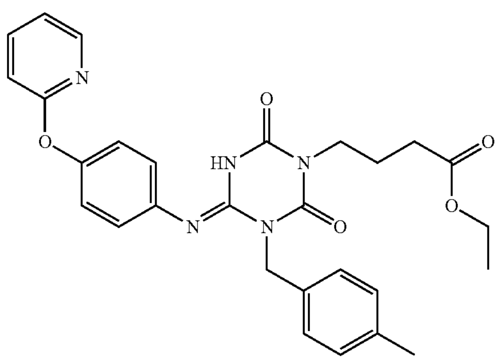 [SMILES: CCOC(=O)CCCn1c(=O)[nH]/c(=N\c2ccc(Oc3ccccn3)cc2)n(Cc2ccc(C)cc2)c1=O] | 516 | 2.26 | 1 |
| R-265 | 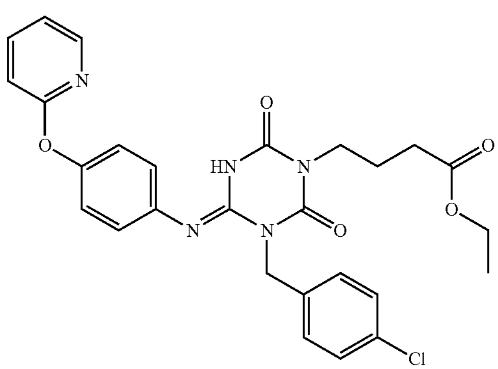 [SMILES: CCOC(=O)CCCn1c(=O)[nH]/c(=N\c2ccc(Oc3ccccn3)cc2)n(Cc2ccc(Cl)cc2)c1=O] | 536 | 2.36 | 1 |

TABLE 110

| Compound No | Structure | [M + H]+ | RT | Method |
|---|---|---|---|---|
| R-266 | 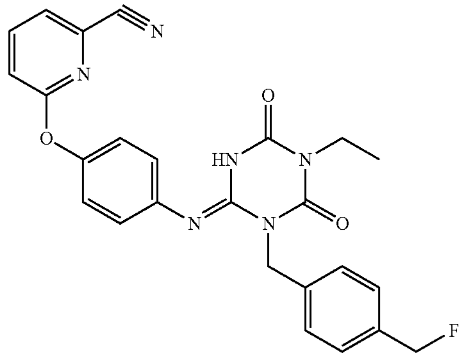 [SMILES: CCn1c(=O)[nH]/c(=N\c2ccc(Oc3cccc(C#N)n3)cc2)n(Cc2ccc(CF)cc2)c1=O] | 473 | 2.04 | 1 |
| R-267 | 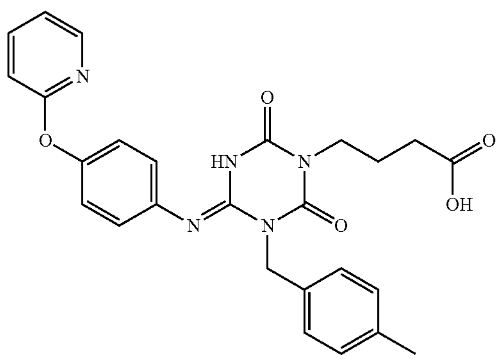 [SMILES: Cc1ccc(Cn2c(=O)n(CCCC(=O)O)c(=O)[nH]/c2=N\c2ccc(Oc3ccccn3)cc2)cc1] | 488 | 1.9 | 1 |
| R-268 | 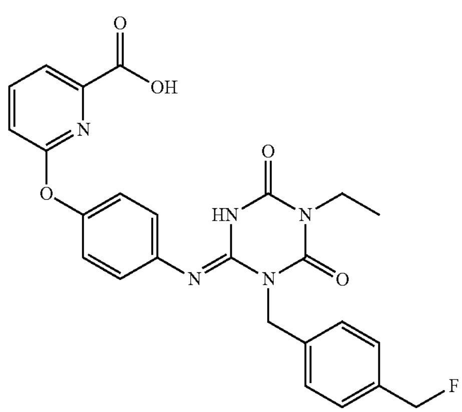 [SMILES: CCn1c(=O)[nH]/c(=N\c2ccc(Oc3cccc(C(=O)O)n3)cc2)n(Cc2ccc(CF)cc2)c1=O] | 492 | 1.85 | 1 |
| R-269 | 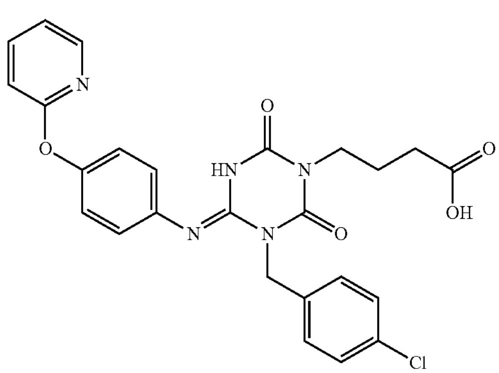 [SMILES: O=C(O)CCCn1c(=O)[nH]/c(=N\c2ccc(Oc3ccccn3)cc2)n(Cc2ccc(Cl)cc2)c1=O] | 508 | 1.99 | 1 |

TABLE 110-continued

| Compound No | Structure | [M + H]+ | RT | Method |
|---|---|---|---|---|
| R-270 | 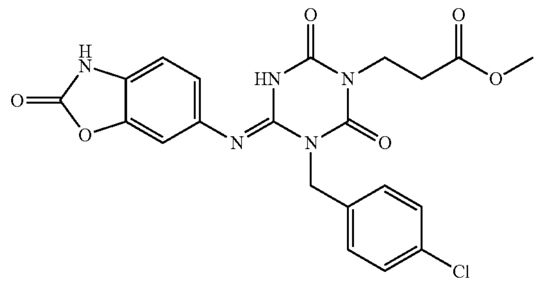 [SMILES: COC(=O)CCn1c(=O)[nH]/c(=N\c2ccc3[nH]c(=O)oc3c2)n(Cc2ccc(Cl)cc2)c1=O] | 472 | 1.73 | 1 |

TABLE 111

| Compound No | Structure | [M + H]+ | RT | Method |
|---|---|---|---|---|
| R-271 | 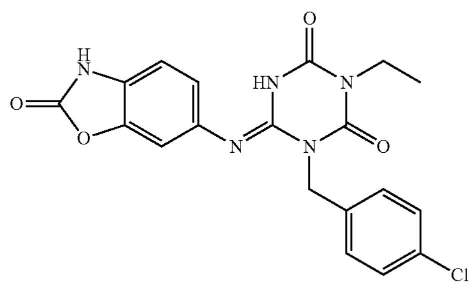 [SMILES: CCn1c(=O)[nH]/c(=N\c2ccc3[nH]c(=O)oc3c2)n(Cc2ccc(Cl)cc2)c1=O] | 414 | 1.77 | 1 |
| R-272 | 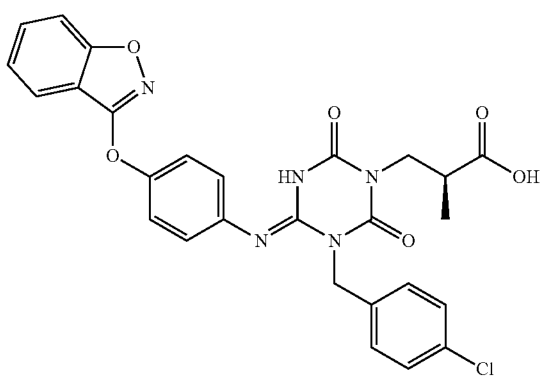 [SMILES: C[C@@H](Cn1c(=O)[nH]/c(=N\c2ccc(Oc3noc4ccccc34)cc2)n(Cc2ccc(Cl)cc2)c1=O)C(=O)O] | 548 | 2.25 | 1 |
| R-273 | 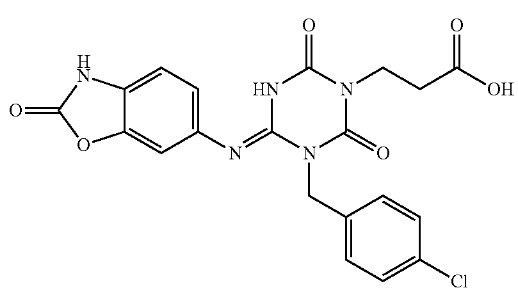 [SMILES: O=C(O)CCn1c(=O)[nH]/c(=N\c2ccc3[nH]c(=O)oc3c2)n(Cc2ccc(Cl)cc2)c1=O] | 458 | 1.5 | 1 |

TABLE 111-continued
| Compound No | Structure | [M + H]+ | RT | Method |
|---|---|---|---|---|
| R-274 | 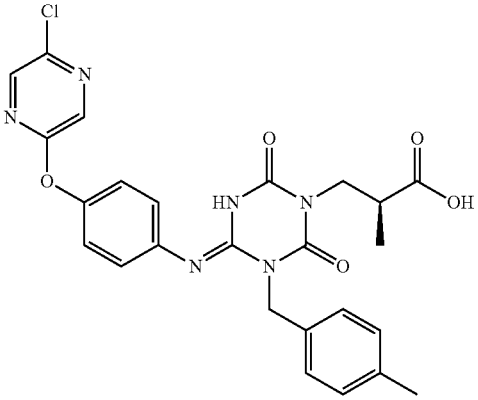 [SMILES: Cc1ccc(Cn2c(=O)n(C[C@H](C)C(=O)O)c(=O)[nH]/c2=N\c2ccc(Oc3cnc(Cl)cn3)cc2)cc1] | 523 | 2.04 | 1 |
TABLE 112
| Compound No | Structure | [M + H]+ | RT | Method |
|---|---|---|---|---|
| R-275 | 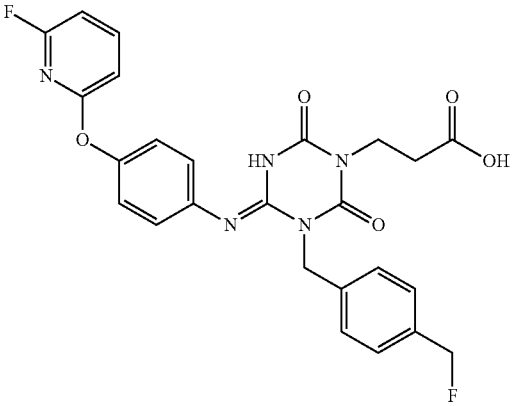 [SMILES: O=C(O)CCn1c(=O)[nH]/c(=N\c2ccc(Oc3cccc(F)n3)cc2)n(Cc2ccc(CF)cc2)c1=O] | 510 | 1.84 | 1 |
| R-276 | 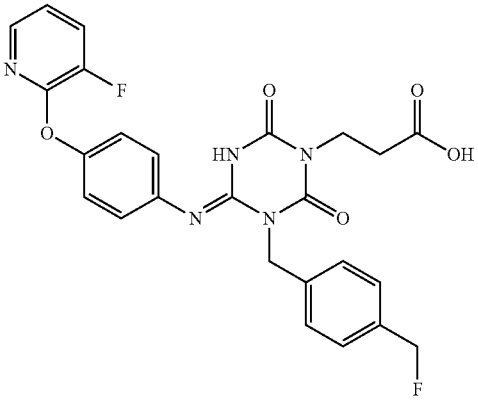 [SMILES: O=C(O)CCn1c(=O)[nH]/c(=N\c2ccc(Oc3ncccc3F)cc2)n(Cc2ccc(CF)cc2)c1=O] | 510 | 1.83 | 1 |

TABLE 112-continued

| Compound No | Structure | [M + H]+ | RT | Method |
|---|---|---|---|---|
| R-277 | 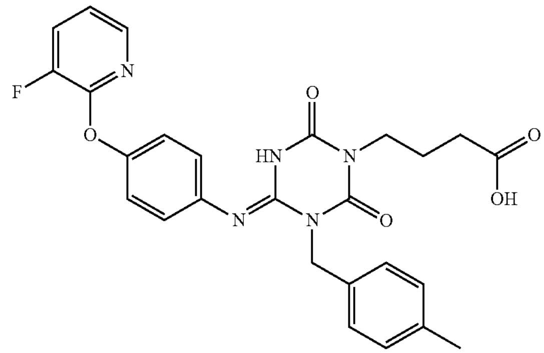 [SMILES: Cc1ccc(Cn2c(=O)n(CCCC(=O)O)c(=O)[nH]/c2=N\c2ccc(Oc3ncccc3F)cc2)cc1] | 506 | 1.98 | 1 |
| R-278 | 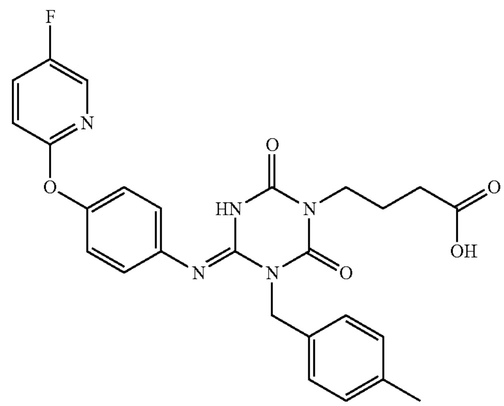 [SMILES: Cc1ccc(Cn2c(=O)n(CCCC(=O)O)c(=O)[nH]/c2=N\c2ccc(Oc3ccc(F)cn3)cc2)cc1] | 506 | 1.99 | 1 |
| R-279 | 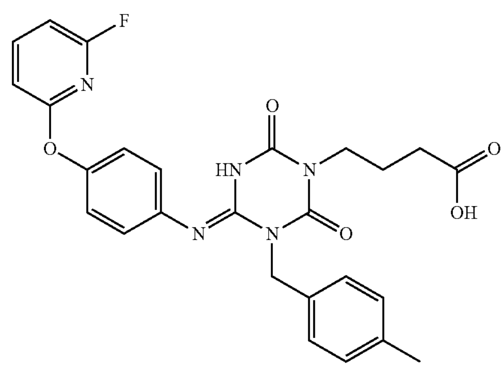 [SMILES: Cc1ccc(Cn2c(=O)n(CCCC(=O)O)c(=O)[nH]/c2=N\c2ccc(Oc3cccc(F)n3)cc2)cc1] | 506 | 2.02 | 1 |

TABLE 113

| Compound No | Structure | [M + H]+ | RT | Method |
|---|---|---|---|---|
| R-280 | 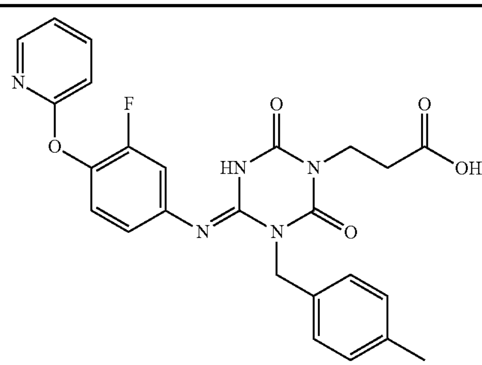 | 492 | 2.06 | 1 |

TABLE 113-continued

| Compound No | Structure | [M + H]+ | RT | Method |
|---|---|---|---|---|
| R-281 | 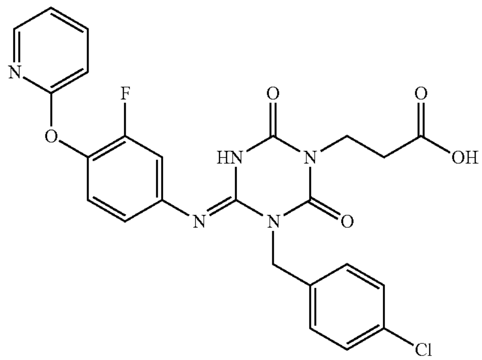 [SMILES: O=C(O)CCn1c(=O)[nH]/c(=N\c2ccc(Oc3ccccn3)c(F)c2)n(Cc2ccc(Cl)cc2)c1=O] | 512 | 2.12 | 1 |
| R-282 | 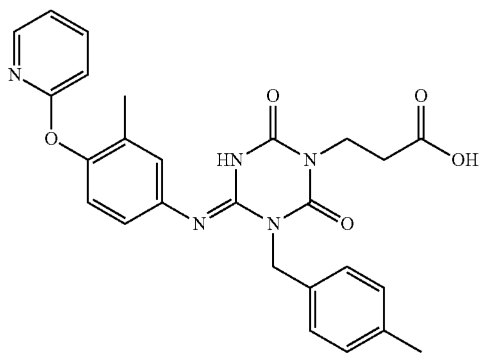 [SMILES: Cc1ccc(Cn2c(=O)n(CCC(=O)O)c(=O)[nH]/c2=N\c2ccc(Oc3ccccn3)c(C)c2)cc1] | 488 | 1.98 | 1 |
| R-283 | 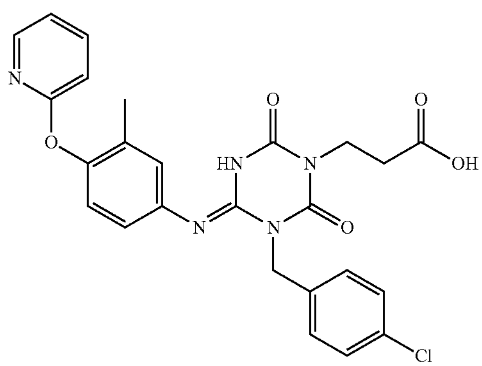 [SMILES: Cc1cc(/N=c2\[nH]c(=O)n(CCC(=O)O)c(=O)n2Cc2ccc(Cl)cc2)ccc1Oc1ccccn1] | 508 | 2.07 | 1 |
| R-284 | 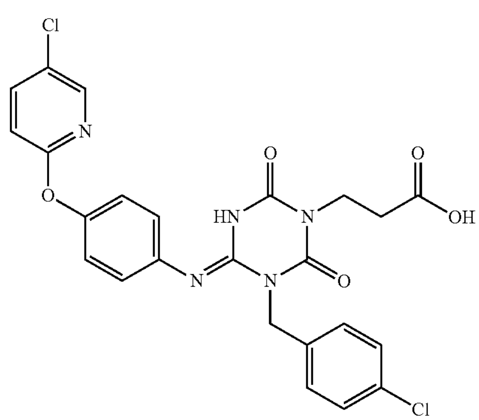 [SMILES: O=C(O)CCn1c(=O)[nH]/c(=N\c2ccc(Oc3ccc(Cl)cn3)cc2)n(Cc2ccc(Cl)cc2)c1=O] | 528 | 2.19 | 1 |

TABLE 114

| Compound No | Structure | [M + H]+ | RT | Method |
|---|---|---|---|---|
| R-285 | 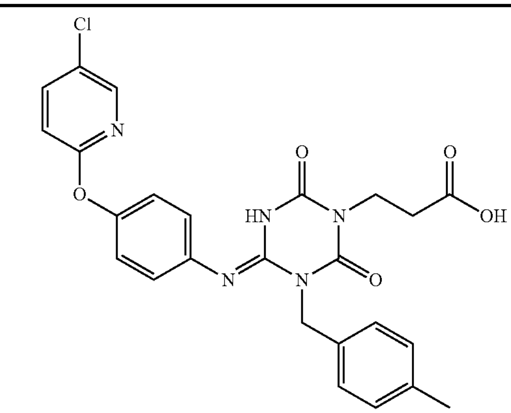 | 508 | 2.11 | 1 |
| R-286 | 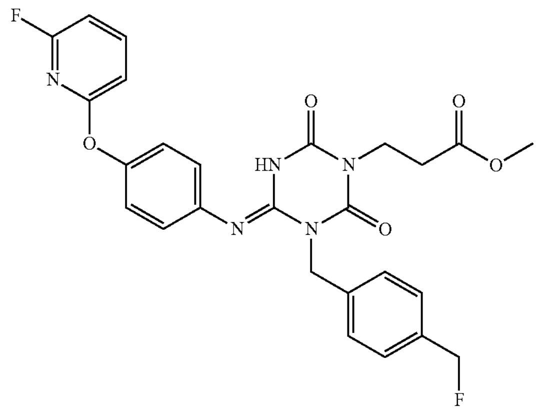 [SMILES: COC(=O)CCn1c(=O)[nH]/c(=N\c2ccc(Oc3cccc(F)n3)cc2)n(Cc2ccc(CF)cc2)c1=O] | 524 | 2.05 | 1 |
| R-287 | 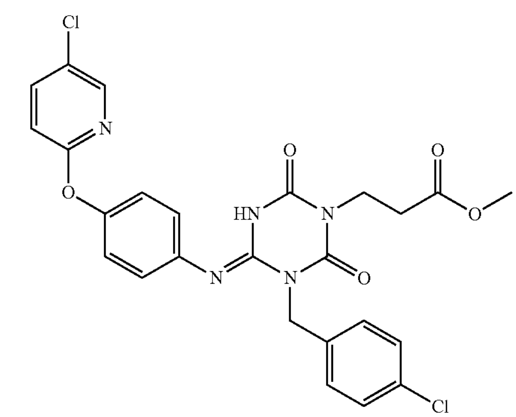 [SMILES: COC(=O)CCn1c(=O)[nH]/c(=N\c2ccc(Oc3ccc(Cl)cn3)cc2)n(Cc2ccc(Cl)cc2)c1=O] | 542 | 2.38 | 1 |
| R-288 | 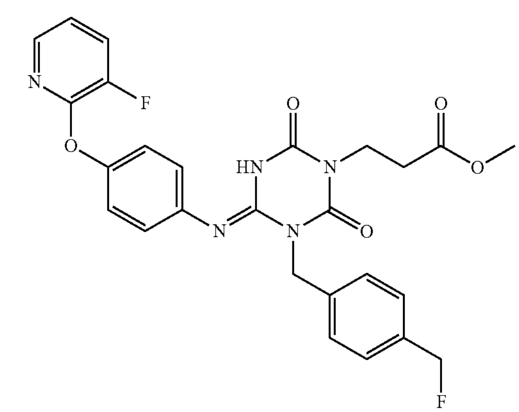 [SMILES: COC(=O)CCn1c(=O)[nH]/c(=N\c2ccc(Oc3ncccc3F)cc2)n(Cc2ccc(CF)cc2)c1=O] | 524 | 2.03 | 1 |

TABLE 114-continued
| Compound No | Structure | [M + H]+ | RT | Method |
|---|---|---|---|---|
| R-289 | 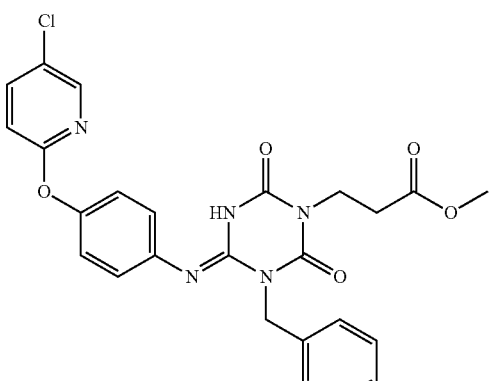 | 522 | 2.3 | 1 |
TABLE 115
| Compound No | Structure | [M + H]+ | RT | Method |
|---|---|---|---|---|
| R-290 | 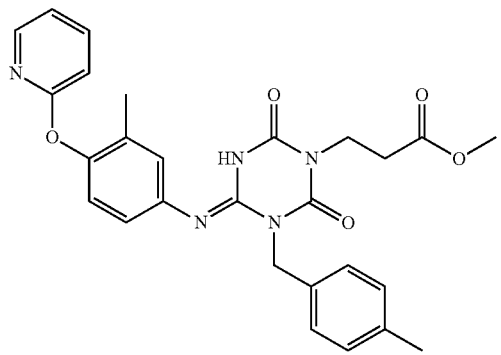 [SMILES: COC(=O)CCn1c(=O)[nH]/c(=N\c2ccc(Oc3ccccn3)c(C)c2)n(Cc2ccc(C)cc2)c1=O] | 502 | 2.23 | 1 |
| R-291 | 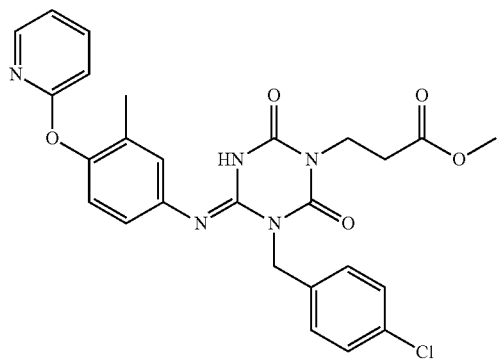 [SMILES: COC(=O)CCn1c(=O)[nH]/c(=N\c2ccc(Oc3ccccn3)c(C)c2)n(Cc2ccc(Cl)cc2)c1=O] | 522 | 2.33 | 1 |

TABLE 115-continued
| Compound No | Structure | [M + H]+ | RT | Method |
|---|---|---|---|---|
| R-292 | 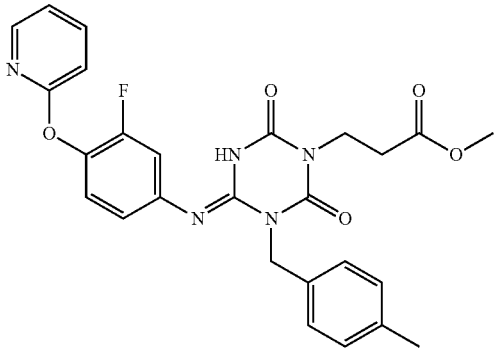 [SMILES: COC(=O)CCn1c(=O)[nH]/c(=N\c2ccc(Oc3ccccn3)c(F)c2)n(Cc2ccc(C)cc2)c1=O] | 506 | 2.29 | 1 |
| R-293 | 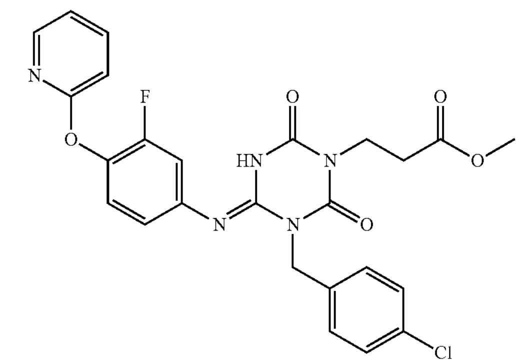 [SMILES: COC(=O)CCn1c(=O)[nH]/c(=N\c2ccc(Oc3ccccn3)c(F)c2)n(Cc2ccc(Cl)cc2)c1=O] | 526 | 2.37 | 1 |
| R-294 | 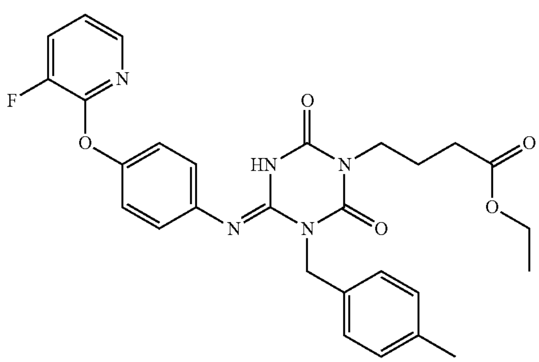 [SMILES: CCOC(=O)CCCn1c(=O)[nH]/c(=N\c2ccc(Oc3ncccc3F)cc2)n(Cc2ccc(C)cc2)c1=O] | 534 | 2.35 | 1 |
TABLE 116
| Compound No | Structure | [M + H]+ | RT | Method |
|---|---|---|---|---|
| R-295 | 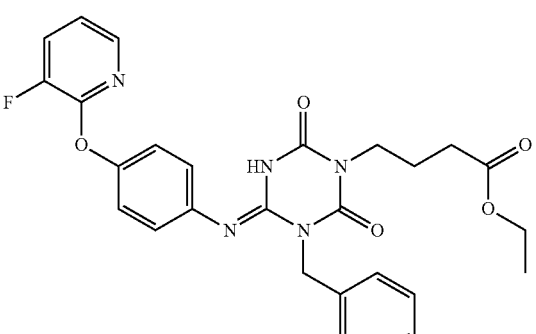 | 534 | 2.34 | 1 |

TABLE 116-continued

| Compound No | Structure | [M + H]+ | RT | Method |
|---|---|---|---|---|
| R-296 | 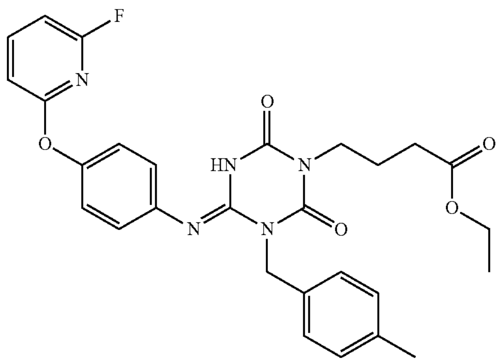 [SMILES: CCOC(=O)CCCn1c(=O)[nH]/c(=N\c2ccc(Oc3cccc(F)n3)cc2)n(Cc2ccc(C)cc2)c1=O] | 534 | 2.36 | 1 |
| R-297 | 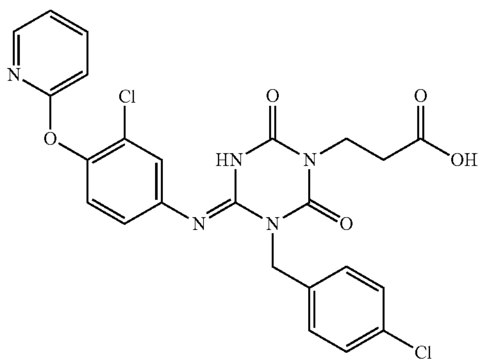 [SMILES: O=C(O)CCn1c(=O)[nH]/c(=N\c2ccc(Oc3ccccn3)c(Cl)c2)n(Cc2ccc(Cl)cc2)c1=O] | 528 | 2.22 | 1 |
| R-298 | 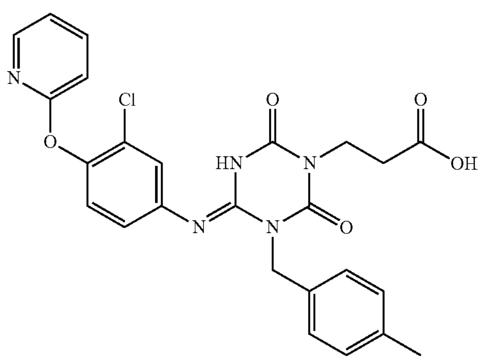 [SMILES: Cc1ccc(Cn2c(=O)n(CCC(=O)O)c(=O)[nH]/c2=N\c2ccc(Oc3ccccn3)c(Cl)c2)cc1] | 508 | 2.14 | 1 |
| R-299 | 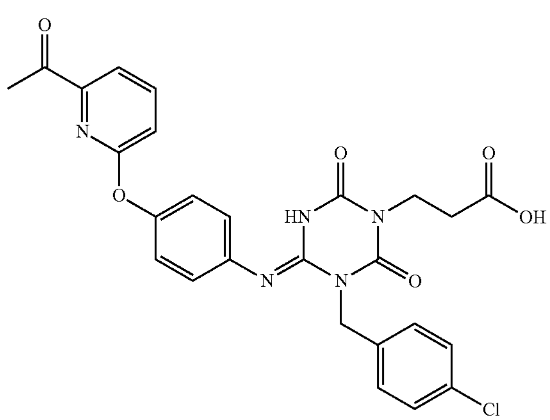 [SMILES: CC(=O)c1cccc(Oc2ccc(/N=c3\[nH]c(=O)n(CCC(=O)O)c(=O)n3Cc3ccc(Cl)cc3)cc2)n1] | 536 | 1.98 | 1 |

TABLE 117
| Compound No | Structure | [M + H]+ | RT | Method |
|---|---|---|---|---|
| R-300 | 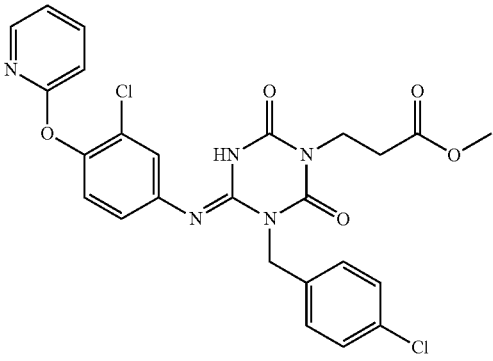 | 542 | 2.46 | 1 |
| R-301 | 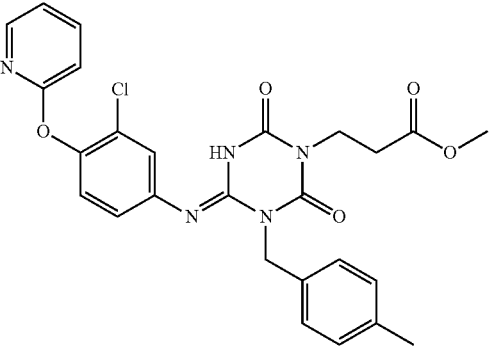 | 522 | 2.38 | 1 |
| R-302 | 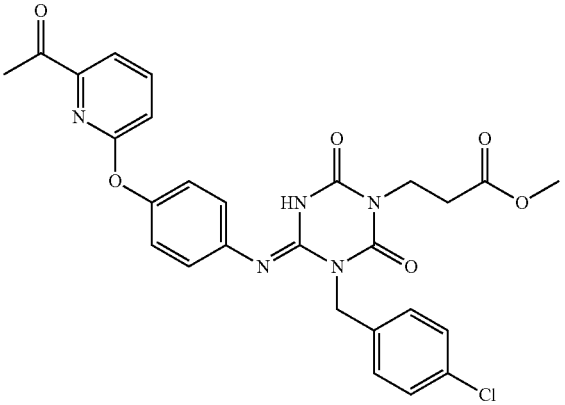 [SMILES: COC(=O)CCn1c(=O)[nH]/c(=N\c2ccc(Oc3cccc(C(C)=O)n3)cc2)n(Cc2ccc(Cl)cc2)c1=O] | 550 | 2.22 | 1 |
| R-303 | 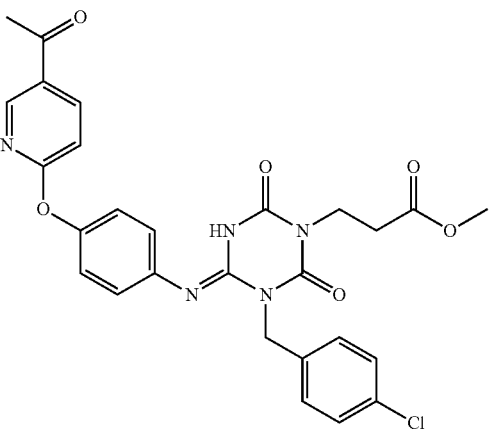 [SMILES: COC(=O)CCn1c(=O)[nH]/c(=N\c2ccc(Oc3ccc(C(C)=O)cn3)cc2)n(Cc2ccc(Cl)cc2)c1=O] | 550 | 2.17 | 1 |

TABLE 117-continued

| Compound No | Structure | [M + H]+ | RT | Method |
|---|---|---|---|---|
| R-304 | 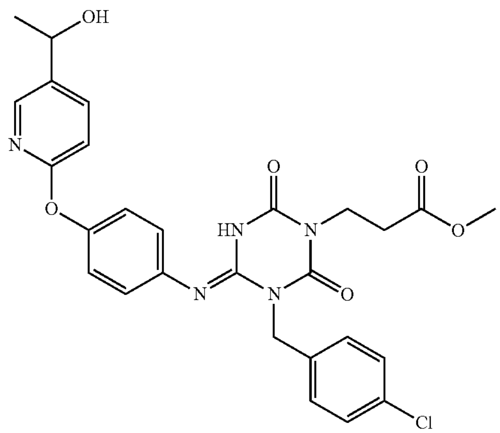 [SMILES: COC(=O)CCn1c(=O)[nH]/c(=N\c2ccc(Oc3ccc(C(C)O)cn3)cc2)n(Cc2ccc(Cl)cc2)c1=O] | 552 | 2 | 1 |

TABLE 118

| Compound No | Structure | [M + H]+ | RT | Method |
|---|---|---|---|---|
| R-305 | 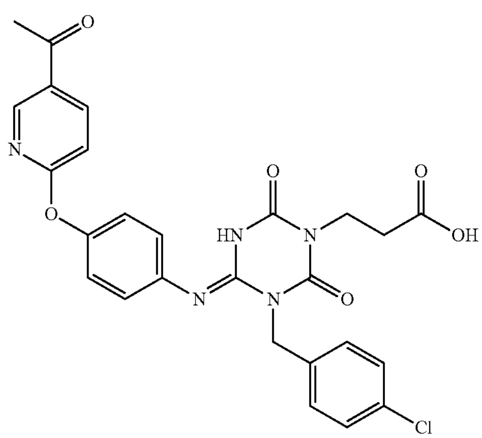 [SMILES: CC(=O)c1ccc(Oc2ccc(/N=c3\[nH]c(=O)n(CCC(=O)O)c(=O)n3Cc3ccc(Cl)cc3)cc2)nc1] | 536 | 1.93 | 1 |
| R-306 | 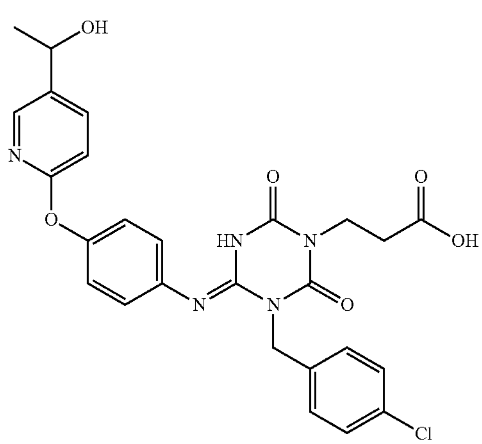 [SMILES: CC(O)c1ccc(Oc2ccc(/N=c3\[nH]c(=O)n(CCC(=O)O)c(=O)n3Cc3ccc(Cl)cc3)cc2)nc1] | 538 | 1.79 | 1 |

TABLE 118-continued

| Compound No | Structure | [M + H]+ | RT | Method |
|---|---|---|---|---|
| R-307 | 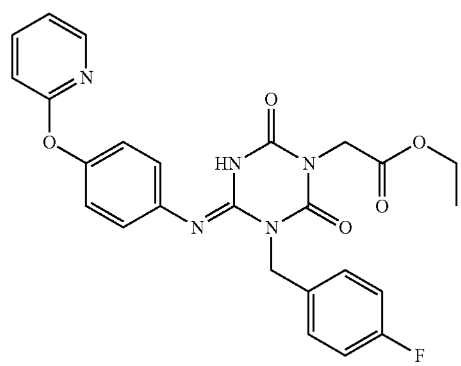 [SMILES: CCOC(=O)Cn1c(=O)[nH]/c(=N\c2ccc(Oc3ccccn3)cc2)n(Cc2ccc(F)cc2)c1=O] | 492 | 2.11 | 1 |
| R-308 | 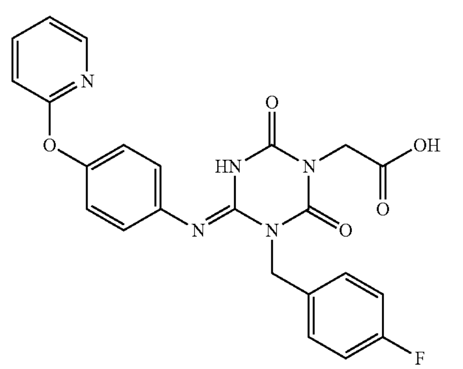 [SMILES: O=C(O)Cn1c(=O)[nH]/c(=N\c2ccc(Oc3ccccn3)cc2)n(Cc2ccc(F)cc2)c1=O] | 464 | 1.78 | 1 |
| R-309 | 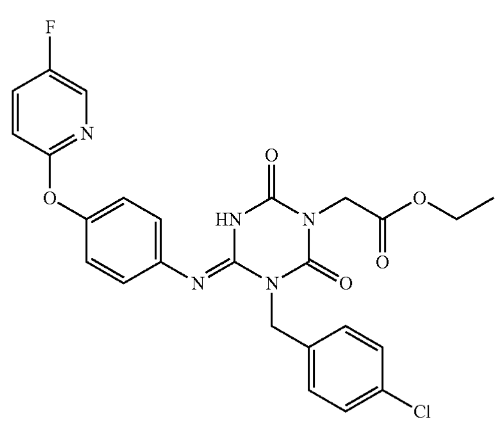 [SMILES: CCOC(=O)Cn1c(=O)[nH]/c(=N\c2ccc(Oc3ccc(F)cn3)cc2)n(Cc2ccc(Cl)cc2)c1=O] | 526 | 2.29 | 1 |

TABLE 119
| Compound No | Structure | [M + H]+ | RT | Method |
|---|---|---|---|---|
| R-310 | 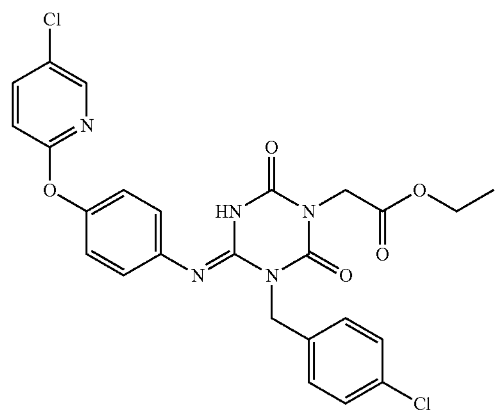 [SMILES: CCOC(=O)Cn1c(=O)[nH]/c(=N\c2ccc(Oc3ccc(Cl)cn3)cc2)n(Cc2ccc(Cl)cc2)c1=O] | 542 | 2.44 | 1 |
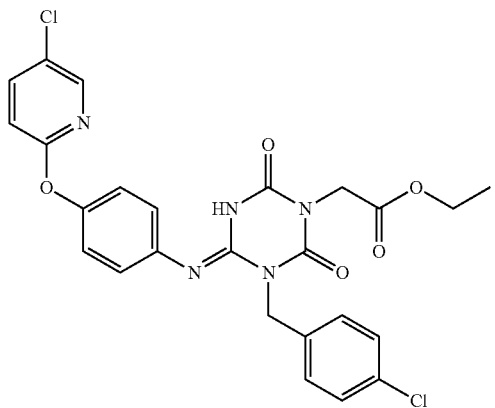
| | | | | |
|---|---|---|---|---|
| R-311 | | 498 | 1.96 | 1 |
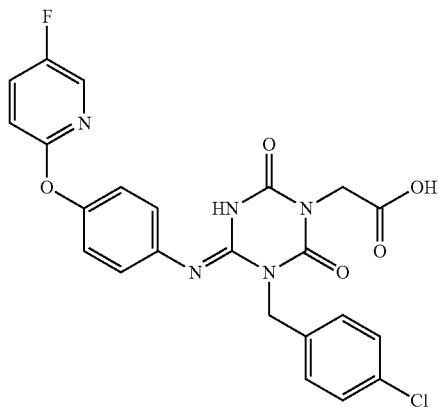 [SMILES: O=C(O)Cn1c(=O)[nH]/c(=N\c2ccc(Oc3ccc(F)cn3)cc2)n(Cc2ccc(Cl)cc2)c1=O]
| | | | | |
|---|---|---|---|---|
| R-312 | | 514 | 2.1 | 1 |
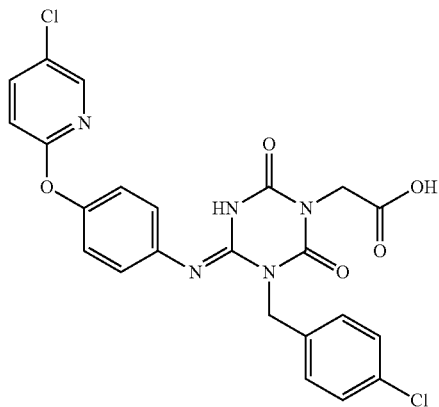 [SMILES: O=C(O)Cn1c(=O)[nH]/c(=N\c2ccc(Oc3ccc(Cl)cn3)cc2)n(Cc2ccc(Cl)cc2)c1=O]

TABLE 119-continued

| Compound No | Structure | [M + H]+ | RT | Method |
|---|---|---|---|---|
| R-313 | 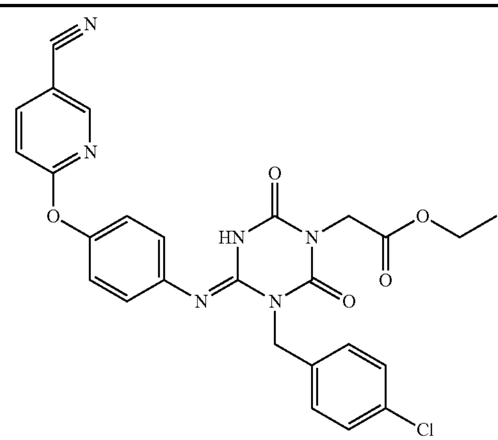 | 533 | 2.23 | 1 |
| R-314 | 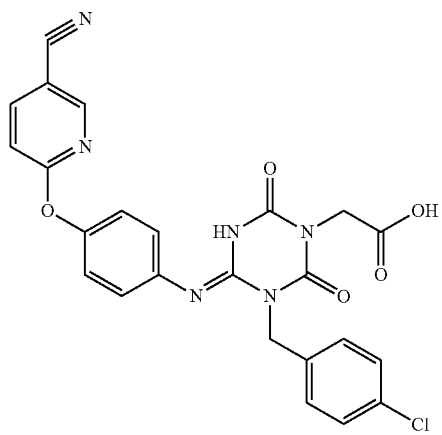 [SMILES: N#Cc1ccc(Oc2ccc(/N=c3\[nH]c(=O)n(CC(=O)O)c(=O)n3Cc3ccc(Cl)cc3)cc2)nc1] | 505 | 1.91 | 1 |

The following compounds of the invention can be synthesized in a similar manner to those described in the above general procedures for the synthesis of the compound of the invention and Examples, with reference to the contents described in WO2010/092966 and WO2012/020749 as needed.

[Chemical Formula 115]

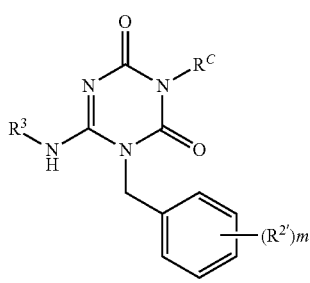

TABLE 120

| $R^3$ | $R^C$ | $(R^{2'})m$ |
|---|---|---|
| 4-(2-Pyridyl)O—Ph | CH$_2$CHMeCOOH | 4-CHF$_2$ |
| 4-(2-Pyridyl)O—Ph | CH(Me)CH(Me)COOHR | 4-Me |
| 4-(3-F-2-Pyridyl)O—Ph | (CH$_2$)$_3$COOH | 4-Me |

TABLE 120-continued

| $R^3$ | $R^C$ | $(R^{2'})m$ |
|---|---|---|
| 4-(5-F-2-Pyridyl)O—Ph | (CH$_2$)$_3$COOH | 4-Me |
| 4-(6-F-2-Pyridyl)O—Ph | (CH$_2$)$_3$COOH | 4-Me |
| 4-(5-F-3-Pyridyl)O—Ph | CH$_2$CHMeCOOH | 4-Me |
| 4-(2-F-4-Pyridyl)O—Ph | CH$_2$C(Me)$_2$COOH | 4-Me |
| 4-(2-F-4-Pyridyl)O—Ph | CH(Me)CH(Me)COOH | 4-Me |
| 4-(5-Cl-2-Pyridyl)O—Ph | (CH$_2$)$_2$COOH | 4-Cl |
| 4-(5-Cl-2-Pyridyl)O—Ph | (CH$_2$)$_2$COOH | 4-Me |
| 4-(5-Cl-3-Pyridyl)O—Ph | CH(Me)CH(Me)COOH | 4-Cl |
| 4-(2-Cl-4-Pyridyl)O—Ph | CH$_2$CHMeCOOH | 4-Me |
| 4-(3-MeO-2-Pyridyl)O—Ph | CH$_2$CHMeCOOH | 4-Me |
| 4-(5-MeO-2-Pyridyl)O—Ph | CH$_2$CHMeCOOH | 4-Me |
| 4-(6-MeO-2-Pyridyl)O—Ph | CH$_2$CHMeCOOH | 4-Me |
| 4-(5-MeO-3-Pyridyl)O—Ph | CH(Me)CH(Me)COOH | 4-Cl |
| 4-(2-MeO-4-Pyridyl)O—Ph | CH$_2$CHMeCOOH | 4-Me |
| 4-(2-MeO-4-Pyridyl)O—Ph | CH$_2$C(Me)$_2$COOH | 4-Cl |
| 4-(5-HOCO-2-thiazolyl)O—Ph | Et | 4-CH$_2$F |
| 4-(5-HOCO-2-Pyridyl)O—Ph | Et | 4-CH$_2$F |
| 4-(5-HOCO-2-Pyridyl)O-3-Me—Ph | Et | 4-CH$_2$F |
| 4-(5-HOCO-3-Pyridyl)O—Ph | Et | 4-CH$_2$F |
| 4-(2-HOCO-4-Pyridyl)O—Ph | Et | 4-CH$_2$F |
| 4-(6-HOCO-3-Pyridazinyl)O—Ph | Et | 4-CH$_2$F |
| 4-(6-H$_2$NCO-3-Pyridazinyl)O—Ph | Et | 4-CH$_2$F |
| 4-(2-Pyrimidyl)O—Ph | CH(Me)CH(Me)COOH | 4-Cl |
| 4-(2-Pyrimidyl)O-3-F—Ph | CH(Me)CH(Me)COOH | 4-Cl |
| 4-(6-Cl-4-Pyrimidyl)O—Ph | CH(Me)CH(Me)COOH | 4-Cl |
| 4-(6-F-4-Pyrimidyl)O—Ph | CH$_2$C(Me)$_2$COOH | 4-Cl |
| 4-(6-F-4-Pyrimidyl)O—Ph | CH(Me)CH(Me)COOH | 4-Cl |
| 4-(2-Me-4-Pyrimidyl)O—Ph | CH(Me)CH(Me)COOH | 4-Cl |
| 4-(2-CN-5-Pyrimidyl)O—Ph | CH$_2$C(Me)$_2$COOH | 4-Cl |

TABLE 120-continued

| R³ | R^C | (R²')m |
|---|---|---|
| 4-(5-Cl-2-Pyrazinyl)O—Ph | CH₂C(Me)₂COOH | 4-Me |
| 4-(5-Cl-2-Pyrazinyl)O—Ph | CH(Me)CH(Me)COOH | 4-Me |
| 4-(5-CF₃-2-Pyrazinyl)O—Ph | CH(Me)CH(Me)COOH | 4-Cl |
| 4-(3-Pyridazinyl)O—Ph | CH₂CHMeCOOH | 4-Me |
| 4-(3-Pyridazinyl)O—Ph | CH(Me)CH(Me)COOH | 4-Cl |
| 4-(3-Pyridazinyl)O-3-F—Ph | CH(Me)CH(Me)COOH | 4-Cl |
| 4-(6-Me-3-Pyridazinyl)O-3-F—Ph | CH(Me)CH(Me)COOH | 4-Cl |
| 4-(6-MeO-3-Pyridazinyl)O—Ph | CH₂CHMeCOOH | 4-Me |
| 4-(6-CF₃-3-Pyridazinyl)O—Ph | CH(Me)CH(Me)COOH | 4-Cl |
| 4-(4-Pyridazinyl)O-3-F—Ph | CH₂CHMeCOOH | 4-Cl |
| 4-(4-Pyridazinyl)O-3-F—Ph | CH₂C(Me)₂COOH | 4-Cl |

TABLE 121

| R³ | R^C | (R²')m |
|---|---|---|
| 4-(2-oxazolyl)O—Ph | CH₂CHMeCOOH | 4-Cl |
| 4-(2-oxazolyl)O—Ph | CH₂CHMeCOOH | 4-Me |
| 4-(2-oxazolyl)O—Ph | CH₂C(Me)₂COOH | 4-Cl |
| 4-(2-oxazolyl)O—Ph | CH(Me)CH(Me)COOH | 4-Cl |
| 4-(1,2,4-oxadiazol-2-yl)O—Ph | CH₂CHMeCOOH | 4-Cl |
| 4-(1,2,4-oxadiazol-2-yl)O—Ph | CH₂CHMeCOOH | 4-Me |
| 4-(1,2,4-oxadiazol-2-yl)O—Ph | CH₂C(Me)₂COOH | 4-Cl |
| 4-(1,2,4-oxadiazol-2-yl)O—Ph | CH(Me)CH(Me)COOH | 4-Cl |
| 4-(1,3,4-oxadiazol-2-yl)O—Ph | CH₂CHMeCOOH | 4-Cl |
| 4-(1,3,4-oxadiazol-2-yl)O—Ph | CH₂CHMeCOOH | 4-Me |
| 4-(1,3,4-oxadiazol-2-yl)O—Ph | CH₂C(Me)₂COOH | 4-Cl |
| 4-(1,3,4-oxadiazol-2-yl)O—Ph | CH(Me)CH(Me)COOH | 4-Cl |
| 4-(3-isothiazolyl)O—Ph | CH₂CHMeCOOH | 4-Cl |
| 4-(3-isothiazolyl)O—Ph | CH₂CHMeCOOH | 4-Me |
| 4-(3-isothiazolyl)O—Ph | CH₂C(Me)₂COOH | 4-Cl |
| 4-(3-isothiazolyl)O—Ph | CH(Me)CH(Me)COOH | 4-Cl |
| 4-(2-thiazolyl)O—Ph | CH₂CHMeCOOH | 4-Me |
| 4-(1,2,4-thiadiazol-5-yl)O—Ph | CH₂CHMeCOOH | 4-Me |
| 4-(1,2,4-thiadiazol-5-yl)O—Ph | CH(Me)CH(Me)COOH | 4-Cl |
| 4-(3-Me-1,2,4-thiadiazol-5-yl)O—Ph | CH₂CHMeCOOH | 4-Me |
| 4-(3-Me-1,2,4-thiadiazol-5-yl)O—Ph | CH₂CHMeCOOH | 4-Cl |
| 4-(3-Me-1,2,4-thiadiazol-5-yl)O—Ph | CH(Me)CH(Me)COOH | 4-Cl |
| 4-(1,2,5-thiadiazol-3-yl)O—Ph | CH₂CHMeCOOH | 4-Cl |
| 4-(1,2,5-thiadiazol-3-yl)O—Ph | CH₂CHMeCOOH | 4-Me |
| 4-(1,2,5-thiadiazol-3-yl)O—Ph | CH₂C(Me)₂COOH | 4-Cl |
| 4-(1,2,5-thiadiazol-3-yl)O—Ph | CH(Me)CH(Me)COOH | 4-Cl |
| 4-(2-Pyridyl)O-3-F—Ph | (CH₂)₂COOH | 4-Cl |
| 4-(2-Pyridyl)O-3-F—Ph | (CH₂)₂COOH | 4-Me |
| 4-(2-Pyridyl)O-3-F—Ph | CH₂CHMeCOOH | 4-Cl |
| 4-(2-Pyridyl)O-3-F—Ph | CH₂CHMeCOOH | 4-Me |
| 4-(2-Pyridyl)O-3-F—Ph | CH₂C(Me)₂COOH | 4-Cl |
| 4-(2-Pyridyl)O-3-F—Ph | CH(Me)CH(Me)COOH | 4-Cl |
| 4-(2-Pyridyl)O-3-Me—Ph | (CH₂)₂COOH | 4-Cl |
| 4-(2-Pyridyl)O-3-Me—Ph | (CH₂)₂COOH | 4-Me |
| 4-(2-Pyridyl)O-3-Me—Ph | CH₂CHMeCOOH | 4-Cl |
| 4-(2-Pyridyl)O-3-Me—Ph | CH₂CHMeCOOH | 4-Me |
| 4-(2-Pyridyl)O-3-Me—Ph | CH₂C(Me)₂COOH | 4-Cl |
| 4-(2-Pyridyl)O-3-Me—Ph | CH(Me)CH(Me)COOH | 4-Cl |
| 4-(5-Et-2-Pyridyl)O—Ph | CH₂CHMeCOOH | 4-Cl |
| 4-(5-Et-2-Pyridyl)O—Ph | CH₂CHMeCOOH | 4-Me |
| 4-(5-Et-2-Pyridyl)O—Ph | CH₂C(Me)₂COOH | 4-Cl |
| 4-(5-Et-2-Pyridyl)O—Ph | CH(Me)CH(Me)COOH | 4-Cl |
| 4-(6-Et-2-Pyridyl)O—Ph | CH₂CHMeCOOH | 4-Cl |
| 4-(6-Et-2-Pyridyl)O—Ph | CH₂CHMeCOOH | 4-Me |

TABLE 122

| R³ | R^C | (R²')m |
|---|---|---|
| 4-(6-Et-2-Pyridyl)O—Ph | CH₂C(Me)₂COOH | 4-Cl |
| 4-(6-Et-2-Pyridyl)O—Ph | CH(Me)CH(Me)COOH | 4-Cl |
| 4-(2-Pyridyl)O—Ph | CH₂CHMeCOOH | 4-CH₂F |
| 4-(3-F-2-Pyridyl)O—Ph | CH₂CHMeCOOH | 4-CH₂F |
| 4-(5-F-2-Pyridyl)O—Ph | CH₂CHMeCOOH | 4-CH₂F |
| 4-(6-F-2-Pyridyl)O—Ph | CH₂CHMeCOOH | 4-CH₂F |
| 4-(5-F-3-Pyridyl)O—Ph | CH₂CHMeCOOH | 4-CH₂F |
| 4-(Benzoxazol-2-yl)O—Ph | CH₂CHMeCOOH | 4-Me |

TABLE 122-continued

| R³ | R^C | (R²')m |
|---|---|---|
| 4-(4-Azabenzoxazol-2-yl)O—Ph | CH₂CHMeCOOH | 4-Me |
| 4-(Benzothiazol-2-yl)O—Ph | CH₂CHMeCOOH | 4-Me |
| 4-(3-Me-1,2-Benzizoxazol-6-yl)O—Ph | CH₂CHMeCOOH | 4-Cl |
| 4-(3-Me-1,2-Benzizoxazol-6-yl)O—Ph | CH₂CHMeCOOH | 4-Me |
| 4-(5-Benzoimidazolyl)O—Ph | CH₂CHMeCOOH | 4-Cl |
| 4-(5-Benzoimidazolyl)O—Ph | CH₂CHMeCOOH | 4-Me |
| 4-(Imidazopyridaziin-3-yl)O—Ph | CH₂CHMeCOOH | 4-Me |
| 4-(Imidazopyridaziin-3-yl)O—Ph | CH₂C(Me)₂COOH | 4-Cl |
| 4-(Imidazopyridaziin-3-yl)O—Ph | CH(Me)CH(Me)COOH | 4-Cl |
| 4-(Imidazopyridaziin-3-yl)O—Ph | (CH₂)₂OH | 4-Cl |
| 4-(Imidazopyridaziin-3-yl)O—Ph | (CH₂)₃OH | 4-Cl |
| 4-(Imidazopyridaziin-3-yl)O—Ph | CH₂CH(OH)CH₂OH | 4-Cl |
| 4-(Imidazopyridaziin-3-yl)O—Ph | CH₂CH(CH₂OH)₂ | 4-Cl |
| 4-(Imidazopyridaziin-3-yl)O—Ph | CH₂CMe(CH₂OH)₂ | 4-Cl |
| 4-(Imidazopyridaziin-3-yl)O—Ph | CH₂COH(CH₂OH)₂ | 4-Cl |

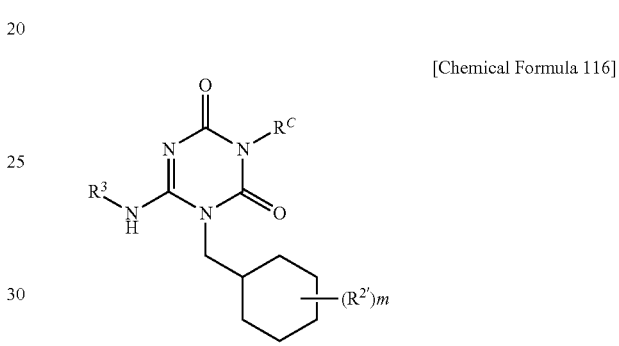

[Chemical Formula 116]

TABLE 123

| R³ | R^C | (R²')m |
|---|---|---|
| 4-(2-Pyridyl)O—Ph | (CH₂)₂COOH | 4-Me |
| 4-(2-Pyridyl)O—Ph | (CH₂)₂COOH | 4,4-(CH₂)₂ |
| 4-(2-Pyridyl)O—Ph | CH₂CHMeCOOH | 4,4-(CH₂)₂ |
| 4-(2-Pyridyl)O-3-F—Ph | (CH₂)₂COOH | 4-Me |
| 4-(2-Pyridyl)O-3-F—Ph | CH₂CHMeCOOH | 4-Me |
| 4-(2-Pyridyl)O-3-F—Ph | (CH₂)₂COOH | 4,4-(CH₂)₂ |
| 4-(2-Pyridyl)O-3-F—Ph | CH₂CHMeCOOH | 4,4-(CH₂)₂ |
| 4-(2-Pyridyl)O-3-Me—Ph | (CH₂)₂COOH | 4-Me |
| 4-(2-Pyridyl)O-3-Me—Ph | CH₂CHMeCOOH | 4-Me |
| 4-(2-Pyridyl)O-3-Me—Ph | (CH₂)₂COOH | 4,4-(CH₂)₂ |
| 4-(2-Pyridyl)O-3-Me—Ph | CH₂CHMeCOOH | 4,4-(CH₂)₂ |
| 4-(3-F-2-Pyridyl)O—Ph | CH₂CHMeCOOH | 4,4-(CH₂)₂ |
| 4-(5-F-2-Pyridyl)O—Ph | CH₂CHMeCOOH | 4,4-(CH₂)₂ |
| 4-(6-F-2-Pyridyl)O—Ph | CH₂CHMeCOOH | 4,4-(CH₂)₂ |
| 4-(5-F-3-Pyridyl)O—Ph | CH₂CHMeCOOH | 4,4-(CH₂)₂ |
| 4-(4-HOCO-2-Pyridyl)O—Ph | Et | 4,4-(CH₂)₂ |
| 4-(5-HOCO-2-Pyridyl)O—Ph | Et | 4,4-(CH₂)₂ |
| 4-(6-HOCO-2-Pyridyl)O—Ph | Et | 4,4-(CH₂)₂ |
| 4-(5-HOCO-2-Pyridyl)O-3-Me—Ph | Et | 4,4-(CH₂)₂ |
| 4-(6-HOCO-2-Pyridyl)O-3-Me—Ph | Et | 4,4-(CH₂)₂ |
| 4-(5-HOCO-2-Pyridyl)O-3-F—Ph | Et | 4,4-(CH₂)₂ |
| 4-(6-HOCO-2-Pyridyl)O-3-F—Ph | Et | 4,4-(CH₂)₂ |

Biological test examples for compounds of the present invention were described below.

TEST EXAMPLES

Test Example 1 Evaluation of Human P2X₃ Receptor Inhibitory Activity

Stably expressing cell line (C6BU-1 cell transfected with human P2X₃ receptor gene (GenBank accession number Y07683) was used. The cells were seeded in a 384-well PDL-coated microtiter plate at a concentration of 3000 cells/well and cultured in the medium (8.3% fetal bovine serum, 8.3% horse serum, and 1% antibiotic and antifungal in DMEM) for one day at 37° C. under 5% carbon dioxide atmosphere. The medium was replaced with 4 μM Fluo-3-AM solution (20 mM HEPES, 137 mM NaCl, 2.7 mM KCl, 0.9 mM $MgCl_2$, 5.0 mM $CaCl_2$, 5.6 mM D-glucose, 2.5 mM probenecid, 0.5% BSA, and 0.04% Pluronic F-127, pH 7.5) and incubated at 37° C. under 5% dioxide carbon atmosphere for one hour. The plate was washed with washing buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH7.5), and each well was added with 20 μL of the washing buffer. The plate was placed in High-Throughput Screening System FLIPR 384 (Molecular Device Co.). Measurement of fluorescence intensity by FLIPR 384 was started, and 20 μL of DMSO solutions containing different concentrations of the test compound as prepared by dilution with dilution buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, 0.1% Pluronic F-127, pH7.5) were dispensed to each well through the built-in automatic dispenser. Five minutes after, 150 nM ATP solution (25 μL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. The specific maximum fluorescence intensity and $IC_{50}$ were calculated using Spotfire (Science & Technology Systems, Inc.)

The data of the compounds of the present invention are as shown in the following Tables.

TABLE 124

| Compound No. | P2X3 IC50 (μM) |
|---|---|
| I-001 | 0.044 |
| I-002 | 0.005 |
| I-003 | 0.007 |
| I-004 | 0.014 |
| I-005 | 0.008 |
| I-006 | 0.005 |
| I-007 | 0.009 |
| I-008 | 0.007 |
| I-009 | 0.007 |
| I-010 | 0.005 |
| I-011 | 0.018 |
| I-012 | 0.025 |
| I-013 | 0.058 |
| I-014 | 0.007 |
| I-015 | 0.009 |
| I-016 | 0.008 |
| I-017 | 0.006 |
| I-018 | 0.012 |
| I-019 | 0.007 |
| I-020 | 0.009 |
| I-021 | 0.025 |
| I-022 | 0.004 |
| I-023 | 0.007 |
| I-024 | 0.034 |

TABLE 124-continued

| Compound No. | P2X3 IC50 (μM) |
|---|---|
| I-025 | 0.023 |
| I-026 | 0.017 |
| I-027 | 0.039 |
| I-028 | 0.02 |
| I-029 | 0.014 |
| I-030 | 0.176 |
| I-031 | 0.199 |
| I-032 | 0.011 |
| I-033 | 0.023 |
| I-034 | 0.009 |
| I-035 | 0.012 |
| I-036 | 0.005 |
| I-037 | 0.006 |
| I-038 | 0.005 |
| I-039 | 0.008 |
| I-040 | 0.006 |
| I-041 | 0.009 |
| I-042 | 0.004 |
| I-043 | 0.117 |
| I-044 | 0.026 |
| I-045 | 0.019 |
| I-046 | 0.019 |
| I-047 | 0.022 |
| I-048 | 0.03 |
| I-049 | 0.015 |
| I-050 | 0.028 |
| I-051 | 0.006 |
| I-052 | 0.006 |
| I-053 | 0.006 |
| I-054 | 0.005 |
| I-055 | 0.009 |
| I-056 | 0.007 |
| I-057 | 0.005 |
| I-058 | 0.006 |
| I-059 | 0.016 |
| I-060 | 0.024 |
| I-061 | 0.062 |
| I-062 | 0.031 |
| I-063 | 0.009 |
| I-064 | 0.01 |
| I-065 | 0.008 |
| I-066 | 0.015 |
| I-067 | 0.011 |
| I-068 | 0.005 |
| I-069 | 0.007 |
| I-070 | 0.005 |
| I-071 | 0.038 |
| I-072 | 0.006 |
| I-073 | 0.015 |
| I-074 | 0.005 |
| I-075 | 0.021 |
| I-076 | 0.022 |
| I-077 | 0.01 |
| I-078 | 0.019 |
| I-079 | 0.005 |
| I-080 | 0.01 |
| I-081 | 0.038 |
| I-082 | 0.112 |
| I-083 | 0.006 |
| I-084 | 0.008 |
| I-085 | 0.225 |
| I-086 | 0.033 |
| I-087 | 0.107 |
| I-088 | 0.015 |
| I-089 | 0.008 |
| I-090 | 0.072 |
| I-091 | 0.01 |
| I-092 | 0.068 |
| I-093 | 0.016 |
| I-094 | 0.011 |
| I-095 | 0.009 |
| I-096 | 0.008 |
| I-097 | 0.005 |
| I-098 | 0.007 |
| I-099 | 0.006 |
| I-100 | 0.004 |
| I-101 | 0.005 |

TABLE 124-continued

| Compound No. | P2X3 IC50 (μM) |
|---|---|
| I-102 | 0.005 |
| I-103 | 0.007 |
| I-104 | 0.005 |
| I-105 | 0.007 |
| I-106 | 0.006 |
| I-107 | 0.031 |
| I-108 | 0.004 |
| I-109 | 0.006 |
| I-110 | 0.004 |
| I-111 | 0.009 |
| I-112 | 0.004 |
| I-113 | 0.005 |
| I-114 | 0.006 |
| I-115 | 0.006 |
| I-116 | 0.007 |
| I-117 | 0.005 |
| I-118 | 0.009 |
| I-119 | 0.006 |
| I-120 | 0.009 |
| I-121 | 0.006 |
| I-122 | 0.004 |
| I-123 | 0.005 |
| I-124 | 0.005 |
| I-125 | 0.005 |
| I-126 | 0.005 |
| I-127 | 0.004 |
| I-128 | 0.008 |
| I-129 | 0.004 |
| I-130 | 0.006 |
| I-131 | 0.008 |
| I-132 | 0.008 |
| I-133 | 0.008 |
| I-134 | 0.007 |
| I-135 | 0.004 |
| I-136 | 0.007 |
| I-137 | 0.014 |
| I-138 | 0.007 |
| I-139 | 0.01 |
| I-140 | 0.003 |
| I-141 | 0.014 |
| I-142 | 0.007 |
| I-143 | 0.005 |
| I-144 | 0.009 |
| I-145 | 0.006 |
| I-146 | 0.005 |
| I-147 | 0.007 |
| I-148 | 0.009 |
| I-149 | 0.005 |
| I-150 | 0.004 |

TABLE 125

| Compound No. | P2X3 IC50 (μM) | Compound No. | P2X3 IC50 (μM) |
|---|---|---|---|
| I-151 | 0.01 | R-001 | 0.007 |
| I-152 | 0.006 | R-002 | 0.363 |
| I-153 | 0.013 | R-003 | 0.004 |
| I-154 | 0.008 | R-004 | 0.123 |
| I-155 | 0.008 | R-005 | 0.608 |
| I-156 | 0.012 | R-006 | 0.004 |
| I-157 | 0.005 | R-007 | 0.301 |
| I-158 | 0.006 | R-009 | 0.007 |
| I-159 | 0.009 | R-010 | 0.01 |
| I-160 | 0.005 | R-011 | 0.049 |
| I-161 | 0.01 | R-012 | 0.005 |
| I-162 | 0.007 | R-013 | 0.006 |
| I-163 | 0.008 | R-014 | 0.005 |
| I-164 | 0.029 | R-015 | 0.104 |
| I-165 | 0.015 | R-016 | 0.006 |
| I-166 | 0.013 | R-017 | 0.006 |
| I-167 | 0.019 | R-018 | 0.005 |
| I-168 | 0.012 | R-019 | 0.006 |
| I-169 | 0.021 | R-020 | 0.013 |
| I-170 | 0.015 | R-021 | 0.015 |
| I-171 | 0.009 | R-022 | 0.012 |
| I-172 | 0.026 | R-023 | 0.021 |
| I-173 | 0.008 | R-024 | 0.018 |
| I-174 | 0.006 | R-025 | 0.005 |
| I-175 | 0.009 | R-026 | 0.008 |
| I-176 | 0.007 | R-027 | 0.006 |
| I-177 | 0.006 | R-028 | 0.007 |
| I-178 | 0.005 | R-029 | 0.007 |
| I-179 | 0.006 | R-030 | 0.008 |
| I-180 | 0.005 | R-031 | 0.012 |
| I-181 | 0.005 | R-032 | 0.004 |
| I-182 | 0.008 | R-033 | 0.006 |
| I-183 | 0.012 | R-034 | 0.005 |
| I-184 | 0.006 | R-035 | 0.008 |
| I-185 | 0.009 | R-036 | 0.011 |
| I-186 | 0.005 | R-037 | 0.007 |
| I-187 | 0.008 | R-038 | 0.007 |
| I-188 | 0.007 | R-039 | 0.006 |
| I-189 | 0.012 | R-040 | 0.007 |
| I-190 | 0.005 | R-041 | 0.011 |
| I-191 | 0.011 | R-042 | 0.005 |
| I-192 | 0.005 | R-043 | 0.005 |
| I-193 | 0.008 | R-044 | 0.01 |
| I-194 | 0.012 | R-045 | 0.014 |
| I-195 | 0.007 | R-046 | 0.006 |
| | | R-047 | 0.009 |
| | | R-048 | 0.006 |
| | | R-049 | 0.008 |
| | | R-050 | 0.014 |
| | | R-053 | 0.052 |
| | | R-054 | 0.026 |
| | | R-055 | 0.007 |
| | | R-056 | 0.01 |
| | | R-057 | 0.006 |
| | | R-058 | 0.004 |
| | | R-059 | 0.005 |
| | | R-060 | 0.016 |
| | | R-061 | 0.007 |
| | | R-062 | 0.318 |
| | | R-063 | 0.456 |
| | | R-064 | 0.012 |
| | | R-066 | 0.058 |
| | | R-068 | 0.04 |
| | | R-069 | 0.051 |
| | | R-070 | 0.007 |
| | | R-071 | 0.006 |
| | | R-072 | 0.016 |
| | | R-073 | 0.031 |
| | | R-074 | 0.013 |
| | | R-075 | 0.013 |
| | | R-076 | 0.013 |
| | | R-077 | 0.024 |
| | | R-078 | 0.01 |
| | | R-079 | 0.011 |
| | | R-080 | 0.013 |
| | | R-081 | 0.005 |
| | | R-082 | 0.007 |
| | | R-083 | 0.007 |
| | | R-084 | 0.006 |
| | | R-085 | 0.006 |
| | | R-086 | 0.007 |
| | | R-087 | 0.012 |
| | | R-088 | 0.006 |
| | | R-089 | 0.007 |
| | | R-090 | 0.07 |
| | | R-091 | 0.108 |
| | | R-092 | 0.01 |
| | | R-093 | 0.013 |
| | | R-094 | 0.029 |
| | | R-095 | 0.045 |
| | | R-096 | 0.156 |
| | | R-097 | 0.212 |
| | | R-098 | 0.08 |
| | | R-099 | 0.004 |
| | | R-100 | 0.006 |
| | | R-101 | 0.201 |

TABLE 125-continued

| Compound No. | P2X3 IC50 (μM) | Compound No. | P2X3 IC50 (μM) |
|---|---|---|---|
|  |  | R-102 | 0.1 |
|  |  | R-105 | 0.007 |
|  |  | R-106 | 0.379 |
|  |  | R-107 | 0.217 |

TABLE 126

| Compound No. | P2X3 IC50 (μM) |
|---|---|
| R-108 | 0.008 |
| R-111 | 0.005 |
| R-112 | 0.017 |
| R-113 | 0.013 |
| R-114 | 0.039 |
| R-115 | 0.065 |
| R-116 | 0.005 |
| R-117 | 0.006 |
| R-118 | 0.005 |
| R-119 | 0.005 |
| R-120 | 0.008 |
| R-121 | 0.005 |
| R-122 | 0.013 |
| R-123 | 0.005 |
| R-124 | 0.009 |
| R-125 | 0.007 |
| R-126 | 0.01 |
| R-127 | 0.09 |
| R-128 | 0.011 |
| R-129 | 0.007 |
| R-130 | 0.009 |
| R-131 | 0.009 |
| R-132 | 0.01 |
| R-133 | 0.006 |
| R-134 | 0.005 |
| R-135 | 0.005 |
| R-136 | 0.006 |
| R-137 | 0.006 |
| R-138 | 0.078 |
| R-139 | 0.119 |
| R-140 | 0.037 |
| R-141 | 0.047 |
| R-142 | 0.069 |
| R-143 | 0.097 |
| R-144 | 0.005 |
| R-145 | 0.011 |
| R-146 | 0.033 |
| R-147 | 0.051 |
| R-148 | 0.005 |
| R-149 | 0.012 |
| R-150 | 0.018 |
| R-151 | 0.011 |
| R-152 | 0.005 |
| R-153 | 0.008 |
| R-154 | 0.008 |
| R-155 | 0.01 |
| R-156 | 0.035 |
| R-157 | 0.006 |
| R-158 | 0.012 |
| R-159 | 0.018 |
| R-160 | 0.008 |
| R-161 | 0.01 |
| R-162 | 0.006 |
| R-163 | 0.014 |
| R-164 | 0.01 |
| R-165 | 0.014 |
| R-166 | 0.048 |
| R-167 | 0.011 |
| R-168 | 0.017 |
| R-169 | 0.304 |
| R-170 | 0.193 |
| R-171 | 0.033 |
| R-172 | 0.033 |
| R-173 | 0.376 |

TABLE 126-continued

| Compound No. | P2X3 IC50 (μM) |
|---|---|
| R-174 | 0.01 |
| R-175 | 0.019 |
| R-176 | 0.007 |
| R-177 | 0.005 |
| R-178 | 0.045 |
| R-179 | 0.056 |
| R-180 | 0.007 |
| R-181 | 0.007 |
| R-182 | 0.026 |
| R-183 | 0.007 |
| R-184 | 0.01 |
| R-185 | 0.012 |
| R-186 | 0.026 |
| R-187 | 0.021 |
| R-188 | 0.009 |
| R-189 | 0.008 |
| R-190 | 0.009 |
| R-191 | 0.012 |
| R-192 | 0.004 |
| R-193 | 0.011 |
| R-194 | 0.013 |
| R-195 | 0.009 |
| R-196 | 0.011 |
| R-197 | 0.007 |
| R-198 | 0.009 |
| R-199 | 0.007 |
| R-200 | 0.008 |
| R-201 | 0.008 |
| R-202 | 0.012 |
| R-203 | 0.006 |
| R-204 | 0.008 |
| R-205 | 0.008 |
| R-206 | 0.005 |
| R-207 | 0.009 |
| R-208 | 0.005 |
| R-209 | 0.005 |
| R-210 | 0.006 |
| R-211 | 0.007 |
| R-212 | 0.008 |
| R-213 | 0.012 |
| R-214 | 0.006 |
| R-215 | 0.006 |
| R-216 | 0.007 |
| R-217 | 0.008 |
| R-218 | 0.006 |
| R-219 | 0.011 |
| R-220 | 0.022 |
| R-221 | 0.005 |
| R-222 | 0.009 |
| R-223 | 0.007 |
| R-224 | 0.012 |
| R-225 | 0.004 |
| R-226 | 0.003 |
| R-227 | 0.035 |
| R-229 | 0.007 |
| R-230 | 0.005 |
| R-231 | 0.005 |
| R-232 | 0.061 |
| R-233 | 0.318 |
| R-234 | 0.003 |
| R-235 | 0.01 |
| R-236 | 0.004 |
| R-237 | 0.009 |
| R-238 | 0.007 |
| R-239 | 0.399 |
| R-240 | 0.011 |
| R-241 | 0.009 |
| R-242 | 0.005 |
| R-243 | 0.004 |
| R-244 | 0.004 |
| R-245 | 0.004 |
| R-246 | 0.006 |
| R-247 | 0.005 |
| R-248 | 0.005 |
| R-249 | 0.006 |
| R-250 | 0.009 |
| R-251 | 0.005 |

TABLE 126-continued

| Compound No. | P2X3 IC50 (µM) |
|---|---|
| R-254 | 0.003 |
| R-255 | 0.005 |
| R-256 | 0.002 |
| R-257 | 0.01 |

TABLE 127

| Compound No. | P2X3 IC50 (µM) | Compound No. | P2X3 IC50 (µM) |
|---|---|---|---|
| I-200 | 0.042 | R-275 | 0.023 |
| I-201 | 0.013 | R-276 | 0.042 |
| I-202 | 0.008 | R-277 | 0.014 |
| I-203 | 0.003 | R-278 | 0.015 |
| I-204 | 0.004 | R-279 | 0.007 |
| I-205 | 0.012 | R-280 | 0.009 |
| I-206 | 0.010 | R-281 | 0.007 |
| I-207 | 0.012 | R-282 | 0.023 |
| I-208 | 0.012 | R-283 | 0.028 |
| I-209 | 0.008 | R-284 | 0.005 |
| I-210 | 0.007 | R-285 | 0.006 |
| I-211 | 0.007 | R-286 | 0.006 |
| I-212 | 0.010 | R-287 | 0.006 |
| I-213 | 0.012 | R-288 | 0.012 |
| I-214 | 0.011 | R-289 | 0.005 |
| I-215 | 0.016 | R-290 | 0.006 |
| I-216 | 0.017 | R-291 | 0.006 |
| I-217 | 0.011 | R-292 | 0.004 |
| I-218 | 0.010 | R-293 | 0.004 |
| I-219 | 0.012 | R-294 | 0.006 |
| I-220 | 0.010 | R-295 | 0.006 |
| I-221 | 0.011 | R-296 | 0.005 |
| I-222 | 0.004 | R-297 | 0.008 |
| I-223 | 0.011 | R-298 | 0.009 |
| I-224 | 0.006 | R-299 | 0.020 |
| I-225 | 0.014 | R-300 | 0.008 |
| I-226 | 0.038 | R-301 | 0.005 |
| I-227 | 0.031 | R-302 | 0.006 |
| I-228 | 0.021 | R-303 | 0.003 |
| I-229 | 0.006 | R-304 | 0.004 |
| I-230 | 0.011 | R-305 | 0.007 |
| I-231 | 0.007 | R-306 | 0.014 |
| I-232 | 0.005 | R-307 | 0.013 |
| I-233 | 0.006 | R-309 | 0.004 |
| I-234 | 0.007 | R-310 | 0.004 |
| I-235 | 0.009 | R-311 | 0.428 |
| I-236 | 0.016 | R-312 | 0.350 |
| I-237 | 0.014 | R-313 | 0.003 |
| I-238 | 0.005 | R-314 | 0.048 |
| I-239 | 0.006 | | |
| I-240 | 0.022 | | |
| I-241 | 0.008 | | |
| I-242 | 0.008 | | |
| I-243 | 0.007 | | |
| I-244 | 0.008 | | |
| I-245 | 0.014 | | |
| I-246 | 0.014 | | |
| I-247 | 0.006 | | |
| I-248 | 0.005 | | |
| I-249 | 0.036 | | |
| I-250 | 0.031 | | |
| I-251 | 0.008 | | |
| I-252 | 0.014 | | |
| I-253 | 0.009 | | |
| I-254 | 0.006 | | |
| I-255 | 0.018 | | |
| I-256 | 0.029 | | |
| I-257 | 0.016 | | |
| I-258 | 0.004 | | |
| I-259 | 0.005 | | |
| I-260 | 0.005 | | |
| I-261 | 0.008 | | |
| I-262 | 0.007 | | |
| I-263 | 0.005 | | |

TABLE 127-continued

| Compound No. | P2X3 IC50 (µM) | Compound No. | P2X3 IC50 (µM) |
|---|---|---|---|
| I-264 | 0.005 | | |
| I-265 | 0.010 | | |
| I-266 | 0.008 | | |
| I-267 | 0.003 | | |
| I-268 | 0.003 | | |
| I-269 | 0.004 | | |
| I-270 | 0.004 | | |
| I-271 | 0.010 | | |
| I-272 | 0.008 | | |
| I-273 | 0.005 | | |
| I-274 | 0.005 | | |
| I-275 | 0.004 | | |
| I-276 | 0.019 | | |
| I-277 | 0.004 | | |
| I-278 | 0.006 | | |

Test Example 2 Evaluation of Human $P2X_3$ Receptor Inhibitory Activity in the Presense of Human Serum Albumin (HSA)

Stably expressing cell line (C6BU-1 cell transfected with human $P2X_3$ receptor gene (GenBank accession number Y07683) was used. The cells were seeded in a 96-well microtiter plate at a concentration of 8000 cells/well and cultured in the medium (7.0% fetal bovine serum, 7.0% horse serum, 1% antibiotic and antifungal, and 2.0% glutamine in DMEM) for one day at 37° C. under 5% carbon dioxide atmosphere. The medium was replaced with 4 µM Fluo-3-AM solution (20 mM HEPES, 137 mM NaCl, 5.37 mM KCl, 0.9 mM $MgCl_2$, 1.26 mM $CaCl_2$, 5.6 mM D-glucose, 2.5 mM probenecid, 0.5% BSA, and 0.04% Pluronic F-127, pH 7.5) and incubated at 37° C. under 5% dioxide carbon atmosphere for one hour. The plate was washed with washing buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH7.5), and each well was added with 40 µL of this buffer. The plate was placed in High-Throughput Screening System FDSS 3000 (Hamamatsu Photonics K.K.). Measurement of fluorescence intensity by FDSS 3000 was started, and 40 µL of DMSO solutions containing 1% HSA (final concentrations) different concentrations of the test compound as prepared by dilution with dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH7.5) were dispensed to each well through the built-in automatic dispenser. Five minutes after, 50 nM ATP solution (50 µL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. $IC_{50}$ was calculated using Microsoft Excel (Microsoft Corporation) and XLfit (idbs Ltd.)

The data of the compounds of the present invention are as shown in the following Tables.

TABLE 128

| Compound No. | P2X3 + HSA IC50 (μM) |
|---|---|
| I-019 | 0.068 |
| I-040 | 0.018 |
| I-056 | 0.023 |
| I-070 | 0.037 |
| I-079 | 0.037 |
| R-123 | 0.018 |

Test Example 3 Evaluation of Rat P2X$_3$ Receptor Inhibitory Activity

Rat P2X$_3$ receptor gene (GenBank accession number NM_031075) was expressed in C6BU-1 cell. The C6BU-1 cells were seeded in a 96-well microtiter plate at a concentration of 2500 cells/well and cultured in the medium (7.0% fetal bovine serum, 7.0% horse serum, and 1% antibiotic and antifungal in DMEM) for one day at 37° C. under 5% carbon dioxide atmosphere. The plasmid was transfected into the cells using transfection reagent FuGENE6 (Promega). The transfected cells were cultured in the medium for one day at 37° C. under 5% carbon dioxide atmosphere. The medium was replaced with 4 μM Fluo-3-AM solution (pH7.5) containing 20 mM HEPES, 137 mM NaCl, 5.27 mM KCl, 0.9 mM MgCl$_2$, 1.26 mM CaCl$_2$, 5.6 mM D-glucose, 2.5 mM probenecid, 1% BSA, and 0.08% Pluronic F-127, and incubated at 37° C. under 5% dioxide carbon atmosphere for one hour. The plate was washed with washing buffer (20 mM HEPES, 137 mM NaCl, 5.27 mM KCl, 0.9 mM MgCl$_2$, 1.26 mM CaCl$_2$, 5.6 mM D-glucose, 2.5 mM probenecid, pH7.5), and each well was added with 40 μL of this buffer. The plate was placed in High-Throughput Screening System FDSS 3000 (Hamamatsu Photonics K.K.). Measurement of fluorescence intensity by FDSS 3000 was started, and 40 μL of DMSO solutions containing different concentrations of the test compound as prepared by dilution with dilution buffer (20 mM HEPES, 137 mM NaCl, 5.27 mM KCl, 0.9 mM MgCl$_2$, 1.26 mM CaCl$_2$, 5.6 mM D-glucose, 2.5 mM probenecid, 0.1% Pluronic F-127, pH7.5) were dispensed to each well through the built-in automatic dispenser. Five minutes after, 50 nM ATP solution (50 μL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. IC$_{50}$ was calculated using Microsoft Excel (Microsoft Corporation) and XLfit (idbs Ltd.).

The data of the compounds of the present invention are as shown in the following Table.

TABLE 129

| Compound No. | ratP2X3 IC50 (μM) |
|---|---|
| I-002 | 0.006 |
| R-009 | 0.004 |

Test Example 4 Evaluation of Rat P2X$_3$ Receptor Inhibitory Activity in the Presence of Rat Serum Albumin (RSA)

Rat P2X$_3$ receptor gene (GenBank accession number NM_031075) was expressed in C6BU-1 cell. The C6BU-1 cells were seeded in a 96-well microtiter plate at a concentration of 2500 cells/well and cultured in the medium (7.0% fetal bovine serum, 7.0% horse serum, and 1% antibiotic and antifungal in DMEM) for one day at 37° C. under 5% carbon dioxide atmosphere. The plasmid was transfected into the cells using transfection reagent FuGENE6 (Promega). The transfected cells were cultured in the medium for one day at 37° C. under 5% carbon dioxide atmosphere. The medium was replaced with 4 μM Fluo-4-AM solution (pH7.5) containing 20 mM HEPES, 137 mM NaCl, 5.27 mM KCl, 0.9 mM MgCl$_2$, 1.26 mM CaCl$_2$, 5.6 mM D-glucose, 2.5 mM probenecid, 10% BSA, and 0.08% Pluronic F-127, and incubated at 37° C. under 5% dioxide carbon atmosphere for one hour. The plate was washed with washing buffer (20 mM HEPES, 137 mM NaCl, 5.27 mM KCl, 0.9 mM MgCl$_2$, 1.26 mM CaCl$_2$, 5.6 mM D-glucose, 2.5 mM probenecid, pH7.5), and each well was added with 40 μL of this buffer. The plate was placed in High-Throughput Screening System FDSS 3000 (Hamamatsu Photonics K.K.). Measurement of fluorescence intensity by FDSS 3000 was started, and 40 μL of DMSO solutions containing 1% RSA (final concentrations) and different concentrations of the test compound as prepared by dilution with dilution buffer (20 mM HEPES, 137 mM NaCl, 5.27 mM KCl, 0.9 mM MgCl$_2$, 1.26 mM CaCl$_2$, 5.6 mM D-glucose, 2.5 mM probenecid, 0.1% Pluronic F-127, pH7.5) were dispensed to each well through the built-in automatic dispenser. Five minutes after, 50 nM ATP solution (50 μL) prepared by dilution with the dilution buffer was dispensed through the built-in automatic dispenser, and the measurement of fluorescence intensity was continued for 4 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. IC$_{50}$ was calculated using Microsoft Excel (Microsoft Corporation) and XLfit (idbs Ltd.).

The data of the compounds of the present invention are as shown in the following Table.

TABLE 130

| Compound No. | ratP2X3 + RSA IC50 (μM) |
|---|---|
| I-019 | 0.011 |
| I-022 | 0.011 |
| I-040 | 0.009 |

TABLE 130-continued

| Compound No. | ratP2X3 + RSA IC50 (μM) |
|---|---|
| I-100 | 0.009 |
| I-113 | 0.010 |
| R-014 | 0.006 |
| R-019 | 0.008 |
| R-037 | 0.008 |

As shown, the compounds described in the present specification showed inhibiting activity on $P2X_3$ receptor. Furthermore, as the compounds of the invention are effective on $P2X_3$ subtype, the compounds are also considered to have inhibiting activity on $P2X_{2/3}$ receptor, which comprises $P2X_2$ subtype.

Test Example 5 Evaluation of the Urinary Function in a Rat Model of Cystitis

Surgery for Cystometry

A rat is fixed in the supine position after being given anesthesia through the inhalation of 2% isoflurane (Anesthetic background; Nitrous oxide:Oxygen=7:3). A midline incision is made in its abdomen to expose the bladder. A cannula (made by processing a polyethylene tube (PE-50: Becton Dickinson)) is inserted through a small incision on top of the bladder and fixed to create a bladder fistula. The other end of the cannula is led through the hypodermal tissue to the back, and the muscular coat and skin are sutured. The cannula, which is led to the back, is protected with a stainless spring in the middle and connected to the cannula swivel.

Acetic Acid Infusion

Two days after the surgery, 0.3% acetic acid is infused into the bladder through the indwelled cannula at a rate of 4 mL/hr for 30 minutes to induce cystitis. The animals, where acetic acid is not infused, are used as normal animals.

Cystometry Measurement

Two or three days after the acetic acid infusion, the other end of the cannula inserted into the bladder is connected to a T shape stopcock and then the intravesical pressure is recorded continuously using a pressure amplifier while infusing warmed normal saline solution at a rate of 3.0 mL/hr from one side and through a pressure transducer on the other side. The baseline of the intravesical pressure is measured (for approximately 40 minutes) after a measurement for stable duration (for approximately 20 minutes). After that, a vehicle, positive control compound or test compound are administered, and the value after administration is measured for approximately 120 minutes. A compound of the present invention is crushed with a mortar and pestle so as to be 0.1-2 mg/mL/kg solution or suspension using 0.5% methylcellulose solution, and administered to an animal orally with an oral sonde. At the same time, the voided urine is received on scales under the cage to measure the variation in weight simultaneously.

Data Adoption Criteria

Based on the voiding interval, normal animals whose voiding interval is 10 minutes or longer were adopted and those whose voiding interval is shorter than that were excluded. In the case of the animals into which acetic acid is infused, those whose voiding interval is less than half the average value of the normal animals are adopted as animals with cystitis and those whose voiding interval is longer than that were excluded.

Collection of Residual Urine

After the completion of the measurement, the infusion of normal saline solution is stopped immediately after urination to collect the residual urine under pentobarbital sodium anesthesia. The collected residual urine is transferred to the voided urine receiver and recorded on the chart.

Analysis Items

Intravesical pressure one to two hours after the start of the measurement (pressure during rest and pressure during urination), voiding interval, voided volume per urination, and residual urine volume The following value is used as an indicator of the effect on the voiding interval:

Improvement rate of the urinary function=(Voiding interval of an animal with cystitis after drug treatment−Voiding interval of an animal with cystitis before drug treatment)/(Mean voiding interval of normal animals before drug treatment−Voiding interval of an animal with cystitis before drug treatment)×100

The following value is used as an indicator of the effect on the voided volume per urination:

Improvement rate of the voided volume per urination=(Voided volume per urination of a rat with cystitis after drug treatment−Voided volume per urination of an animal with cystitis before drug treatment)/(Mean voided volume per urination of normal animals before drug treatment−Voided volume per urination of an animal with cystitis before drug treatment)×100

Test Example 6 Analgesic Effect in a Seltzer Model

Preparation of Partial Sciatic Nerve Ligation Model in Rats

Rats were anaesthetized using isoflurane/O2 inhalation anaesthesia. After induction of anesthesia, the left thigh was shaved. An incision was made in the skin just below the hip bone. The muscle was bluntly dissected to expose the sciatic nerve. One third (⅓) to one half (½) of the sciatic nerve thickness was tightly ligated and the wound was closed. The right thigh is used as a sham-operated control. The right thigh undergoes an identical procedure with the left hind limb, however, the sciatic nerve is not manipulated or ligated.

Evaluation (1)

Two weeks after nerve ligation, the effect on mechanical allodynia was assessed using a series of von Frey filaments. For habituation, the rats were placed into a plastic cage on a wire mesh bottom. The mechanical sensitivity (mechanical threshold) of the hind paws was estimated with a series of von Frey filaments (0.4-26 g). The measurement of mechanical sensitivity of the right and left hind paws was performed to obtain predose mechanical sensitivity. The rats showing the threshold change from 0.6 to 2 g (in nerve ligated side) and 8 to 15 g (in sham operated side) were used in the experiments. On the day before the experiment, the rats were evaluated with a series of von Frey filaments to familiarize them with the test procedure. The adopted animal was administrated with the test compounds. The test compounds were homogenized with mortar and pestle and suspended or diluted in 0.5% Methyl Cellulose to prepare 0.1-2.0 mg/mL/kg suspension and orally administered to rat using a syringe attached with a sonde. Post-dose mechanical sensitivities of the right and left hind paws were measured at approximately 1 to 5 hours after drug administration. Percent reversal of mechanical allodynia for each rat was calculated using the following formula. The analgesic effects of the compounds were compared.

$$\% \text{ Reversal} = \frac{\text{Log}_{10}(\text{Postdose mechanical sensitivity in nerve ligated side}) - \text{Log}_{10}(\text{Predose mechanical sensitivity in nerve ligated side})}{\text{Log}_{10}(\text{Predose mechanical sensitivity in sham operated side}) - \text{Log}_{10}(\text{Predose mechanical sensitivity in nerve ligated side})}$$

The analgesic effects of the compounds of the present invention after single administration of 1 mg/kg at 3 hours are as shown in the following Table.

TABLE 131

| Compound No. | % reversal |
|---|---|
| I-019 | 27.9 |
| I-057 | 21.4 |

Evaluation (2)

Mechanical hyperalgesia is evaluated using an analgesy meter. Two weeks after nerve ligation, the paw pressure test is performed using an analgesy meter (stimulus pressure increased 16 g per second) to obtain paw withdrawal thresholds (PWT). Measurements are made on both sides of the hind paw and to obtain pre-dose PWT. The rats showing the threshold change from 60 to 90 g (in nerve ligated side) and 100 to 175 g (in sham operated side) are used in the experiments. On the day before the experiment, the rats have their hind paws set on the apparatus to familiarize them with the test procedure. The adopted animal is administrated with the test compounds. The test compounds are homogenized with mortar and pestle and suspended or diluted in 0.5% Methyl Cellulose to prepare 0.03-100 mg/2 mL/kg suspension and orally administered to rat using a syringe attached with a sonde. Post-dose PWT of the right and left hind paws are measured at approximately 1 to 5 hours after drug administration. Percent reversal of mechanical hyperalgesia for each rat is calculated using the following formula. The analgesic effects of the compounds are compared.

Postdose PWT in nerve ligated side−Predose PWT in nerve ligated % Reversal=side

Predose PWT in sham operated side−Predose PWT in nerve ligated side

Test Example 7 CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 1.56, 3.125, 6.25, 12.5, 25, 50 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile:0.5 mol/L Tris (trishydroxyaminomethane)=4:1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile:0.5 mol/L Tris (trishydroxyaminomethane)=4:1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

The results of the compounds of the present invention are as shown in the following Table.

TABLE 132

| Compound No. | MBI |
|---|---|
| I-041 | (—) |
| I-057 | (—) |
| I-063 | (—) |
| I-069 | (—) |
| I-106 | (—) |
| R-010 | (—) |
| R-014 | (—) |
| R-027 | (—) |
| R-058 | (—) |

Test Example 8 CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1.0, 5.0, 10, 20 µmol/L (four points).

Each five kinds of substrates, human hepatic microsome, or a test drug in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

The data of the compounds of the present invention are as shown in the following Table.

TABLE 133

| Compound No. | CYP1A2 (μmol/L) | CYP2C9 (μmol/L) | CYP2C19 (μmol/L) | CYP2D6 (μmol/L) | CYP3A4 (μmol/L) |
|---|---|---|---|---|---|
| I-041 | >20 | >20 | >20 | >20 | >20 |
| I-057 | >20 | >20 | >20 | >20 | >20 |
| I-063 | >20 | >20 | >20 | >20 | >20 |
| I-069 | >20 | >20 | >20 | >20 | >20 |
| I-106 | >20 | >20 | >20 | >20 | >20 |
| R-010 | >20 | >20 | >20 | >20 | >20 |
| R-014 | >20 | >20 | >20 | >20 | >20 |
| R-027 | >20 | >20 | >20 | >20 | >20 |
| R-058 | >20 | >20 | >20 | >20 | >20 |

Test Example 9 Fluctuation Ames Test

Mutagenicity of compounds of the present invention was evaluated.

20 μL of freezing-stored rat typhoid bacillus (Salmonella typhimurium TA98 strain, TA100 strain) was inoculated on 10 mL of a liquid nutrient medium (2.5% Oxoid nutrient broth No. 2), and this was cultured before shaking at 37° C. for 10 hours. 7.70 mL of a bacterial solution of the TA98 strain was centrifuged (2000×g, 10 minutes) to remove a culturing solution. The bacteria was suspended in 7.70 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), the suspension was added to 110 mL of an Exposure medium (Micro F buffer containing Biotin: 8 μg/mL, histidine: 0.2 μg/mL, glucose: 8 mg/mL). The TA100 strain was added to 120 mL of the Exposure medium relative to 3.42 mL of the bacterial solution to prepare a test bacterial solution. Each 12 μL of DMSO solution of a compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 5884 of the test bacterial solution (a mixed solution of 498 μl of the test bacterial solution and 90 μL of S9 mix under the metabolism activating condition) were mixed, and this was shaking-cultured at 37° C. for 90 minutes. 460 μL of the bacterial solution exposed to a compound of the present invention was mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.

The data of the compounds of the present invention are as shown in the following Table.

TABLE 134

| Compound No. | FAT |
|---|---|
| I-002 | (—) |
| I-019 | (—) |
| I-040 | (—) |
| I-057 | (—) |
| I-070 | (—) |

Test Example 10 Solubility Test

The solubility of a compound was determined under a condition in which 1% DMSO was added. 10 mmol/L compound solution was prepared using DMSO, and then 2 μL of the compound solution was added to 198 μL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1), and then a concentration in the filtration was measured with HPLC or LC/MS/MS by the absolute calibration method.

The reslults of the compounds of the present invention are as shown in the following Table.

TABLE 135

| Compound No. | Solubility (μmol/L) |
|---|---|
| I-002 | >50 |
| I-019 | >50 |
| I-038 | >50 |
| I-039 | >50 |
| I-040 | >50 |
| I-041 | >50 |
| I-057 | >50 |
| I-063 | >50 |

Test Example 11 Metabolism Stability Test

Using commercially available pooled human hepatic microsomes, a test compound is reacted for a constant time, a remaining rate is calculated by comparing a reacted sample and an unreacted sample, thereby, a degree of metabolism in liver is assessed.

A reaction was performed (oxidative reaction) at 37° C. for 0 minute or 30 minutes in the presence of 1 mmol/L NADPH in 0.2 mL of a buffer (50 mmol/L tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%.

The data of the compounds of the present invention are as shown in the following Table. The remaining rate at the compound concentration 0.5 μmol/L are shown below.

TABLE 136

| Compound No. | Metabolism Stability (%) |
|---|---|
| I-002 | 99 |
| I-019 | 96 |
| I-029 | 100 |
| I-057 | 91 |
| I-063 | 97 |
| I-070 | 103 |

Test Example 12 Metabolism Stability Test

The test compound is reacted for a given period of time using cryopreserved rat hepatocytes that are prepared and the residual ratio is calculated based on the comparison between reacted and unreacted samples to evaluate the degree of hepatic metabolism.

The compound is reacted in the Williams E medium containing $1.0 \times 10^6$ cells/mL of cryopreserved rat hepatocytes at a temperature of 37.0 for 0, 1 or 2 hours. After reaction, 50 μL of reaction solution is added to and mixed with 100 μL of a solution containing methanol and acetonitrile in the proportion of one to one (v/v) and the mixture is centrifuged at 3000 rpm for 15 minutes. The test compound contained in the centrifugal supernatant is quantitated using a LC/MS/MS system and the residual ratio of the test compound after reaction is calculated regarding the amount of compound after the reaction for 0 minute as 100%.

Test Example 13 hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, CaCl$_2$: 2 mmol/L, MgCl$_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

The data of the compounds of the present invention are as shown in the following Table.

TABLE 137

| Compound No. | hERG Inhibition (%) |
|---|---|
| I-002 | 7.3 |
| I-006 | 5.3 |

Test Example 14 Protein Binding Test

The unbound fraction of the present compound in serum was measured using serum of various species.

The reactive conditions are as follows: Evaluation method, Equilibrium dialysis; Reaction time, 24 hours; Reaction temperature, 37° C.; Concentration of the present compound, 2 μg/mL The test solution was added to each serum and the mixture was agitated to prepare the serum samples at the concentration mentioned above. Each serum sample was added into one side of the cell and phosphate buffered saline (PBS) was added into the other side to perform equilibrium dialysis at 37° C. for 24 hours. Then, the concentration of the compounds in the samples that were obtained from both sides was measured by LC/MS/MS.

The data of the compounds of the present invention are as shown in the following Table. The ratio of PBS concentration to serum concentration is expressed as unbound fraction (fu).

TABLE 138

| Compound No. | fu (%) |
|---|---|
| I-019 | 1 |
| I-029 | 1.7 |
| I-040 | 3.5 |
| I-056 | 1.8 |
| I-057 | 1.7 |
| R-019 | 1.8 |

Test Example 15 Pharmacokinetic Test

Materials and Methods
(1) Animals: SD rats were used
(2) Breeding conditions: SD rats were allowed to freely take solid food and sterilized tap water.
(3) Dose and grouping: orally or intravenously administered at a predetermined dose; grouping was as follows (Dose depends on the compound)
Oral administration: 1 mg/kg (n=2)
Intravenous administration: 0.5 mg/kg (n=2)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe (6) Evaluation items: blood was collected over time, and the plasma concentration of drug was measured by LC/MS/MS (7) Statistical analysis: regarding the transition of the plasma concentration of the present compound, the area under the plasma concentration-time curve (AUC) was calculated by non-linear least squares program WinNonlin (Registered trade name), and the bioavailability (BA) was calculated from the AUCs of the oral administration group and intravenous administration group. The total body clearance (CLtot) was calculated by dividing the dose by the AUC of the intravenous administration group.

The data of the compounds of the present invention are as shown in the following Table.

TABLE 139

| Compound No. | AUC (po) (ng · hr/mL) | AUC (iv) (ng · hr/mL) | BA (%) | CLtot (mL/min/kg) |
|---|---|---|---|---|
| I-014 | 4890 | 2300 | 106.2 | 4 |
| I-017 | 6110 | 3790 | 80.7 | 2.3 |
| I-040 | 410 | 291 | 70.3 | 28.6 |
| I-057 | 487 | 367 | 66.4 | 22.9 |
| I-058 | 2030 | 1510 | 67.2 | 5.8 |
| I-127 | 2460 | 2330 | 52.8 | 3.8 |

Test Example 16 Powder Solubility Test

Appropriate quantity of the compound of the present invention is put in a suitable container and 200 µL of JP-1 solution (water was added to 2.0 g of sodium chloride and 7.0 mL of hydrochloric acid to reach 1000 mL), JP-2 solution (500 mL of water is added to 500 mL of phosphate buffer with a pH of 6.8) or 20 mmol/L sodium taurocholate (TCA)/JP-2 solution (JP-2 solution was added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol was added to 100 µL of each filtrate to dilute two-fold. The dilution rate is changed as necessary. After checking that there is no bubble and deposit, the container is sealed and shaken. The compound of the present invention is measured using HPLC by absolute calibration curve method.

Preparation Example

The following Formulation Examples are only exemplified and not intended to limit the scope of the invention.

Formulation Example 1: Tablet

| Compound of the present invention | 15 mg |
|---|---|
| Lactose | 15 mg |
| Calcium Stearate | 3 mg |

The above ingredients other than Calcium Stearate are uniformly mixed, crushed, granule, dried to prepare granules of suitable size. After addition of Calcium Stearate, the mixture is compressed to prepare tables.

Formulation Example 2: Capsules

| Compound of the present invention | 10 mg |
|---|---|
| Magnecium Stearate | 10 mg |
| Lactose | 80 mg |

The above ingredients are uniformly mixed to prepare powdered medicine as powder or fine particles, which are put into capsule containers to prepare capsules.

Formulation Example 3: Granules

| Compound of the present invention | 30 g |
|---|---|
| Lactose | 265 g |
| Magnecium Stearate | 5 g |

The above ingredients are fully mixed, compressed, crushed, selected the size to prepare granules of suitable size.

Formulation Example 4: Orally Dispersing Tablets

The compounds of the present invention and crystalline cellulose are mixed, granulated and tablets are made to give orally dispersing tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injection.

Formulation Example 7: Infusions

The compounds of the present invention and phosphate buffer are mixed to give injection.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compounds represented by Formula (I) have an antagonistic activity on $P2X_3$ and/or $P2X_{2/3}$ receptor and are useful in the treatment of diseases or conditions associated with a $P2X_3$ and/or $P2X_{2/3}$ receptor, such as chronic pain, urination disorder, respiratory disease, and the like.

The invention claimed is:

1. A method for treating pain, comprising administering to a person in need thereof a pharmaceutically effective amount of a compound:

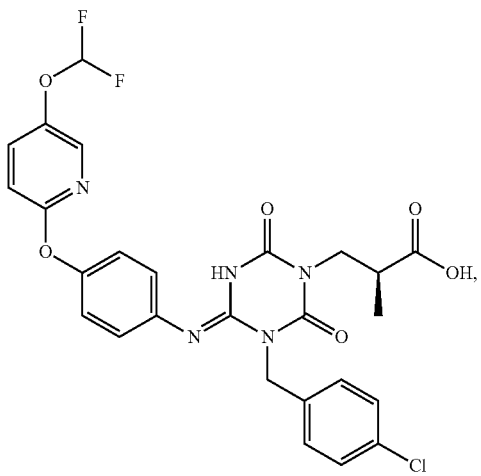

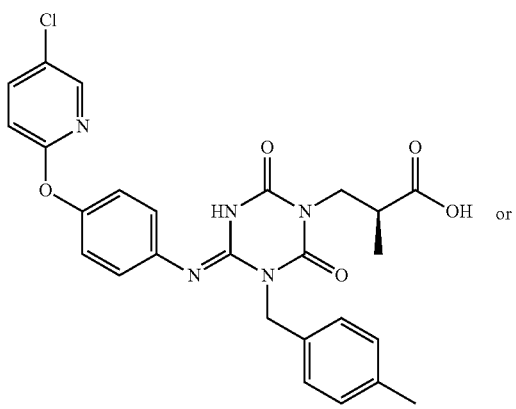 or

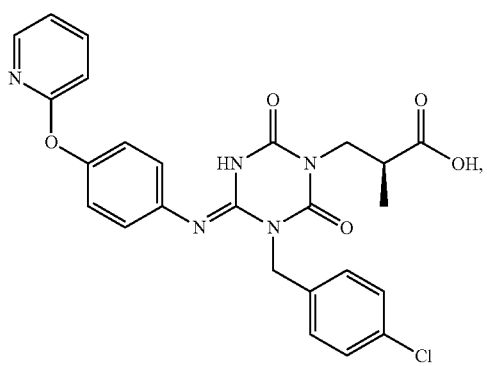

or its pharmaceutically acceptable salt.

2. The method according to claim 1, wherein the compound is the following formula:

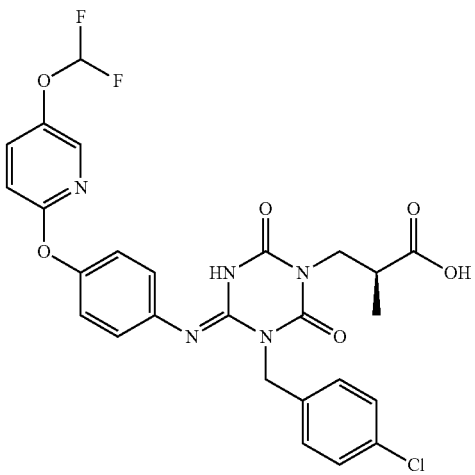 [SMILES: C[C@@H](Cn1c(=O)[nH]/c(=N\c2ccc(Oc3ccc(OC(F)F)cn3)cc2)n(Cc2ccc(Cl)cc2)c1=O)C(=O)O]

or its pharmaceutically acceptable salt.

3. The method according to claim 1, wherein the compound is the following formula:

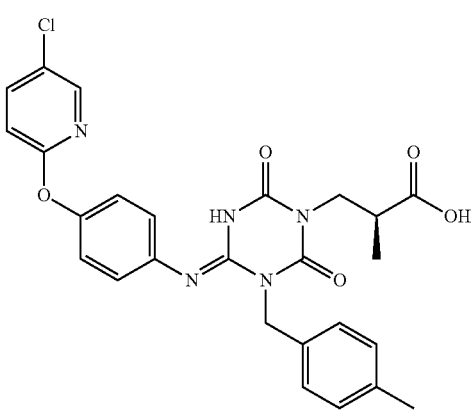 [SMILES: Cc1ccc(Cn2c(=O)n(C[C@H](C)C(=O)O)c(=O)[nH]/c2=N\c2ccc(Oc3ccc(Cl)cn3)cc2)cc1]

or its pharmaceutically acceptable salt.

4. The method according to claim 1, wherein the compound is the following formula:

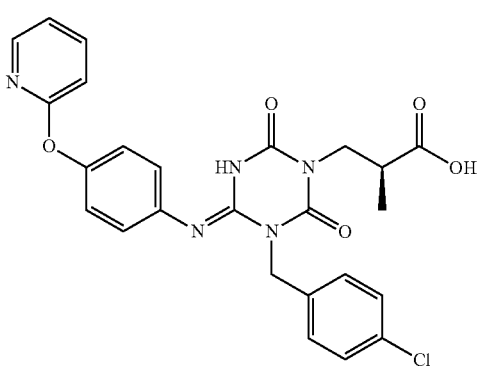

or its pharmaceutically acceptable salt.

* * * * *